(12) United States Patent
Drescher et al.

(10) Patent No.: US 8,470,810 B2
(45) Date of Patent: Jun. 25, 2013

(54) HETEROCYCLIC COMPOUNDS SUITABLE FOR TREATING DISORDERS THAT RESPOND TO MODULATION OF THE DOPAMINE D3 RECEPTOR

(75) Inventors: Karla Drescher, Dossenheim (DE); Andreas Haupt, Schwetzingen (DE); Liliane Unger, Ludwigshafen (DE); Sean C. Turner, Mannheim (DE); Wilfried Braje, Mannheim (DE); Roland Grandel, Bad Rappenau (DE); Christophe Henry, München (DE); Gisela Backfisch, Dossenheim (DE); Armin Beyerbach, Allschwil (CH); Wilfried Lubisch, Heidelberg (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/868,480

(22) Filed: Aug. 25, 2010

(65) Prior Publication Data
US 2011/0160176 A1  Jun. 30, 2011

Related U.S. Application Data

(62) Division of application No. 11/665,399, filed as application No. PCT/EP2005/011106 on Oct. 14, 2005, now Pat. No. 7,851,463.

(60) Provisional application No. 60/618,878, filed on Oct. 14, 2004.

(51) Int. Cl.
*A61K 31/397* (2006.01)
*C07D 413/02* (2006.01)

(52) U.S. Cl.
USPC ........................................ 514/210.2; 548/235

(58) Field of Classification Search
USPC .............. 514/210.2, 428, 256, 361, 374, 315; 548/567, 950, 127, 215; 546/268.1, 184; 544/242
See application file for complete search history.

(56) References Cited

U.S. PATENT DOCUMENTS

| | | | |
|---|---|---|---|
| 4,818,275 A | 4/1989 | Theodoridis | |
| 5,464,810 A | 11/1995 | Haas et al. | |
| 5,708,018 A | 1/1998 | Haadsma-Svensson et al. | |
| 6,423,717 B1 | 7/2002 | Bromidge et al. | |
| 7,851,463 B2 * | 12/2010 | Drescher et al. | 514/210.2 |
| 2009/0306175 A1 * | 12/2009 | Grandel et al. | 514/429 |

FOREIGN PATENT DOCUMENTS

| | | |
|---|---|---|
| EP | 0609734 | 8/1994 |
| WO | 87/03782 | 7/1987 |
| WO | 90/09787 | 9/1990 |
| WO | 9504713 | 2/1995 |
| WO | 9623760 | 8/1996 |
| WO | 9745503 | 12/1997 |
| WO | 9827081 | 6/1998 |
| WO | 9958499 | 11/1999 |
| WO | 0005225 | 2/2000 |

OTHER PUBLICATIONS

"Autism," [retrieved on Apr. 14, 2008]. Retrieved online via Internet, URL: http://www.nlm.nih.gov/medlineplus/autism.html.*

(Continued)

*Primary Examiner* — Kristin Bianchi
(74) *Attorney, Agent, or Firm* — Lisa V. Mueller; Michael Best & Friedrich LLP

(57) ABSTRACT

The invention relates to compounds of the formula (I) wherein n is 0, 1 or 2; G is $CH_2$ or $CHR^3$; $R^1$ is H, $C_1$-$C_6$-alkyl, $C_1$-$C_6$-alkyl substituted by $C_3$-$C_6$-cycloalkyl, $C_1$-$C_6$-hydroxyalkyl, fluorinated $C_1$-$C_6$-alkyl, $C_3$-$C_6$-cycloalkyl, fluorinated $C_3$-$C_6$-cycloalkyl, $C_3$-$C_6$ alkenyl, fluorinated $C_3$-$C_6$-alkenyl, formyl, acetyl or propionyl; $R^2$, $R^3$ and $R^4$ are, independently of each other, H, methyl, fluoromethyl, difluoromethyl, or trifluoromethyl; A is phenylene, pyridylene, pyrimidylene, pyrazinylene, pyridazinylene or thiophenylene, which can be substituted by one or more substituents selected from halogen, methyl, methoxy and $CF_3$; E is $NR^5$ or $CH_2$, wherein $R^5$ is H or $C_1$-$C_3$-alkyl; Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$alkylcarbonyl or fluorinated $C_1$-$C_4$-alkylcarbonyl, and where the cyclic radical Ar may carry 1, 2 or 3 substituents $R^a$, wherein the variable $R^a$ has the meanings given in the claims and in the description; and physiologically tolerated acid addition salts thereof. The invention also relates to the use of a compound of the formula I or a pharmaceutically acceptable salt thereof for preparing a pharmaceutical composition for the treatment of a medical disorder susceptible to treatment with a dopamine D3 receptor ligand.

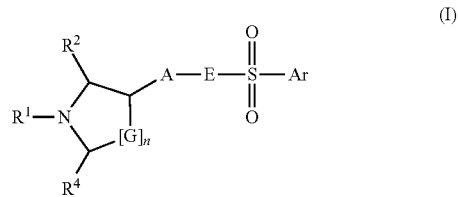

(I)

20 Claims, No Drawings

OTHER PUBLICATIONS

"Anxiety," [retrieved on Apr. 14, 2008]. Retrieved online via Internet, URL: http://www.nlm.nih.gov/medlineplus/anxiety.html.*

Joyce, J.N., Dopamine D3 receptor as a therapeutic target for antipsychotic and antiparkinsonian drugs. Pharmacology and Therapeutics, 2001, 90, pp. 231-259.

Laszy, J., et al. Dopamine D3 receptor antagonists improve the learning performance in memory-impaired rats. Psychopharmacology, 2005, 179, pp. 567-575.

Heidbreder, C.A., et al., The role of central dopamine D3 receptors in drug addiction: a review of pharmacological evidence. Brain Research Reviews, 2005, 49, 77-105.

Rogoz, Z., et al., Anxiolytic-like effects of preferential dopamine D3 receptor agonists in an animal model. Polish Journal of Pharmacology, 2003, 55, pp. 449-454.

Muhlbauer, B., et al., Dopamine D3 receptors in the rat kidney: role in physiology and pathophysiology. Acta Physiologica Scandinavica, 2000, 168(1), pp. 219-223.

Benoit, S.C., et al., Altered feeding responses in mice with targeted disruption of the dopamine-3 receptor gene. Behavioral Neuroscience, 2003, 117(1), 46-54.

Schwartz, J.C., et al., The Dopamine D1 Receptor as a Target for Antipsychotics, in Novel Antipsychotic Drugs, H. Y. Meitzer, Ed. Raven Press, New York, 1992, pp. 135-144.

Dooley, M, et al., Drugs and Aging, 1998, 12, pp. 495-514.

Joyce, J.N., Pharmacology and Therapeutics, 2001, 90, pp. 231-259, "The Dopamine D1 Receptor as a Therapeutic Target for Antipsychotic and Antiparkinsonian Drugs."

Sokoloff, P., et al., Molecular Cloning and Characterization of a Novel Dopamine Receptor (D3) as a Target for Neuroleptics, Nature, 347, 146 (1990).

Sokoloff, P., et al., Localization and Function of the D3 Dopamine Receptor, Arzneim, Frosch/Drug Res. 42(1), 224 (1992).

* cited by examiner

HETEROCYCLIC COMPOUNDS SUITABLE FOR TREATING DISORDERS THAT RESPOND TO MODULATION OF THE DOPAMINE D3 RECEPTOR

CROSS-REFERENCE TO RELATED APPLICATIONS

This is a divisional of U.S. patent application Ser. No. 11/665,399, filed on Sep. 24, 2007, now U.S. Pat. No. 7,851,463 which is the U.S. national stage of PCT/EP2005/011106, filed on Oct. 14, 2005, which claims priority to U.S. provisional patent application No. 60/618,878, filed on Oct. 14, 2004, the contents of all of which are hereby incorporated by reference.

BACKGROUND OF THE INVENTION

The present invention relates to novel heterocyclic compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and anti parkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

Compounds having an affinity for the dopamine $D_3$ receptor have been described in the prior art on various occasions, e.g. in WO 95/04713, WO 96/23760, WO 97/45503, WO98/27081 and WO 99/58499. Some of these compounds possess moderate affinities and or selectivities for the dopamine $D_3$ receptor. They have therefore been proposed as being suitable for treating diseases of the central nervous system. Some of the compounds described in these publications possess a pyrrolidinylphenyl structure. Unfortunately their affinity and selectivity towards the $D_3$ receptor or their pharmacological profile are not satisfactory. Consequently there is an ongoing need to provide new compounds, which either have an high affinity and an improved selectivity. The compounds should also have good pharmacological profile, e.g. a high brain plasma ratio, a high bioavailability, good metabolic stability, or a decreased inhibition of the mitochondrial respiration.

SUMMARY OF THE INVENTION

The invention is based on the object of providing compounds which act as highly selective dopamine $D_3$ receptor ligands. This object is surprisingly achieved by means of compounds of the formula I

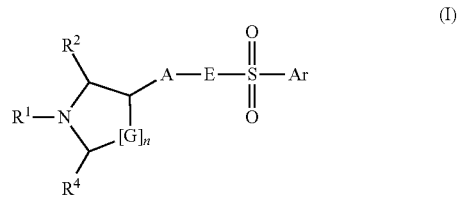

wherein
n is 0, 1 or 2;
G is $CH_2$ or $CHR^3$;
$R^1$ is H, $C_1$-$C_6$-alkyl, $C_1$-$C_6$-alkyl substituted by $C_3$-$C_6$-cycloalkyl, $C_1$-$C_6$-hydroxyalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl;
$R^2$, $R^3$ and $R^4$ are, independently of each other, H, methyl, fluoromethyl, difluoromethyl, or trifluoromethyl;
A is phenylene, pyridylene, pyrimidylene, pyrazinylene, pyridazinylene or thiophenylene, which can be substituted by one or more substituents selected from halogen, methyl, methoxy and $CF_3$;
E is $NR^5$ or $CH_2$, wherein $R^5$ is H or $C_1$-$C_3$-alkyl;
Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl, and where the cyclic radical Ar may carry 1, 2 or 3 substituents $R^a$;
$R^a$ is halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, benzyloxy, phenoxy, where the phenyl radical in the 3 last-mentioned radicals may be unsubstituted or may carry 1 to 3 substituents selected from $C_1$-$C_4$-alkyl, fluorinated $C_1$-$C_4$-alkyl and halogen, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, NH—C(O)—$NR^6R^7$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring, or is a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the heterocyclic ring may carry 1, 2 or 3 substituents selected from hydroxy, halogen, $C_1$-$C_6$-alkyl, fluorinated $C_1$-$C_6$-alkyl and $C_1$-$C_6$-alkoxy;

and physiologically tolerated acid addition salts thereof.

The present invention therefore relates to compounds of the general formula I and to their physiologically tolerated acid addition salts.

The present invention also relates to a pharmaceutical composition which comprises at least one compound of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

Particularly, the carbon atom of the nitrogen-containing ring carrying the group A may have (S) or (R) configuration. However, the (S) configuration is preferred.

Moreover, the radical A may be in a cis or trans position to either of the substituents $R^2$, $R^3$ or $R^4$ (if at least one of those is not hydrogen). However, the cis position is preferred.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$—$C_m$ indicates in each case the possible number of carbon atoms in the group.

The term halogen denotes in each case fluorine, bromine, chlorine or iodine, in particular fluorine, chlorine or bromine.

$C_1$-$C_4$ Alkyl is a straight-chain or branched alkyl group having from 1 to 4 carbon atoms. Examples of an alkyl group are methyl, ethyl, n-propyl, iso-propyl, n-butyl, 2-butyl, isobutyl or tert-butyl. $C_1$-$C_2$ Alkyl is methyl or ethyl, $C_1$-$C_3$ alkyl is additionally n-propyl or isopropyl.

$C_1$-$C_6$ Alkyl is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methyl pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_6$ alkyl is a straight-chain or branched alkyl group having from 1 to 6, especially 1 to 4 carbon atoms, in particular 1 to 3 carbon atoms, wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl, 1-methyl-1-ethylpropyl.

Fluorinated branched $C_3$-$C_6$ alkyl is alkyl having 3 to 6 carbon atoms at least one being a secondary or tertiary carbon atom wherein at least one, e.g. 1, 2, 3, 4 or all of the hydrogen atoms are replaced by a fluorine atom.

$C_1$-$C_6$ Alkoxy is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Fluorinated $C_1$-$C_6$ alkoxy is a straight-chain or branched alkoxy group having from 1 to 6, in particular 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_6$ Hydroxyalkyl is a straight-chain or branched alkyl group having from 1 to 6, especially 1 to 4 carbon atoms, in particular 1 to 3 carbon atoms, wherein one of the hydrogen atoms is replaced by a hydroxy group, such as in 2-hydroxyethyl or 3-hydroxypropyl.

$C_1$-$C_6$-Alkoxy-$C_1$-$C_6$-alkyl is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in methoxymethyl, 2-methoxyethyl, ethoxymethyl, 3-methoxypropyl, 3-ethoxypropyl and the like.

$C_1$-$C_6$-Alkoxy-$C_1$-$C_6$-alkoxy is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in 2-methoxyethoxy, ethoxymethoxy, 2-ethoxyethoxy, 3-methoxypropoxy, 3-ethoxypropoxy and the like.

$C_1$-$C_6$-Alkylcarbonyl is a straight-chain or branched alkyl group having from 1 to 6, especially 1 to 4 carbon atoms, in particular 1 to 3 carbon atoms, wherein one of the hydrogen atoms is replaced by a carbonyl group (CO), such as in acetyl and propionyl.

Fluorinated $C_1$-$C_6$-alkylcarbonyl is a straight-chain or branched alkyl group having from 1 to 6, especially 1 to 4 carbon atoms, in particular 1 to 3 carbon atoms, wherein one of the hydrogen atoms is replaced by a carbonyl group (CO) and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_6$-Alkylcarbonylamino is a straight-chain or branched alkyl group having from 1 to 6, especially 1 to 4 carbon atoms, in particular 1 to 3 carbon atoms, wherein one of the hydrogen atoms is replaced by a carbonylamino group (CO—NH—), such as in acetamido ($CH_3CONH$—) and propionamido ($CH_3CH_2CONH$—).

Fluorinated $C_1$-$C_6$-alkylcarbonylamino is a straight-chain or branched alkyl group having from 1 to 6, especially 1 to 4 carbon atoms, in particular 1 to 3 carbon atoms, wherein one of the hydrogen atoms is replaced by a carbonylamino group (CO—NH—) and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_6$ Alkylthio (also termed as $C_1$-$C_6$-alkylsulfanyl) (or $C_1$-$C_6$-alkylsulfinyl or $C_1$-$C_6$-alkylsulfonyl, respectively) refer to straight-chain or branched alkyl groups having 1 to 6 carbon atoms, e.g. 1 to 4 carbon atoms, which are bound to the remainder of the molecule via a sulfur atom (or S(O)O in case of alkylsulfinyl or S(O)$_2$O in case of alkylsulfonyl, respectively), at any bond in the alkyl group. Examples for $C_1$-$C_4$-alkylthio include methylthio, ethylthio, propylthio, isopropylthio, and n-butylthio. Examples for $C_1$-$C_4$-alkylsulfinyl include methylsulfinyl, ethylsulfinyl, propylsulfinyl, isopropylsulfinyl, and n-butylsulfinyl. Examples for $C_1$-$C_4$-alkylsulfonyl include methylsulfonyl, ethylsulfonyl, propylsulfonyl, isopropylsulfonyl, and n-butylsulfonyl.

Fluorinated $C_1$-$C_6$ alkylthio (also termed fluorinated $C_1$-$C_6$-alkylsulfanyl) is a straight-chain or branched alkylthio group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfinyl is a straight-chain or branched alkylsulfinyl group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfonyl is a straight-chain or branched alkylsulfonyl group having from 1 to 6, in particular 1 to 4 carbon atoms, wherein at least one, e.g. 1, 2, 3, 4 or all of the hydrogen atoms are replaced by fluorine atoms.

$C_3$-$C_6$ Cycloalkyl is a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl) and the like. $C_3$-$C_6$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_1$-$C_6$-Alkylene is a hydrocarbon bridging group having 1, 2, 3, 4, 5 or 6 carbon atoms, like methylene, ethylene, 1,2- and 1,3-propylene, 1,4-butylene and the like.

Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 3-, 4- or 5-pyrazolyl, 2-, 4- or 5-imidazolyl, 2- or 5-[1,3,4]oxadiazolyl, 4- or 5-[1,2,3] oxadiazolyl, 3- or 5-[1,2,4]oxadiazolyl, 2- or 5-[1,3,4]thiadiazolyl, 2- or 5-[1,3,4]thiadiazolyl, 4- or 5-[1,2,3]thiadiazolyl, 3- or 5-[1,2,4]thiadiazolyl 1H-, 2H- or 3H-1,2,3-triazol-4-yl, 2H-triazol-3-yl, 1H-, 2H-, or 4H-1,2,4-triazolyl and 1H- or 2H-tetrazolyl, which may be unsubstituted or which may carry 1, 2 or 3 of the aforementioned radicals $R^a$.

Examples of a phenyl ring fused to a saturated or unsaturated 5- or 6-membered carbocyclic or heterocyclic ring comprise indenyl, indanyl, naphthyl, 1,2- or 2,3-dihydronaphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals $R^a$. This fused system may be bonded to the remainder of the molecule (more precisely to the sulfonyl group) via carbon atoms of the phenyl moiety or via ring atoms (C- or N-atoms) of the ring fused to phenyl.

Examples for saturated or unsaturated 3- to 7-membered heterocyclic rings (as radicals $R^a$) comprise saturated or unsaturated, aromatic or non-aromatic heterocyclic rings. Examples therefore include, apart from the above-defined 5- or 6-membered heteroaromatic radicals, aziridyl, diaziridinyl, oxiranyl, azetidinyl, azetinyl, di- and tetrahydrofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl and the like.

If $R^6$ and $R^7$ form together with N a 4-, 5- or 6-membered ring, examples for this type of radical comprise, apart from the above-defined 5- or 6-membered heteroaromatic radicals containing at least one N atom as ring member, azetidinyl, azetinyl, pyrrolinyl, pyrrolidinyl, pyrazolinyl, pyrazolidinyl, imidazolinyl, imidazolidinyl, oxazolinyl, oxazolidinyl, piperidinyl, piperazinyl, morpholinyl and the like.

In a specific embodiment,
$R^1$ is H, $C_1$-$C_6$-alkyl which may be substituted by $C_3$-$C_6$-cycloalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl; and
Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S, and where the cyclic radical may carry 1, 2 or 3 substituents $R^a$ selected from the group consisting of halogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, CN, acetyl, carboxy, $NR^6R^7$, $NR^6R^7$—$C_1$-$C_6$-alkylene, where $R^6$ and $R^7$ are, independently of each other, H, $C_1$-$C_4$-alkyl or fluorinated $C_1$-$C_4$-alkyl or may form, together with N, a 4-, 5- or 6-membered saturated or unsaturated ring, and a saturated or unsaturated 5- or 6-membered heterocyclic ring comprising as ring members 1, 2 or 3 heteroatoms selected from N, O and S.

In compounds of formula I, n preferably is 0 or 1; i.e. the nitrogen-containing ring is an azetidinyl group or a pyrrolidinyl group; and particularly, n is 1, which means that in a particularly preferred embodiment, the nitrogen-containing ring is a pyrrolidinyl ring.

Preferably, the radical $R^1$ is selected from H, $C_1$-$C_4$-alkyl, $C_1$-$C_4$-alkyl which is substituted by $C_3$-$C_6$-cycloalkyl or hydroxy, fluorinated $C_1$-$C_4$-alkyl and $C_2$-$C_4$-alkenyl. More preference is given to H, propyl, cyclopropylmethylene, fluorinated ethyl, e.g. 2-fluoroethyl, fluorinated propyl, e.g. 3-fluoropropyl, hydroxypropyl, e.g. 3-hydroxypropyl, propionyl and allyl. More preferably, $R^1$ is selected from H, propyl, cyclopropylmethylene, 2-fluoroethyl, 3-fluoropropyl, 3-hydroxypropyl, and allyl. In a particularly preferred embodiment, $R^1$ is n-propyl or allyl and especially n-propyl.

In an alternative embodiment, $R^1$ is preferably selected from H, $C_1$-$C_4$-alkyl, $C_1$-$C_4$-alkyl which is substituted by $C_3$-$C_6$-cycloalkyl, fluorinated $C_1$-$C_4$-alkyl and $C_2$-$C_4$-alkenyl. More preference is given to H, propyl, cyclopropylmethylene, fluorinated ethyl, e.g. 2-fluoroethyl, fluorinated propyl, e.g. 3-fluoropropyl, and allyl. In a particularly preferred embodiment, $R^1$ is n-propyl or allyl and especially n-propyl.

Preferably, $R^2$, $R^3$ and $R^4$ are H.

The group A is preferably phenylene, pyridylene or pyrimidylene. In a more preferred embodiment, A is 1,4-phenylene, 1,2-phenylene, 2,5-pyridylene 3,6-pyridylene or 2,5-pyrimidylene, where A may be substituted as described above. In an even more preferred embodiment, A is 1,4-phenylene, 1,2-phenylene, 3,6-pyridylene or 2,5-pyrimidylene. If A is substituted, preferred substituents are selected from halogen, in particular fluorine, and methoxy. Examples include 2-fluoro-1,4-phenylene, 3-fluoro-1,4-phenylene, 2-methoxy-1,4-phenylene, and 3-methoxy-1,4-phenylene. In a specific embodiment, A is not substituted. Particularly, A is 1,4-phenylene.

The group E is preferably $NR^5$, more preferably NH or $NCH_3$ and in particular NH.

Preferred cyclic radicals of the group Ar are phenyl, 2- or 3-thienyl, in particular 3-thienyl, imidazolyl, in particular 4-imidazolyl, isoxazolyl, in particular 4-isoxazolyl, thiazolyl, in particular 2-thiazolyl, triazolyl, in particular 3-[1,2,4]triazolyl, thiadiazolyl, in particular 3- and 5-[1,2,4]thiadiazolyl and 2-[1,3,4]thiadiazolyl, 2-, 3- or 4-pyridyl, 2- and 5-pyrimidinl, 1-, 2-, 3-, 4- or 5-indanyl, 2-, 3-, 4- or 5-benzofuranyl, quinolinyl, in particular 8-quinolinyl, isoquinolinyl, in particular 5-isoquinolinyl, 1,2,3,4-tetrahydroisoquinolinyl, in particular 7-1,2,3,4-tetrahydroisoquinolin-7-yl, benzothienyl, in particular 2-benzothienyl, benzothiazolyl, in particular 6-benzothiazolyl, benzoxadiazolyl, in particular 4-[2,1,3]benzoxadiazolyl, benzothiadiazolyl, in particular 4-[2,1,3]benzothiadiazolyl, benzoxazin and dihydrobenzoxazin. The numbers indicate the position at which Ar is bound to the sulfonyl group. More preferred radicals Ar are phenyl, 2-thienyl, 3-pyridyl, 5-pyridyl, 5-indanyl, 2-benzofuranyl, and 2,3-dihydrobenzofuran-2-yl. Even more preferred radicals Ar are phenyl, 2-thienyl, 5-indanyl, benzofuran-2-yl and 2,3-dihydrobenzofuran-2-yl. Specifically, Ar is phenyl.

In an alternative embodiment, preferred cyclic radicals of the group Ar are phenyl, 2- or 3-thienyl, 2-, 3- or 4-pyridyl, 1-, 2-, 3-, 4- or 5-indanyl, 2-, 3-, 4- or 5-benzofuranyl, in particular 2-thienyl, 2- or 3-pyridinyl, 5-indanyl, 5-benzofuranyl, and especially phenyl.

Preferably, $R^a$ selected from the group consisting of halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-alkoxy-$C_1$-$C_6$-alkoxy, fluorinated $C_1$-$C_6$-alkoxy, fluorinated $C_1$-$C_6$-alkylthio, $C_1$-$C_6$-alkylsulfonyl, phenylsulfonyl, benzyloxy, phenoxy, CN, nitro, acetyl, trifluoroacetyl, acetamido, carboxy, NH—C(O)—$NH_2$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy, and a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the 3- to 7-membered heterocyclic ring may carry 1, 2 or 3 substituents selected from hydroxy, halogen, $C_1$-$C_6$-alkyl, fluorinated $C_1$-$C_6$-alkyl and $C_1$-$C_6$-alkoxy.

Preferably, the saturated or unsaturated 3- to 7-membered heterocyclic ring is selected from azetidin-1-yl, 2-methylazetidinyl, 3-methoxyazetidinyl, 3-hydroxyazetidinyl, 3-fluoroazetidinyl, pyrrolidin-1-yl, pyrrolidin-2-yl, pyrrolidin-3-yl, 2- and 3-fluoropyrrolidin-1-yl, 2,2-difluoropyrrolidin-1-y 3,3-difluoropyrrolidin-1-yl, 2- and 3-methylpyrrolidin-1-yl, 1-methylpyrrolidin-2-yl, 2,2-dimethylpyrrolidin-1-yl 3,3-dimethylpyrrolidin-1-yl, 2-oxo-pyrrolidin-1-yl, 2- and 3-trifluoromethylpyrrolidin-1-yl, 2-oxo-oxazolidin-1-yl, piperidin-1-yl, 2-methylpiperidin-1-yl, piperazin-1-yl, 4-methylpiperazin-1-yl, morpholin-4-yl, thiomorpholin-4-yl, 1-oxothiomorpholin-4-yl, 1,1-dioxothiomorpholin-4-yl, pyrrol-1-yl, pyrrol-2-yl, pyrrol-3-yl, 1-methylpyrrol-2-yl, 1-methylpyrrol-3-yl, furan-2-yl, furan-3-yl, thiophen-2-yl, thiophen-3-yl, 5-propylthiophen-2-yl, pyrazol-1-yl, pyrazol-3-yl, pyrazol-4-yl, 1-methylpyrazol-4-yl, imidazol-1-yl, imidazol-2-yl, 1-methylimidazol-2-yl, oxazol-2-yl, oxazol-4-yl, oxazol-5-yl, isoxazol-3-yl, isoxazol-4-yl, isoxazol-5-yl, [1,2,3]triazol-1-yl, [1,2,4]triazol-1-yl, [1,2,3]triazol-2-yl, [1,2,4]triazol-3-yl, [1,2,4]triazol-4-yl, 4-methyl-[1,2,4]triazol-3-yl, 2-methyl-[1,2,3]-triazol-4-yl, [1,3,4]-oxadiazol-2-yl, [1,2,4]-oxadiazol-3-yl, [1,2,4]-oxadiazol-5-yl, [1,2,3]-oxadiazol-5-yl, [1,2,3]thiadiazol-4-yl, tetrazol-1-yl, tetrazol-5-yl, 2-methyltetrazol-5-yl, 1-methyltetrazol-5-yl, furazan-3-yl, pyrid-2-yl, pyrid-3-yl, pyrid-4-yl, pyrimidin-2-yl, pyrimidin-4-yl and pyrimidin-5-yl. More preferably, the saturated or unsaturated 3- to 7-membered heterocyclic ring is selected from azetidin-1-yl, pyrrolidin-1-yl, 3,3-difluoropyrrolidin-1-yl, 2-oxo-pyrrolidin-1-yl, 2-oxo-oxazolidin-1-yl, morpholin-4-yl, 2-furanyl, 5-propylthien-2-yl, pyrrol-1-yl, pyrazol-1-yl, 1-methylpyrazol-4-yl, 1-ethylpyrazol-4-yl, oxazol-5-yl, isoxazol-3-yl, isoxazol-5-yl, 4-[1,2,3]thiadiazolyl. Even more preferably, the saturated or unsaturated 3- to 7-membered heterocyclic ring is selected from azetidin-1-yl, pyrrolidin-1-yl, 3,3-difluoropyrrolidin-1-yl, 2-oxo-pyrrolidin-1-yl, morpholin-4-yl, pyrrol-1-yl, furan-2-yl, pyrazol-1-yl, 1-methylpyrazol-4-yl, oxazol-5-yl, isoxazol-5-yl, 4-[1,2,3]thiadiazolyl.

In a preferred embodiment, the cyclic radical Ar is unsubstituted or substituted by 1, 2 or 3 substituents $R^a$ selected from the group consisting of halogen, $C_1$-$C_6$-alkyl, $C_1$-$C_6$-hydroxyalkyl, fluorinated $C_1$-$C_4$-alkyl, $C_1$-$C_4$-alkoxy, fluorinated $C_1$-$C_4$-alkoxy, $C_1$-$C_4$-alkoxy-$C_1$-$C_4$-alkoxy, $C_2$-$C_4$-alkenyl, fluorinated $C_2$-$C_4$-alkenyl, $NR^6R^7$, $ONR^6R^7$, $C_1$-$C_6$-alkylene-$NR^6R^7$, where $R^6$ and $R^7$ are independently of each other H, $C_1$-$C_4$-alkyl or $C_1$-$C_4$-alkoxy, ureido ($NHCONH_2$) $C_3$-$C_6$-cycloalkyl, fluorinated $C_3$-$C_6$-cycloalkyl, acetyl, carboxyl, hydroxy, cyano, nitro, benzoxy, methylsulfanyl, fluoromethylsulfanyl, difluoromethylsulfanyl, trifluoromethylsulfanyl, methylsulfonyl and one of the above-mentioned saturated or unsaturated 3- to 7-membered heterocyclic rings. In a more preferred embodiment, $R^a$ is selected from the group consisting of halogen, $C_1$-$C_6$-alkyl, fluorinated $C_1$-$C_4$-alkyl, $C_1$-$C_4$-alkoxy, $OCF_3$, $OCHF_2$, $OCH_2F$, $C_2$-$C_4$-alkenyl, $C_3$-$C_6$-cycloalkyl, fluorinated $C_3$-$C_6$-cycloalkyl, ureido, acetyl, carboxyl, hydroxy, cyano, benzoxy, trifluoromethylsulfanyl, methylsulfonyl, azetidin-1-yl, pyrrolidin-1-yl, 3,3-difluoropyrrolidin-1-yl, 2-oxo-pyrrolidin-1-yl, 2-oxo-oxazolidin-1-yl, morpholin-4-yl, 2-furanyl, 5-propylthien-2-yl, pyrrol-1-yl, pyrazol-1-yl, 1-methylpyrazol-4-yl, 1-ethylpyrazol-4-yl, oxazol-5-yl, isoxazol-3-yl, isoxazol-5-yl, and 4-[1,2,3]thiadiazolyl. Even more preferably, $R^a$ is selected from the group consisting of halogen, $C_1$-$C_6$-alkyl, fluorinated $C_1$-$C_4$-alkyl, $C_1$-$C_4$-alkoxy, $OCF_3$, $OCHF_2$, $C_2$-$C_4$-alkenyl, $C_3$-$C_6$-cycloalkyl, fluorinated $C_3$-$C_6$-cycloalkyl, ureido, acetyl, carboxyl, hydroxy, benzoxy, trifluoromethylsulfanyl, azetidin-1-yl, pyrrolidin-1-yl, 3,3-difluoropyrrolidin-1-yl, 2-oxo-pyrrolidin-1-yl, morpholin-4-yl, pyrrol-1-yl, furan-2-yl, pyrazol-1-yl, 1-methylpyrazol-4-yl, oxazol-5-yl, isoxazol-5-yl, and 4-[1,2,3]thiadiazolyl.

If Ar is a heteroaromatic ring, $R^a$ in this case is in particular selected from halogen, $C_2$-$C_4$-alkenyl, oxazolyl and isoxazolyl. If Ar is a fused system, it is preferentially not substituted.

In an alternative embodiment, the cyclic radical is substituted by 1, 2 or 3 substituents $R^a$ selected from the group consisting of halogen, $C_1$-$C_6$-alkyl, fluorinated $C_1$-$C_4$-alkyl, $C_1$-$C_4$-alkoxy, fluorinated $C_1$-$C_4$-alkoxy, $C_2$-$C_4$-alkenyl, fluorinated $C_2$-$C_4$-alkenyl, $NR^6R^7$, $C_1$-$C_6$-alkylene-$NR^6R^7$, where $R^6$ and $R^7$ are independently of each other H, $C_1$-$C_4$-alkyl or fluorinated $C_1$-$C_4$-alkyl or may form, together with N, a 4-, 5- or 6-membered saturated or unsaturated ring, like $CH_2N(CH_3)_2$, $C_3$-$C_6$-cycloalkyl optionally substituted by halogen, acetyl or carboxyl. In a more preferred embodiment, Ar is phenyl which is substituted by 1, 2 or 3 substituents selected from the group consisting of halogen, $C_1$-$C_6$-alkyl, fluorinated $C_1$-$C_4$-alkyl, $C_1$-$C_4$-alkoxy, $OCF_3$, $OCHF_2$, $OCH_2F$, $C_2$-$C_4$-alkenyl, fluorinated $C_2$-$C_4$-alkenyl, $CH_2N(CH_3)_2$, $NR^6R^7$, where $R^6$ and $R^7$ are independently of each other H, $C_1$-$C_4$-alkyl or fluorinated $C_1$-$C_4$-alkyl, $C_3$-$C_6$-cycloalkyl optionally substituted by halogen, acetyl or carboxyl, or Ar is thienyl, pyridyl, benzofuranyl or indanyl, which are optionally substituted by halogen, $C_1$-$C_4$-alkyl or $C_1$-$C_4$-alkenyl. More preferably, Ar is phenyl which is substituted by 1, 2 or 3 substituents $R^a$ selected from fluorine or bromine, $C_1$-$C_6$-alkyl, especially methyl, ethyl, n-propyl, isopropyl, sec-butyl, isobutyl, dimethylpropyl, and particularly isopropyl, fluorinated $C_1$-$C_4$-alkyl, especially $CF_3$ or fluorinated isopropyl, $C_1$-$C_4$-alkoxy, especially methoxy, ethoxy, propoxy, isopropoxy or butoxy, $OCF_3$, $OCHF_2$, $OCH_2F$, isopropenyl, $CH_2N(CH_3)_2$, $NR^6R^7$, where $R^6$ and $R^7$ are independently of each other H, $C_1$-$C_4$-alkyl or fluorinated $C_1$-$C_4$-alkyl, $C_3$-$C_6$-cycloalkyl, especially cyclopentyl, fluorinated $C_3$-$C_6$-cycloalkyl, especially 2,2-difluorocyclopropyl, acetyl or carboxyl. Alternatively, Ar is thienyl or pyridyl which carry 1, 2 or 3 substituents selected from halogen, especially chlorine, and $C_1$-$C_4$-alkenyl, especially isopropenyl, or Ar is benzofuranyl or indanyl.

In the aforementioned 5-membered heteroaromatic radicals, Ar preferably carries one radical $R^a$ in the 5-position (related to the 2-position of the $SO_2$-radical) and optionally one or two further radicals selected from halogen, in particular fluorine or chlorine.

Phenyl and the aforementioned 6-membered heteroaromatic radicals Ar preferably carry one radical $R^a$ in the 4-position (related to the 1-position of the $SO_2$-radical) and optionally one or two further radicals selected from halogen, in particular fluorine or bromine.

In a very preferred embodiment of the invention Ar is phenyl that carries one radical $R^a$ in the 4-position of the phenyl ring and optionally 1 or 2 halogen atoms, which are selected from halogen, in particular from fluorine or chlorine.

In a even more preferred embodiment, Ar preferably carries one radical $R^a$, which has the formula $R^{a'}$

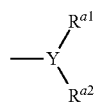

wherein
Y is N, CH or CF,
$R^{a1}$ and $R^{a2}$ are independently of each other selected from $C_1$-$C_2$-alkyl, in particular methyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or
$R^{a1}$ and $R^{a2}$ form a radical $(CH_2)_m$ wherein 1 or 2 of the hydrogen atoms may be replaced by fluorine and wherein m is 2, 3 or 4, in particular $CH_2$—$CH_2$, CHF—$CH_2$ $CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, $CH_2$—$CF_2$—$CH_2$.

In case $R^{a1}$ and $R^{a2}$ are different from each other, the radical of the aforementioned formula Ra may have either (R)- or (S)-configuration with regard to the Y-moiety.

Examples for preferred radicals of the formula $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl cyclopropyl, cyclobutyl, 1-fluorocyclopropyl, (S)- and (R)-2,2-difluorocyclopropyl and 2-fluorocyclopropyl.

Amongst the radicals of the formula $R^{a'}$ those are preferred which carry 1, 2, 3 or 4, in particular 1, 2 or 3 fluorine atoms.
In a particularly preferred embodiment, radical $R^{a'}$ is in the 4-position of the phenyl ring.
Preferred examples for Ar are in particular the following: 4-methylphenyl, 4-ethylphenyl, 4-propylphenyl, 4-isopropylphenyl, 4-sec-butylphenyl, 4-isobutylphenyl, 4-(1,1-dimethylpropyl)-phenyl, 4-vinylphenyl, 4-isopropenylphenyl, 4-fluorophenyl, 4-chlorophenyl, 4-bromophenyl, 4-(fluoromethyl)phenyl, 3-(fluoromethyl)phenyl, 2-(fluoromethyl)phenyl, 4-(difluoromethyl)phenyl, 3-(difluoromethyl)phenyl, 2-(difluoromethyl)phenyl, 4-(trifluoromethyl)phenyl, 3-(trifluoromethyl)phenyl, 2-(trifluoromethyl)phenyl, 4-(1-fluoroethyl)-phenyl, 4-((S)-1-fluoroethyl)-phenyl, 4-((R)-1-fluoroethyl)-phenyl, 4-(2-fluoroethyl)-phenyl, 4-(1,1-difluoroethyl)-phenyl, 4-(2,2-difluoroethyl)-phenyl, 4-(2,2,2-trifluoroethyl)-phenyl, 4-(3-fluoropropyl)-phenyl, 4-(2-fluoropropyl)-phenyl, 4-((S)-2-fluoropropyl)-phenyl, 4-((R)-2-fluoropropyl)-phenyl, 4-(3,3-difluoropropyl)-phenyl, 4-(3,3,3-trifluoropropyl)-phenyl, 4-(1-fluoro-1-methylethyl)-phenyl, 4-(2-fluoro-1-methylethyl)-phenyl, 4-((S)-2-fluoro-1-methylethyl)-phenyl, 4-((R)-2-fluoro-1-methylethyl)-phenyl, 4-(2,2-difluoro-1-methylethyl)-phenyl, 4-((S)-2,2-difluoro-1-methylethyl)-phenyl, 4-((R)-2,2-difluoro-1-methylethyl)-phenyl, 4-(2,2,2-trifluoro-1-methylethyl)-phenyl, 4-((S)-2,2,2-trifluoro-1-methylethyl)-phenyl, 4-((R)-2,2,2-trifluoro-1-methylethyl)-phenyl, 4-(2-fluoro-1-fluoromethylethyl)-phenyl, 4-(1-difluoromethyl-2,2-difluoroethyl)-phenyl, 4-(1,1-dimethyl-2-fluoroethyl)-phenyl, 4-methoxyphenyl, 4-ethoxyphenyl, 4-propoxyphenyl, 4-isopropoxyphenyl, 4-butoxyphenyl, 4-(fluoromethoxy)-phenyl, 4-(difluoromethoxy)-phenyl, 4-(trifluoromethoxy)-phenyl, 3-(trifluoromethoxy)-phenyl, 4-(2-fluoroethoxy)-phenyl, 4-(2,2-difluoroethoxy)-phenyl, 4-(2,2,2-trifluoroethoxy)-phenyl, 4-(1,1,2,2-tetrafluoroethoxy)-phenyl, 4-cyclopropylphenyl, 4-cyclobutylphenyl, 4-cyclopentylphenyl, 4-(2,2-difluorocyclopropyl)-phenyl, 3,4-difluorophenyl, 4-bromo-3-fluorophenyl, 4-bromo-2-fluorophenyl, 4-bromo-2,5-difluorophenyl, 2-fluoro-4-isopropylphenyl, 3-fluoro-4-isopropylphenyl, 4-(1-hydroxy-1-methylethyl)-phenyl, 4-(2-hydroxy-2-methylpropyl)-phenyl, 4-acetylphenyl, 4-carboxyphenyl, 4-cyanophenyl, 4-hydroxyphenyl, 4-(O-benzyl)-phenyl, 4-(2-methoxyethoxy)-phenyl, 4-($CH_2$—$N(CH_3)_2$)phenyl, 4-(NH—CO—$NH_2$)-phenyl, 4-(methylsulfanyl)-phenyl, 4-(fluoromethylsulfanyl)phenyl, 4-(difluoromethylsulfanyl)-phenyl, 4-(trifluoromethylsulfanyl)-phenyl, 4-(methylsulfonyl)-phenyl, 4-(N-methoxy-N-methyl-amino)-phenyl, 4-(methoxyamino)phenyl, 4-(ethoxyamino)-phenyl, 4-(N-methylaminooxy)-phenyl, 4-(N,N-dimethylaminooxy)-phenyl, 4-(azetidin-1-yl)-phenyl, 4-(2-methylazetidin-1-yl)-phenyl, 4-((S)-2-methylazetidin-1-yl)-phenyl, 4-((R)-2-methylazetidin-1-yl)-phenyl, 4-(3-fluoroazetidin-1-yl)-phenyl, 4-(3-methoxyazetidin-1-yl)-phenyl, 4-(3-hydroxyazetidin-1-yl)-phenyl, 4-(pyrrolidin-1-yl)-phenyl, 4-(pyrrolidin-2-yl)-phenyl, 4-((S)-pyrrolidin-2-yl)phenyl, 4-((R)-pyrrolidin-2-yl)-phenyl, 4-(pyrrolidin-3-yl)-phenyl, 4-((S)-pyrrolidin-3-yl)phenyl, 4-((R)-pyrrolidin-3-yl)-phenyl, 4-(2-fluoropyrrolidin-1-yl)-phenyl, 4-((S)-2-fluoropyrrolidin-1-yl)-phenyl, 4-((R)-2-fluoropyrrolidin-1-yl)-phenyl, 4-(3-fluoropyrrolidin-1-yl)-phenyl, 4-((S)-3-fluoropyrrolidin-1-yl)-phenyl, 4-((R)-3-fluoropyrrolidin-1-yl)-phenyl, 4-(2,2-difluoropyrrolidin-1-yl)-phenyl, 4-(3,3-difluoropyrrolidin-1-yl)-phenyl, 4-(2-methylpyrrolidin-1-yl)-phenyl, 4-((S)-2-methylpyrrolidin-1-yl)-phenyl, 4-((R)-2-methylpyrrolidin-1-yl)-phenyl, 4-(3-methylpyrrolidin-1-yl)-phenyl, 4-((S)-3-methylpyrrolidin-1-yl)-phenyl, 4-((R)-3-methylpyrrolidin-1-yl)-phenyl, 4-(1-methylpyrrolidin-2-yl)-phenyl, 4-((S)-1-methylpyrrolidin-2-yl)-phenyl, 4-((R)-1-methylpyrrolidin-2-yl)-phenyl, 4-(1-methylpyrrolidin-3-yl)-phenyl, 4-((S)-1-methylpyrrolidin-3-yl)-phenyl, 4-((R)-1-methylpyrrolidin-3-yl)-phenyl, 4-(2,2-dimethylpyrrolidin-1-yl)-phenyl, 4-(3,3-dimethylpyrrolidin-1-yl)-phenyl, 4-(2-trifluoromethylpyrrolidin-1-yl)-phenyl, 4-((S)-2-trifluoromethylpyrrolidin-1-yl)-phenyl, 4-((R)-2-trifluoromethylpyrrolidin-1-yl)-phenyl, 4-(3-trifluoromethylpyrrolidin-1-yl)-phenyl, 4-((S)-3-trifluoromethylpyrrolidin-1-yl)-phenyl, 4-((R)-3-trifluoromethylpyrrolidin-1-yl)phenyl, 4-(2-oxopyrrolidin-1-yl)-phenyl, 4-(2-oxo-oxazolidin-3-yl)-phenyl, 4-(piperidin-1-yl)-phenyl, 4-(2-methylpiperidin-1-yl)-phenyl, 4-((S)-2-methylpiperidin-1-yl)-phenyl, 4-((R)-2-methylpiperidin-1-yl)-phenyl, 4-(piperazin-1-yl)-phenyl, 4-(4-methylpiperazin-1-yl)-phenyl, 4-(morpholin-4-yl)-phenyl, 4-(thiomorpholin-4-yl)-phenyl, 4-(1-oxothiomorpholin-4-yl)-phenyl, 4-(1,1-dioxo-thiomorpholin-4-yl)-phenyl, 4-(pyrrol-1-yl)phenyl, 4-(pyrrol-2-yl)-phenyl, 4-(pyrrol-3-yl)-phenyl, 4-(1-methylpyrrol-2-yl)-phenyl, 4-(1-methylpyrrol-3-yl)-phenyl, 4-(furan-2-yl)-phenyl, 4-(furan-3-yl)-phenyl, 4-(thiophen-2-yl)-phenyl, 4-(thiophen-3-yl)-phenyl, 4-(5-propylthien-2-yl)-phenyl, 4-(pyrazol-1-yl)-phenyl, 4-(pyrazol-3-yl)-phenyl, 4-(pyrazol-4-yl)-phenyl, 4-(1-methyl-1H-pyrazol-4-yl)-phenyl, 4-(1-ethyl-1H-pyrazol-4-yl)-phenyl, 4-(1-methyl-1H-pyrazol-5-yl)-phenyl, 4-(1H-imidazol-2-yl)-phenyl, 4-(imidazol-1-yl)-phenyl, 4-(1-methylimidazol-2-yl)-phenyl, 4-(oxazol-2-yl)-phenyl, 4-(oxazol-4-yl)-phenyl, 4-(oxazol-5-yl)-phenyl, 4-(isoxazol- 3-yl)phenyl, 4-(isoxazol-4-yl)-phenyl, 4-(isoxazol-5-yl)-phenyl, 4-([1,2,3]-triazol-1-yl)-phenyl, 4-([1,2,4]-triazol-1-yl)-phenyl, 4-([1,2,3]-triazol-2-yl)-phenyl, 4-(4H-[1,2,4]-triazol-3-yl)phenyl, 4-([1,2,4]-triazol-4-yl)-phenyl, 4-(2H[1,2,3]-triazol-4-yl)-phenyl, 4-(4-methyl-4H-[1,2,4]-triazol-3-yl)-phenyl, 4-(2-methyl-2H-[1,2,3]-triazol-4-yl)-phenyl, 4-([1,3,4]-oxadiazol-2-yl)-phenyl, 4-([1,2,4]-oxadiazol-3-yl)-phenyl, 4-([1,2,4]-oxadiazol-5-yl)phenyl, 4-([1,2,3]-oxadiazol-4-yl)-phenyl, 4-([1,2,3]-oxadiazol-5-yl)-phenyl, 4-([1,2,3]-thiadiazol-4-yl)-phenyl, 4-(1H-tetrazol-5-yl)-phenyl, 4-(tetrazol-1-yl)-phenyl, 4-(2-methyl-2H-tetrazol-5-yl)-phenyl, 4-(1-methyl-1H-tetrazol-5-yl)-phenyl, 4-furazan-3-yl-phenyl, 4-(pyrid-2-yl)-phenyl, 4-(pyrid-3-yl)-phenyl, 4-(pyrid-4-yl)-phenyl, 4-(pyrimidin-2-yl)phenyl, 4-(pyrimidin-4-yl)-phenyl, 4-(pyrimidin-5-yl)-phenyl, 5-isopropylthiophen-2-yl, 2-chlorothiophen-5-yl, 2,5-dichlorothiophen-4-yl, 2,3-dichlorothiophen-5-yl, 2-chloro-3-nitrothiophen-5-yl, 2-(phenylsulfonyl)-thiophen-5-yl, 2-(pyridin-2-yl)thiophen-5-yl, 2-(5-(trifluoromethyl)isoxazol-3-yl)-thiophen-5-yl, 2-(2-methylthiazol-4-yl)-thiophen-5-yl, 1-methyl-1H-imidazol-4-yl, 1,2-dimethyl-1H-imidazol-4-yl, 3,5-dimethylisoxazol-4-yl, thiazol-2-yl, 4-methylthiazol-2-yl, 4-isopropylthiazol-2-yl, 4-trifluoromethylthiazol-2-yl, 5-methylthiazol-2-yl, 5-isopropylthiazol-2-yl, 5-trifluoromethylthiazol-2-yl, 2,4-dimethylthiazol-5-yl, 2-acetamido-4-methylthiazol-5-yl, 4H-[1,2,4]triazol-3-yl, 5-methyl-4H-[1,2,4]triazol-3-yl, 4-methyl-4H-[1,2,4]-triazol-3-yl, 5-isopropyl-4H-[1,2,4]triazol-3-yl, 5-trifluoromethyl-4H-[1,2,4]triazol-3-yl, 4,5-dimethyl-4H-[1,2,4]triazol-3-yl, 5-isopropyl-4-methyl-4H-[1,2,4]triazol-3-yl, 5-trifluoromethyl-4-methyl-4H-[1,2,4]triazol-3-yl, [1,3,4]thiadiazol-2-yl, 5-methyl-[1,3,4]thiadiazol-2-yl, 5-isopropyl-[1,3,4]thiadiazol-2-yl, 5-trifluoromethyl-[1,3,4,]thiadiazol-2-yl, 3-bromo-2-chloropyrid-5-yl, 2-(4-morpholino)pyrid-5-yl, 2-phenoxy-pyrid-5-yl, (2-isopropyl)-pyrimidin-5-yl, (5-isopropyl)-pyrimidin-2-yl, 8-quinolyl, 5-isoquinolyl, 2-(trifluoroacetyl)-1,2,3,4-tetrahydroisoquinolin-7-yl, 5-chloro-3-methylbenzothiophen-2-yl, 3,4-dihydro-4-methyl-2H-benzo[b][1,4]oxazinyl, benzothiazol-6-yl, benzo[2,1,3]oxadiazol-4-yl, 5-chlorobenzo[2,1,3]oxadiazol-4-yl, 7-chlorobenzo[2,1,3]oxadiazol-4-yl and benzo[2,1,3]thiadiazol-4-yl.

Particularly preferred compounds I are those of formulae I.a, I.b, I.c, I.d, I.e, I.f, I.g, I.h, I.i, I.k, I.l, I.m, I.n, I.o, I.p, I.q, I.r, I.s and I.t, wherein R¹ and Ar have the above-defined meanings. Preferred meanings of R¹ and Ar are as defined above.

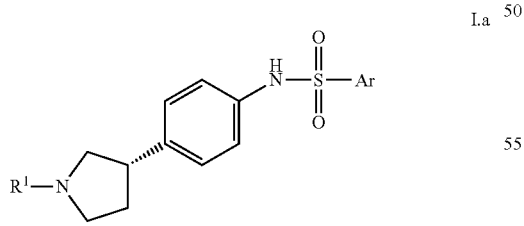

I.a

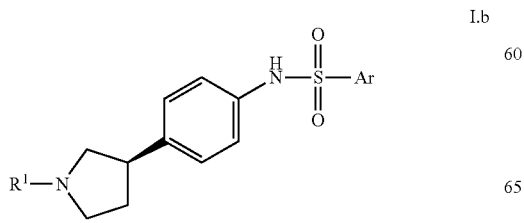

I.b

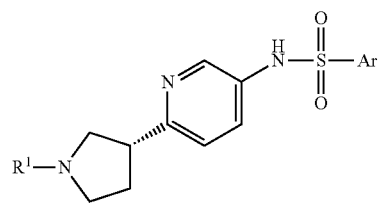

I.c

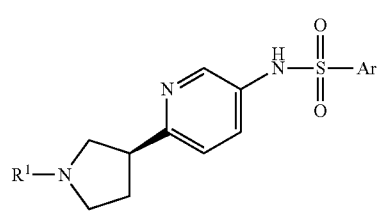

I.d

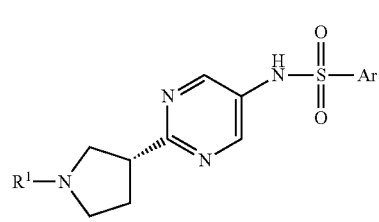

I.e

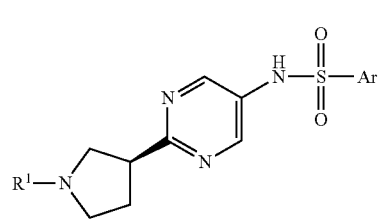

I.f

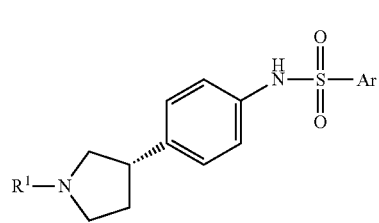

I.g

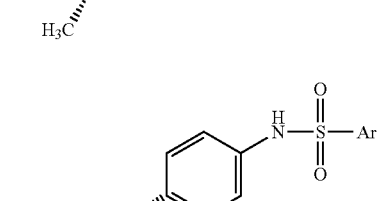

I.h

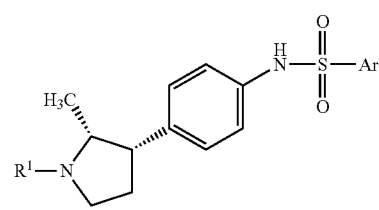

I.i

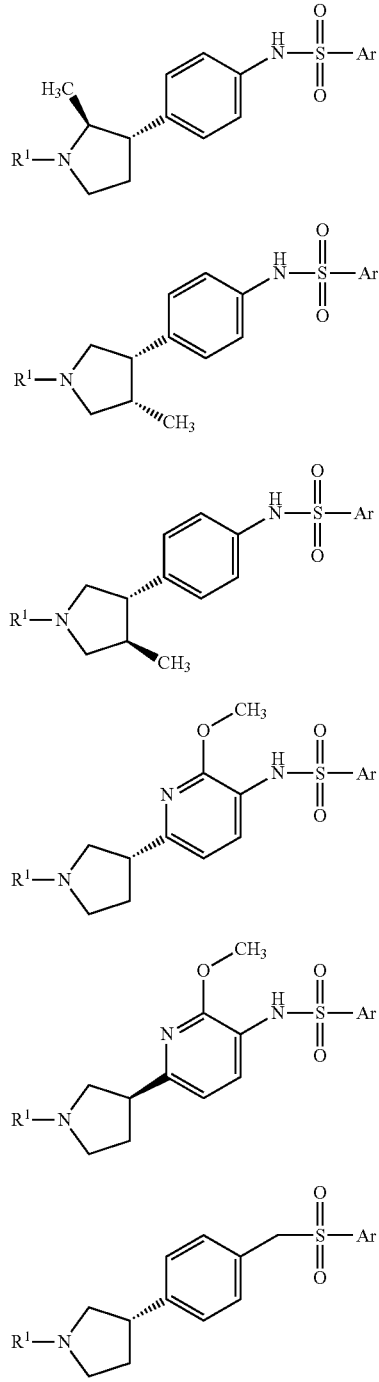
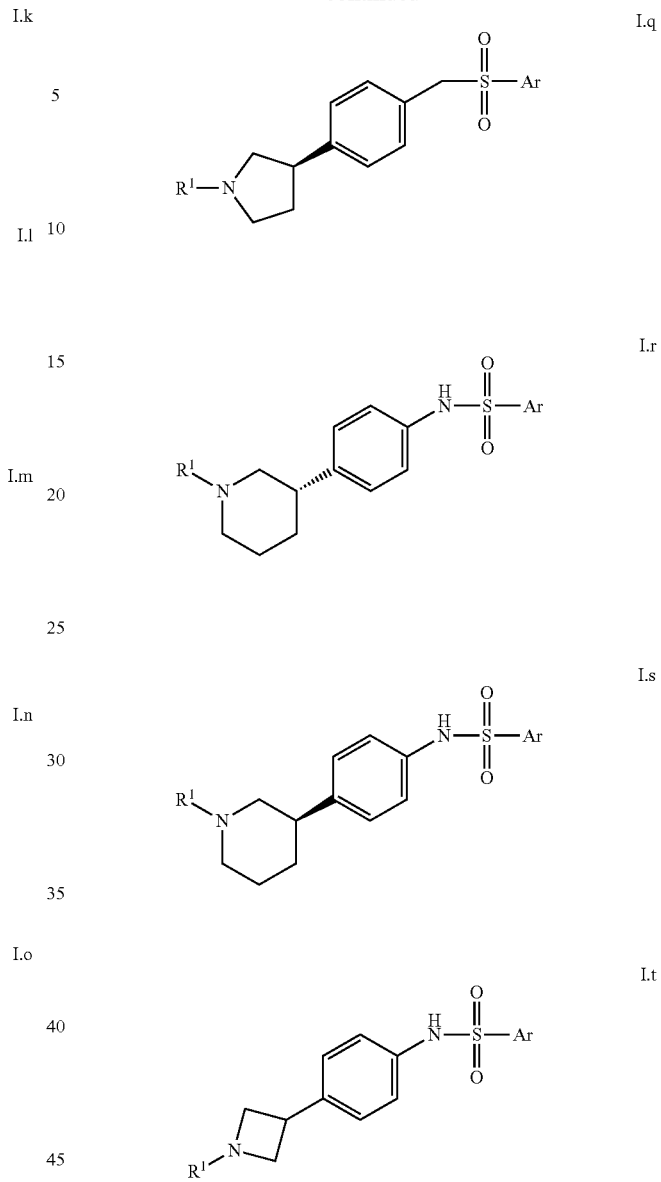

Examples of preferred compounds which are represented by the formulae I.a, I.b, I.c, I.d, I.e, I.f, I.g, I.h, I.i, I.k, I.l, I.m, I.n, I.o, I.p, I.q, I.r, I.s and I.t are the individual compounds listed above, where the variables Ar and R¹ have the meanings given in one row of table A.

TABLE A

| No. | R¹ | Ar |
|---|---|---|
| 1. | propyl | 4-methylphenyl |
| 2. | propyl | 4-ethylphenyl |
| 3. | propyl | 4-propylphenyl |
| 4. | propyl | 4-isopropylphenyl |
| 5. | propyl | 4-sec-butylphenyl |
| 6. | propyl | 4-isobutylphenyl |
| 7. | propyl | 4-(1,1-dimethylpropyl)-phenyl |
| 8. | propyl | 4-vinylphenyl |
| 9. | propyl | 4-isopropenylphenyl |

TABLE A-continued

| No. | R¹ | Ar |
|---|---|---|
| 10. | propyl | 4-fluorophenyl |
| 11. | propyl | 4-chlorophenyl |
| 12. | propyl | 4-bromophenyl |
| 13. | propyl | 4-(fluoromethyl)phenyl |
| 14. | propyl | 3-(fluoromethyl)phenyl |
| 15. | propyl | 2-(fluoromethyl)phenyl |
| 16. | propyl | 4-(difluoromethyl)phenyl |
| 17. | propyl | 3-(difluoromethyl)phenyl |
| 18. | propyl | 2-(difluoromethyl)phenyl |
| 19. | propyl | 4-(trifluoromethyl)phenyl |
| 20. | propyl | 3-(trifluoromethyl)phenyl |
| 21. | propyl | 2-(trifluoromethyl)phenyl |
| 22. | propyl | 4-(1-fluoroethyl)-phenyl |
| 23. | propyl | 4-((S)-1-fluoroethyl)-phenyl |
| 24. | propyl | 4-((R)-1-fluoroethyl)-phenyl |
| 25. | propyl | 4-(2-fluoroethyl)-phenyl |
| 26. | propyl | 4-(1,1-difluoroethyl)-phenyl |
| 27. | propyl | 4-(2,2-difluoroethyl)-phenyl |
| 28. | propyl | 4-(2,2,2-trifluoroethyl)-phenyl |
| 29. | propyl | 4-(3-fluoropropyl)-phenyl |
| 30. | propyl | 4-(2-fluoropropyl)-phenyl |
| 31. | propyl | 4-((S)-2-fluoropropyl)-phenyl |
| 32. | propyl | 4-((R)-2-fluoropropyl)-phenyl |
| 33. | propyl | 4-(3,3-difluoropropyl)-phenyl |
| 34. | propyl | 4-(3,3,3-trifluoropropyl)-phenyl |
| 35. | propyl | 4-(1-fluoro-1-methylethyl)-phenyl |
| 36. | propyl | 4-(2-fluoro-1-methylethyl)-phenyl |
| 37. | propyl | 4-((S)-2-fluoro-1-methylethyl)-phenyl |
| 38. | propyl | 4-((R)-2-fluoro-1-methylethyl)-phenyl |
| 39. | propyl | 4-(2,2-difluoro-1-methylethyl)-phenyl |
| 40. | propyl | 4-((S)-2,2-difluoro-1-methylethyl)-phenyl |
| 41. | propyl | 4-((R)-2,2-difluoro-1-methylethyl)-phenyl |
| 42. | propyl | 4-(2,2,2-trifluoro-1-methylethyl)-phenyl |
| 43. | propyl | 4-((S)-2,2,2-trifluoro-1-methylethyl)-phenyl |
| 44. | propyl | 4-((R)-2,2,2-trifluoro-1-methylethyl)-phenyl |
| 45. | propyl | 4-(2-fluoro-1-fluoromethylethyl)-phenyl |
| 46. | propyl | 4-(1-difluoromethyl-2,2-difluoroethyl)-phenyl |
| 47. | propyl | 4-(1,1-dimethyl-2-fluoroethyl)-phenyl |
| 48. | propyl | 4-methoxyphenyl |
| 49. | propyl | 4-ethoxyphenyl |
| 50. | propyl | 4-propoxyphenyl |
| 51. | propyl | 4-isopropoxyphenyl |
| 52. | propyl | 4-butoxyphenyl |
| 53. | propyl | 4-(fluoromethoxy)-phenyl |
| 54. | propyl | 4-(difluoromethoxy)-phenyl |
| 55. | propyl | 4-(trifluoromethoxy)-phenyl |
| 56. | propyl | 3-(trifluoromethoxy)-phenyl |
| 57. | propyl | 4-(2-fluoroethoxy)-phenyl |
| 58. | propyl | 4-(2,2-difluoroethoxy)-phenyl |
| 59. | propyl | 4-(2,2,2-trifluoroethoxy)-phenyl |
| 60. | propyl | 4-(1,1,2,2-tetrafluoroethoxy)-phenyl |
| 61. | propyl | 4-cyclopropylphenyl |
| 62. | propyl | 4-cyclobutylphenyl |
| 63. | propyl | 4-cyclopentylphenyl |
| 64. | propyl | 4-(2,2-difluorocyclopropyl)-phenyl |
| 65. | propyl | 3,4-difluorophenyl |
| 66. | propyl | 4-bromo-3-fluorophenyl |
| 67. | propyl | 4-bromo-2-fluorophenyl |
| 68. | propyl | 4-bromo-2,5-difluorophenyl |
| 69. | propyl | 2-fluoro-4-isopropylphenyl |
| 70. | propyl | 3-fluoro-4-isopropylphenyl |
| 71. | propyl | 4-(1-hydroxy-1-methylethyl)-phenyl |
| 72. | propyl | 4-(2-hydroxy-2-methylpropyl)-phenyl |
| 73. | propyl | 4-acetylphenyl |
| 74. | propyl | 4-carboxyphenyl |
| 75. | propyl | 4-cyanophenyl |
| 76. | propyl | 4-hydroxyphenyl |
| 77. | propyl | 4-(O-benzyl)-phenyl |
| 78. | propyl | 4-(2-methoxyethoxy)-phenyl |
| 79. | propyl | 4-($CH_2$—$N(CH_3)_2$)-phenyl |
| 80. | propyl | 4-(NH—CO—$NH_2$)-phenyl |
| 81. | propyl | 4-(methylsulfanyl)-phenyl |
| 82. | propyl | 4-(fluoromethylsulfanyl)-phenyl |
| 83. | propyl | 4-(difluoromethylsulfanyl)-phenyl |
| 84. | propyl | 4-(trifluoromethylsulfanyl)-phenyl |
| 85. | propyl | 4-(methylsulfonyl)-phenyl |
| 86. | propyl | 4-(N-methoxy-N-methyl-amino)-phenyl |
| 87. | propyl | 4-(methoxyamino)-phenyl |

TABLE A-continued

| No. | R¹ | Ar |
|---|---|---|
| 88. | propyl | 4-(ethoxyamino)-phenyl |
| 89. | propyl | 4-(N-methylaminooxy)-phenyl |
| 90. | propyl | 4-(N,N-dimethylaminooxy)-phenyl |
| 91. | propyl | 4-(azetidin-1-yl)-phenyl |
| 92. | propyl | 4-(2-methylazetidin-1-yl)-phenyl |
| 93. | propyl | 4-((S)-2-methylazetidin-1-yl)-phenyl |
| 94. | propyl | 4-((R)-2-methylazetidin-1-yl)-phenyl |
| 95. | propyl | 4-(3-fluoroazetidin-1-yl)-phenyl |
| 96. | propyl | 4-(3-methoxyazetidin-1-yl)-phenyl |
| 97. | propyl | 4-(3-hydroxyazetidin-1-yl)-phenyl |
| 98. | propyl | 4-(pyrrolidin-1-yl)-phenyl |
| 99. | propyl | 4-(pyrrolidin-2-yl)-phenyl |
| 100. | propyl | 4-((S)-pyrrolidin-2-yl)-phenyl |
| 101. | propyl | 4-((R)-pyrrolidin-2-yl)-phenyl |
| 102. | propyl | 4-(pyrrolidin-3-yl)-phenyl |
| 103. | propyl | 4-((S)-pyrrolidin-3-yl)-phenyl |
| 104. | propyl | 4-((R)-pyrrolidin-3-yl)-phenyl |
| 105. | propyl | 4-(2-fluoropyrrolidin-1-yl)-phenyl |
| 106. | propyl | 4-((S)-2-fluoropyrrolidin-1-yl)-phenyl |
| 107. | propyl | 4-((R)-2-fluoropyrrolidin-1-yl)-phenyl |
| 108. | propyl | 4-(3-fluoropyrrolidin-1-yl)-phenyl |
| 109. | propyl | 4-((S)-3-fluoropyrrolidin-1-yl)-phenyl |
| 110. | propyl | 4-((R)-3-fluoropyrrolidin-1-yl)-phenyl |
| 111. | propyl | 4-(2,2-difluoropyrrolidin-1-yl)-phenyl |
| 112. | propyl | 4-(3,3-difluoropyrrolidin-1-yl)-phenyl |
| 113. | propyl | 4-(2-methylpyrrolidin-1-yl)-phenyl |
| 114. | propyl | 4-((S)-2-methylpyrrolidin-1-yl)-phenyl |
| 115. | propyl | 4-((R)-2-methylpyrrolidin-1-yl)-phenyl |
| 116. | propyl | 4-(3-methylpyrrolidin-1-yl)-phenyl |
| 117. | propyl | 4-((S)-3-methylpyrrolidin-1-yl)-phenyl |
| 118. | propyl | 4-((R)-3-methylpyrrolidin-1-yl)-phenyl |
| 119. | propyl | 4-(1-methylpyrrolidin-2-yl)-phenyl |
| 120. | propyl | 4-((S)-1-methylpyrrolidin-2-yl)-phenyl |
| 121. | propyl | 4-((R)-1-methylpyrrolidin-2-yl)-phenyl |
| 122. | propyl | 4-(1-methylpyrrolidin-3-yl)-phenyl |
| 123. | propyl | 4-((S)-1-methylpyrrolidin-3-yl)-phenyl |
| 124. | propyl | 4-((R)-1-methylpyrrolidin-3-yl)-phenyl |
| 125. | propyl | 4-(2,2-dimethylpyrrolidin-1-yl)-phenyl |
| 126. | propyl | 4-(3,3-dimethylpyrrolidin-1-yl)-phenyl |
| 127. | propyl | 4-(2-trifluoromethylpyrrolidin-1-yl)-phenyl |
| 128. | propyl | 4-((S)-2-trifluoromethylpyrrolidin-1-yl)-phenyl |
| 129. | propyl | 4-((R)-2-trifluoromethylpyrrolidin-1-yl)-phenyl |
| 130. | propyl | 4-(3-trifluoromethylpyrrolidin-1-yl)-phenyl |
| 131. | propyl | 4-((S)-3-trifluoromethylpyrrolidin-1-yl)-phenyl |
| 132. | propyl | 4-((R)-3-trifluoromethylpyrrolidin-1-yl)-phenyl |
| 133. | propyl | 4-(2-oxopyrrolidin-1-yl)-phenyl |
| 134. | propyl | 4-(2-oxo-oxazolidin-3-yl)-phenyl |
| 135. | propyl | 4-(piperidin-1-yl)-phenyl |
| 136. | propyl | 4-(2-methylpiperidin-1-yl)-phenyl |
| 137. | propyl | 4-((S)-2-methylpiperidin-1-yl)-phenyl |
| 138. | propyl | 4-((R)-2-methylpiperidin-1-yl)-phenyl |
| 139. | propyl | 4-(piperazin-1-yl)-phenyl |
| 140. | propyl | 4-(4-methylpiperazin-1-yl)-phenyl |
| 141. | propyl | 4-(morpholin-4-yl)-phenyl |
| 142. | propyl | 4-(thiomorpholin-4-yl)-phenyl |
| 143. | propyl | 4-(1-oxo-thiomorpholin-4-yl)-phenyl |
| 144. | propyl | 4-(1,1-dioxo-thiomorpholin-4-yl)-phenyl |
| 145. | propyl | 4-(pyrrol-1-yl)-phenyl |
| 146. | propyl | 4-(pyrrol-2-yl)-phenyl |
| 147. | propyl | 4-(pyrrol-3-yl)-phenyl |
| 148. | propyl | 4-(1-methylpyrrol-2-yl)-phenyl |
| 149. | propyl | 4-(1-methylpyrrol-3-yl)-phenyl |
| 150. | propyl | 4-(furan-2-yl)-phenyl |
| 151. | propyl | 4-(furan-3-yl)-phenyl |
| 152. | propyl | 4-(thiophen-2-yl)-phenyl |
| 153. | propyl | 4-(thiophen-3-yl)-phenyl |
| 154. | propyl | 4-(5-propylthien-2-yl)-phenyl |
| 155. | propyl | 4-(pyrazol-1-yl)-phenyl |
| 156. | propyl | 4-(pyrazol-3-yl)-phenyl |
| 157. | propyl | 4-(pyrazol-4-yl)-phenyl |
| 158. | propyl | 4-(1-methyl-1H-pyrazol-4-yl)-phenyl |
| 159. | propyl | 4-(1-ethyl-1H-pyrazol-4-yl)-phenyl |
| 160. | propyl | 4-(1-methyl-1H-pyrazol-5-yl)-phenyl |
| 161. | propyl | 4-(1H-imidazol-2-yl)-phenyl |
| 162. | propyl | 4-(imidazol-1-yl)-phenyl |
| 163. | propyl | 4-(1-methylimidazol-2-yl)-phenyl |
| 164. | propyl | 4-(oxazol-2-yl)-phenyl |
| 165. | propyl | 4-(oxazol-4-yl)-phenyl |

TABLE A-continued

| No. | R¹ | Ar |
|---|---|---|
| 166. | propyl | 4-(oxazol-5-yl)-phenyl |
| 167. | propyl | 4-(isoxazol-3-yl)-phenyl |
| 168. | propyl | 4-(isoxazol-4-yl)-phenyl |
| 169. | propyl | 4-(isoxazol-5-yl)-phenyl |
| 170. | propyl | 4-([1,2,3]-triazol-1-yl)-phenyl |
| 171. | propyl | 4-([1,2,4]-triazol-1-yl)-phenyl |
| 172. | propyl | 4-([1,2,3]-triazol-2-yl)-phenyl |
| 173. | propyl | 4-(4H-[1,2,4]-triazol-3-yl)-phenyl |
| 174. | propyl | 4-([1,2,4]-triazol-4-yl)-phenyl |
| 175. | propyl | 4-(2H-[1,2,3]-triazol-4-yl)-phenyl |
| 176. | propyl | 4-(4-methyl-4H-[1,2,4]-triazol-3-yl)-phenyl |
| 177. | propyl | 4-(2-methyl-2H-[1,2,3]-triazol-4-yl)-phenyl |
| 178. | propyl | 4-([1,3,4]-oxadiazol-2-yl)-phenyl |
| 179. | propyl | 4-([1,2,4]-oxadiazol-3-yl)-phenyl |
| 180. | propyl | 4-([1,2,4]-oxadiazol-5-yl)-phenyl |
| 181. | propyl | 4-([1,2,3]-oxadiazol-4-yl)-phenyl |
| 182. | propyl | 4-([1,2,3]-oxadiazol-5-yl)-phenyl |
| 183. | propyl | 4-([1,2,3]-thiadiazol-4-yl)-phenyl |
| 184. | propyl | 4-(1H-tetrazol-5-yl)-phenyl |
| 185. | propyl | 4-(tetrazol-1-yl)-phenyl |
| 186. | propyl | 4-(2-methyl-2H-tetrazol-5-yl)-phenyl |
| 187. | propyl | 4-(1-methyl-1H-tetrazol-5-yl)-phenyl |
| 188. | propyl | 4-furazan-3-yl-phenyl |
| 189. | propyl | 4-(pyrid-2-yl)-phenyl |
| 190. | propyl | 4-(pyrid-3-yl)-phenyl |
| 191. | propyl | 4-(pyrid-4-yl)-phenyl |
| 192. | propyl | 4-(pyrimidin-2-yl)-phenyl |
| 193. | propyl | 4-(pyrimidin-4-yl)-phenyl |
| 194. | propyl | 4-(pyrimidin-5-yl)-phenyl |
| 195. | propyl | 5-isopropylthiophen-2-yl |
| 196. | propyl | 2-chlorothiophen-5-yl |
| 197. | propyl | 2,5-dichlorothiophen-4-yl |
| 198. | propyl | 2,3-dichlorothiophen-5-yl |
| 199. | propyl | 2-chloro-3-nitrothiophen-5-yl |
| 200. | propyl | 2-(phenylsulfonyl)-thiophen-5-yl |
| 201. | propyl | 2-(pyridin-2-yl)thiophen-5-yl |
| 202. | propyl | 2-(5-(trifluoromethyl)isoxazol-3-yl)-thiophen-5-yl |
| 203. | propyl | 2-(2-methylthiazol-4-yl)-thiophen-5-yl |
| 204. | propyl | 1-methyl-1H-imidazol-4-yl |
| 205. | propyl | 1,2-dimethyl-1H-imidazol-4-yl |
| 206. | propyl | 3,5-dimethylisoxazol-4-yl |
| 207. | propyl | thiazol-2-yl |
| 208. | propyl | 4-methylthiazol-2-yl |
| 209. | propyl | 4-isopropylthiazol-2-yl |
| 210. | propyl | 4-trifluoromethylthiazol-2-yl |
| 211. | propyl | 5-methylthiazol-2-yl |
| 212. | propyl | 5-isopropylthiazol-2-yl |
| 213. | propyl | 5-trifluoromethylthiazol-2-yl |
| 214. | propyl | 2,4-dimethylthiazol-5-yl |
| 215. | propyl | 2-acetamido-4-methylthiazol-5-yl |
| 216. | propyl | 4H-[1,2,4]triazol-3-yl |
| 217. | propyl | 5-methyl-4H-[1,2,4]triazol-3-yl |
| 218. | propyl | 4-methyl-4H-[1,2,4]triazol-3-yl |
| 219. | propyl | 5-isopropyl-4H-[1,2,4]triazol-3-yl |
| 220. | propyl | 5-trifluoromethyl-4H-[1,2,4]triazol-3-yl |
| 221. | propyl | 4,5-dimethyl-4H-[1,2,4]triazol-3-yl |
| 222. | propyl | 5-isopropyl-4-methyl-4H-[1,2,4]triazol-3-yl |
| 223. | propyl | 5-trifluoromethyl-4-methyl-4H-[1,2,4]triazol-3-yl |
| 224. | propyl | [1,3,4]thiadiazol-2-yl |
| 225. | propyl | 5-methyl-[1,3,4]thiadiazol-2-yl |
| 226. | propyl | 5-isopropyl-[1,3,4]thiadiazol-2-yl |
| 227. | propyl | 5-trifluoromethyl-[1,3,4]thiadiazol-2-yl |
| 228. | propyl | 3-bromo-2-chloropyrid-5-yl |
| 229. | propyl | 2-(4-morpholino)-pyrid-5-yl |
| 230. | propyl | 2-phenoxypyrid-5-yl |
| 231. | propyl | (2-isopropyl)-pyrimidin-5-yl |
| 232. | propyl | (5-isopropyl)-pyrimidin-2-yl |
| 233. | propyl | 8-quinolyl |
| 234. | propyl | 5-isoquinolyl |
| 235. | propyl | 2-(trifluoroacetyl)-1,2,3,4-tetrahydroisoquinolin-7-yl |
| 236. | propyl | 5-chloro-3-methylbenzothiophen-2-yl |
| 237. | propyl | 3,4-dihydro-4-methyl-2H-benzo[b][1,4]oxazinyl |
| 238. | propyl | benzothiazol-6-yl |
| 239. | propyl | benzo[2,1,3]oxadiazol-4-yl |
| 240. | propyl | 5-chlorobenzo[2,1,3]oxadiazol-4-yl |
| 241. | propyl | 7-chlorobenzo[2,1,3]oxadiazol-4-yl |
| 242. | propyl | benzo[2,1,3]thiadiazol-4-yl |
| 243. | ethyl | 4-methylphenyl |

TABLE A-continued

| No. | R¹ | Ar |
|---|---|---|
| 244. | ethyl | 4-ethylphenyl |
| 245. | ethyl | 4-propylphenyl |
| 246. | ethyl | 4-isopropylphenyl |
| 247. | ethyl | 4-sec-butylphenyl |
| 248. | ethyl | 4-isobutylphenyl |
| 249. | ethyl | 4-(1,1-dimethylpropyl)-phenyl |
| 250. | ethyl | 4-vinylphenyl |
| 251. | ethyl | 4-isopropenylphenyl |
| 252. | ethyl | 4-fluorophenyl |
| 253. | ethyl | 4-chlorophenyl |
| 254. | ethyl | 4-bromophenyl |
| 255. | ethyl | 4-(fluoromethyl)phenyl |
| 256. | ethyl | 3-(fluoromethyl)phenyl |
| 257. | ethyl | 2-(fluoromethyl)phenyl |
| 258. | ethyl | 4-(difluoromethyl)phenyl |
| 259. | ethyl | 3-(difluoromethyl)phenyl |
| 260. | ethyl | 2-(difluoromethyl)phenyl |
| 261. | ethyl | 4-(trifluoromethyl)phenyl |
| 262. | ethyl | 3-(trifluoromethyl)phenyl |
| 263. | ethyl | 2-(trifluoromethyl)phenyl |
| 264. | ethyl | 4-(1-fluoroethyl)-phenyl |
| 265. | ethyl | 4-((S)-1-fluoroethyl)-phenyl |
| 266. | ethyl | 4-((R)-1-fluoroethyl)-phenyl |
| 267. | ethyl | 4-(2-fluoroethyl)-phenyl |
| 268. | ethyl | 4-(1,1-difluoroethyl)-phenyl |
| 269. | ethyl | 4-(2,2-difluoroethyl)-phenyl |
| 270. | ethyl | 4-(2,2,2-trifluoroethyl)-phenyl |
| 271. | ethyl | 4-(3-fluoropropyl)-phenyl |
| 272. | ethyl | 4-(2-fluoropropyl)-phenyl |
| 273. | ethyl | 4-((S)-2-fluoropropyl)-phenyl |
| 274. | ethyl | 4-((R)-2-fluoropropyl)-phenyl |
| 275. | ethyl | 4-(3,3-difluoropropyl)-phenyl |
| 276. | ethyl | 4-(3,3,3-trifluoropropyl)-phenyl |
| 277. | ethyl | 4-(1-fluoro-1-methylethyl)-phenyl |
| 278. | ethyl | 4-(2-fluoro-1-methylethyl)-phenyl |
| 279. | ethyl | 4-((S)-2-fluoro-1-methylethyl)-phenyl |
| 280. | ethyl | 4-((R)-2-fluoro-1-methylethyl)-phenyl |
| 281. | ethyl | 4-(2,2-difluoro-1-methylethyl)-phenyl |
| 282. | ethyl | 4-((S)-2,2-difluoro-1-methylethyl)-phenyl |
| 283. | ethyl | 4-((R)-2,2-difluoro-1-methylethyl)-phenyl |
| 284. | ethyl | 4-(2,2,2-trifluoro-1-methylethyl)-phenyl |
| 285. | ethyl | 4-((S)-2,2,2-trifluoro-1-methylethyl)-phenyl |
| 286. | ethyl | 4-((R)-2,2,2-trifluoro-1-methylethyl)-phenyl |
| 287. | ethyl | 4-(2-fluoro-1-fluoromethylethyl)-phenyl |
| 288. | ethyl | 4-(1-difluoromethyl-2,2-difluoroethyl)-phenyl |
| 289. | ethyl | 4-(1,1-dimethyl-2-fluoroethyl)-phenyl |
| 290. | ethyl | 4-methoxyphenyl |
| 291. | ethyl | 4-ethoxyphenyl |
| 292. | ethyl | 4-propoxyphenyl |
| 293. | ethyl | 4-isopropoxyphenyl |
| 294. | ethyl | 4-butoxyphenyl |
| 295. | ethyl | 4-(fluoromethoxy)-phenyl |
| 296. | ethyl | 4-(difluoromethoxy)-phenyl |
| 297. | ethyl | 4-(trifluoromethoxy)-phenyl |
| 298. | ethyl | 3-(trifluoromethoxy)-phenyl |
| 299. | ethyl | 4-(2-fluoroethoxy)-phenyl |
| 300. | ethyl | 4-(2,2-difluoroethoxy)-phenyl |
| 301. | ethyl | 4-(2,2,2-trifluoroethoxy)-phenyl |
| 302. | ethyl | 4-(1,1,2,2-tetrafluoroethoxy)-phenyl |
| 303. | ethyl | 4-cyclopropylphenyl |
| 304. | ethyl | 4-cyclobutylphenyl |
| 305. | ethyl | 4-cyclopentylphenyl |
| 306. | ethyl | 4-(2,2-difluorocyclopropyl)-phenyl |
| 307. | ethyl | 3,4-difluorophenyl |
| 308. | ethyl | 4-bromo-3-fluorophenyl |
| 309. | ethyl | 4-bromo-2-fluorophenyl |
| 310. | ethyl | 4-bromo-2,5-difluorophenyl |
| 311. | ethyl | 2-fluoro-4-isopropylphenyl |
| 312. | ethyl | 3-fluoro-4-isopropylphenyl |
| 313. | ethyl | 4-(1-hydroxy-1-methylethyl)-phenyl |
| 314. | ethyl | 4-(2-hydroxy-2-methylpropyl)-phenyl |
| 315. | ethyl | 4-acetylphenyl |
| 316. | ethyl | 4-carboxyphenyl |
| 317. | ethyl | 4-cyanophenyl |
| 318. | ethyl | 4-hydroxyphenyl |
| 319. | ethyl | 4-(O-benzyl)-phenyl |
| 320. | ethyl | 4-(2-methoxyethoxy)-phenyl |
| 321. | ethyl | 4-($CH_2$—$N(CH_3)_2$)-phenyl |

TABLE A-continued

| No. | R¹ | Ar |
|---|---|---|
| 322. | ethyl | 4-(NH—CO—NH$_2$)-phenyl |
| 323. | ethyl | 4-(methylsulfanyl)-phenyl |
| 324. | ethyl | 4-(fluoromethylsulfanyl)-phenyl |
| 325. | ethyl | 4-(difluoromethylsulfanyl)-phenyl |
| 326. | ethyl | 4-(trifluoromethylsulfanyl)-phenyl |
| 327. | ethyl | 4-(methylsulfonyl)-phenyl |
| 328. | ethyl | 4-(N-methoxy-N-methyl-amino)-phenyl |
| 329. | ethyl | 4-(methoxyamino)-phenyl |
| 330. | ethyl | 4-(ethoxyamino)-phenyl |
| 331. | ethyl | 4-(N-methylaminooxy)-phenyl |
| 332. | ethyl | 4-(N,N-dimethylaminooxy)-phenyl |
| 333. | ethyl | 4-(azetidin-1-yl)-phenyl |
| 334. | ethyl | 4-(2-methylazetidin-1-yl)-phenyl |
| 335. | ethyl | 4-((S)-2-methylazetidin-1-yl)-phenyl |
| 336. | ethyl | 4-((R)-2-methylazetidin-1-yl)-phenyl |
| 337. | ethyl | 4-(3-fluoroazetidin-1-yl)-phenyl |
| 338. | ethyl | 4-(3-methoxyazetidin-1-yl)-phenyl |
| 339. | ethyl | 4-(3-hydroxyazetidin-1-yl)-phenyl |
| 340. | ethyl | 4-(pyrrolidin-1-yl)-phenyl |
| 341. | ethyl | 4-(pyrrolidin-2-yl)-phenyl |
| 342. | ethyl | 4-((S)-pyrrolidin-2-yl)-phenyl |
| 343. | ethyl | 4-((R)-pyrrolidin-2-yl)-phenyl |
| 344. | ethyl | 4-(pyrrolidin-3-yl)-phenyl |
| 345. | ethyl | 4-((S)-pyrrolidin-3-yl)-phenyl |
| 346. | ethyl | 4-((R)-pyrrolidin-3-yl)-phenyl |
| 347. | ethyl | 4-(2-fluoropyrrolidin-1-yl)-phenyl |
| 348. | ethyl | 4-((S)-2-fluoropyrrolidin-1-yl)-phenyl |
| 349. | ethyl | 4-((R)-2-fluoropyrrolidin-1-yl)-phenyl |
| 350. | ethyl | 4-(3-fluoropyrrolidin-1-yl)-phenyl |
| 351. | ethyl | 4-((S)-3-fluoropyrrolidin-1-yl)-phenyl |
| 352. | ethyl | 4-((R)-3-fluoropyrrolidin-1-yl)-phenyl |
| 353. | ethyl | 4-(2,2-difluoropyrrolidin-1-yl)-phenyl |
| 354. | ethyl | 4-(3,3-difluoropyrrolidin-1-yl)-phenyl |
| 355. | ethyl | 4-(2-methylpyrrolidin-1-yl)-phenyl |
| 356. | ethyl | 4-((S)-2-methylpyrrolidin-1-yl)-phenyl |
| 357. | ethyl | 4-((R)-2-methylpyrrolidin-1-yl)-phenyl |
| 358. | ethyl | 4-(3-methylpyrrolidin-1-yl)-phenyl |
| 359. | ethyl | 4-((S)-3-methylpyrrolidin-1-yl)-phenyl |
| 360. | ethyl | 4-((R)-3-methylpyrrolidin-1-yl)-phenyl |
| 361. | ethyl | 4-(1-methylpyrrolidin-2-yl)-phenyl |
| 362. | ethyl | 4-((S)-1-methylpyrrolidin-2-yl)-phenyl |
| 363. | ethyl | 4-((R)-1-methylpyrrolidin-2-yl)-phenyl |
| 364. | ethyl | 4-(1-methylpyrrolidin-3-yl)-phenyl |
| 365. | ethyl | 4-((S)-1-methylpyrrolidin-3-yl)-phenyl |
| 366. | ethyl | 4-((R)-1-methylpyrrolidin-3-yl)-phenyl |
| 367. | ethyl | 4-(2,2-dimethylpyrrolidin-1-yl)-phenyl |
| 368. | ethyl | 4-(3,3-dimethylpyrrolidin-1-yl)-phenyl |
| 369. | ethyl | 4-(2-trifluoromethylpyrrolidin-1-yl)-phenyl |
| 370. | ethyl | 4-((S)-2-trifluoromethylpyrrolidin-1-yl)-phenyl |
| 371. | ethyl | 4-((R)-2-trifluoromethylpyrrolidin-1-yl)-phenyl |
| 372. | ethyl | 4-(3-trifluoromethylpyrrolidin-1-yl)-phenyl |
| 373. | ethyl | 4-((S)-3-trifluoromethylpyrrolidin-1-yl)-phenyl |
| 374. | ethyl | 4-((R)-3-trifluoromethylpyrrolidin-1-yl)-phenyl |
| 375. | ethyl | 4-(2-oxopyrrolidin-1-yl)-phenyl |
| 376. | ethyl | 4-(2-oxo-oxazolidin-3-yl)-phenyl |
| 377. | ethyl | 4-(piperidin-1-yl)-phenyl |
| 378. | ethyl | 4-(2-methylpiperidin-1-yl)-phenyl |
| 379. | ethyl | 4-((S)-2-methylpiperidin-1-yl)-phenyl |
| 380. | ethyl | 4-((R)-2-methylpiperidin-1-yl)-phenyl |
| 381. | ethyl | 4-(piperazin-1-yl)-phenyl |
| 382. | ethyl | 4-(4-methylpiperazin-1-yl)-phenyl |
| 383. | ethyl | 4-(morpholin-4-yl)-phenyl |
| 384. | ethyl | 4-(thiomorpholin-4-yl)-phenyl |
| 385. | ethyl | 4-(1-oxo-thiomorpholin-4-yl)-phenyl |
| 386. | ethyl | 4-(1,1-dioxo-thiomorpholin-4-yl)-phenyl |
| 387. | ethyl | 4-(pyrrol-1-yl)-phenyl |
| 388. | ethyl | 4-(pyrrol-2-yl)-phenyl |
| 389. | ethyl | 4-(pyrrol-3-yl)-phenyl |
| 390. | ethyl | 4-(1-methylpyrrol-2-yl)-phenyl |
| 391. | ethyl | 4-(1-methylpyrrol-3-yl)-phenyl |
| 392. | ethyl | 4-(furan-2-yl)-phenyl |
| 393. | ethyl | 4-(furan-3-yl)-phenyl |
| 394. | ethyl | 4-(thiophen-2-yl)-phenyl |
| 395. | ethyl | 4-(thiophen-3-yl)-phenyl |
| 396. | ethyl | 4-(5-propylthien-2-yl)-phenyl |
| 397. | ethyl | 4-(pyrazol-1-yl)-phenyl |
| 398. | ethyl | 4-(pyrazol-3-yl)-phenyl |
| 399. | ethyl | 4-(pyrazol-4-yl)-phenyl |

TABLE A-continued

| No. | R¹ | Ar |
| --- | --- | --- |
| 400. | ethyl | 4-(1-methyl-1H-pyrazol-4-yl)-phenyl |
| 401. | ethyl | 4-(1-ethyl-1H-pyrazol-4-yl)-phenyl |
| 402. | ethyl | 4-(1-methyl-1H-pyrazol-5-yl)-phenyl |
| 403. | ethyl | 4-(1H-imidazol-2-yl)-phenyl |
| 404. | ethyl | 4-(imidazol-1-yl)-phenyl |
| 405. | ethyl | 4-(1-methylimidazol-2-yl)-phenyl |
| 406. | ethyl | 4-(oxazol-2-yl)-phenyl |
| 407. | ethyl | 4-(oxazol-4-yl)-phenyl |
| 408. | ethyl | 4-(oxazol-5-yl)-phenyl |
| 409. | ethyl | 4-(isoxazol-3-yl)-phenyl |
| 410. | ethyl | 4-(isoxazol-4-yl)-phenyl |
| 411. | ethyl | 4-(isoxazol-5-yl)-phenyl |
| 412. | ethyl | 4-([1,2,3]-triazol-1-yl)-phenyl |
| 413. | ethyl | 4-([1,2,4]-triazol-1-yl)-phenyl |
| 414. | ethyl | 4-([1,2,3]-triazol-2-yl)-phenyl |
| 415. | ethyl | 4-(4H-[1,2,4]-triazol-3-yl)-phenyl |
| 416. | ethyl | 4-([1,2,4]-triazol-4-yl)-phenyl |
| 417. | ethyl | 4-(2H-[1,2,3]-triazol-4-yl)-phenyl |
| 418. | ethyl | 4-(4-methyl-4H-[1,2,4]-triazol-3-yl)-phenyl |
| 419. | ethyl | 4-(2-methyl-2H-[1,2,3]-triazol-4-yl)-phenyl |
| 420. | ethyl | 4-([1,3,4]-oxadiazol-2-yl)-phenyl |
| 421. | ethyl | 4-([1,2,4]-oxadiazol-3-yl)-phenyl |
| 422. | ethyl | 4-([1,2,4]-oxadiazol-5-yl)-phenyl |
| 423. | ethyl | 4-([1,2,3]-oxadiazol-4-yl)-phenyl |
| 424. | ethyl | 4-([1,2,3]-oxadiazol-5-yl)-phenyl |
| 425. | ethyl | 4-([1,2,3]-thiadiazol-4-yl)-phenyl |
| 426. | ethyl | 4-(1H-tetrazol-5-yl)-phenyl |
| 427. | ethyl | 4-(tetrazol-1-yl)-phenyl |
| 428. | ethyl | 4-(2-methyl-2H-tetrazol-5-yl)-phenyl |
| 429. | ethyl | 4-(1-methyl-1H-tetrazol-5-yl)-phenyl |
| 430. | ethyl | 4-furazan-3-yl-phenyl |
| 431. | ethyl | 4-(pyrid-2-yl)-phenyl |
| 432. | ethyl | 4-(pyrid-3-yl)-phenyl |
| 433. | ethyl | 4-(pyrid-4-yl)-phenyl |
| 434. | ethyl | 4-(pyrimidin-2-yl)-phenyl |
| 435. | ethyl | 4-(pyrimidin-4-yl)-phenyl |
| 436. | ethyl | 4-(pyrimidin-5-yl)-phenyl |
| 437. | ethyl | 5-isopropylthiophen-2-yl |
| 438. | ethyl | 2-chlorothiophen-5-yl |
| 439. | ethyl | 2,5-dichlorothiophen-4-yl |
| 440. | ethyl | 2,3-dichlorothiophen-5-yl |
| 441. | ethyl | 2-chloro-3-nitrothiophen-5-yl |
| 442. | ethyl | 2-(phenylsulfonyl)-thiophen-5-yl |
| 443. | ethyl | 2-(pyridin-2-yl)thiophen-5-yl |
| 444. | ethyl | 2-(5-(trifluoromethyl)isoxazol-3-yl)-thiophen-5-yl |
| 445. | ethyl | 2-(2-methylthiazol-4-yl)-thiophen-5-yl |
| 446. | ethyl | 1-methyl-1H-imidazol-4-yl |
| 447. | ethyl | 1,2-dimethyl-1H-imidazol-4-yl |
| 448. | ethyl | 3,5-dimethylisoxazol-4-yl |
| 449. | ethyl | thiazol-2-yl |
| 450. | ethyl | 4-methylthiazol-2-yl |
| 451. | ethyl | 4-isopropylthiazol-2-yl |
| 452. | ethyl | 4-trifluoromethylthiazol-2-yl |
| 453. | ethyl | 5-methylthiazol-2-yl |
| 454. | ethyl | 5-isopropylthiazol-2-yl |
| 455. | ethyl | 5-trifluoromethylthiazol-2-yl |
| 456. | ethyl | 2,4-dimethylthiazol-5-yl |
| 457. | ethyl | 2-acetamido-4-methylthiazol-5-yl |
| 458. | ethyl | 4H-[1,2,4]triazol-3-yl |
| 459. | ethyl | 5-methyl-4H-[1,2,4]triazol-3-yl |
| 460. | ethyl | 4-methyl-4H-[1,2,4]triazol-3-yl |
| 461. | ethyl | 5-isopropyl-4H-[1,2,4]triazol-3-yl |
| 462. | ethyl | 5-trifluoromethyl-4H-[1,2,4]triazol-3-yl |
| 463. | ethyl | 4,5-dimethyl-4H-[1,2,4]triazol-3-yl |
| 464. | ethyl | 5-isopropyl-4-methyl-4H-[1,2,4]triazol-3-yl |
| 465. | ethyl | 5-trifluoromethyl-4-methyl-4H-[1,2,4]triazol-3-yl |
| 466. | ethyl | [1,3,4]thiadiazol-2-yl |
| 467. | ethyl | 5-methyl-[1,3,4]thiadiazol-2-yl |
| 468. | ethyl | 5-isopropyl-[1,3,4]thiadiazol-2-yl |
| 469. | ethyl | 5-trifluoromethyl-[1,3,4]thiadiazol-2-yl |
| 470. | ethyl | 3-bromo-2-chloropyrid-5-yl |
| 471. | ethyl | 2-(4-morpholino)-pyrid-5-yl |
| 472. | ethyl | 2-phenoxypyrid-5-yl |
| 473. | ethyl | (2-isopropyl)-pyrimidin-5-yl |
| 474. | ethyl | (5-isopropyl)-pyrimidin-2-yl |
| 475. | ethyl | 8-quinolyl |
| 476. | ethyl | 5-isoquinolyl |
| 477. | ethyl | 2-(trifluoroacetyl)-1,2,3,4-tetrahydroisoquinolin-7-yl |

TABLE A-continued

| No. | R¹ | Ar |
|---|---|---|
| 478. | ethyl | 5-chloro-3-methylbenzothiophen-2-yl |
| 479. | ethyl | 3,4-dihydro-4-methyl-2H-benzo[b][1,4]oxazinyl |
| 480. | ethyl | benzothiazol-6-yl |
| 481. | ethyl | benzo[2,1,3]oxadiazol-4-yl |
| 482. | ethyl | 5-chlorobenzo[2,1,3]oxadiazol-4-yl |
| 483. | ethyl | 7-chlorobenzo[2,1,3]oxadiazol-4-yl |
| 484. | ethyl | benzo[2,1,3]thiadiazol-4-yl |
| 485. | methyl | 4-methylphenyl |
| 486. | methyl | 4-ethylphenyl |
| 487. | methyl | 4-propylphenyl |
| 488. | methyl | 4-isopropylphenyl |
| 489. | methyl | 4-sec-butylphenyl |
| 490. | methyl | 4-isobutylphenyl |
| 491. | methyl | 4-(1,1-dimethylpropyl)-phenyl |
| 492. | methyl | 4-vinylphenyl |
| 493. | methyl | 4-isopropenylphenyl |
| 494. | methyl | 4-fluorophenyl |
| 495. | methyl | 4-chlorophenyl |
| 496. | methyl | 4-bromophenyl |
| 497. | methyl | 4-(fluoromethyl)phenyl |
| 498. | methyl | 3-(fluoromethyl)phenyl |
| 499. | methyl | 2-(fluoromethyl)phenyl |
| 500. | methyl | 4-(difluoromethyl)phenyl |
| 501. | methyl | 3-(difluoromethyl)phenyl |
| 502. | methyl | 2-(difluoromethyl)phenyl |
| 503. | methyl | 4-(trifluoromethyl)phenyl |
| 504. | methyl | 3-(trifluoromethyl)phenyl |
| 505. | methyl | 2-(trifluoromethyl)phenyl |
| 506. | methyl | 4-(1-fluoroethyl)-phenyl |
| 507. | methyl | 4-((S)-1-fluoroethyl)-phenyl |
| 508. | methyl | 4-((R)-1-fluoroethyl)-phenyl |
| 509. | methyl | 4-(2-fluoroethyl)-phenyl |
| 510. | methyl | 4-(1,1-difluoroethyl)-phenyl |
| 511. | methyl | 4-(2,2-difluoroethyl)-phenyl |
| 512. | methyl | 4-(2,2,2-trifluoroethyl)-phenyl |
| 513. | methyl | 4-(3-fluoropropyl)-phenyl |
| 514. | methyl | 4-(2-fluoropropyl)-phenyl |
| 515. | methyl | 4-((S)-2-fluoropropyl)-phenyl |
| 516. | methyl | 4-((R)-2-fluoropropyl)-phenyl |
| 517. | methyl | 4-(3,3-difluoropropyl)-phenyl |
| 518. | methyl | 4-(3,3,3-trifluoropropyl)-phenyl |
| 519. | methyl | 4-(1-fluoro-1-methylethyl)-phenyl |
| 520. | methyl | 4-(2-fluoro-1-methylethyl)-phenyl |
| 521. | methyl | 4-((S)-2-fluoro-1-methylethyl)-phenyl |
| 522. | methyl | 4-((R)-2-fluoro-1-methylethyl)-phenyl |
| 523. | methyl | 4-(2,2-difluoro-1-methylethyl)-phenyl |
| 524. | methyl | 4-((S)-2,2-difluoro-1-methylethyl)-phenyl |
| 525. | methyl | 4-((R)-2,2-difluoro-1-methylethyl)-phenyl |
| 526. | methyl | 4-(2,2,2-trifluoro-1-methylethyl)-phenyl |
| 527. | methyl | 4-((S)-2,2,2-trifluoro-1-methylethyl)-phenyl |
| 528. | methyl | 4-((R)-2,2,2-trifluoro-1-methylethyl)-phenyl |
| 529. | methyl | 4-(2-fluoro-1-fluoromethylethyl)-phenyl |
| 530. | methyl | 4-(1-difluoromethyl-2,2-difluoroethyl)-phenyl |
| 531. | methyl | 4-(1,1-dimethyl-2-fluoroethyl)-phenyl |
| 532. | methyl | 4-methoxyphenyl |
| 533. | methyl | 4-ethoxyphenyl |
| 534. | methyl | 4-propoxyphenyl |
| 535. | methyl | 4-isopropoxyphenyl |
| 536. | methyl | 4-butoxyphenyl |
| 537. | methyl | 4-(fluoromethoxy)-phenyl |
| 538. | methyl | 4-(difluoromethoxy)-phenyl |
| 539. | methyl | 4-(trifluoromethoxy)-phenyl |
| 540. | methyl | 3-(trifluoromethoxy)-phenyl |
| 541. | methyl | 4-(2-fluoroethoxy)-phenyl |
| 542. | methyl | 4-(2,2-difluoroethoxy)-phenyl |
| 543. | methyl | 4-(2,2,2-trifluoroethoxy)-phenyl |
| 544. | methyl | 4-(1,1,2,2-tetrafluoroethoxy)-phenyl |
| 545. | methyl | 4-cyclopropylphenyl |
| 546. | methyl | 4-cyclobutylphenyl |
| 547. | methyl | 4-cyclopentylphenyl |
| 548. | methyl | 4-(2,2-difluorocyclopropyl)-phenyl |
| 549. | methyl | 3,4-difluorophenyl |
| 550. | methyl | 4-bromo-3-fluorophenyl |
| 551. | methyl | 4-bromo-2-fluorophenyl |
| 552. | methyl | 4-bromo-2,5-difluorophenyl |
| 553. | methyl | 2-fluoro-4-isopropylphenyl |
| 554. | methyl | 3-fluoro-4-isopropylphenyl |
| 555. | methyl | 4-(1-hydroxy-1-methylethyl)-phenyl |

TABLE A-continued

| No. | R¹ | Ar |
|---|---|---|
| 556. | methyl | 4-(2-hydroxy-2-methylpropyl)-phenyl |
| 557. | methyl | 4-acetylphenyl |
| 558. | methyl | 4-carboxyphenyl |
| 559. | methyl | 4-cyanophenyl |
| 560. | methyl | 4-hydroxyphenyl |
| 561. | methyl | 4-(O-benzyl)-phenyl |
| 562. | methyl | 4-(2-methoxyethoxy)-phenyl |
| 563. | methyl | 4-(CH₂—N(CH₃)₂)-phenyl |
| 564. | methyl | 4-(NH—CO—NH₂)-phenyl |
| 565. | methyl | 4-(methylsulfanyl)-phenyl |
| 566. | methyl | 4-(fluoromethylsulfanyl)-phenyl |
| 567. | methyl | 4-(difluoromethylsulfanyl)-phenyl |
| 568. | methyl | 4-(trifluoromethylsulfanyl)-phenyl |
| 569. | methyl | 4-(methylsulfonyl)-phenyl |
| 570. | methyl | 4-(N-methoxy-N-methyl-amino)-phenyl |
| 571. | methyl | 4-(methoxyamino)-phenyl |
| 572. | methyl | 4-(ethoxyamino)-phenyl |
| 573. | methyl | 4-(N-methylaminooxy)-phenyl |
| 574. | methyl | 4-(N,N-dimethylaminooxy)-phenyl |
| 575. | methyl | 4-(azetidin-1-yl)-phenyl |
| 576. | methyl | 4-(2-methylazetidin-1-yl)-phenyl |
| 577. | methyl | 4-((S)-2-methylazetidin-1-yl)-phenyl |
| 578. | methyl | 4-((R)-2-methylazetidin-1-yl)-phenyl |
| 579. | methyl | 4-(3-fluoroazetidin-1-yl)-phenyl |
| 580. | methyl | 4-(3-methoxyazetidin-1-yl)-phenyl |
| 581. | methyl | 4-(3-hydroxyazetidin-1-yl)-phenyl |
| 582. | methyl | 4-(pyrrolidin-1-yl)-phenyl |
| 583. | methyl | 4-(pyrrolidin-2-yl)-phenyl |
| 584. | methyl | 4-((S)-pyrrolidin-2-yl)-phenyl |
| 585. | methyl | 4-((R)-pyrrolidin-2-yl)-phenyl |
| 586. | methyl | 4-(pyrrolidin-3-yl)-phenyl |
| 587. | methyl | 4-((S)-pyrrolidin-3-yl)-phenyl |
| 588. | methyl | 4-((R)-pyrrolidin-3-yl)-phenyl |
| 589. | methyl | 4-(2-fluoropyrrolidin-1-yl)-phenyl |
| 590. | methyl | 4-((S)-2-fluoropyrrolidin-1-yl)-phenyl |
| 591. | methyl | 4-((R)-2-fluoropyrrolidin-1-yl)-phenyl |
| 592. | methyl | 4-(3-fluoropyrrolidin-1-yl)-phenyl |
| 593. | methyl | 4-((S)-3-fluoropyrrolidin-1-yl)-phenyl |
| 594. | methyl | 4-((R)-3-fluoropyrrolidin-1-yl)-phenyl |
| 595. | methyl | 4-(2,2-difluoropyrrolidin-1-yl)-phenyl |
| 596. | methyl | 4-(3,3-difluoropyrrolidin-1-yl)-phenyl |
| 597. | methyl | 4-(2-methylpyrrolidin-1-yl)-phenyl |
| 598. | methyl | 4-((S)-2-methylpyrrolidin-1-yl)-phenyl |
| 599. | methyl | 4-((R)-2-methylpyrrolidin-1-yl)-phenyl |
| 600. | methyl | 4-(3-methylpyrrolidin-1-yl)-phenyl |
| 601. | methyl | 4-((S)-3-methylpyrrolidin-1-yl)-phenyl |
| 602. | methyl | 4-((R)-3-methylpyrrolidin-1-yl)-phenyl |
| 603. | methyl | 4-(1-methylpyrrolidin-2-yl)-phenyl |
| 604. | methyl | 4-((S)-1-methylpyrrolidin-2-yl)-phenyl |
| 605. | methyl | 4-((R)-1-methylpyrrolidin-2-yl)-phenyl |
| 606. | methyl | 4-(1-methylpyrrolidin-3-yl)-phenyl |
| 607. | methyl | 4-((S)-1-methylpyrrolidin-3-yl)-phenyl |
| 608. | methyl | 4-((R)-1-methylpyrrolidin-3-yl)-phenyl |
| 609. | methyl | 4-(2,2-dimethylpyrrolidin-1-yl)-phenyl |
| 610. | methyl | 4-(3,3-dimethylpyrrolidin-1-yl)-phenyl |
| 611. | methyl | 4-(2-trifluoromethylpyrrolidin-1-yl)-phenyl |
| 612. | methyl | 4-((S)-2-trifluoromethylpyrrolidin-1-yl)-phenyl |
| 613. | methyl | 4-((R)-2-trifluoromethylpyrrolidin-1-yl)-phenyl |
| 614. | methyl | 4-(3-trifluoromethylpyrrolidin-1-yl)-phenyl |
| 615. | methyl | 4-((S)-3-trifluoromethylpyrrolidin-1-yl)-phenyl |
| 616. | methyl | 4-((R)-3-trifluoromethylpyrrolidin-1-yl)-phenyl |
| 617. | methyl | 4-(2-oxopyrrolidin-1-yl)-phenyl |
| 618. | methyl | 4-(2-oxo-oxazolidin-3-yl)-phenyl |
| 619. | methyl | 4-(piperidin-1-yl)-phenyl |
| 620. | methyl | 4-(2-methylpiperidin-1-yl)-phenyl |
| 621. | methyl | 4-((S)-2-methylpiperidin-1-yl)-phenyl |
| 622. | methyl | 4-((R)-2-methylpiperidin-1-yl)-phenyl |
| 623. | methyl | 4-(piperazin-1-yl)-phenyl |
| 624. | methyl | 4-(4-methylpiperazin-1-yl)-phenyl |
| 625. | methyl | 4-(morpholin-4-yl)-phenyl |
| 626. | methyl | 4-(thiomorpholin-4-yl)-phenyl |
| 627. | methyl | 4-(1-oxo-thiomorpholin-4-yl)-phenyl |
| 628. | methyl | 4-(1,1-dioxo-thiomorpholin-4-yl)-phenyl |
| 629. | methyl | 4-(pyrrol-1-yl)-phenyl |
| 630. | methyl | 4-(pyrrol-2-yl)-phenyl |
| 631. | methyl | 4-(pyrrol-3-yl)-phenyl |
| 632. | methyl | 4-(1-methylpyrrol-2-yl)-phenyl |
| 633. | methyl | 4-(1-methylpyrrol-3-yl)-phenyl |

TABLE A-continued

| No. | R¹ | Ar |
|---|---|---|
| 634. | methyl | 4-(furan-2-yl)-phenyl |
| 635. | methyl | 4-(furan-3-yl)-phenyl |
| 636. | methyl | 4-(thiophen-2-yl)-phenyl |
| 637. | methyl | 4-(thiophen-3-yl)-phenyl |
| 638. | methyl | 4-(5-propylthien-2-yl)-phenyl |
| 639. | methyl | 4-(pyrazol-1-yl)-phenyl |
| 640. | methyl | 4-(pyrazol-3-yl)-phenyl |
| 641. | methyl | 4-(pyrazol-4-yl)-phenyl |
| 642. | methyl | 4-(1-methyl-1H-pyrazol-4-yl)-phenyl |
| 643. | methyl | 4-(1-ethyl-1H-pyrazol-4-yl)-phenyl |
| 644. | methyl | 4-(1-methyl-1H-pyrazol-5-yl)-phenyl |
| 645. | methyl | 4-(1H-imidazol-2-yl)-phenyl |
| 646. | methyl | 4-(imidazol-1-yl)-phenyl |
| 647. | methyl | 4-(1-methylimidazol-2-yl)-phenyl |
| 648. | methyl | 4-(oxazol-2-yl)-phenyl |
| 649. | methyl | 4-(oxazol-4-yl)-phenyl |
| 650. | methyl | 4-(oxazol-5-yl)-phenyl |
| 651. | methyl | 4-(isoxazol-3-yl)-phenyl |
| 652. | methyl | 4-(isoxazol-4-yl)-phenyl |
| 653. | methyl | 4-(isoxazol-5-yl)-phenyl |
| 654. | methyl | 4-([1,2,3]-triazol-1-yl)-phenyl |
| 655. | methyl | 4-([1,2,4]-triazol-1-yl)-phenyl |
| 656. | methyl | 4-([1,2,3]-triazol-2-yl)-phenyl |
| 657. | methyl | 4-(4H-[1,2,4]-triazol-3-yl)-phenyl |
| 658. | methyl | 4-([1,2,4]-triazol-4-yl)-phenyl |
| 659. | methyl | 4-(2H-[1,2,3]-triazol-4-yl)-phenyl |
| 660. | methyl | 4-(4-methyl-4H-[1,2,4]-triazol-3-yl)-phenyl |
| 661. | methyl | 4-(2-methyl-2H-[1,2,3]-triazol-4-yl)-phenyl |
| 662. | methyl | 4-([1,3,4]-oxadiazol-2-yl)-phenyl |
| 663. | methyl | 4-([1,2,4]-oxadiazol-3-yl)-phenyl |
| 664. | methyl | 4-([1,2,4]-oxadiazol-5-yl)-phenyl |
| 665. | methyl | 4-([1,2,3]-oxadiazol-4-yl)-phenyl |
| 666. | methyl | 4-([1,2,3]-oxadiazol-5-yl)-phenyl |
| 667. | methyl | 4-([1,2,3]-thiadiazol-4-yl)-phenyl |
| 668. | methyl | 4-(1H-tetrazol-5-yl)-phenyl |
| 669. | methyl | 4-(tetrazol-1-yl)-phenyl |
| 670. | methyl | 4-(2-methyl-2H-tetrazol-5-yl)-phenyl |
| 671. | methyl | 4-(1-methyl-1H-tetrazol-5-yl)-phenyl |
| 672. | methyl | 4-furazan-3-yl-phenyl |
| 673. | methyl | 4-(pyrid-2-yl)-phenyl |
| 674. | methyl | 4-(pyrid-3-yl)-phenyl |
| 675. | methyl | 4-(pyrid-4-yl)-phenyl |
| 676. | methyl | 4-(pyrimidin-2-yl)-phenyl |
| 677. | methyl | 4-(pyrimidin-4-yl)-phenyl |
| 678. | methyl | 4-(pyrimidin-5-yl)-phenyl |
| 679. | methyl | 5-isopropylthiophen-2-yl |
| 680. | methyl | 2-chlorothiophen-5-yl |
| 681. | methyl | 2,5-dichlorothiophen-4-yl |
| 682. | methyl | 2,3-dichlorothiophen-5-yl |
| 683. | methyl | 2-chloro-3-nitrothiophen-5-yl |
| 684. | methyl | 2-(phenylsulfonyl)-thiophen-5-yl |
| 685. | methyl | 2-(pyridin-2-yl)thiophen-5-yl |
| 686. | methyl | 2-(5-(trifluoromethyl)isoxazol-3-yl)-thiophen-5-yl |
| 687. | methyl | 2-(2-methylthiazol-4-yl)-thiophen-5-yl |
| 688. | methyl | 1-methyl-1H-imidazol-4-yl |
| 689. | methyl | 1,2-dimethyl-1H-imidazol-4-yl |
| 690. | methyl | 3,5-dimethylisoxazol-4-yl |
| 691. | methyl | thiazol-2-yl |
| 692. | methyl | 4-methylthiazol-2-yl |
| 693. | methyl | 4-isopropylthiazol-2-yl |
| 694. | methyl | 4-trifluoromethylthiazol-2-yl |
| 695. | methyl | 5-methylthiazol-2-yl |
| 696. | methyl | 5-isopropylthiazol-2-yl |
| 697. | methyl | 5-trifluoromethylthiazol-2-yl |
| 698. | methyl | 2,4-dimethylthiazol-5-yl |
| 699. | methyl | 2-acetamido-4-methylthiazol-5-yl |
| 700. | methyl | 4H-[1,2,4]triazol-3-yl |
| 701. | methyl | 5-methyl-4H-[1,2,4]triazol-3-yl |
| 702. | methyl | 4-methyl-4H-[1,2,4]triazol-3-yl |
| 703. | methyl | 5-isopropyl-4H-[1,2,4]triazol-3-yl |
| 704. | methyl | 5-trifluoromethyl-4H-[1,2,4]triazol-3-yl |
| 705. | methyl | 4,5-dimethyl-4H-[1,2,4]triazol-3-yl |
| 706. | methyl | 5-isopropyl-4-methyl-4H-[1,2,4]triazol-3-yl |
| 707. | methyl | 5-trifluoromethyl-4-methyl-4H-[1,2,4]triazol-3-yl |
| 708. | methyl | [1,3,4]thiadiazol-2-yl |
| 709. | methyl | 5-methyl-[1,3,4]thiadiazol-2-yl |
| 710. | methyl | 5-isopropyl-[1,3,4]thiadiazol-2-yl |
| 711. | methyl | 5-trifluoromethyl-[1,3,4]thiadiazol-2-yl |

TABLE A-continued

| No. | R¹ | Ar |
|---|---|---|
| 712. | methyl | 3-bromo-2-chloropyrid-5-yl |
| 713. | methyl | 2-(4-morpholino)-pyrid-5-yl |
| 714. | methyl | 2-phenoxypyrid-5-yl |
| 715. | methyl | (2-isopropyl)-pyrimidin-5-yl |
| 716. | methyl | (5-isopropyl)-pyrimidin-2-yl |
| 717. | methyl | 8-quinolyl |
| 718. | methyl | 5-isoquinolyl |
| 719. | methyl | 2-(trifluoroacetyl)-1,2,3,4-tetrahydroisoquinolin-7-yl |
| 720. | methyl | 5-chloro-3-methylbenzothiophen-2-yl |
| 721. | methyl | 3,4-dihydro-4-methyl-2H-benzo[b][1,4]oxazinyl |
| 722. | methyl | benzothiazol-6-yl |
| 723. | methyl | benzo[2,1,3]oxadiazol-4-yl |
| 724. | methyl | 5-chlorobenzo[2,1,3]oxadiazol-4-yl |
| 725. | methyl | 7-chlorobenzo[2,1,3]oxadiazol-4-yl |
| 726. | methyl | benzo[2,1,3]thiadiazol-4-yl |
| 727. | H | 4-methylphenyl |
| 728. | H | 4-ethylphenyl |
| 729. | H | 4-propylphenyl |
| 730. | H | 4-isopropylphenyl |
| 731. | H | 4-sec-butylphenyl |
| 732. | H | 4-isobutylphenyl |
| 733. | H | 4-(1,1-dimethylpropyl)-phenyl |
| 734. | H | 4-vinylphenyl |
| 735. | H | 4-isopropenylphenyl |
| 736. | H | 4-fluorophenyl |
| 737. | H | 4-chlorophenyl |
| 738. | H | 4-bromophenyl |
| 739. | H | 4-(fluoromethyl)phenyl |
| 740. | H | 3-(fluoromethyl)phenyl |
| 741. | H | 2-(fluoromethyl)phenyl |
| 742. | H | 4-(difluoromethyl)phenyl |
| 743. | H | 3-(difluoromethyl)phenyl |
| 744. | H | 2-(difluoromethyl)phenyl |
| 745. | H | 4-(trifluoromethyl)phenyl |
| 746. | H | 3-(trifluoromethyl)phenyl |
| 747. | H | 2-(trifluoromethyl)phenyl |
| 748. | H | 4-(1-fluoroethyl)-phenyl |
| 749. | H | 4-((S)-1-fluoroethyl)-phenyl |
| 750. | H | 4-((R)-1-fluoroethyl)-phenyl |
| 751. | H | 4-(2-fluoroethyl)-phenyl |
| 752. | H | 4-(1,1-difluoroethyl)-phenyl |
| 753. | H | 4-(2,2-difluoroethyl)-phenyl |
| 754. | H | 4-(2,2,2-trifluoroethyl)-phenyl |
| 755. | H | 4-(3-fluoropropyl)-phenyl |
| 756. | H | 4-(2-fluoropropyl)-phenyl |
| 757. | H | 4-((S)-2-fluoropropyl)-phenyl |
| 758. | H | 4-((R)-2-fluoropropyl)-phenyl |
| 759. | H | 4-(3,3-difluoropropyl)-phenyl |
| 760. | H | 4-(3,3,3-trifluoropropyl)-phenyl |
| 761. | H | 4-(1-fluoro-1-methylethyl)-phenyl |
| 762. | H | 4-(2-fluoro-1-methylethyl)-phenyl |
| 763. | H | 4-((S)-2-fluoro-1-methylethyl)-phenyl |
| 764. | H | 4-((R)-2-fluoro-1-methylethyl)-phenyl |
| 765. | H | 4-(2,2-difluoro-1-methylethyl)-phenyl |
| 766. | H | 4-((S)-2,2-difluoro-1-methylethyl)-phenyl |
| 767. | H | 4-((R)-2,2-difluoro-1-methylethyl)-phenyl |
| 768. | H | 4-(2,2,2-trifluoro-1-methylethyl)-phenyl |
| 769. | H | 4-((S)-2,2,2-trifluoro-1-methylethyl)-phenyl |
| 770. | H | 4-((R)-2,2,2-trifluoro-1-methylethyl)-phenyl |
| 771. | H | 4-(2-fluoro-1-fluoromethylethyl)-phenyl |
| 772. | H | 4-(1-difluoromethyl-2,2-difluoroethyl)-phenyl |
| 773. | H | 4-(1,1-dimethyl-2-fluoroethyl)-phenyl |
| 774. | H | 4-methoxyphenyl |
| 775. | H | 4-ethoxyphenyl |
| 776. | H | 4-propoxyphenyl |
| 777. | H | 4-isopropoxyphenyl |
| 778. | H | 4-butoxyphenyl |
| 779. | H | 4-(fluoromethoxy)-phenyl |
| 780. | H | 4-(difluoromethoxy)-phenyl |
| 781. | H | 4-(trifluoromethoxy)-phenyl |
| 782. | H | 3-(trifluoromethoxy)-phenyl |
| 783. | H | 4-(2-fluoroethoxy)-phenyl |
| 784. | H | 4-(2,2-difluoroethoxy)-phenyl |
| 785. | H | 4-(2,2,2-trifluoroethoxy)-phenyl |
| 786. | H | 4-(1,1,2,2-tetrafluoroethoxy)-phenyl |
| 787. | H | 4-cyclopropylphenyl |
| 788. | H | 4-cyclobutylphenyl |
| 789. | H | 4-cyclopentylphenyl |

TABLE A-continued

| No. | R¹ | Ar |
|---|---|---|
| 790. | H | 4-(2,2-difluorocyclopropyl)-phenyl |
| 791. | H | 3,4-difluorophenyl |
| 792. | H | 4-bromo-3-fluorophenyl |
| 793. | H | 4-bromo-2-fluorophenyl |
| 794. | H | 4-bromo-2,5-difluorophenyl |
| 795. | H | 2-fluoro-4-isopropylphenyl |
| 796. | H | 3-fluoro-4-isopropylphenyl |
| 797. | H | 4-(1-hydroxy-1-methylethyl)-phenyl |
| 798. | H | 4-(2-hydroxy-2-methylpropyl)-phenyl |
| 799. | H | 4-acetylphenyl |
| 800. | H | 4-carboxyphenyl |
| 801. | H | 4-cyanophenyl |
| 802. | H | 4-hydroxyphenyl |
| 803. | H | 4-(O-benzyl)-phenyl |
| 804. | H | 4-(2-methoxyethoxy)-phenyl |
| 805. | H | 4-($CH_2$—$N(CH_3)_2$)-phenyl |
| 806. | H | 4-(NH—CO—$NH_2$)-phenyl |
| 807. | H | 4-(methylsulfanyl)-phenyl |
| 808. | H | 4-(fluoromethylsulfanyl)-phenyl |
| 809. | H | 4-(difluoromethylsulfanyl)-phenyl |
| 810. | H | 4-(trifluoromethylsulfanyl)-phenyl |
| 811. | H | 4-(methylsulfonyl)-phenyl |
| 812. | H | 4-(N-methoxy-N-methyl-amino)-phenyl |
| 813. | H | 4-(methoxyamino)-phenyl |
| 814. | H | 4-(ethoxyamino)-phenyl |
| 815. | H | 4-(N-methylaminooxy)-phenyl |
| 816. | H | 4-(N,N-dimethylaminooxy)-phenyl |
| 817. | H | 4-(azetidin-1-yl)-phenyl |
| 818. | H | 4-(2-methylazetidin-1-yl)-phenyl |
| 819. | H | 4-((S)-2-methylazetidin-1-yl)-phenyl |
| 820. | H | 4-((R)-2-methylazetidin-1-yl)-phenyl |
| 821. | H | 4-(3-fluoroazetidin-1-yl)-phenyl |
| 822. | H | 4-(3-methoxyazetidin-1-yl)-phenyl |
| 823. | H | 4-(3-hydroxyazetidin-1-yl)-phenyl |
| 824. | H | 4-(pyrrolidin-1-yl)-phenyl |
| 825. | H | 4-(pyrrolidin-2-yl)-phenyl |
| 826. | H | 4-((S)-pyrrolidin-2-yl)-phenyl |
| 827. | H | 4-((R)-pyrrolidin-2-yl)-phenyl |
| 828. | H | 4-(pyrrolidin-3-yl)-phenyl |
| 829. | H | 4-((S)-pyrrolidin-3-yl)-phenyl |
| 830. | H | 4-((R)-pyrrolidin-3-yl)-phenyl |
| 831. | H | 4-(2-fluoropyrrolidin-1-yl)-phenyl |
| 832. | H | 4-((S)-2-fluoropyrrolidin-1-yl)-phenyl |
| 833. | H | 4-((R)-2-fluoropyrrolidin-1-yl)-phenyl |
| 834. | H | 4-(3-fluoropyrrolidin-1-yl)-phenyl |
| 835. | H | 4-((S)-3-fluoropyrrolidin-1-yl)-phenyl |
| 836. | H | 4-((R)-3-fluoropyrrolidin-1-yl)-phenyl |
| 837. | H | 4-(2,2-difluoropyrrolidin-1-yl)-phenyl |
| 838. | H | 4-(3,3-difluoropyrrolidin-1-yl)-phenyl |
| 839. | H | 4-(2-methylpyrrolidin-1-yl)-phenyl |
| 840. | H | 4-((S)-2-methylpyrrolidin-1-yl)-phenyl |
| 841. | H | 4-((R)-2-methylpyrrolidin-1-yl)-phenyl |
| 842. | H | 4-(3-methylpyrrolidin-1-yl)-phenyl |
| 843. | H | 4-((S)-3-methylpyrrolidin-1-yl)-phenyl |
| 844. | H | 4-((R)-3-methylpyrrolidin-1-yl)-phenyl |
| 845. | H | 4-(1-methylpyrrolidin-2-yl)-phenyl |
| 846. | H | 4-((S)-1-methylpyrrolidin-2-yl)-phenyl |
| 847. | H | 4-((R)-1-methylpyrrolidin-2-yl)-phenyl |
| 848. | H | 4-(1-methylpyrrolidin-3-yl)-phenyl |
| 849. | H | 4-((S)-1-methylpyrrolidin-3-yl)-phenyl |
| 850. | H | 4-((R)-1-methylpyrrolidin-3-yl)-phenyl |
| 851. | H | 4-(2,2-dimethylpyrrolidin-1-yl)-phenyl |
| 852. | H | 4-(3,3-dimethylpyrrolidin-1-yl)-phenyl |
| 853. | H | 4-(2-trifluoromethylpyrrolidin-1-yl)-phenyl |
| 854. | H | 4-((S)-2-trifluoromethylpyrrolidin-1-yl)-phenyl |
| 855. | H | 4-((R)-2-trifluoromethylpyrrolidin-1-yl)-phenyl |
| 856. | H | 4-(3-trifluoromethylpyrrolidin-1-yl)-phenyl |
| 857. | H | 4-((S)-3-trifluoromethylpyrrolidin-1-yl)-phenyl |
| 858. | H | 4-((R)-3-trifluoromethylpyrrolidin-1-yl)-phenyl |
| 859. | H | 4-(2-oxopyrrolidin-1-yl)-phenyl |
| 860. | H | 4-(2-oxo-oxazolidin-3-yl)-phenyl |
| 861. | H | 4-(piperidin-1-yl)-phenyl |
| 862. | H | 4-(2-methylpiperidin-1-yl)-phenyl |
| 863. | H | 4-((S)-2-methylpiperidin-1-yl)-phenyl |
| 864. | H | 4-((R)-2-methylpiperidin-1-yl)-phenyl |
| 865. | H | 4-(piperazin-1-yl)-phenyl |
| 866. | H | 4-(4-methylpiperazin-1-yl)-phenyl |
| 867. | H | 4-(morpholin-4-yl)-phenyl |

TABLE A-continued

| No. | R¹ | Ar |
|---|---|---|
| 868. | H | 4-(thiomorpholin-4-yl)-phenyl |
| 869. | H | 4-(1-oxo-thiomorpholin-4-yl)-phenyl |
| 870. | H | 4-(1,1-dioxo-thiomorpholin-4-yl)-phenyl |
| 871. | H | 4-(pyrrol-1-yl)-phenyl |
| 872. | H | 4-(pyrrol-2-yl)-phenyl |
| 873. | H | 4-(pyrrol-3-yl)-phenyl |
| 874. | H | 4-(1-methylpyrrol-2-yl)-phenyl |
| 875. | H | 4-(1-methylpyrrol-3-yl)-phenyl |
| 876. | H | 4-(furan-2-yl)-phenyl |
| 877. | H | 4-(furan-3-yl)-phenyl |
| 878. | H | 4-(thiophen-2-yl)-phenyl |
| 879. | H | 4-(thiophen-3-yl)-phenyl |
| 880. | H | 4-(5-propylthien-2-yl)-phenyl |
| 881. | H | 4-(pyrazol-1-yl)-phenyl |
| 882. | H | 4-(pyrazol-3-yl)-phenyl |
| 883. | H | 4-(pyrazol-4-yl)-phenyl |
| 884. | H | 4-(1-methyl-1H-pyrazol-4-yl)-phenyl |
| 885. | H | 4-(1-ethyl-1H-pyrazol-4-yl)-phenyl |
| 886. | H | 4-(1-methyl-1H-pyrazol-5-yl)-phenyl |
| 887. | H | 4-(1H-imidazol-2-yl)-phenyl |
| 888. | H | 4-(imidazol-1-yl)-phenyl |
| 889. | H | 4-(1-methylimidazol-2-yl)-phenyl |
| 890. | H | 4-(oxazol-2-yl)-phenyl |
| 891. | H | 4-(oxazol-4-yl)-phenyl |
| 892. | H | 4-(oxazol-5-yl)-phenyl |
| 893. | H | 4-(isoxazol-3-yl)-phenyl |
| 894. | H | 4-(isoxazol-4-yl)-phenyl |
| 895. | H | 4-(isoxazol-5-yl)-phenyl |
| 896. | H | 4-([1,2,3]-triazol-1-yl)-phenyl |
| 897. | H | 4-([1,2,4]-triazol-1-yl)-phenyl |
| 898. | H | 4-([1,2,3]-triazol-2-yl)-phenyl |
| 899. | H | 4-(4H-[1,2,4]-triazol-3-yl)-phenyl |
| 900. | H | 4-([1,2,4]-triazol-4-yl)-phenyl |
| 901. | H | 4-(2H-[1,2,3]-triazol-4-yl)-phenyl |
| 902. | H | 4-(4-methyl-4H-[1,2,4]-triazol-3-yl)-phenyl |
| 903. | H | 4-(2-methyl-2H-[1,2,3]-triazol-4-yl)-phenyl |
| 904. | H | 4-([1,3,4]-oxadiazol-2-yl)-phenyl |
| 905. | H | 4-([1,2,4]-oxadiazol-3-yl)-phenyl |
| 906. | H | 4-([1,2,4]-oxadiazol-5-yl)-phenyl |
| 907. | H | 4-([1,2,3]-oxadiazol-4-yl)-phenyl |
| 908. | H | 4-([1,2,3]-oxadiazol-5-yl)-phenyl |
| 909. | H | 4-([1,2,3]-thiadiazol-4-yl)-phenyl |
| 910. | H | 4-(1H-tetrazol-5-yl)-phenyl |
| 911. | H | 4-(tetrazol-1-yl)-phenyl |
| 912. | H | 4-(2-methyl-2H-tetrazol-5-yl)-phenyl |
| 913. | H | 4-(1-methyl-1H-tetrazol-5-yl)-phenyl |
| 914. | H | 4-furazan-3-yl-phenyl |
| 915. | H | 4-(pyrid-2-yl)-phenyl |
| 916. | H | 4-(pyrid-3-yl)-phenyl |
| 917. | H | 4-(pyrid-4-yl)-phenyl |
| 918. | H | 4-(pyrimidin-2-yl)-phenyl |
| 919. | H | 4-(pyrimidin-4-yl)-phenyl |
| 920. | H | 4-(pyrimidin-5-yl)-phenyl |
| 921. | H | 5-isopropylthiophen-2-yl |
| 922. | H | 2-chlorothiophen-5-yl |
| 923. | H | 2,5-dichlorothiophen-4-yl |
| 924. | H | 2,3-dichlorothiophen-5-yl |
| 925. | H | 2-chloro-3-nitrothiophen-5-yl |
| 926. | H | 2-(phenylsulfonyl)-thiophen-5-yl |
| 927. | H | 2-(pyridin-2-yl)thiophen-5-yl |
| 928. | H | 2-(5-(trifluoromethyl)isoxazol-3-yl)-thiophen-5-yl |
| 929. | H | 2-(2-methylthiazol-4-yl)-thiophen-5-yl |
| 930. | H | 1-methyl-1H-imidazol-4-yl |
| 931. | H | 1,2-dimethyl-1H-imidazol-4-yl |
| 932. | H | 3,5-dimethylisoxazol-4-yl |
| 933. | H | thiazol-2-yl |
| 934. | H | 4-methylthiazol-2-yl |
| 935. | H | 4-isopropylthiazol-2-yl |
| 936. | H | 4-trifluoromethylthiazol-2-yl |
| 937. | H | 5-methylthiazol-2-yl |
| 938. | H | 5-isopropylthiazol-2-yl |
| 939. | H | 5-trifluoromethylthiazol-2-yl |
| 940. | H | 2,4-dimethylthiazol-5-yl |
| 941. | H | 2-acetamido-4-methylthiazol-5-yl |
| 942. | H | 4H-[1,2,4]triazol-3-yl |
| 943. | H | 5-methyl-4H-[1,2,4]triazol-3-yl |
| 944. | H | 4-methyl-4H-[1,2,4]triazol-3-yl |
| 945. | H | 5-isopropyl-4H-[1,2,4]triazol-3-yl |

TABLE A-continued

| No. | R¹ | Ar |
|---|---|---|
| 946. | H | 5-trifluoromethyl-4H-[1,2,4]triazol-3-yl |
| 947. | H | 4,5-dimethyl-4H-[1,2,4]triazol-3-yl |
| 948. | H | 5-isopropyl-4-methyl-4H-[1,2,4]triazol-3-yl |
| 949. | H | 5-trifluoromethyl-4-methyl-4H-[1,2,4]triazol-3-yl |
| 950. | H | [1,3,4]thiadiazol-2-yl |
| 951. | H | 5-methyl-[1,3,4]thiadiazol-2-yl |
| 952. | H | 5-isopropyl-[1,3,4]thiadiazol-2-yl |
| 953. | H | 5-trifluoromethyl-[1,3,4]thiadiazol-2-yl |
| 954. | H | 3-bromo-2-chloropyrid-5-yl |
| 955. | H | 2-(4-morpholino)-pyrid-5-yl |
| 956. | H | 2-phenoxypyrid-5-yl |
| 957. | H | (2-isopropyl)-pyrimidin-5-yl |
| 958. | H | (5-isopropyl)-pyrimidin-2-yl |
| 959. | H | 8-quinolyl |
| 960. | H | 5-isoquinolyl |
| 961. | H | 2-(trifluoroacetyl)-1,2,3,4-tetrahydroisoquinolin-7-yl |
| 962. | H | 5-chloro-3-methylbenzothiophen-2-yl |
| 963. | H | 3,4-dihydro-4-methyl-2H-benzo[b][1,4]oxazinyl |
| 964. | H | benzothiazol-6-yl |
| 965. | H | benzo[2,1,3]oxadiazol-4-yl |
| 966. | H | 5-chlorobenzo[2,1,3]oxadiazol-4-yl |
| 967. | H | 7-chlorobenzo[2,1,3]oxadiazol-4-yl |
| 968. | H | benzo[2,1,3]thiadiazol-4-yl |
| 969. | 3-fluoropropyl | 4-methylphenyl |
| 970. | 3-fluoropropyl | 4-ethylphenyl |
| 971. | 3-fluoropropyl | 4-propylphenyl |
| 972. | 3-fluoropropyl | 4-isopropylphenyl |
| 973. | 3-fluoropropyl | 4-sec-butylphenyl |
| 974. | 3-fluoropropyl | 4-isobutylphenyl |
| 975. | 3-fluoropropyl | 4-(1,1-dimethylpropyl)-phenyl |
| 976. | 3-fluoropropyl | 4-vinylphenyl |
| 977. | 3-fluoropropyl | 4-isopropenylphenyl |
| 978. | 3-fluoropropyl | 4-fluorophenyl |
| 979. | 3-fluoropropyl | 4-chlorophenyl |
| 980. | 3-fluoropropyl | 4-bromophenyl |
| 981. | 3-fluoropropyl | 4-(fluoromethyl)phenyl |
| 982. | 3-fluoropropyl | 3-(fluoromethyl)phenyl |
| 983. | 3-fluoropropyl | 2-(fluoromethyl)phenyl |
| 984. | 3-fluoropropyl | 4-(difluoromethyl)phenyl |
| 985. | 3-fluoropropyl | 3-(difluoromethyl)phenyl |
| 986. | 3-fluoropropyl | 2-(difluoromethyl)phenyl |
| 987. | 3-fluoropropyl | 4-(trifluoromethyl)phenyl |
| 988. | 3-fluoropropyl | 3-(trifluoromethyl)phenyl |
| 989. | 3-fluoropropyl | 2-(trifluoromethyl)phenyl |
| 990. | 3-fluoropropyl | 4-(1-fluoroethyl)-phenyl |
| 991. | 3-fluoropropyl | 4-((S)-1-fluoroethyl)-phenyl |
| 992. | 3-fluoropropyl | 4-((R)-1-fluoroethyl)-phenyl |
| 993. | 3-fluoropropyl | 4-(2-fluoroethyl)-phenyl |
| 994. | 3-fluoropropyl | 4-(1,1-difluoroethyl)-phenyl |
| 995. | 3-fluoropropyl | 4-(2,2-difluoroethyl)-phenyl |
| 996. | 3-fluoropropyl | 4-(2,2,2-trifluoroethyl)-phenyl |
| 997. | 3-fluoropropyl | 4-(3-fluoropropyl)-phenyl |
| 998. | 3-fluoropropyl | 4-(2-fluoropropyl)-phenyl |
| 999. | 3-fluoropropyl | 4-((S)-2-fluoropropyl)-phenyl |
| 1000. | 3-fluoropropyl | 4-((R)-2-fluoropropyl)-phenyl |
| 1001. | 3-fluoropropyl | 4-(3,3-difluoropropyl)-phenyl |
| 1002. | 3-fluoropropyl | 4-(3,3,3-trifluoropropyl)-phenyl |
| 1003. | 3-fluoropropyl | 4-(1-fluoro-1-methylethyl)-phenyl |
| 1004. | 3-fluoropropyl | 4-(2-fluoro-1-methylethyl)-phenyl |
| 1005. | 3-fluoropropyl | 4-((S)-2-fluoro-1-methylethyl)-phenyl |
| 1006. | 3-fluoropropyl | 4-((R)-2-fluoro-1-methylethyl)-phenyl |
| 1007. | 3-fluoropropyl | 4-(2,2-difluoro-1-methylethyl)-phenyl |
| 1008. | 3-fluoropropyl | 4-((S)-2,2-difluoro-1-methylethyl)-phenyl |
| 1009. | 3-fluoropropyl | 4-((R)-2,2-difluoro-1-methylethyl)-phenyl |
| 1010. | 3-fluoropropyl | 4-(2,2,2-trifluoro-1-methylethyl)-phenyl |
| 1011. | 3-fluoropropyl | 4-((S)-2,2,2-trifluoro-1-methylethyl)-phenyl |
| 1012. | 3-fluoropropyl | 4-((R)-2,2,2-trifluoro-1-methylethyl)-phenyl |
| 1013. | 3-fluoropropyl | 4-(2-fluoro-1-fluoromethylethyl)-phenyl |
| 1014. | 3-fluoropropyl | 4-(1-difluoromethyl-2,2-difluoroethyl)-phenyl |
| 1015. | 3-fluoropropyl | 4-(1,1-dimethyl-2-fluoroethyl)-phenyl |
| 1016. | 3-fluoropropyl | 4-methoxyphenyl |
| 1017. | 3-fluoropropyl | 4-ethoxyphenyl |
| 1018. | 3-fluoropropyl | 4-propoxyphenyl |
| 1019. | 3-fluoropropyl | 4-isopropoxyphenyl |
| 1020. | 3-fluoropropyl | 4-butoxyphenyl |
| 1021. | 3-fluoropropyl | 4-(fluoromethoxy)-phenyl |
| 1022. | 3-fluoropropyl | 4-(difluoromethoxy)-phenyl |
| 1023. | 3-fluoropropyl | 4-(trifluoromethoxy)-phenyl |

TABLE A-continued

| No. | R¹ | Ar |
|---|---|---|
| 1024. | 3-fluoropropyl | 3-(trifluoromethoxy)-phenyl |
| 1025. | 3-fluoropropyl | 4-(2-fluoroethoxy)-phenyl |
| 1026. | 3-fluoropropyl | 4-(2,2-difluoroethoxy)-phenyl |
| 1027. | 3-fluoropropyl | 4-(2,2,2-trifluoroethoxy)-phenyl |
| 1028. | 3-fluoropropyl | 4-(1,1,2,2-tetrafluoroethoxy)-phenyl |
| 1029. | 3-fluoropropyl | 4-cyclopropylphenyl |
| 1030. | 3-fluoropropyl | 4-cyclobutylphenyl |
| 1031. | 3-fluoropropyl | 4-cyclopentylphenyl |
| 1032. | 3-fluoropropyl | 4-(2,2-difluorocyclopropyl)-phenyl |
| 1033. | 3-fluoropropyl | 3,4-difluorophenyl |
| 1034. | 3-fluoropropyl | 4-bromo-3-fluorophenyl |
| 1035. | 3-fluoropropyl | 4-bromo-2-fluorophenyl |
| 1036. | 3-fluoropropyl | 4-bromo-2,5-difluorophenyl |
| 1037. | 3-fluoropropyl | 2-fluoro-4-isopropylphenyl |
| 1038. | 3-fluoropropyl | 3-fluoro-4-isopropylphenyl |
| 1039. | 3-fluoropropyl | 4-(1-hydroxy-1-methylethyl)-phenyl |
| 1040. | 3-fluoropropyl | 4-(2-hydroxy-2-methylpropyl)-phenyl |
| 1041. | 3-fluoropropyl | 4-acetylphenyl |
| 1042. | 3-fluoropropyl | 4-carboxyphenyl |
| 1043. | 3-fluoropropyl | 4-cyanophenyl |
| 1044. | 3-fluoropropyl | 4-hydroxyphenyl |
| 1045. | 3-fluoropropyl | 4-(O-benzyl)-phenyl |
| 1046. | 3-fluoropropyl | 4-(2-methoxyethoxy)-phenyl |
| 1047. | 3-fluoropropyl | 4-(CH$_2$—N(CH$_3$)$_2$)-phenyl |
| 1048. | 3-fluoropropyl | 4-(NH—CO—NH$_2$)-phenyl |
| 1049. | 3-fluoropropyl | 4-(methylsulfanyl)-phenyl |
| 1050. | 3-fluoropropyl | 4-(fluoromethylsulfanyl)-phenyl |
| 1051. | 3-fluoropropyl | 4-(difluoromethylsulfanyl)-phenyl |
| 1052. | 3-fluoropropyl | 4-(trifluoromethylsulfanyl)-phenyl |
| 1053. | 3-fluoropropyl | 4-(methylsulfonyl)-phenyl |
| 1054. | 3-fluoropropyl | 4-(N-methoxy-N-methyl-amino)-phenyl |
| 1055. | 3-fluoropropyl | 4-(methoxyamino)-phenyl |
| 1056. | 3-fluoropropyl | 4-(ethoxyamino)-phenyl |
| 1057. | 3-fluoropropyl | 4-(N-methylaminooxy)-phenyl |
| 1058. | 3-fluoropropyl | 4-(N,N-dimethylaminooxy)-phenyl |
| 1059. | 3-fluoropropyl | 4-(azetidin-1-yl)-phenyl |
| 1060. | 3-fluoropropyl | 4-(2-methylazetidin-1-yl)-phenyl |
| 1061. | 3-fluoropropyl | 4-((S)-2-methylazetidin-1-yl)-phenyl |
| 1062. | 3-fluoropropyl | 4-((R)-2-methylazetidin-1-yl)-phenyl |
| 1063. | 3-fluoropropyl | 4-(3-fluoroazetidin-1-yl)-phenyl |
| 1064. | 3-fluoropropyl | 4-(3-methoxyazetidin-1-yl)-phenyl |
| 1065. | 3-fluoropropyl | 4-(3-hydroxyazetidin-1-yl)-phenyl |
| 1066. | 3-fluoropropyl | 4-(pyrrolidin-1-yl)-phenyl |
| 1067. | 3-fluoropropyl | 4-(pyrrolidin-2-yl)-phenyl |
| 1068. | 3-fluoropropyl | 4-((S)-pyrrolidin-2-yl)-phenyl |
| 1069. | 3-fluoropropyl | 4-((R)-pyrrolidin-2-yl)-phenyl |
| 1070. | 3-fluoropropyl | 4-(pyrrolidin-3-yl)-phenyl |
| 1071. | 3-fluoropropyl | 4-((S)-pyrrolidin-3-yl)-phenyl |
| 1072. | 3-fluoropropyl | 4-((R)-pyrrolidin-3-yl)-phenyl |
| 1073. | 3-fluoropropyl | 4-(2-fluoropyrrolidin-1-yl)-phenyl |
| 1074. | 3-fluoropropyl | 4-((S)-2-fluoropyrrolidin-1-yl)-phenyl |
| 1075. | 3-fluoropropyl | 4-((R)-2-fluoropyrrolidin-1-yl)-phenyl |
| 1076. | 3-fluoropropyl | 4-(3-fluoropyrrolidin-1-yl)-phenyl |
| 1077. | 3-fluoropropyl | 4-((S)-3-fluoropyrrolidin-1-yl)-phenyl |
| 1078. | 3-fluoropropyl | 4-((R)-3-fluoropyrrolidin-1-yl)-phenyl |
| 1079. | 3-fluoropropyl | 4-(2,2-difluoropyrrolidin-1-yl)-phenyl |
| 1080. | 3-fluoropropyl | 4-(3,3-difluoropyrrolidin-1-yl)-phenyl |
| 1081. | 3-fluoropropyl | 4-(2-methylpyrrolidin-1-yl)-phenyl |
| 1082. | 3-fluoropropyl | 4-((S)-2-methylpyrrolidin-1-yl)-phenyl |
| 1083. | 3-fluoropropyl | 4-((R)-2-methylpyrrolidin-1-yl)-phenyl |
| 1084. | 3-fluoropropyl | 4-(3-methylpyrrolidin-1-yl)-phenyl |
| 1085. | 3-fluoropropyl | 4-((S)-3-methylpyrrolidin-1-yl)-phenyl |
| 1086. | 3-fluoropropyl | 4-((R)-3-methylpyrrolidin-1-yl)-phenyl |
| 1087. | 3-fluoropropyl | 4-(1-methylpyrrolidin-2-yl)-phenyl |
| 1088. | 3-fluoropropyl | 4-((S)-1-methylpyrrolidin-2-yl)-phenyl |
| 1089. | 3-fluoropropyl | 4-((R)-1-methylpyrrolidin-2-yl)-phenyl |
| 1090. | 3-fluoropropyl | 4-(1-methylpyrrolidin-3-yl)-phenyl |
| 1091. | 3-fluoropropyl | 4-((S)-1-methylpyrrolidin-3-yl)-phenyl |
| 1092. | 3-fluoropropyl | 4-((R)-1-methylpyrrolidin-3-yl)-phenyl |
| 1093. | 3-fluoropropyl | 4-(2,2-dimethylpyrrolidin-1-yl)-phenyl |
| 1094. | 3-fluoropropyl | 4-(3,3-dimethylpyrrolidin-1-yl)-phenyl |
| 1095. | 3-fluoropropyl | 4-(2-trifluoromethylpyrrolidin-1-yl)-phenyl |
| 1096. | 3-fluoropropyl | 4-((S)-2-trifluoromethylpyrrolidin-1-yl)-phenyl |
| 1097. | 3-fluoropropyl | 4-((R)-2-trifluoromethylpyrrolidin-1-yl)-phenyl |
| 1098. | 3-fluoropropyl | 4-(3-trifluoromethylpyrrolidin-1-yl)-phenyl |
| 1099. | 3-fluoropropyl | 4-((S)-3-trifluoromethylpyrrolidin-1-yl)-phenyl |
| 1100. | 3-fluoropropyl | 4-((R)-3-trifluoromethylpyrrolidin-1-yl)-phenyl |
| 1101. | 3-fluoropropyl | 4-(2-oxopyrrolidin-1-yl)-phenyl |

TABLE A-continued

| No. | R¹ | Ar |
|---|---|---|
| 1102. | 3-fluoropropyl | 4-(2-oxo-oxazolidin-3-yl)-phenyl |
| 1103. | 3-fluoropropyl | 4-(piperidin-1-yl)-phenyl |
| 1104. | 3-fluoropropyl | 4-(2-methylpiperidin-1-yl)-phenyl |
| 1105. | 3-fluoropropyl | 4-((S)-2-methylpiperidin-1-yl)-phenyl |
| 1106. | 3-fluoropropyl | 4-((R)-2-methylpiperidin-1-yl)-phenyl |
| 1107. | 3-fluoropropyl | 4-(piperazin-1-yl)-phenyl |
| 1108. | 3-fluoropropyl | 4-(4-methylpiperazin-1-yl)-phenyl |
| 1109. | 3-fluoropropyl | 4-(morpholin-4-yl)-phenyl |
| 1110. | 3-fluoropropyl | 4-(thiomorpholin-4-yl)-phenyl |
| 1111. | 3-fluoropropyl | 4-(1-oxo-thiomorpholin-4-yl)-phenyl |
| 1112. | 3-fluoropropyl | 4-(1,1-dioxo-thiomorpholin-4-yl)-phenyl |
| 1113. | 3-fluoropropyl | 4-(pyrrol-1-yl)-phenyl |
| 1114. | 3-fluoropropyl | 4-(pyrrol-2-yl)-phenyl |
| 1115. | 3-fluoropropyl | 4-(pyrrol-3-yl)-phenyl |
| 1116. | 3-fluoropropyl | 4-(1-methylpyrrol-2-yl)-phenyl |
| 1117. | 3-fluoropropyl | 4-(1-methylpyrrol-3-yl)-phenyl |
| 1118. | 3-fluoropropyl | 4-(furan-2-yl)-phenyl |
| 1119. | 3-fluoropropyl | 4-(furan-3-yl)-phenyl |
| 1120. | 3-fluoropropyl | 4-(thiophen-2-yl)-phenyl |
| 1121. | 3-fluoropropyl | 4-(thiophen-3-yl)-phenyl |
| 1122. | 3-fluoropropyl | 4-(5-propylthien-2-yl)-phenyl |
| 1123. | 3-fluoropropyl | 4-(pyrazol-1-yl)-phenyl |
| 1124. | 3-fluoropropyl | 4-(pyrazol-3-yl)-phenyl |
| 1125. | 3-fluoropropyl | 4-(pyrazol-4-yl)-phenyl |
| 1126. | 3-fluoropropyl | 4-(1-methyl-1H-pyrazol-4-yl)-phenyl |
| 1127. | 3-fluoropropyl | 4-(1-ethyl-1H-pyrazol-4-yl)-phenyl |
| 1128. | 3-fluoropropyl | 4-(1-methyl-1H-pyrazol-5-yl)-phenyl |
| 1129. | 3-fluoropropyl | 4-(1H-imidazol-2-yl)-phenyl |
| 1130. | 3-fluoropropyl | 4-(imidazol-1-yl)-phenyl |
| 1131. | 3-fluoropropyl | 4-(1-methylimidazol-2-yl)-phenyl |
| 1132. | 3-fluoropropyl | 4-(oxazol-2-yl)-phenyl |
| 1133. | 3-fluoropropyl | 4-(oxazol-4-yl)-phenyl |
| 1134. | 3-fluoropropyl | 4-(oxazol-5-yl)-phenyl |
| 1135. | 3-fluoropropyl | 4-(isoxazol-3-yl)-phenyl |
| 1136. | 3-fluoropropyl | 4-(isoxazol-4-yl)-phenyl |
| 1137. | 3-fluoropropyl | 4-(isoxazol-5-yl)-phenyl |
| 1138. | 3-fluoropropyl | 4-([1,2,3]-triazol-1-yl)-phenyl |
| 1139. | 3-fluoropropyl | 4-([1,2,4]-triazol-1-yl)-phenyl |
| 1140. | 3-fluoropropyl | 4-([1,2,3]-triazol-2-yl)-phenyl |
| 1141. | 3-fluoropropyl | 4-(4H-[1,2,4]-triazol-3-yl)-phenyl |
| 1142. | 3-fluoropropyl | 4-([1,2,4]-triazol-4-yl)-phenyl |
| 1143. | 3-fluoropropyl | 4-(2H-[1,2,3]-triazol-4-yl)-phenyl |
| 1144. | 3-fluoropropyl | 4-(4-methyl-4H-[1,2,4]-triazol-3-yl)-phenyl |
| 1145. | 3-fluoropropyl | 4-(2-methyl-2H-[1,2,3]-triazol-4-yl)-phenyl |
| 1146. | 3-fluoropropyl | 4-([1,3,4]-oxadiazol-2-yl)-phenyl |
| 1147. | 3-fluoropropyl | 4-([1,2,4]-oxadiazol-3-yl)-phenyl |
| 1148. | 3-fluoropropyl | 4-([1,2,4]-oxadiazol-5-yl)-phenyl |
| 1149. | 3-fluoropropyl | 4-([1,2,3]-oxadiazol-4-yl)-phenyl |
| 1150. | 3-fluoropropyl | 4-([1,2,3]-oxadiazol-5-yl)-phenyl |
| 1151. | 3-fluoropropyl | 4-([1,2,3]-thiadiazol-4-yl)-phenyl |
| 1152. | 3-fluoropropyl | 4-(1H-tetrazol-5-yl)-phenyl |
| 1153. | 3-fluoropropyl | 4-(tetrazol-1-yl)-phenyl |
| 1154. | 3-fluoropropyl | 4-(2-methyl-2H-tetrazol-5-yl)-phenyl |
| 1155. | 3-fluoropropyl | 4-(1-methyl-1H-tetrazol-5-yl)-phenyl |
| 1156. | 3-fluoropropyl | 4-furazan-3-yl-phenyl |
| 1157. | 3-fluoropropyl | 4-(pyrid-2-yl)-phenyl |
| 1158. | 3-fluoropropyl | 4-(pyrid-3-yl)-phenyl |
| 1159. | 3-fluoropropyl | 4-(pyrid-4-yl)-phenyl |
| 1160. | 3-fluoropropyl | 4-(pyrimidin-2-yl)-phenyl |
| 1161. | 3-fluoropropyl | 4-(pyrimidin-4-yl)-phenyl |
| 1162. | 3-fluoropropyl | 4-(pyrimidin-5-yl)-phenyl |
| 1163. | 3-fluoropropyl | 5-isopropylthiophen-2-yl |
| 1164. | 3-fluoropropyl | 2-chlorothiophen-5-yl |
| 1165. | 3-fluoropropyl | 2,5-dichlorothiophen-4-yl |
| 1166. | 3-fluoropropyl | 2,3-dichlorothiophen-5-yl |
| 1167. | 3-fluoropropyl | 2-chloro-3-nitrothiophen-5-yl |
| 1168. | 3-fluoropropyl | 2-(phenylsulfonyl)-thiophen-5-yl |
| 1169. | 3-fluoropropyl | 2-(pyridin-2-yl)thiophen-5-yl |
| 1170. | 3-fluoropropyl | 2-(5-(trifluoromethyl)isoxazol-3-yl)-thiophen-5-yl |
| 1171. | 3-fluoropropyl | 2-(2-methylthiazol-4-yl)-thiophen-5-yl |
| 1172. | 3-fluoropropyl | 1-methyl-1H-imidazol-4-yl |
| 1173. | 3-fluoropropyl | 1,2-dimethyl-1H-imidazol-4-yl |
| 1174. | 3-fluoropropyl | 3,5-dimethylisoxazol-4-yl |
| 1175. | 3-fluoropropyl | thiazol-2-yl |
| 1176. | 3-fluoropropyl | 4-methylthiazol-2-yl |
| 1177. | 3-fluoropropyl | 4-isopropylthiazol-2-yl |
| 1178. | 3-fluoropropyl | 4-trifluoromethylthiazol-2-yl |
| 1179. | 3-fluoropropyl | 5-methylthiazol-2-yl |

TABLE A-continued

| No. | R¹ | Ar |
|---|---|---|
| 1180. | 3-fluoropropyl | 5-isopropylthiazol-2-yl |
| 1181. | 3-fluoropropyl | 5-trifluoromethylthiazol-2-yl |
| 1182. | 3-fluoropropyl | 2,4-dimethylthiazol-5-yl |
| 1183. | 3-fluoropropyl | 2-acetamido-4-methylthiazol-5-yl |
| 1184. | 3-fluoropropyl | 4H-[1,2,4]triazol-3-yl |
| 1185. | 3-fluoropropyl | 5-methyl-4H-[1,2,4]triazol-3-yl |
| 1186. | 3-fluoropropyl | 4-methyl-4H-[1,2,4]triazol-3-yl |
| 1187. | 3-fluoropropyl | 5-isopropyl-4H-[1,2,4]triazol-3-yl |
| 1188. | 3-fluoropropyl | 5-trifluoromethyl-4H-[1,2,4]triazol-3-yl |
| 1189. | 3-fluoropropyl | 4,5-dimethyl-4H-[1,2,4]triazol-3-yl |
| 1190. | 3-fluoropropyl | 5-isopropyl-4-methyl-4H-[1,2,4]triazol-3-yl |
| 1191. | 3-fluoropropyl | 5-trifluoromethyl-4-methyl-4H-[1,2,4]triazol-3-yl |
| 1192. | 3-fluoropropyl | [1,3,4]thiadiazol-2-yl |
| 1193. | 3-fluoropropyl | 5-methyl-[1,3,4]thiadiazol-2-yl |
| 1194. | 3-fluoropropyl | 5-isopropyl-[1,3,4]thiadiazol-2-yl |
| 1195. | 3-fluoropropyl | 5-trifluoromethyl-[1,3,4]thiadiazol-2-yl |
| 1196. | 3-fluoropropyl | 3-bromo-2-chloropyrid-5-yl |
| 1197. | 3-fluoropropyl | 2-(4-morpholino)-pyrid-5-yl |
| 1198. | 3-fluoropropyl | 2-phenoxypyrid-5-yl |
| 1199. | 3-fluoropropyl | (2-isopropyl)-pyrimidin-5-yl |
| 1200. | 3-fluoropropyl | (5-isopropyl)-pyrimidin-2-yl |
| 1201. | 3-fluoropropyl | 8-quinolyl |
| 1202. | 3-fluoropropyl | 5-isoquinolyl |
| 1203. | 3-fluoropropyl | 2-(trifluoroacetyl)-1,2,3,4-tetrahydroisoquinolin-7-yl |
| 1204. | 3-fluoropropyl | 5-chloro-3-methylbenzothiophen-2-yl |
| 1205. | 3-fluoropropyl | 3,4-dihydro-4-methyl-2H-benzo[b][1,4]oxazinyl |
| 1206. | 3-fluoropropyl | benzothiazol-6-yl |
| 1207. | 3-fluoropropyl | benzo[2,1,3]oxadiazol-4-yl |
| 1208. | 3-fluoropropyl | 5-chlorobenzo[2,1,3]oxadiazol-4-yl |
| 1209. | 3-fluoropropyl | 7-chlorobenzo[2,1,3]oxadiazol-4-yl |
| 1210. | 3-fluoropropyl | benzo[2,1,3]thiadiazol-4-yl |
| 1211. | 2-fluoroethyl | 4-methylphenyl |
| 1212. | 2-fluoroethyl | 4-ethylphenyl |
| 1213. | 2-fluoroethyl | 4-propylphenyl |
| 1214. | 2-fluoroethyl | 4-isopropylphenyl |
| 1215. | 2-fluoroethyl | 4-sec-butylphenyl |
| 1216. | 2-fluoroethyl | 4-isobutylphenyl |
| 1217. | 2-fluoroethyl | 4-(1,1-dimethylpropyl)-phenyl |
| 1218. | 2-fluoroethyl | 4-vinylphenyl |
| 1219. | 2-fluoroethyl | 4-isopropenylphenyl |
| 1220. | 2-fluoroethyl | 4-fluorophenyl |
| 1221. | 2-fluoroethyl | 4-chlorophenyl |
| 1222. | 2-fluoroethyl | 4-bromophenyl |
| 1223. | 2-fluoroethyl | 4-(fluoromethyl)phenyl |
| 1224. | 2-fluoroethyl | 3-(fluoromethyl)phenyl |
| 1225. | 2-fluoroethyl | 2-(fluoromethyl)phenyl |
| 1226. | 2-fluoroethyl | 4-(difluoromethyl)phenyl |
| 1227. | 2-fluoroethyl | 3-(difluoromethyl)phenyl |
| 1228. | 2-fluoroethyl | 2-(difluoromethyl)phenyl |
| 1229. | 2-fluoroethyl | 4-(trifluoromethyl)phenyl |
| 1230. | 2-fluoroethyl | 3-(trifluoromethyl)phenyl |
| 1231. | 2-fluoroethyl | 2-(trifluoromethyl)phenyl |
| 1232. | 2-fluoroethyl | 4-(1-fluoroethyl)-phenyl |
| 1233. | 2-fluoroethyl | 4-((S)-1-fluoroethyl)-phenyl |
| 1234. | 2-fluoroethyl | 4-((R)-1-fluoroethyl)-phenyl |
| 1235. | 2-fluoroethyl | 4-(2-fluoroethyl)-phenyl |
| 1236. | 2-fluoroethyl | 4-(1,1-difluoroethyl)-phenyl |
| 1237. | 2-fluoroethyl | 4-(2,2-difluoroethyl)-phenyl |
| 1238. | 2-fluoroethyl | 4-(2,2,2-trifluoroethyl)-phenyl |
| 1239. | 2-fluoroethyl | 4-(3-fluoropropyl)-phenyl |
| 1240. | 2-fluoroethyl | 4-(2-fluoropropyl)-phenyl |
| 1241. | 2-fluoroethyl | 4-((S)-2-fluoropropyl)-phenyl |
| 1242. | 2-fluoroethyl | 4-((R)-2-fluoropropyl)-phenyl |
| 1243. | 2-fluoroethyl | 4-(3,3-difluoropropyl)-phenyl |
| 1244. | 2-fluoroethyl | 4-(3,3,3-trifluoropropyl)-phenyl |
| 1245. | 2-fluoroethyl | 4-(1-fluoro-1-methylethyl)-phenyl |
| 1246. | 2-fluoroethyl | 4-(2-fluoro-1-methylethyl)-phenyl |
| 1247. | 2-fluoroethyl | 4-((S)-2-fluoro-1-methylethyl)-phenyl |
| 1248. | 2-fluoroethyl | 4-((R)-2-fluoro-1-methylethyl)-phenyl |
| 1249. | 2-fluoroethyl | 4-(2,2-difluoro-1-methylethyl)-phenyl |
| 1250. | 2-fluoroethyl | 4-((S)-2,2-difluoro-1-methylethyl)-phenyl |
| 1251. | 2-fluoroethyl | 4-((R)-2,2-difluoro-1-methylethyl)-phenyl |
| 1252. | 2-fluoroethyl | 4-(2,2,2-trifluoro-1-methylethyl)-phenyl |
| 1253. | 2-fluoroethyl | 4-((S)-2,2,2-trifluoro-1-methylethyl)-phenyl |
| 1254. | 2-fluoroethyl | 4-((R)-2,2,2-trifluoro-1-methylethyl)-phenyl |
| 1255. | 2-fluoroethyl | 4-(2-fluoro-1-fluoromethylethyl)-phenyl |
| 1256. | 2-fluoroethyl | 4-(1-difluoromethyl-2,2-difluoroethyl)-phenyl |
| 1257. | 2-fluoroethyl | 4-(1,1-dimethyl-2-fluoroethyl)-phenyl |

TABLE A-continued

| No. | R¹ | Ar |
|---|---|---|
| 1258. | 2-fluoroethyl | 4-methoxyphenyl |
| 1259. | 2-fluoroethyl | 4-ethoxyphenyl |
| 1260. | 2-fluoroethyl | 4-propoxyphenyl |
| 1261. | 2-fluoroethyl | 4-isopropoxyphenyl |
| 1262. | 2-fluoroethyl | 4-butoxyphenyl |
| 1263. | 2-fluoroethyl | 4-(fluoromethoxy)-phenyl |
| 1264. | 2-fluoroethyl | 4-(difluoromethoxy)-phenyl |
| 1265. | 2-fluoroethyl | 4-(trifluoromethoxy)-phenyl |
| 1266. | 2-fluoroethyl | 3-(trifluoromethoxy)-phenyl |
| 1267. | 2-fluoroethyl | 4-(2-fluoroethoxy)-phenyl |
| 1268. | 2-fluoroethyl | 4-(2,2-difluoroethoxy)-phenyl |
| 1269. | 2-fluoroethyl | 4-(2,2,2-trifluoroethoxy)-phenyl |
| 1270. | 2-fluoroethyl | 4-(1,1,2,2-tetrafluoroethoxy)-phenyl |
| 1271. | 2-fluoroethyl | 4-cyclopropylphenyl |
| 1272. | 2-fluoroethyl | 4-cyclobutylphenyl |
| 1273. | 2-fluoroethyl | 4-cyclopentylphenyl |
| 1274. | 2-fluoroethyl | 4-(2,2-difluorocyclopropyl)-phenyl |
| 1275. | 2-fluoroethyl | 3,4-difluorophenyl |
| 1276. | 2-fluoroethyl | 4-bromo-3-fluorophenyl |
| 1277. | 2-fluoroethyl | 4-bromo-2-fluorophenyl |
| 1278. | 2-fluoroethyl | 4-bromo-2,5-difluorophenyl |
| 1279. | 2-fluoroethyl | 2-fluoro-4-isopropylphenyl |
| 1280. | 2-fluoroethyl | 3-fluoro-4-isopropylphenyl |
| 1281. | 2-fluoroethyl | 4-(1-hydroxy-1-methylethyl)-phenyl |
| 1282. | 2-fluoroethyl | 4-(2-hydroxy-2-methylpropyl)-phenyl |
| 1283. | 2-fluoroethyl | 4-acetylphenyl |
| 1284. | 2-fluoroethyl | 4-carboxyphenyl |
| 1285. | 2-fluoroethyl | 4-cyanophenyl |
| 1286. | 2-fluoroethyl | 4-hydroxyphenyl |
| 1287. | 2-fluoroethyl | 4-(O-benzyl)-phenyl |
| 1288. | 2-fluoroethyl | 4-(2-methoxyethoxy)-phenyl |
| 1289. | 2-fluoroethyl | 4-($CH_2$—$N(CH_3)_2$)-phenyl |
| 1290. | 2-fluoroethyl | 4-(NH—CO—$NH_2$)-phenyl |
| 1291. | 2-fluoroethyl | 4-(methylsulfanyl)-phenyl |
| 1292. | 2-fluoroethyl | 4-(fluoromethylsulfanyl)-phenyl |
| 1293. | 2-fluoroethyl | 4-(difluoromethylsulfanyl)-phenyl |
| 1294. | 2-fluoroethyl | 4-(trifluoromethylsulfanyl)-phenyl |
| 1295. | 2-fluoroethyl | 4-(methylsulfonyl)-phenyl |
| 1296. | 2-fluoroethyl | 4-(N-methoxy-N-methyl-amino)-phenyl |
| 1297. | 2-fluoroethyl | 4-(methoxyamino)-phenyl |
| 1298. | 2-fluoroethyl | 4-(ethoxyamino)-phenyl |
| 1299. | 2-fluoroethyl | 4-(N-methylaminooxy)-phenyl |
| 1300. | 2-fluoroethyl | 4-(N,N-dimethylaminooxy)-phenyl |
| 1301. | 2-fluoroethyl | 4-(azetidin-1-yl)-phenyl |
| 1302. | 2-fluoroethyl | 4-(2-methylazetidin-1-yl)-phenyl |
| 1303. | 2-fluoroethyl | 4-((S)-2-methylazetidin-1-yl)-phenyl |
| 1304. | 2-fluoroethyl | 4-((R)-2-methylazetidin-1-yl)-phenyl |
| 1305. | 2-fluoroethyl | 4-(3-fluoroazetidin-1-yl)-phenyl |
| 1306. | 2-fluoroethyl | 4-(3-methoxyazetidin-1-yl)-phenyl |
| 1307. | 2-fluoroethyl | 4-(3-hydroxyazetidin-1-yl)-phenyl |
| 1308. | 2-fluoroethyl | 4-(pyrrolidin-1-yl)-phenyl |
| 1309. | 2-fluoroethyl | 4-(pyrrolidin-2-yl)-phenyl |
| 1310. | 2-fluoroethyl | 4-((S)-pyrrolidin-2-yl)-phenyl |
| 1311. | 2-fluoroethyl | 4-((R)-pyrrolidin-2-yl)-phenyl |
| 1312. | 2-fluoroethyl | 4-(pyrrolidin-3-yl)-phenyl |
| 1313. | 2-fluoroethyl | 4-((S)-pyrrolidin-3-yl)-phenyl |
| 1314. | 2-fluoroethyl | 4-((R)-pyrrolidin-3-yl)-phenyl |
| 1315. | 2-fluoroethyl | 4-(2-fluoropyrrolidin-1-yl)-phenyl |
| 1316. | 2-fluoroethyl | 4-((S)-2-fluoropyrrolidin-1-yl)-phenyl |
| 1317. | 2-fluoroethyl | 4-((R)-2-fluoropyrrolidin-1-yl)-phenyl |
| 1318. | 2-fluoroethyl | 4-(3-fluoropyrrolidin-1-yl)-phenyl |
| 1319. | 2-fluoroethyl | 4-((S)-3-fluoropyrrolidin-1-yl)-phenyl |
| 1320. | 2-fluoroethyl | 4-((R)-3-fluoropyrrolidin-1-yl)-phenyl |
| 1321. | 2-fluoroethyl | 4-(2,2-difluoropyrrolidin-1-yl)-phenyl |
| 1322. | 2-fluoroethyl | 4-(3,3-difluoropyrrolidin-1-yl)-phenyl |
| 1323. | 2-fluoroethyl | 4-(2-methylpyrrolidin-1-yl)-phenyl |
| 1324. | 2-fluoroethyl | 4-((S)-2-methylpyrrolidin-1-yl)-phenyl |
| 1325. | 2-fluoroethyl | 4-((R)-2-methylpyrrolidin-1-yl)-phenyl |
| 1326. | 2-fluoroethyl | 4-(3-methylpyrrolidin-1-yl)-phenyl |
| 1327. | 2-fluoroethyl | 4-((S)-3-methylpyrrolidin-1-yl)-phenyl |
| 1328. | 2-fluoroethyl | 4-((R)-3-methylpyrrolidin-1-yl)-phenyl |
| 1329. | 2-fluoroethyl | 4-(1-methylpyrrolidin-2-yl)-phenyl |
| 1330. | 2-fluoroethyl | 4-((S)-1-methylpyrrolidin-2-yl)-phenyl |
| 1331. | 2-fluoroethyl | 4-((R)-1-methylpyrrolidin-2-yl)-phenyl |
| 1332. | 2-fluoroethyl | 4-(1-methylpyrrolidin-3-yl)-phenyl |
| 1333. | 2-fluoroethyl | 4-((S)-1-methylpyrrolidin-3-yl)-phenyl |
| 1334. | 2-fluoroethyl | 4-((R)-1-methylpyrrolidin-3-yl)-phenyl |
| 1335. | 2-fluoroethyl | 4-(2,2-dimethylpyrrolidin-1-yl)-phenyl |

TABLE A-continued

| No. | R¹ | Ar |
|---|---|---|
| 1336. | 2-fluoroethyl | 4-(3,3-dimethylpyrrolidin-1-yl)-phenyl |
| 1337. | 2-fluoroethyl | 4-(2-trifluoromethylpyrrolidin-1-yl)-phenyl |
| 1338. | 2-fluoroethyl | 4-((S)-2-trifluoromethylpyrrolidin-1-yl)-phenyl |
| 1339. | 2-fluoroethyl | 4-((R)-2-trifluoromethylpyrrolidin-1-yl)-phenyl |
| 1340. | 2-fluoroethyl | 4-(3-trifluoromethylpyrrolidin-1-yl)-phenyl |
| 1341. | 2-fluoroethyl | 4-((S)-3-trifluoromethylpyrrolidin-1-yl)-phenyl |
| 1342. | 2-fluoroethyl | 4-((R)-3-trifluoromethylpyrrolidin-1-yl)-phenyl |
| 1343. | 2-fluoroethyl | 4-(2-oxopyrrolidin-1-yl)-phenyl |
| 1344. | 2-fluoroethyl | 4-(2-oxo-oxazolidin-3-yl)-phenyl |
| 1345. | 2-fluoroethyl | 4-(piperidin-1-yl)-phenyl |
| 1346. | 2-fluoroethyl | 4-(2-methylpiperidin-1-yl)-phenyl |
| 1347. | 2-fluoroethyl | 4-((S)-2-methylpiperidin-1-yl)-phenyl |
| 1348. | 2-fluoroethyl | 4-((R)-2-methylpiperidin-1-yl)-phenyl |
| 1349. | 2-fluoroethyl | 4-(piperazin-1-yl)-phenyl |
| 1350. | 2-fluoroethyl | 4-(4-methylpiperazin-1-yl)-phenyl |
| 1351. | 2-fluoroethyl | 4-(morpholin-4-yl)-phenyl |
| 1352. | 2-fluoroethyl | 4-(thiomorpholin-4-yl)-phenyl |
| 1353. | 2-fluoroethyl | 4-(1-oxo-thiomorpholin-4-yl)-phenyl |
| 1354. | 2-fluoroethyl | 4-(1,1-dioxo-thiomorpholin-4-yl)-phenyl |
| 1355. | 2-fluoroethyl | 4-(pyrrol-1-yl)-phenyl |
| 1356. | 2-fluoroethyl | 4-(pyrrol-2-yl)-phenyl |
| 1357. | 2-fluoroethyl | 4-(pyrrol-3-yl)-phenyl |
| 1358. | 2-fluoroethyl | 4-(1-methylpyrrol-2-yl)-phenyl |
| 1359. | 2-fluoroethyl | 4-(1-methylpyrrol-3-yl)-phenyl |
| 1360. | 2-fluoroethyl | 4-(furan-2-yl)-phenyl |
| 1361. | 2-fluoroethyl | 4-(furan-3-yl)-phenyl |
| 1362. | 2-fluoroethyl | 4-(thiophen-2-yl)-phenyl |
| 1363. | 2-fluoroethyl | 4-(thiophen-3-yl)-phenyl |
| 1364. | 2-fluoroethyl | 4-(5-propylthien-2-yl)-phenyl |
| 1365. | 2-fluoroethyl | 4-(pyrazol-1-yl)-phenyl |
| 1366. | 2-fluoroethyl | 4-(pyrazol-3-yl)-phenyl |
| 1367. | 2-fluoroethyl | 4-(pyrazol-4-yl)-phenyl |
| 1368. | 2-fluoroethyl | 4-(1-methyl-1H-pyrazol-4-yl)-phenyl |
| 1369. | 2-fluoroethyl | 4-(1-ethyl-1H-pyrazol-4-yl)-phenyl |
| 1370. | 2-fluoroethyl | 4-(1-methyl-1H-pyrazol-5-yl)-phenyl |
| 1371. | 2-fluoroethyl | 4-(1H-imidazol-2-yl)-phenyl |
| 1372. | 2-fluoroethyl | 4-(imidazol-1-yl)-phenyl |
| 1373. | 2-fluoroethyl | 4-(1-methylimidazol-2-yl)-phenyl |
| 1374. | 2-fluoroethyl | 4-(oxazol-2-yl)-phenyl |
| 1375. | 2-fluoroethyl | 4-(oxazol-4-yl)-phenyl |
| 1376. | 2-fluoroethyl | 4-(oxazol-5-yl)-phenyl |
| 1377. | 2-fluoroethyl | 4-(isoxazol-3-yl)-phenyl |
| 1378. | 2-fluoroethyl | 4-(isoxazol-4-yl)-phenyl |
| 1379. | 2-fluoroethyl | 4-(isoxazol-5-yl)-phenyl |
| 1380. | 2-fluoroethyl | 4-([1,2,3]-triazol-1-yl)-phenyl |
| 1381. | 2-fluoroethyl | 4-([1,2,4]-triazol-1-yl)-phenyl |
| 1382. | 2-fluoroethyl | 4-([1,2,3]-triazol-2-yl)-phenyl |
| 1383. | 2-fluoroethyl | 4-(4H-[1,2,4]-triazol-3-yl)-phenyl |
| 1384. | 2-fluoroethyl | 4-([1,2,4]-triazol-4-yl)-phenyl |
| 1385. | 2-fluoroethyl | 4-(2H-[1,2,3]-triazol-4-yl)-phenyl |
| 1386. | 2-fluoroethyl | 4-(4-methyl-4H-[1,2,4]-triazol-3-yl)-phenyl |
| 1387. | 2-fluoroethyl | 4-(2-methyl-2H-[1,2,3]-triazol-4-yl)-phenyl |
| 1388. | 2-fluoroethyl | 4-([1,3,4]-oxadiazol-2-yl)-phenyl |
| 1389. | 2-fluoroethyl | 4-([1,2,4]-oxadiazol-3-yl)-phenyl |
| 1390. | 2-fluoroethyl | 4-([1,2,4]-oxadiazol-5-yl)-phenyl |
| 1391. | 2-fluoroethyl | 4-([1,2,3]-oxadiazol-4-yl)-phenyl |
| 1392. | 2-fluoroethyl | 4-([1,2,3]-oxadiazol-5-yl)-phenyl |
| 1393. | 2-fluoroethyl | 4-([1,2,3]-thiadiazol-4-yl)-phenyl |
| 1394. | 2-fluoroethyl | 4-(1H-tetrazol-5-yl)-phenyl |
| 1395. | 2-fluoroethyl | 4-(tetrazol-1-yl)-phenyl |
| 1396. | 2-fluoroethyl | 4-(2-methyl-2H-tetrazol-5-yl)-phenyl |
| 1397. | 2-fluoroethyl | 4-(1-methyl-1H-tetrazol-5-yl)-phenyl |
| 1398. | 2-fluoroethyl | 4-furazan-3-yl-phenyl |
| 1399. | 2-fluoroethyl | 4-(pyrid-2-yl)-phenyl |
| 1400. | 2-fluoroethyl | 4-(pyrid-3-yl)-phenyl |
| 1401. | 2-fluoroethyl | 4-(pyrid-4-yl)-phenyl |
| 1402. | 2-fluoroethyl | 4-(pyrimidin-2-yl)-phenyl |
| 1403. | 2-fluoroethyl | 4-(pyrimidin-4-yl)-phenyl |
| 1404. | 2-fluoroethyl | 4-(pyrimidin-5-yl)-phenyl |
| 1405. | 2-fluoroethyl | 5-isopropylthiophen-2-yl |
| 1406. | 2-fluoroethyl | 2-chlorothiophen-5-yl |
| 1407. | 2-fluoroethyl | 2,5-dichlorothiophen-4-yl |
| 1408. | 2-fluoroethyl | 2,3-dichlorothiophen-5-yl |
| 1409. | 2-fluoroethyl | 2-chloro-3-nitrothiophen-5-yl |
| 1410. | 2-fluoroethyl | 2-(phenylsulfonyl)-thiophen-5-yl |
| 1411. | 2-fluoroethyl | 2-(pyridin-2-yl)thiophen-5-yl |
| 1412. | 2-fluoroethyl | 2-(5-(trifluoromethyl)isoxazol-3-yl)-thiophen-5-yl |
| 1413. | 2-fluoroethyl | 2-(2-methylthiazol-4-yl)-thiophen-5-yl |

TABLE A-continued

| No. | R¹ | Ar |
|---|---|---|
| 1414. | 2-fluoroethyl | 1-methyl-1H-imidazol-4-yl |
| 1415. | 2-fluoroethyl | 1,2-dimethyl-1H-imidazol-4-yl |
| 1416. | 2-fluoroethyl | 3,5-dimethylisoxazol-4-yl |
| 1417. | 2-fluoroethyl | thiazol-2-yl |
| 1418. | 2-fluoroethyl | 4-methylthiazol-2-yl |
| 1419. | 2-fluoroethyl | 4-isopropylthiazol-2-yl |
| 1420. | 2-fluoroethyl | 4-trifluoromethylthiazol-2-yl |
| 1421. | 2-fluoroethyl | 5-methylthiazol-2-yl |
| 1422. | 2-fluoroethyl | 5-isopropylthiazol-2-yl |
| 1423. | 2-fluoroethyl | 5-trifluoromethylthiazol-2-yl |
| 1424. | 2-fluoroethyl | 2,4-dimethylthiazol-5-yl |
| 1425. | 2-fluoroethyl | 2-acetamido-4-methylthiazol-5-yl |
| 1426. | 2-fluoroethyl | 4H-[1,2,4]triazol-3-yl |
| 1427. | 2-fluoroethyl | 5-methyl-4H-[1,2,4]triazol-3-yl |
| 1428. | 2-fluoroethyl | 4-methyl-4H-[1,2,4]triazol-3-yl |
| 1429. | 2-fluoroethyl | 5-isopropyl-4H-[1,2,4]triazol-3-yl |
| 1430. | 2-fluoroethyl | 5-trifluoromethyl-4H-[1,2,4]triazol-3-yl |
| 1431. | 2-fluoroethyl | 4,5-dimethyl-4H-[1,2,4]triazol-3-yl |
| 1432. | 2-fluoroethyl | 5-isopropyl-4-methyl-4H-[1,2,4]triazol-3-yl |
| 1433. | 2-fluoroethyl | 5-trifluoromethyl-4-methyl-4H-[1,2,4]triazol-3-yl |
| 1434. | 2-fluoroethyl | [1,3,4]thiadiazol-2-yl |
| 1435. | 2-fluoroethyl | 5-methyl-[1,3,4]thiadiazol-2-yl |
| 1436. | 2-fluoroethyl | 5-isopropyl-[1,3,4]thiadiazol-2-yl |
| 1437. | 2-fluoroethyl | 5-trifluoromethyl-[1,3,4]thiadiazol-2-yl |
| 1438. | 2-fluoroethyl | 3-bromo-2-chloropyrid-5-yl |
| 1439. | 2-fluoroethyl | 2-(4-morpholino)-pyrid-5-yl |
| 1440. | 2-fluoroethyl | 2-phenoxypyrid-5-yl |
| 1441. | 2-fluoroethyl | (2-isopropyl)-pyrimidin-5-yl |
| 1442. | 2-fluoroethyl | (5-isopropyl)-pyrimidin-2-yl |
| 1443. | 2-fluoroethyl | 8-quinolyl |
| 1444. | 2-fluoroethyl | 5-isoquinolyl |
| 1445. | 2-fluoroethyl | 2-(trifluoroacetyl)-1,2,3,4-tetrahydroisoquinolin-7-yl |
| 1446. | 2-fluoroethyl | 5-chloro-3-methylbenzothiophen-2-yl |
| 1447. | 2-fluoroethyl | 3,4-dihydro-4-methyl-2H-benzo[b][1,4]oxazinyl |
| 1448. | 2-fluoroethyl | benzothiazol-6-yl |
| 1449. | 2-fluoroethyl | benzo[2,1,3]oxadiazol-4-yl |
| 1450. | 2-fluoroethyl | 5-chlorobenzo[2,1,3]oxadiazol-4-yl |
| 1451. | 2-fluoroethyl | 7-chlorobenzo[2,1,3]oxadiazol-4-yl |
| 1452. | 2-fluoroethyl | benzo[2,1,3]thiadiazol-4-yl |
| 1453. | cyclopropylmethyl | 4-methylphenyl |
| 1454. | cyclopropylmethyl | 4-ethylphenyl |
| 1455. | cyclopropylmethyl | 4-propylphenyl |
| 1456. | cyclopropylmethyl | 4-isopropylphenyl |
| 1457. | cyclopropylmethyl | 4-sec-butylphenyl |
| 1458. | cyclopropylmethyl | 4-isobutylphenyl |
| 1459. | cyclopropylmethyl | 4-(1,1-dimethylpropyl)-phenyl |
| 1460. | cyclopropylmethyl | 4-vinylphenyl |
| 1461. | cyclopropylmethyl | 4-isopropenylphenyl |
| 1462. | cyclopropylmethyl | 4-fluorophenyl |
| 1463. | cyclopropylmethyl | 4-chlorophenyl |
| 1464. | cyclopropylmethyl | 4-bromophenyl |
| 1465. | cyclopropylmethyl | 4-(fluoromethyl)phenyl |
| 1466. | cyclopropylmethyl | 3-(fluoromethyl)phenyl |
| 1467. | cyclopropylmethyl | 2-(fluoromethyl)phenyl |
| 1468. | cyclopropylmethyl | 4-(difluoromethyl)phenyl |
| 1469. | cyclopropylmethyl | 3-(difluoromethyl)phenyl |
| 1470. | cyclopropylmethyl | 2-(difluoromethyl)phenyl |
| 1471. | cyclopropylmethyl | 4-(trifluoromethyl)phenyl |
| 1472. | cyclopropylmethyl | 3-(trifluoromethyl)phenyl |
| 1473. | cyclopropylmethyl | 2-(trifluoromethyl)phenyl |
| 1474. | cyclopropylmethyl | 4-(1-fluoroethyl)-phenyl |
| 1475. | cyclopropylmethyl | 4-((S)-1-fluoroethyl)-phenyl |
| 1476. | cyclopropylmethyl | 4-((R)-1-fluoroethyl)-phenyl |
| 1477. | cyclopropylmethyl | 4-(2-fluoroethyl)-phenyl |
| 1478. | cyclopropylmethyl | 4-(1,1-difluoroethyl)-phenyl |
| 1479. | cyclopropylmethyl | 4-(2,2-difluoroethyl)-phenyl |
| 1480. | cyclopropylmethyl | 4-(2,2,2-trifluoroethyl)-phenyl |
| 1481. | cyclopropylmethyl | 4-(3-fluoropropyl)-phenyl |
| 1482. | cyclopropylmethyl | 4-(2-fluoropropyl)-phenyl |
| 1483. | cyclopropylmethyl | 4-((S)-2-fluoropropyl)-phenyl |
| 1484. | cyclopropylmethyl | 4-((R)-2-fluoropropyl)-phenyl |
| 1485. | cyclopropylmethyl | 4-(3,3-difluoropropyl)-phenyl |
| 1486. | cyclopropylmethyl | 4-(3,3,3-trifluoropropyl)-phenyl |
| 1487. | cyclopropylmethyl | 4-(1-fluoro-1-methylethyl)-phenyl |
| 1488. | cyclopropylmethyl | 4-(2-fluoro-1-methylethyl)-phenyl |
| 1489. | cyclopropylmethyl | 4-((S)-2-fluoro-1-methylethyl)-phenyl |
| 1490. | cyclopropylmethyl | 4-((R)-2-fluoro-1-methylethyl)-phenyl |
| 1491. | cyclopropylmethyl | 4-(2,2-difluoro-1-methylethyl)-phenyl |

TABLE A-continued

| No. | R¹ | Ar |
|---|---|---|
| 1492. | cyclopropylmethyl | 4-((S)-2,2-difluoro-1-methylethyl)-phenyl |
| 1493. | cyclopropylmethyl | 4-((R)-2,2-difluoro-1-methylethyl)-phenyl |
| 1494. | cyclopropylmethyl | 4-(2,2,2-trifluoro-1-methylethyl)-phenyl |
| 1495. | cyclopropylmethyl | 4-((S)-2,2,2-trifluoro-1-methylethyl)-phenyl |
| 1496. | cyclopropylmethyl | 4-((R)-2,2,2-trifluoro-1-methylethyl)-phenyl |
| 1497. | cyclopropylmethyl | 4-(2-fluoro-1-fluoromethylethyl)-phenyl |
| 1498. | cyclopropylmethyl | 4-(1-difluoromethyl-2,2-difluoroethyl)-phenyl |
| 1499. | cyclopropylmethyl | 4-(1,1-dimethyl-2-fluoroethyl)-phenyl |
| 1500. | cyclopropylmethyl | 4-methoxyphenyl |
| 1501. | cyclopropylmethyl | 4-ethoxyphenyl |
| 1502. | cyclopropylmethyl | 4-propoxyphenyl |
| 1503. | cyclopropylmethyl | 4-isopropoxyphenyl |
| 1504. | cyclopropylmethyl | 4-butoxyphenyl |
| 1505. | cyclopropylmethyl | 4-(fluoromethoxy)-phenyl |
| 1506. | cyclopropylmethyl | 4-(difluoromethoxy)-phenyl |
| 1507. | cyclopropylmethyl | 4-(trifluoromethoxy)-phenyl |
| 1508. | cyclopropylmethyl | 3-(trifluoromethoxy)-phenyl |
| 1509. | cyclopropylmethyl | 4-(2-fluoroethoxy)-phenyl |
| 1510. | cyclopropylmethyl | 4-(2,2-difluoroethoxy)-phenyl |
| 1511. | cyclopropylmethyl | 4-(2,2,2-trifluoroethoxy)-phenyl |
| 1512. | cyclopropylmethyl | 4-(1,1,2,2-tetrafluoroethoxy)-phenyl |
| 1513. | cyclopropylmethyl | 4-cyclopropylphenyl |
| 1514. | cyclopropylmethyl | 4-cyclobutylphenyl |
| 1515. | cyclopropylmethyl | 4-cyclopentylphenyl |
| 1516. | cyclopropylmethyl | 4-(2,2-difluorocyclopropyl)-phenyl |
| 1517. | cyclopropylmethyl | 3,4-difluorophenyl |
| 1518. | cyclopropylmethyl | 4-bromo-3-fluorophenyl |
| 1519. | cyclopropylmethyl | 4-bromo-2-fluorophenyl |
| 1520. | cyclopropylmethyl | 4-bromo-2,5-difluorophenyl |
| 1521. | cyclopropylmethyl | 2-fluoro-4-isopropylphenyl |
| 1522. | cyclopropylmethyl | 3-fluoro-4-isopropylphenyl |
| 1523. | cyclopropylmethyl | 4-(1-hydroxy-1-methylethyl)-phenyl |
| 1524. | cyclopropylmethyl | 4-(2-hydroxy-2-methylpropyl)-phenyl |
| 1525. | cyclopropylmethyl | 4-acetylphenyl |
| 1526. | cyclopropylmethyl | 4-carboxyphenyl |
| 1527. | cyclopropylmethyl | 4-cyanophenyl |
| 1528. | cyclopropylmethyl | 4-hydroxyphenyl |
| 1529. | cyclopropylmethyl | 4-(O-benzyl)-phenyl |
| 1530. | cyclopropylmethyl | 4-(2-methoxyethoxy)-phenyl |
| 1531. | cyclopropylmethyl | 4-(CH₂—N(CH₃)₂)-phenyl |
| 1532. | cyclopropylmethyl | 4-(NH—CO—NH₂)-phenyl |
| 1533. | cyclopropylmethyl | 4-(methylsulfanyl)-phenyl |
| 1534. | cyclopropylmethyl | 4-(fluoromethylsulfanyl)-phenyl |
| 1535. | cyclopropylmethyl | 4-(difluoromethylsulfanyl)-phenyl |
| 1536. | cyclopropylmethyl | 4-(trifluoromethylsulfanyl)-phenyl |
| 1537. | cyclopropylmethyl | 4-(methylsulfonyl)-phenyl |
| 1538. | cyclopropylmethyl | 4-(N-methoxy-N-methyl-amino)-phenyl |
| 1539. | cyclopropylmethyl | 4-(methoxyamino)-phenyl |
| 1540. | cyclopropylmethyl | 4-(ethoxyamino)-phenyl |
| 1541. | cyclopropylmethyl | 4-(N-methylaminooxy)-phenyl |
| 1542. | cyclopropylmethyl | 4-(N,N-dimethylaminooxy)-phenyl |
| 1543. | cyclopropylmethyl | 4-(azetidin-1-yl)-phenyl |
| 1544. | cyclopropylmethyl | 4-(2-methylazetidin-1-yl)-phenyl |
| 1545. | cyclopropylmethyl | 4-((S)-2-methylazetidin-1-yl)-phenyl |
| 1546. | cyclopropylmethyl | 4-((R)-2-methylazetidin-1-yl)-phenyl |
| 1547. | cyclopropylmethyl | 4-(3-fluoroazetidin-1-yl)-phenyl |
| 1548. | cyclopropylmethyl | 4-(3-methoxyazetidin-1-yl)-phenyl |
| 1549. | cyclopropylmethyl | 4-(3-hydroxyazetidin-1-yl)-phenyl |
| 1550. | cyclopropylmethyl | 4-(pyrrolidin-1-yl)-phenyl |
| 1551. | cyclopropylmethyl | 4-(pyrrolidin-2-yl)-phenyl |
| 1552. | cyclopropylmethyl | 4-((S)-pyrrolidin-2-yl)-phenyl |
| 1553. | cyclopropylmethyl | 4-((R)-pyrrolidin-2-yl)-phenyl |
| 1554. | cyclopropylmethyl | 4-(pyrrolidin-3-yl)-phenyl |
| 1555. | cyclopropylmethyl | 4-((S)-pyrrolidin-3-yl)-phenyl |
| 1556. | cyclopropylmethyl | 4-((R)-pyrrolidin-3-yl)-phenyl |
| 1557. | cyclopropylmethyl | 4-(2-fluoropyrrolidin-1-yl)-phenyl |
| 1558. | cyclopropylmethyl | 4-((S)-2-fluoropyrrolidin-1-yl)-phenyl |
| 1559. | cyclopropylmethyl | 4-((R)-2-fluoropyrrolidin-1-yl)-phenyl |
| 1560. | cyclopropylmethyl | 4-(3-fluoropyrrolidin-1-yl)-phenyl |
| 1561. | cyclopropylmethyl | 4-((S)-3-fluoropyrrolidin-1-yl)-phenyl |
| 1562. | cyclopropylmethyl | 4-((R)-3-fluoropyrrolidin-1-yl)-phenyl |
| 1563. | cyclopropylmethyl | 4-(2,2-difluoropyrrolidin-1-yl)-phenyl |
| 1564. | cyclopropylmethyl | 4-(3,3-difluoropyrrolidin-1-yl)-phenyl |
| 1565. | cyclopropylmethyl | 4-(2-methylpyrrolidin-1-yl)-phenyl |
| 1566. | cyclopropylmethyl | 4-((S)-2-methylpyrrolidin-1-yl)-phenyl |
| 1567. | cyclopropylmethyl | 4-((R)-2-methylpyrrolidin-1-yl)-phenyl |
| 1568. | cyclopropylmethyl | 4-(3-methylpyrrolidin-1-yl)-phenyl |
| 1569. | cyclopropylmethyl | 4-((S)-3-methylpyrrolidin-1-yl)-phenyl |

TABLE A-continued

| No. | R¹ | Ar |
|---|---|---|
| 1570. | cyclopropylmethyl | 4-((R)-3-methylpyrrolidin-1-yl)-phenyl |
| 1571. | cyclopropylmethyl | 4-(1-methylpyrrolidin-2-yl)-phenyl |
| 1572. | cyclopropylmethyl | 4-((S)-1-methylpyrrolidin-2-yl)-phenyl |
| 1573. | cyclopropylmethyl | 4-((R)-1-methylpyrrolidin-2-yl)-phenyl |
| 1574. | cyclopropylmethyl | 4-(1-methylpyrrolidin-3-yl)-phenyl |
| 1575. | cyclopropylmethyl | 4-((S)-1-methylpyrrolidin-3-yl)-phenyl |
| 1576. | cyclopropylmethyl | 4-((R)-1-methylpyrrolidin-3-yl)-phenyl |
| 1577. | cyclopropylmethyl | 4-(2,2-dimethylpyrrolidin-1-yl)-phenyl |
| 1578. | cyclopropylmethyl | 4-(3,3-dimethylpyrrolidin-1-yl)-phenyl |
| 1579. | cyclopropylmethyl | 4-(2-trifluoromethylpyrrolidin-1-yl)-phenyl |
| 1580. | cyclopropylmethyl | 4-((S)-2-trifluoromethylpyrrolidin-1-yl)-phenyl |
| 1581. | cyclopropylmethyl | 4-((R)-2-trifluoromethylpyrrolidin-1-yl)-phenyl |
| 1582. | cyclopropylmethyl | 4-(3-trifluoromethylpyrrolidin-1-yl)-phenyl |
| 1583. | cyclopropylmethyl | 4-((S)-3-trifluoromethylpyrrolidin-1-yl)-phenyl |
| 1584. | cyclopropylmethyl | 4-((R)-3-trifluoromethylpyrrolidin-1-yl)-phenyl |
| 1585. | cyclopropylmethyl | 4-(2-oxopyrrolidin-1-yl)-phenyl |
| 1586. | cyclopropylmethyl | 4-(2-oxo-oxazolidin-3-yl)-phenyl |
| 1587. | cyclopropylmethyl | 4-(piperidin-1-yl)-phenyl |
| 1588. | cyclopropylmethyl | 4-(2-methylpiperidin-1-yl)-phenyl |
| 1589. | cyclopropylmethyl | 4-((S)-2-methylpiperidin-1-yl)-phenyl |
| 1590. | cyclopropylmethyl | 4-((R)-2-methylpiperidin-1-yl)-phenyl |
| 1591. | cyclopropylmethyl | 4-(piperazin-1-yl)-phenyl |
| 1592. | cyclopropylmethyl | 4-(4-methylpiperazin-1-yl)-phenyl |
| 1593. | cyclopropylmethyl | 4-(morpholin-4-yl)-phenyl |
| 1594. | cyclopropylmethyl | 4-(thiomorpholin-4-yl)-phenyl |
| 1595. | cyclopropylmethyl | 4-(1-oxo-thiomorpholin-4-yl)-phenyl |
| 1596. | cyclopropylmethyl | 4-(1,1-dioxo-thiomorpholin-4-yl)-phenyl |
| 1597. | cyclopropylmethyl | 4-(pyrrol-1-yl)-phenyl |
| 1598. | cyclopropylmethyl | 4-(pyrrol-2-yl)-phenyl |
| 1599. | cyclopropylmethyl | 4-(pyrrol-3-yl)-phenyl |
| 1600. | cyclopropylmethyl | 4-(1-methylpyrrol-2-yl)-phenyl |
| 1601. | cyclopropylmethyl | 4-(1-methylpyrrol-3-yl)-phenyl |
| 1602. | cyclopropylmethyl | 4-(furan-2-yl)-phenyl |
| 1603. | cyclopropylmethyl | 4-(furan-3-yl)-phenyl |
| 1604. | cyclopropylmethyl | 4-(thiophen-2-yl)-phenyl |
| 1605. | cyclopropylmethyl | 4-(thiophen-3-yl)-phenyl |
| 1606. | cyclopropylmethyl | 4-(5-propylthien-2-yl)-phenyl |
| 1607. | cyclopropylmethyl | 4-(pyrazol-1-yl)-phenyl |
| 1608. | cyclopropylmethyl | 4-(pyrazol-3-yl)-phenyl |
| 1609. | cyclopropylmethyl | 4-(pyrazol-4-yl)-phenyl |
| 1610. | cyclopropylmethyl | 4-(1-methyl-1H-pyrazol-4-yl)-phenyl |
| 1611. | cyclopropylmethyl | 4-(1-ethyl-1H-pyrazol-4-yl)-phenyl |
| 1612. | cyclopropylmethyl | 4-(1-methyl-1H-pyrazol-5-yl)-phenyl |
| 1613. | cyclopropylmethyl | 4-(1H-imidazol-2-yl)-phenyl |
| 1614. | cyclopropylmethyl | 4-(imidazol-1-yl)-phenyl |
| 1615. | cyclopropylmethyl | 4-(1-methylimidazol-2-yl)-phenyl |
| 1616. | cyclopropylmethyl | 4-(oxazol-2-yl)-phenyl |
| 1617. | cyclopropylmethyl | 4-(oxazol-4-yl)-phenyl |
| 1618. | cyclopropylmethyl | 4-(oxazol-5-yl)-phenyl |
| 1619. | cyclopropylmethyl | 4-(isoxazol-3-yl)-phenyl |
| 1620. | cyclopropylmethyl | 4-(isoxazol-4-yl)-phenyl |
| 1621. | cyclopropylmethyl | 4-(isoxazol-5-yl)-phenyl |
| 1622. | cyclopropylmethyl | 4-([1,2,3]-triazol-1-yl)-phenyl |
| 1623. | cyclopropylmethyl | 4-([1,2,4]-triazol-1-yl)-phenyl |
| 1624. | cyclopropylmethyl | 4-([1,2,3]-triazol-2-yl)-phenyl |
| 1625. | cyclopropylmethyl | 4-(4H-[1,2,4]-triazol-3-yl)-phenyl |
| 1626. | cyclopropylmethyl | 4-([1,2,4]-triazol-4-yl)-phenyl |
| 1627. | cyclopropylmethyl | 4-(2H-[1,2,3]-triazol-4-yl)-phenyl |
| 1628. | cyclopropylmethyl | 4-(4-methyl-4H-[1,2,4]-triazol-3-yl)-phenyl |
| 1629. | cyclopropylmethyl | 4-(2-methyl-2H-[1,2,3]-triazol-4-yl)-phenyl |
| 1630. | cyclopropylmethyl | 4-([1,3,4]-oxadiazol-2-yl)-phenyl |
| 1631. | cyclopropylmethyl | 4-([1,2,4]-oxadiazol-3-yl)-phenyl |
| 1632. | cyclopropylmethyl | 4-([1,2,4]-oxadiazol-5-yl)-phenyl |
| 1633. | cyclopropylmethyl | 4-([1,2,3]-oxadiazol-4-yl)-phenyl |
| 1634. | cyclopropylmethyl | 4-([1,2,3]-oxadiazol-5-yl)-phenyl |
| 1635. | cyclopropylmethyl | 4-([1,2,3]-thiadiazol-4-yl)-phenyl |
| 1636. | cyclopropylmethyl | 4-(1H-tetrazol-5-yl)-phenyl |
| 1637. | cyclopropylmethyl | 4-(tetrazol-1-yl)-phenyl |
| 1638. | cyclopropylmethyl | 4-(2-methyl-2H-tetrazol-5-yl)-phenyl |
| 1639. | cyclopropylmethyl | 4-(1-methyl-1H-tetrazol-5-yl)-phenyl |
| 1640. | cyclopropylmethyl | 4-furazan-3-yl-phenyl |
| 1641. | cyclopropylmethyl | 4-(pyrid-2-yl)-phenyl |
| 1642. | cyclopropylmethyl | 4-(pyrid-3-yl)-phenyl |
| 1643. | cyclopropylmethyl | 4-(pyrid-4-yl)-phenyl |
| 1644. | cyclopropylmethyl | 4-(pyrimidin-2-yl)-phenyl |
| 1645. | cyclopropylmethyl | 4-(pyrimidin-4-yl)-phenyl |
| 1646. | cyclopropylmethyl | 4-(pyrimidin-5-yl)-phenyl |
| 1647. | cyclopropylmethyl | 5-isopropylthiophen-2-yl |

TABLE A-continued

| No. | R¹ | Ar |
|---|---|---|
| 1648. | cyclopropylmethyl | 2-chlorothiophen-5-yl |
| 1649. | cyclopropylmethyl | 2,5-dichlorothiophen-4-yl |
| 1650. | cyclopropylmethyl | 2,3-dichlorothiophen-5-yl |
| 1651. | cyclopropylmethyl | 2-chloro-3-nitrothiophen-5-yl |
| 1652. | cyclopropylmethyl | 2-(phenylsulfonyl)-thiophen-5-yl |
| 1653. | cyclopropylmethyl | 2-(pyridin-2-yl)thiophen-5-yl |
| 1654. | cyclopropylmethyl | 2-(5-(trifluoromethyl)isoxazol-3-yl)-thiophen-5-yl |
| 1655. | cyclopropylmethyl | 2-(2-methylthiazol-4-yl)-thiophen-5-yl |
| 1656. | cyclopropylmethyl | 1-methyl-1H-imidazol-4-yl |
| 1657. | cyclopropylmethyl | 1,2-dimethyl-1H-imidazol-4-yl |
| 1658. | cyclopropylmethyl | 3,5-dimethylisoxazol-4-yl |
| 1659. | cyclopropylmethyl | thiazol-2-yl |
| 1660. | cyclopropylmethyl | 4-methylthiazol-2-yl |
| 1661. | cyclopropylmethyl | 4-isopropylthiazol-2-yl |
| 1662. | cyclopropylmethyl | 4-trifluoromethylthiazol-2-yl |
| 1663. | cyclopropylmethyl | 5-methylthiazol-2-yl |
| 1664. | cyclopropylmethyl | 5-isopropylthiazol-2-yl |
| 1665. | cyclopropylmethyl | 5-trifluoromethylthiazol-2-yl |
| 1666. | cyclopropylmethyl | 2,4-dimethylthiazol-5-yl |
| 1667. | cyclopropylmethyl | 2-acetamido-4-methylthiazol-5-yl |
| 1668. | cyclopropylmethyl | 4H-[1,2,4]triazol-3-yl |
| 1669. | cyclopropylmethyl | 5-methyl-4H-[1,2,4]triazol-3-yl |
| 1670. | cyclopropylmethyl | 4-methyl-4H-[1,2,4]triazol-3-yl |
| 1671. | cyclopropylmethyl | 5-isopropyl-4H-[1,2,4]triazol-3-yl |
| 1672. | cyclopropylmethyl | 5-trifluoromethyl-4H-[1,2,4]triazol-3-yl |
| 1673. | cyclopropylmethyl | 4,5-dimethyl-4H-[1,2,4]triazol-3-yl |
| 1674. | cyclopropylmethyl | 5-isopropyl-4-methyl-4H-[1,2,4]triazol-3-yl |
| 1675. | cyclopropylmethyl | 5-trifluoromethyl-4-methyl-4H-[1,2,4]triazol-3-yl |
| 1676. | cyclopropylmethyl | [1,3,4]thiadiazol-2-yl |
| 1677. | cyclopropylmethyl | 5-methyl-[1,3,4]thiadiazol-2-yl |
| 1678. | cyclopropylmethyl | 5-isopropyl-[1,3,4]thiadiazol-2-yl |
| 1679. | cyclopropylmethyl | 5-trifluoromethyl-[1,3,4]thiadiazol-2-yl |
| 1680. | cyclopropylmethyl | 3-bromo-2-chloropyrid-5-yl |
| 1681. | cyclopropylmethyl | 2-(4-morpholino)-pyrid-5-yl |
| 1682. | cyclopropylmethyl | 2-phenoxypyrid-5-yl |
| 1683. | cyclopropylmethyl | (2-isopropyl)-pyrimidin-5-yl |
| 1684. | cyclopropylmethyl | (5-isopropyl)-pyrimidin-2-yl |
| 1685. | cyclopropylmethyl | 8-quinolyl |
| 1686. | cyclopropylmethyl | 5-isoquinolyl |
| 1687. | cyclopropylmethyl | 2-(trifluoroacetyl)-1,2,3,4-tetrahydroisoquinolin-7-yl |
| 1688. | cyclopropylmethyl | 5-chloro-3-methylbenzothiophen-2-yl |
| 1689. | cyclopropylmethyl | 3,4-dihydro-4-methyl-2H-benzo[b][1,4]oxazinyl |
| 1690. | cyclopropylmethyl | benzothiazol-6-yl |
| 1691. | cyclopropylmethyl | benzo[2,1,3]oxadiazol-4-yl |
| 1692. | cyclopropylmethyl | 5-chlorobenzo[2,1,3]oxadiazol-4-yl |
| 1693. | cyclopropylmethyl | 7-chlorobenzo[2,1,3]oxadiazol-4-yl |
| 1694. | cyclopropylmethyl | benzo[2,1,3]thiadiazol-4-yl |
| 1695. | allyl | 4-methylphenyl |
| 1696. | allyl | 4-ethylphenyl |
| 1697. | allyl | 4-propylphenyl |
| 1698. | allyl | 4-isopropylphenyl |
| 1699. | allyl | 4-sec-butylphenyl |
| 1700. | allyl | 4-isobutylphenyl |
| 1701. | allyl | 4-(1,1-dimethylpropyl)-phenyl |
| 1702. | allyl | 4-vinylphenyl |
| 1703. | allyl | 4-isopropenylphenyl |
| 1704. | allyl | 4-fluorophenyl |
| 1705. | allyl | 4-chlorophenyl |
| 1706. | allyl | 4-bromophenyl |
| 1707. | allyl | 4-(fluoromethyl)phenyl |
| 1708. | allyl | 3-(fluoromethyl)phenyl |
| 1709. | allyl | 2-(fluoromethyl)phenyl |
| 1710. | allyl | 4-(difluoromethyl)phenyl |
| 1711. | allyl | 3-(difluoromethyl)phenyl |
| 1712. | allyl | 2-(difluoromethyl)phenyl |
| 1713. | allyl | 4-(trifluoromethyl)phenyl |
| 1714. | allyl | 3-(trifluoromethyl)phenyl |
| 1715. | allyl | 2-(trifluoromethyl)phenyl |
| 1716. | allyl | 4-(1-fluoroethyl)-phenyl |
| 1717. | allyl | 4-((S)-1-fluoroethyl)-phenyl |
| 1718. | allyl | 4-((R)-1-fluoroethyl)-phenyl |
| 1719. | allyl | 4-(2-fluoroethyl)-phenyl |
| 1720. | allyl | 4-(1,1-difluoroethyl)-phenyl |
| 1721. | allyl | 4-(2,2-difluoroethyl)-phenyl |
| 1722. | allyl | 4-(2,2,2-trifluoroethyl)-phenyl |
| 1723. | allyl | 4-(3-fluoropropyl)-phenyl |
| 1724. | allyl | 4-(2-fluoropropyl)-phenyl |
| 1725. | allyl | 4-((S)-2-fluoropropyl)-phenyl |

TABLE A-continued

| No. | R¹ | Ar |
|---|---|---|
| 1726. | allyl | 4-((R)-2-fluoropropyl)-phenyl |
| 1727. | allyl | 4-(3,3-difluoropropyl)-phenyl |
| 1728. | allyl | 4-(3,3,3-trifluoropropyl)-phenyl |
| 1729. | allyl | 4-(1-fluoro-1-methylethyl)-phenyl |
| 1730. | allyl | 4-(2-fluoro-1-methylethyl)-phenyl |
| 1731. | allyl | 4-((S)-2-fluoro-1-methylethyl)-phenyl |
| 1732. | allyl | 4-((R)-2-fluoro-1-methylethyl)-phenyl |
| 1733. | allyl | 4-(2,2-difluoro-1-methylethyl)-phenyl |
| 1734. | allyl | 4-((S)-2,2-difluoro-1-methylethyl)-phenyl |
| 1735. | allyl | 4-((R)-2,2-difluoro-1-methylethyl)-phenyl |
| 1736. | allyl | 4-(2,2,2-trifluoro-1-methylethyl)-phenyl |
| 1737. | allyl | 4-((S)-2,2,2-trifluoro-1-methylethyl)-phenyl |
| 1738. | allyl | 4-((R)-2,2,2-trifluoro-1-methylethyl)-phenyl |
| 1739. | allyl | 4-(2-fluoro-1-fluoromethylethyl)-phenyl |
| 1740. | allyl | 4-(1-difluoromethyl-2,2-difluoroethyl)-phenyl |
| 1741. | allyl | 4-(1,1-dimethyl-2-fluoroethyl)-phenyl |
| 1742. | allyl | 4-methoxyphenyl |
| 1743. | allyl | 4-ethoxyphenyl |
| 1744. | allyl | 4-propoxyphenyl |
| 1745. | allyl | 4-isopropoxyphenyl |
| 1746. | allyl | 4-butoxyphenyl |
| 1747. | allyl | 4-(fluoromethoxy)-phenyl |
| 1748. | allyl | 4-(difluoromethoxy)-phenyl |
| 1749. | allyl | 4-(trifluoromethoxy)-phenyl |
| 1750. | allyl | 3-(trifluoromethoxy)-phenyl |
| 1751. | allyl | 4-(2-fluoroethoxy)-phenyl |
| 1752. | allyl | 4-(2,2-difluoroethoxy)-phenyl |
| 1753. | allyl | 4-(2,2,2-trifluoroethoxy)-phenyl |
| 1754. | allyl | 4-(1,1,2,2-tetrafluoroethoxy)-phenyl |
| 1755. | allyl | 4-cyclopropylphenyl |
| 1756. | allyl | 4-cyclobutylphenyl |
| 1757. | allyl | 4-cyclopentylphenyl |
| 1758. | allyl | 4-(2,2-difluorocyclopropyl)-phenyl |
| 1759. | allyl | 3,4-difluorophenyl |
| 1760. | allyl | 4-bromo-3-fluorophenyl |
| 1761. | allyl | 4-bromo-2-fluorophenyl |
| 1762. | allyl | 4-bromo-2,5-difluorophenyl |
| 1763. | allyl | 2-fluoro-4-isopropylphenyl |
| 1764. | allyl | 3-fluoro-4-isopropylphenyl |
| 1765. | allyl | 4-(1-hydroxy-1-methylethyl)-phenyl |
| 1766. | allyl | 4-(2-hydroxy-2-methylpropyl)-phenyl |
| 1767. | allyl | 4-acetylphenyl |
| 1768. | allyl | 4-carboxyphenyl |
| 1769. | allyl | 4-cyanophenyl |
| 1770. | allyl | 4-hydroxyphenyl |
| 1771. | allyl | 4-(O-benzyl)-phenyl |
| 1772. | allyl | 4-(2-methoxyethoxy)-phenyl |
| 1773. | allyl | 4-(CH₂—N(CH₃)₂)-phenyl |
| 1774. | allyl | 4-(NH—CO—NH₂)-phenyl |
| 1775. | allyl | 4-(methylsulfanyl)-phenyl |
| 1776. | allyl | 4-(fluoromethylsulfanyl)-phenyl |
| 1777. | allyl | 4-(difluoromethylsulfanyl)-phenyl |
| 1778. | allyl | 4-(trifluoromethylsulfanyl)-phenyl |
| 1779. | allyl | 4-(methylsulfonyl)-phenyl |
| 1780. | allyl | 4-(N-methoxy-N-methyl-amino)-phenyl |
| 1781. | allyl | 4-(methoxyamino)-phenyl |
| 1782. | allyl | 4-(ethoxyamino)-phenyl |
| 1783. | allyl | 4-(N-methylaminooxy)-phenyl |
| 1784. | allyl | 4-(N,N-dimethylaminooxy)-phenyl |
| 1785. | allyl | 4-(azetidin-1-yl)-phenyl |
| 1786. | allyl | 4-(2-methylazetidin-1-yl)-phenyl |
| 1787. | allyl | 4-((S)-2-methylazetidin-1-yl)-phenyl |
| 1788. | allyl | 4-((R)-2-methylazetidin-1-yl)-phenyl |
| 1789. | allyl | 4-(3-fluoroazetidin-1-yl)-phenyl |
| 1790. | allyl | 4-(3-methoxyazetidin-1-yl)-phenyl |
| 1791. | allyl | 4-(3-hydroxyazetidin-1-yl)-phenyl |
| 1792. | allyl | 4-(pyrrolidin-1-yl)-phenyl |
| 1793. | allyl | 4-(pyrrolidin-2-yl)-phenyl |
| 1794. | allyl | 4-((S)-pyrrolidin-2-yl)-phenyl |
| 1795. | allyl | 4-((R)-pyrrolidin-2-yl)-phenyl |
| 1796. | allyl | 4-(pyrrolidin-3-yl)-phenyl |
| 1797. | allyl | 4-((S)-pyrrolidin-3-yl)-phenyl |
| 1798. | allyl | 4-((R)-pyrrolidin-3-yl)-phenyl |
| 1799. | allyl | 4-(2-fluoropyrrolidin-1-yl)-phenyl |
| 1800. | allyl | 4-((S)-2-fluoropyrrolidin-1-yl)-phenyl |
| 1801. | allyl | 4-((R)-2-fluoropyrrolidin-1-yl)-phenyl |
| 1802. | allyl | 4-(3-fluoropyrrolidin-1-yl)-phenyl |
| 1803. | allyl | 4-((S)-3-fluoropyrrolidin-1-yl)-phenyl |

TABLE A-continued

| No. | R¹ | Ar |
|---|---|---|
| 1804. | allyl | 4-((R)-3-fluoropyrrolidin-1-yl)-phenyl |
| 1805. | allyl | 4-(2,2-difluoropyrrolidin-1-yl)-phenyl |
| 1806. | allyl | 4-(3,3-difluoropyrrolidin-1-yl)-phenyl |
| 1807. | allyl | 4-(2-methylpyrrolidin-1-yl)-phenyl |
| 1808. | allyl | 4-((S)-2-methylpyrrolidin-1-yl)-phenyl |
| 1809. | allyl | 4-((R)-2-methylpyrrolidin-1-yl)-phenyl |
| 1810. | allyl | 4-(3-methylpyrrolidin-1-yl)-phenyl |
| 1811. | allyl | 4-((S)-3-methylpyrrolidin-1-yl)-phenyl |
| 1812. | allyl | 4-((R)-3-methylpyrrolidin-1-yl)-phenyl |
| 1813. | allyl | 4-(1-methylpyrrolidin-2-yl)-phenyl |
| 1814. | allyl | 4-((S)-1-methylpyrrolidin-2-yl)-phenyl |
| 1815. | allyl | 4-((R)-1-methylpyrrolidin-2-yl)-phenyl |
| 1816. | allyl | 4-(1-methylpyrrolidin-3-yl)-phenyl |
| 1817. | allyl | 4-((S)-1-methylpyrrolidin-3-yl)-phenyl |
| 1818. | allyl | 4-((R)-1-methylpyrrolidin-3-yl)-phenyl |
| 1819. | allyl | 4-(2,2-dimethylpyrrolidin-1-yl)-phenyl |
| 1820. | allyl | 4-(3,3-dimethylpyrrolidin-1-yl)-phenyl |
| 1821. | allyl | 4-(2-trifluoromethylpyrrolidin-1-yl)-phenyl |
| 1822. | allyl | 4-((S)-2-trifluoromethylpyrrolidin-1-yl)-phenyl |
| 1823. | allyl | 4-((R)-2-trifluoromethylpyrrolidin-1-yl)-phenyl |
| 1824. | allyl | 4-(3-trifluoromethylpyrrolidin-1-yl)-phenyl |
| 1825. | allyl | 4-((S)-3-trifluoromethylpyrrolidin-1-yl)-phenyl |
| 1826. | allyl | 4-((R)-3-trifluoromethylpyrrolidin-1-yl)-phenyl |
| 1827. | allyl | 4-(2-oxopyrrolidin-1-yl)-phenyl |
| 1828. | allyl | 4-(2-oxo-oxazolidin-3-yl)-phenyl |
| 1829. | allyl | 4-(piperidin-1-yl)-phenyl |
| 1830. | allyl | 4-(2-methylpiperidin-1-yl)-phenyl |
| 1831. | allyl | 4-((S)-2-methylpiperidin-1-yl)-phenyl |
| 1832. | allyl | 4-((R)-2-methylpiperidin-1-yl)-phenyl |
| 1833. | allyl | 4-(piperazin-1-yl)-phenyl |
| 1834. | allyl | 4-(4-methylpiperazin-1-yl)-phenyl |
| 1835. | allyl | 4-(morpholin-4-yl)-phenyl |
| 1836. | allyl | 4-(thiomorpholin-4-yl)-phenyl |
| 1837. | allyl | 4-(1-oxo-thiomorpholin-4-yl)-phenyl |
| 1838. | allyl | 4-(1,1-dioxo-thiomorpholin-4-yl)-phenyl |
| 1839. | allyl | 4-(pyrrol-1-yl)-phenyl |
| 1840. | allyl | 4-(pyrrol-2-yl)-phenyl |
| 1841. | allyl | 4-(pyrrol-3-yl)-phenyl |
| 1842. | allyl | 4-(1-methylpyrrol-2-yl)-phenyl |
| 1843. | allyl | 4-(1-methylpyrrol-3-yl)-phenyl |
| 1844. | allyl | 4-(furan-2-yl)-phenyl |
| 1845. | allyl | 4-(furan-3-yl)-phenyl |
| 1846. | allyl | 4-(thiophen-2-yl)-phenyl |
| 1847. | allyl | 4-(thiophen-3-yl)-phenyl |
| 1848. | allyl | 4-(5-propylthien-2-yl)-phenyl |
| 1849. | allyl | 4-(pyrazol-1-yl)-phenyl |
| 1850. | allyl | 4-(pyrazol-3-yl)-phenyl |
| 1851. | allyl | 4-(pyrazol-4-yl)-phenyl |
| 1852. | allyl | 4-(1-methyl-1H-pyrazol-4-yl)-phenyl |
| 1853. | allyl | 4-(1-ethyl-1H-pyrazol-4-yl)-phenyl |
| 1854. | allyl | 4-(1-methyl-1H-pyrazol-5-yl)-phenyl |
| 1855. | allyl | 4-(1H-imidazol-2-yl)-phenyl |
| 1856. | allyl | 4-(imidazol-1-yl)-phenyl |
| 1857. | allyl | 4-(1-methylimidazol-2-yl)-phenyl |
| 1858. | allyl | 4-(oxazol-2-yl)-phenyl |
| 1859. | allyl | 4-(oxazol-4-yl)-phenyl |
| 1860. | allyl | 4-(oxazol-5-yl)-phenyl |
| 1861. | allyl | 4-(isoxazol-3-yl)-phenyl |
| 1862. | allyl | 4-(isoxazol-4-yl)-phenyl |
| 1863. | allyl | 4-(isoxazol-5-yl)-phenyl |
| 1864. | allyl | 4-([1,2,3]-triazol-1-yl)-phenyl |
| 1865. | allyl | 4-([1,2,4]-triazol-1-yl)-phenyl |
| 1866. | allyl | 4-([1,2,3]-triazol-2-yl)-phenyl |
| 1867. | allyl | 4-(4H-[1,2,4]-triazol-3-yl)-phenyl |
| 1868. | allyl | 4-([1,2,4]-triazol-4-yl)-phenyl |
| 1869. | allyl | 4-(2H-[1,2,3]-triazol-4-yl)-phenyl |
| 1870. | allyl | 4-(4-methyl-4H-[1,2,4]-triazol-3-yl)-phenyl |
| 1871. | allyl | 4-(2-methyl-2H-[1,2,3]-triazol-4-yl)-phenyl |
| 1872. | allyl | 4-([1,3,4]-oxadiazol-2-yl)-phenyl |
| 1873. | allyl | 4-([1,2,4]-oxadiazol-3-yl)-phenyl |
| 1874. | allyl | 4-([1,2,4]-oxadiazol-5-yl)-phenyl |
| 1875. | allyl | 4-([1,2,3]-oxadiazol-4-yl)-phenyl |
| 1876. | allyl | 4-([1,2,3]-oxadiazol-5-yl)-phenyl |
| 1877. | allyl | 4-([1,2,3]-thiadiazol-4-yl)-phenyl |
| 1878. | allyl | 4-(1H-tetrazol-5-yl)-phenyl |
| 1879. | allyl | 4-(tetrazol-1-yl)-phenyl |
| 1880. | allyl | 4-(2-methyl-2H-tetrazol-5-yl)-phenyl |
| 1881. | allyl | 4-(1-methyl-1H-tetrazol-5-yl)-phenyl |

TABLE A-continued

| No. | R¹ | Ar |
|---|---|---|
| 1882. | allyl | 4-furazan-3-yl-phenyl |
| 1883. | allyl | 4-(pyrid-2-yl)-phenyl |
| 1884. | allyl | 4-(pyrid-3-yl)-phenyl |
| 1885. | allyl | 4-(pyrid-4-yl)-phenyl |
| 1886. | allyl | 4-(pyrimidin-2-yl)-phenyl |
| 1887. | allyl | 4-(pyrimidin-4-yl)-phenyl |
| 1888. | allyl | 4-(pyrimidin-5-yl)-phenyl |
| 1889. | allyl | 5-isopropylthiophen-2-yl |
| 1890. | allyl | 2-chlorothiophen-5-yl |
| 1891. | allyl | 2,5-dichlorothiophen-4-yl |
| 1892. | allyl | 2,3-dichlorothiophen-5-yl |
| 1893. | allyl | 2-chloro-3-nitrothiophen-5-yl |
| 1894. | allyl | 2-(phenylsulfonyl)-thiophen-5-yl |
| 1895. | allyl | 2-(pyridin-2-yl)thiophen-5-yl |
| 1896. | allyl | 2-(5-(trifluoromethyl)isoxazol-3-yl)-thiophen-5-yl |
| 1897. | allyl | 2-(2-methylthiazol-4-yl)-thiophen-5-yl |
| 1898. | allyl | 1-methyl-1H-imidazol-4-yl |
| 1899. | allyl | 1,2-dimethyl-1H-imidazol-4-yl |
| 1900. | allyl | 3,5-dimethylisoxazol-4-yl |
| 1901. | allyl | thiazol-2-yl |
| 1902. | allyl | 4-methylthiazol-2-yl |
| 1903. | allyl | 4-isopropylthiazol-2-yl |
| 1904. | allyl | 4-trifluoromethylthiazol-2-yl |
| 1905. | allyl | 5-methylthiazol-2-yl |
| 1906. | allyl | 5-isopropylthiazol-2-yl |
| 1907. | allyl | 5-trifluoromethylthiazol-2-yl |
| 1908. | allyl | 2,4-dimethylthiazol-5-yl |
| 1909. | allyl | 2-acetamido-4-methylthiazol-5-yl |
| 1910. | allyl | 4H-[1,2,4]triazol-3-yl |
| 1911. | allyl | 5-methyl-4H-[1,2,4]triazol-3-yl |
| 1912. | allyl | 4-methyl-4H-[1,2,4]triazol-3-yl |
| 1913. | allyl | 5-isopropyl-4H-[1,2,4]triazol-3-yl |
| 1914. | allyl | 5-trifluoromethyl-4H-[1,2,4]triazol-3-yl |
| 1915. | allyl | 4,5-dimethyl-4H-[1,2,4]triazol-3-yl |
| 1916. | allyl | 5-isopropyl-4-methyl-4H-[1,2,4]triazol-3-yl |
| 1917. | allyl | 5-trifluoromethyl-4-methyl-4H-[1,2,4]triazol-3-yl |
| 1918. | allyl | [1,3,4]thiadiazol-2-yl |
| 1919. | allyl | 5-methyl-[1,3,4]thiadiazol-2-yl |
| 1920. | allyl | 5-isopropyl-[1,3,4]thiadiazol-2-yl |
| 1921. | allyl | 5-trifluoromethyl-[1,3,4]thiadiazol-2-yl |
| 1922. | allyl | 3-bromo-2-chloropyrid-5-yl |
| 1923. | allyl | 2-(4-morpholino)-pyrid-5-yl |
| 1924. | allyl | 2-phenoxypyrid-5-yl |
| 1925. | allyl | (2-isopropyl)-pyrimidin-5-yl |
| 1926. | allyl | (5-isopropyl)-pyrimidin-2-yl |
| 1927. | allyl | 8-quinolyl |
| 1928. | allyl | 5-isoquinolyl |
| 1929. | allyl | 2-(trifluoroacetyl)-1,2,3,4-tetrahydroisoquinolin-7-yl |
| 1930. | allyl | 5-chloro-3-methylbenzothiophen-2-yl |
| 1931. | allyl | 3,4-dihydro-4-methyl-2H-benzo[b][1,4]oxazinyl |
| 1932. | allyl | benzothiazol-6-yl |
| 1933. | allyl | benzo[2,1,3]oxadiazol-4-yl |
| 1934. | allyl | 5-chlorobenzo[2,1,3]oxadiazol-4-yl |
| 1935. | allyl | 7-chlorobenzo[2,1,3]oxadiazol-4-yl |
| 1936. | allyl | benzo[2,1,3]thiadiazol-4-yl |
| 1937. | allyl | 6-chloroimidazo[2,1-b]thiazolyl |

Compounds I of the present invention can be synthesized as outlined in the synthetic routes A, B and C below.

Scheme 1:

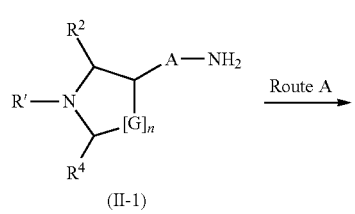

(II-1)

Route A

-continued

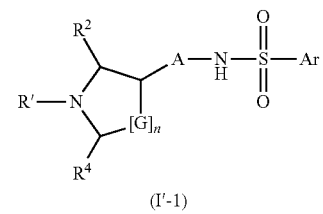

(I'-1)

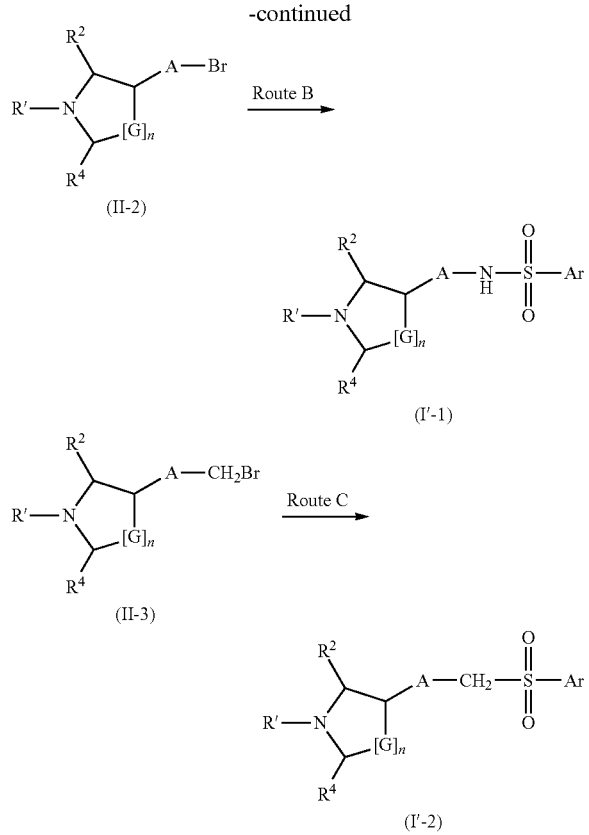

In scheme 1, A, Ar, G, n, $R^2$, and $R^4$ are as defined above. R' is either $R^1$ or is a precursor of $R^1$.

Route A

In route A, the amino compound (II-1) is reacted with a suitable sulfonic acid derivative to give the sulfonamide (I-1) (E=NH). A suitable sulfonic acid derivative is e.g. the sulfonyl chloride Ar—$SO_2$Cl. The sulfonation reaction is preferably carried out in the presence of a base, according to standard procedures in the art. In the reaction depicted in the above scheme 1, the sulfonation takes place under the reaction conditions which are customary for preparing arylsulfonamide compounds or arylsulfonic esters, respectively, and which are described, for example, in J. March, Advanced Organic Chemistry, $3^{rd}$ edition, John Wiley & Sons, New York, 1985 page 444ff and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction with Cl—$SO_2$—Ar is customarily carried out in the presence of an auxiliary base. Suitable bases are inorganic bases, such as sodium carbonate or potassium carbonate, or sodium hydrogencarbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound (II-1).

Prior to the sulfonation reaction, the radical $NH_2$ can be converted into a $NR^{5'}$ group, in which $R^{5'}$ has the meanings different from hydrogen which are specified for $R^5$ (not shown in scheme 1).

If in the resulting sulfonamide (I'-1) R' is not the desired radical $R^1$ but a precursor thereof, the compound can be modified as outlined below to obtain the desired substituent $R^1$. A precursor is a radical which can be easily removed and replaced by the desired group $R^1$ or which can be modified to give $R^1$. The precursor can also be an N-protective group.

If R' is allyl, the allyl group can be cleaved to obtain a compound wherein R' is hydrogen. The cleavage of the allyl group is achieved, for example, by reacting compound (I'-1) [R'=allyl] with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis(triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391).

If R' is benzyl, this substituent may also be cleaved to obtain a compound (I'-1) wherein R' is H. The reaction conditions for the cleavage are known in the art. Typically, the benzyl group is removed by a hydrogenation reaction in the presence of a suitable Pd catalyst, such as Pd on carbon or palladium hydroxide.

R' can also be a protective group. The protective group may be removed to yield a compound (I'-1) wherein R' is H. Suitable protective groups are known in the art and are, for example, selected from tert-butoxycarbonyl (boc), benzyloxycarbonyl (Cbz), 9-fluorenylmethoxycarbonyl (Fmoc), triphenylmethyl (Trt) and nitrobenzenesulfenyl (Nps). A preferred protective group is boc. The protective groups can be removed by known methods, such as treatment of the protected amine with an acid, e.g halogen acid, such as HCl or HBr, or trifluoroacetic acid, or by hydrogenation, optionally in the presence of a Pd catalyst.

The resulting compound, wherein R' is H, can then be reacted, in a known manner, in the sense of an alkylation, with a compound $R^1$—X. In this compound, $R^1$ is $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl or $C_3$-$C_6$-cycloalkyl-$C_1$-$C_4$-alkyl and X is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

The alkylation can also be achieved, in the sense of a reductive amination, by reacting the compound (I'-1), wherein R'=H, with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

In case R' is hydrogen, the resulting sulfonamide (I'-1) can further be reacted with an acyl halide to obtain a compound of the formula I wherein $R^1$ is $C_1$-$C_3$-alkylcarbonyl. The carbonyl group in these compounds can be reduced with diborane to obtain compounds of the general formula I, wherein $R^1$ is $C_2$-$C_4$-alkyl. The carbonyl group can also be reacted with a fluorinating agent to obtain a compound I wherein $R^1$ is 1,1-difluoroalkyl. Acylation and reduction can be achieved by standard methods, which are discussed in Jerry March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

Route B

In route B, the bromo substituted compound (II-2) is reacted with an appropriate sulfonamide $ArSO_2NHR^5$ to give the sulfonamide (I-1). The reaction is generally carried out under activating conditions, e.g. under microwave conditions. Pd, especially Pd(0), or Cu catalysts may also be used for coupling (see, e.g. Org. Lett. 2000, 2, 1101; J. Am. Chem. Soc. 2002, 124, 6043; Org. Lett. 2003, 5, 4373; Tetrahedron Lett. 2003, 44, 3385). Examples for suitable Pd (0) catalysts are tetrakis(triphenylphosphine)palladium(0) and $Pd_2(dba)_3$ (tris(dibenzylideneacetone)-dipalladium(0)), which are customarily used in the presence of a tri(substituted)phosphine, e.g. a triarylphosphine such as triphenylphosphine, tritolylphosphine or xantphos, tri(cyclo)alkylphosphine such as tris-n-butylphosphine, tris(tert.-butyl)phosphine or tris(cyclohexylphosphine). This route is especially useful in cases where the corresponding sulfonyl chloride is not available.

Alternatively, the bromo substituent may be replaced by an amino substituent, e.g. by reacting with a benzophenone imine or with lithium bis(trimethylsilyl)amide in the presence of a palladium(0) compound such as tris(dibenzylideneacetone)dipalladium(0) in the presence of a tri(substituted) phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexylphosphine), preferably in the presence of a base such as sodium hydride according to the method described in (see, e.g. J. Org. Chem., 68 (2993) pp 8274-8276, J. Org. Chem. 2000, 65, 2612). The resulting amino compound may then be subjected to the sulfonation reaction of route A.

Route C

In route C, compound (II-3) is reacted with a mercapto compound HS—Ar in the presence of a base, such as sodium hydride or sodium alkoxide or with an alkali metal salt thereof thereby yielding a thioether compound. The thioether moiety is then oxidized to a sulfone moiety, e.g. by oxone, to yield the sulfone (I'-2).

The substituent Ar can be varied by either using different sulfonyl chlorides or by modifying the substituents of the cyclic group Ar after the formation of the sulfonamide (I'-1) by known methods. For example, a bromine substituent of the Ar group may be replaced by an N-bound pyrrolidinyl group according to the procedure described in Tetrahedron Asym. 1999, 10, 1831. A bromine substituent of the Ar group may be replaced by an isopropenyl group according to a Stille coupling where the bromo compound is reacted with an alkenyl tributyl stannate in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). The isopropenyl group may then be converted into the isopropyl group by known hydrogenation methods.

Compounds of formula (II) (II-1, II-2 and II-3) can be synthesized by as shown below.

1. Synthesis of Compounds (II-1)

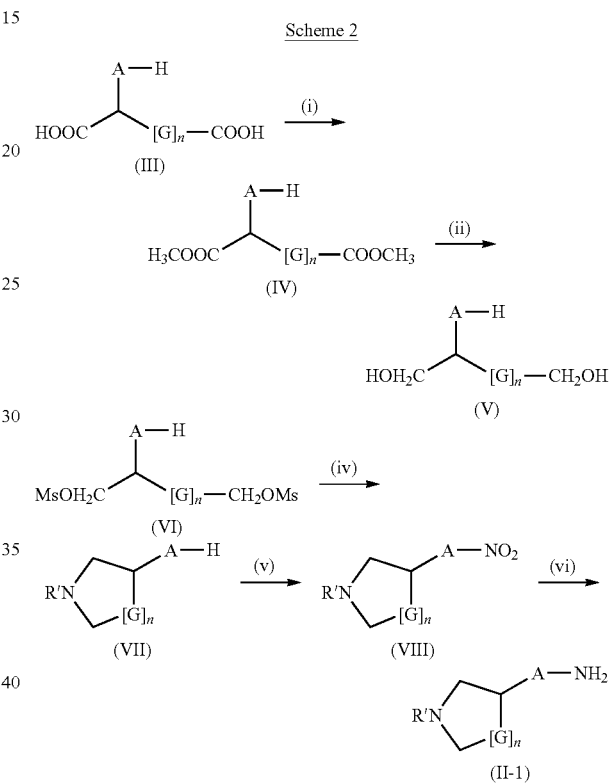

Scheme 2

In scheme 2, A, G, n and R' are as defined above.

The conversion of the acid (III) into its methyl ester (IV) is performed by standard techniques, e.g. as described in Jerry March, Advanced Organic Chemistry, John Wiley, $3^{rd}$ edition, page 348ff. For instance, the acid is transformed into the corresponding acid chloride, e.g by reacting it with $SOCl_2$. The chloride is then converted into the ester by reaction with methanol.

The reduction in step (ii) is suitably carried out under standard conditions for the conversion of carboxylic esters into alcohols. Appropriate reaction conditions and reducing agents are described, e.g. in Jerry March, Advanced Organic Chemistry, John Wiley, $3^{rd}$ edition, page 1093ff. Typical reducing agents are metal hydrides and complex hydrides. Examples of suitable metal hydrides include $BH_3$, 9-BBN, $AlH_3$ and AlH(i-Bu)$_2$ (DIBAL-H), suitably in the presence of complexing solvents, such as tetrahydrofuran and diethylether. Complex hydrides are e.g. $NaBH_4$, $LiAlH_4$ and LiAlH(OR)$_3$, where R is $C_1$-$C_4$-alkyl, such as methyl, ethyl, isobutyl or tert-butyl. A preferred reducing agent is $LiAlH_4$. The reduction is suitably carried out in complexing solvents, such as open-chain and cyclic ethers, e.g. tetrahydrofuran, diethyl ether, dipropyl ether, diisopropyl ether, dibutyl ether and methylbutyl ether. A preferred solvent is tetrahydrofuran.

In the mesylation step (iii), the alcohol functionality is converted into a better leaving group. The mesylation is performed under standard conditions, e.g. by reacting the alcohol with methansulfonyl chloride in the presence of a base. Suitable bases are, among others, alkyl amines, such as diethyl amine, triethyl amine and ethyldiisopropyl amine. In this step, other functionalties representing good leaving groups, such as trifluoroacetate, other alkylsulfonates, arylsulfonates, e.g. tosylates, alkyl sulfates and the like tosylate, may be introduced instead of the methansulfonyl group.

In the cyclisation step (iv), compound (VI) or a suitable derivative thereof is reacted with a primary amine $NH_2R'$. In case the primary amine is a liquid, it may also be used as solvent, no further solvent being necessary. If the amine is visquous or a solid, the reaction is advantageously carried out in a suitable solvent.

The reaction of step (v) takes place under the reaction conditions which are customary for a nitration reaction on an aromatic radical and which are described, for example, in Jerry March, Advanced Organic Chemistry, John Wiley, 3$^{rd}$ edition, page 468ff, Tetrahedron 1999, 55(33), pp. 10243-10252, J. Med. Chem. 1997, 40(22), pp. 3679-3686 and Synthetic Communications, 1993, 23(5), pp. 591-599. For example, compound (VII) is reacted with concentrated nitric acid or a nitrate, such as potassium or sodium nitrate, in the presence of concentrated sulfuric acid. The resulting product (VIII) may in the form of different regioisomers (e.g. ortho, meta or para, if A is phenyl or a 6-membered hetaryl. In the case of A being phenyl or a 6-membered hetaryl, the para-nitro compound generally predominates. However, some ortho product may also be obtained, whereas the meta product is not produced at all or only in neglectable amounts. By separating ortho and para products, compounds of formula I, wherein A is 1,4-bound aryl or hetaryl as well as compounds I, wherein A is 1,2-bound aryl or hetarly, are accessible via the reaction path shown in scheme 2.

In step (vi), the nitro group in (VIII) is reduced to an $NH_2$ group. Subsequently, the $NH_2$ group can be converted into a —$NR^{5'}$ group, in which $R^{5'}$ has the meanings different from hydrogen which are specified for $R^5$. The reaction conditions which are required for step (vi) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound VII with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2$ $(P(phenyl)_3)_2$, or $CoCl_2$, (see Ono et al. Chem. Ind. (London), 1983 p. 480), or using $NaBH_2S_3$ (see Lalancette at al. Can. J. Chem. 49, 1971, p. 2990), with it being possible to carry out these reductions, depending on the given reagent, in substance or in a solvent or diluent. Alternatively, the reduction can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of nitro compound, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VII with tin(II) chloride is preferably carried out in an inert organic solvent, preferably an alcohol such as methanol, ethanol, isopropanol or butanol.

For compounds, wherein n is 1 and A is phenylene (i.e. (I) is N-(pyrrolidin-3-yl)-phenylsulfonamide), starting compound (III) is e.g. commercially available (S) or (R) phenylsuccinic acid or a racemic mixture thereof. By starting from enantiomerically pure (S)- or (R)-compound (III), pure (S)- or (R) may be obtained:

a) (S) Isomer

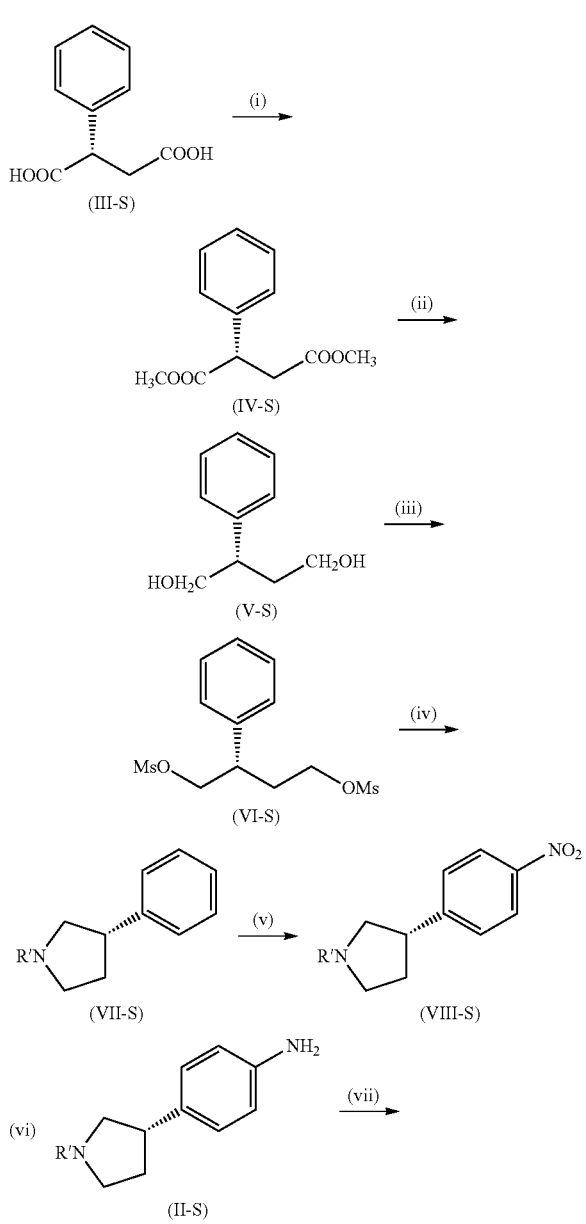

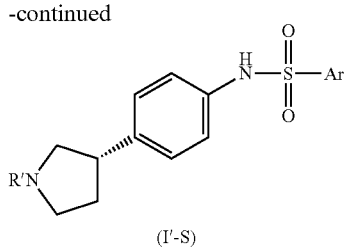

(I'-S)

In step (i), commercially available (S)-phenylsuccinic acid (II-S) is converted into the methyl ester (III); this is reduced to the alcohol (IV) which is reacted with methylsulfonylchloride. Cyclisation with a primary amine gives the phenyl pyrrolidine (VI). The phenyl group is first nitrated, then the nitro group is reduced to an amino function which is reacted with a sulfonyl chloride to give the desired sulfonyl amide (I'-S).

a) (R) Isomer

The (R)-isomer can be obtained in an analogous way starting from commercially available (R)-phenylsuccinic acid (III-R):

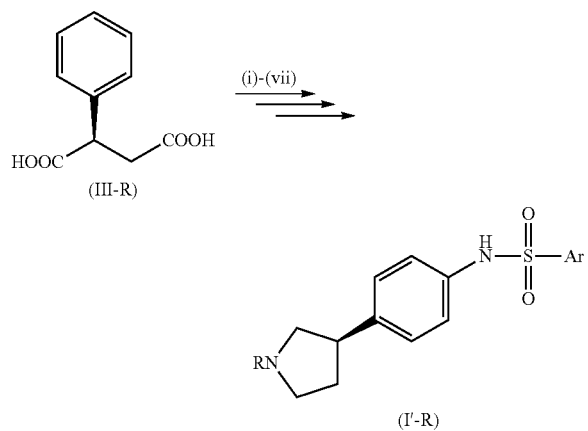

c) Isomeric Mixtures

Isomeric mixtures of compound I'-S and I'-R can be obtained by starting from racemic III or from a mixture of III-S and III-R.

The skilled person will appreciate that the synthesis described in scheme 2 is also suitable for the preparation of compounds (II) and consequently for compounds (I), wherein $R^2$, $R^3$ and $R^4$ are different from H, e.g. by starting from the correspondingly substituted compound (III). The same applies to the synthesis of enantiomerically pure (I) which can be synthesized by starting from the corresponding enantiomer (III).

2. Synthesis of Compounds (II-2)

Compounds of formula (II-2) can be synthesized by carrying out in step (v) of scheme 2 a halogenation instead of a nitration. Halogenation reactions of aryl and hetaryl groups are widespread standard methods and are, e.g., discussed in Jerry March, Advanced Organic Chemistry, John Wiley, 3$^{rd}$ edition page 476 ff.

3. Synthesis of Compounds (II-3)

The synthesis of these compounds also belongs to standard reaction methods and can be performed by monohalogenating the methyl group of a methyl-substituted aryl or hetaryl compound.

4. Specific Syntheses 4.1 Synthesis of Compounds, Wherein n is 5 (Pyrrolidinyl Sulfone Derivatives)

4.1.1

Scheme 3:

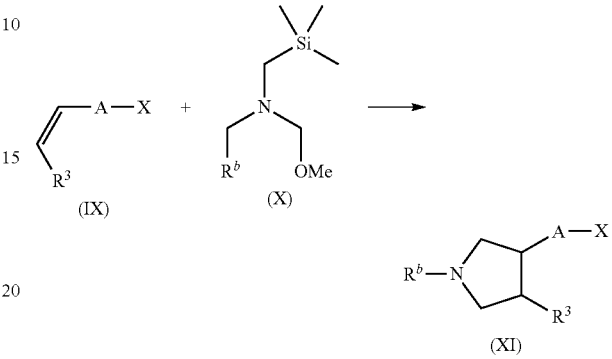

In scheme 3, A and $R^3$ are as defined above.

The pyrrolidine ring is also available by a [3+2] dipolar cycloaddition of a non-stabilized azomethine ylid to a 1-alkenylaryl or hetaryl derivative (IX) (e.g. a vinyl benzene, $R^3$=H). This procedure is generally described in J. Org. Chem. 1987, 52, 235. The precursor of the ylid, the amine $N(CH_2R^b)(CH_2SiMe_3)(CH_2OCH_3)$ (X), is commercially available or can be synthesized from $NH_2(CH_2R^b)$, $Me_3SiCH_2Cl$ and HCHO in the presence of methanol.

The 1-alkenyl-(hetero)aromatic compound (IX) can be synthesized e.g. by a Stille coupling of a halogeno benzene, e.g. a bromo benzene, with the corresponding alkenyl tributyl stannate, such as vinyl or isobutenyl tributyl stannate, in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). By choosing a special Stille isomer (e.g. cis- or trans-isobutenyl tributyl stannate), the corresponding cis- or trans alkyl phenyl pyrrolidine can be prepared selectively.

Alternatively, the 1-alkenyl-(hetero)aromatic compound (IX) can be synthesized by a Wittig reaction of aryl aldehyde with a Wittig reagent such as $PPh_3$=CHR(R is H, or $C_1$-$C_3$-alkyl). Conditions for the Wittig reaction are well known in the art and are, e.g. discussed in Jerry March, Advanced Organic Chemistry, John Wiley, 3$^{rd}$ edition, page 845ff.

Advantageously, the 1-(hetero)alkenyl-aromatic compound (IX) further carries a nitro group or another halogeno substituent (X=$NO_2$ or halogen). In this case, the subsequent reaction steps can be carried out as outlined in route A or B. If X=H, the A ring may be first nitrated as described in scheme 2, step (v) and then subjected to the reaction of scheme 2, step (vi) and scheme 1, route A; or ring A may be halogenated and then subjected to the procedure of route B.

The group $CH_2R^b$ of the precursor amine advantageously corresponds either to the desired group $R^1$ of the final compound I or is alternatively a cleavable group, such as benzyl, which can be removed to give the N-unsubstituted pyrrolidine. The latter can subsequently be functionalized as described above (see route A).

The synthesis of hetarylpyrrolidines is e.g. described in Chem. Pharm. Bull., 1985, 33, 2762-66; J. Heterocyclic Chemistry, 1996, 1995-2005; J. Heterocyclic Chemistry, 2001, 38, 1039-1044; Tetrahedron Letters, 1992, 33, 44, 6607-10; Heterocycles, 1998, 48, 12, 2535-2541 for A being pyridylene. The synthesis of vinyl-substituted thiophene and thiazol is e.g. described in Bioorg. Med. Chem. 1999, 7(5), 665.

4.1.2

Scheme 4:

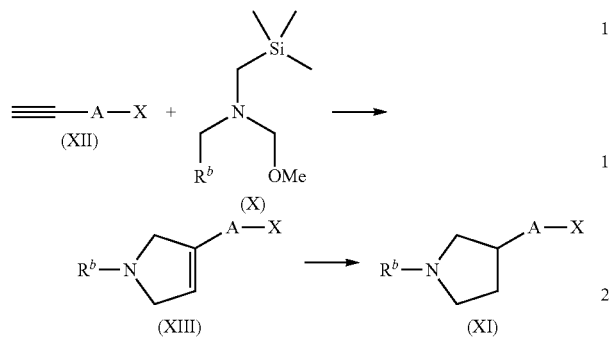

Phenylpyrrolidines can also be prepared by a [3+2] dipolar cycloaddition of a non-stabilized azomethine ylid to a 1-alkynylbenzene (XII) (see, e.g., Tetrahedron 1996, 52, 59). The resulting pyrroline (XIII) or the final product (I') is then hydrogenated to the corresponding pyrrolidine (XI). If the hydrogenation is carried out under chiral conditions, e.g. by using chiral catalysts, the enantiomerically pure phenylpyrrolidine compounds can be obtained. Chiral hydrogenation catalysts are well known in the art. The subsequent conversion to the desired sulfonamide can be carried out as described in route A or B.

4.1.3

Alternatively, hetarylpyrrolidinyl compounds can be prepared from hetaryl halides which are subjected to a Pd-mediated cross coupling with an organozinc pyrrolidine compound. This process is described in further detail below in route F. In this alternative, too, the hetaryl halide advantageously carries a nitro group. In this case, the conversion to the desired sulfonamides can be carried out as described in route A. Alternatively, the hetaryl halide carries a halogen atom. In this case, the conversion to the desired sulfonamides can be achieved as described in route B.

4.1.4

Compounds I, wherein n is 1, G is $CH_2$, A is 1,3-bound arylene or hetarylyene and E is NH, can be prepared in a similar way compared to the 1,4-bound compound from a 3-aminoaryl or hetaryl-pyrrolidine which is reacted with an appropriate sulfonyl chloride. Advantageously, the N-atom of the pyrrolidine ring is protected by a urethane-based protective group, like benzyloxycarbonyl (cbz) and tert-butyloxycarbonyl (boc). This group may be replaced by the desired substituent $R^1$ by treating the compound with an acid, such as hydrochloric acid, thus removing the acid group, and then introducing the desired substituent as described in route A.

The 3-aminoaryl or hetaryl-pyrrolidine may be prepared by way of a Heck reaction where a protected pyrroline is reacted with 1-iodo-3-nitrobenzene under typical Heck conditions. Catalytic hydrogenation of the pyrroline double bond and reduction of the nitro group according to the procedure described in scheme 2 yields the desired product.

4.2 Synthesis of N-(azetidin-3-yl)-sulfonamides

Compounds I, wherein n is 0 (azetidine compounds) can be synthesized as follows:

Scheme 5:

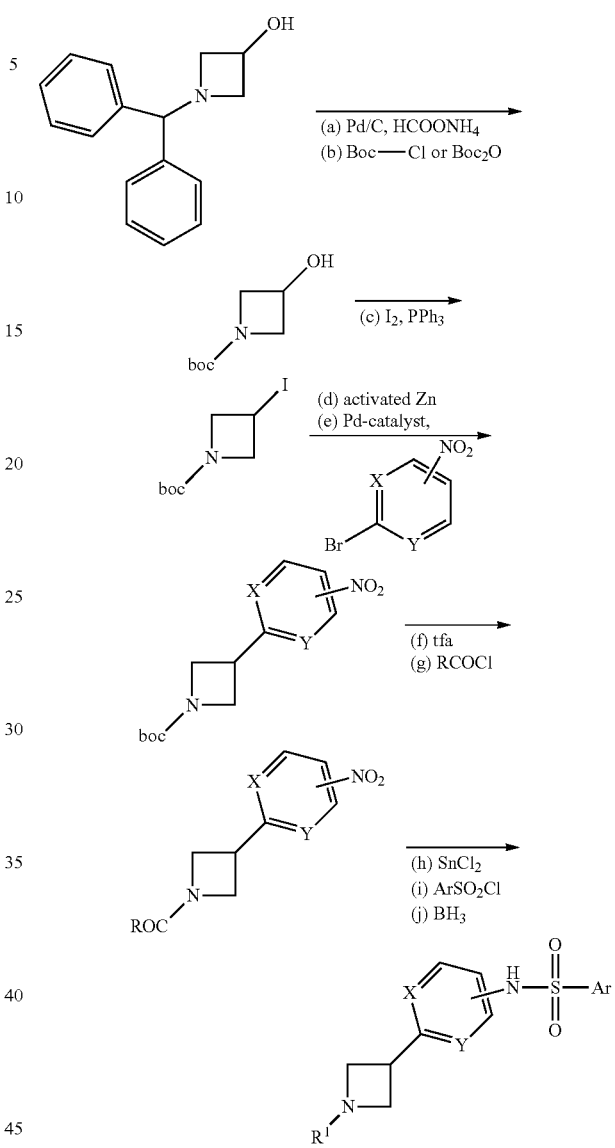

In scheme 5, Ar and R1 are as defined above. X and Y are, independently of each other, CH or N.

Starting from 1-benzhydryl-azetidin-3-ol, Pd-mediated deprotection of the amine (Tetrahedron 2002, 58, 9865-9870), carbamate formation and subsequent halogenation generate an intermediate that undergoes Zn insertion (Tetrahedron 1987, 43, 2203-2212; J. Org. Chem. 1988, 53, 2390-2392). The thus obtained organozinc species can react with an appropriate 2-halo-nitro-ring (Synlett 1998, 4, 379-380; J. Am. Chem. Soc. 2003, 125, 12527-12530) to give the nitroaryl-azetidine core. If one utilizes a 2-halo-halo-ring, there is also the possibility to realize the direct coupling between the aryl-azetidine halide and the appropriate sulfonamides (Org. Lett. 2000, 2, 1101-1104; J. Am. Chem. Soc. 2002, 124, 6043-6048; Org. Lett. 2003, 5, 4373-4376; Tetrahedron Lett. 2003, 44, 3385-3386). The amine may be regenerated by cleavage of the carbamate (e.g. with trifluoroacetic acid in the case of a Boc carbamate) and subsequently converted into an amide by reaction with the appropriate acyl chloride. The nitro group can be reduced to the amine via tin chloride or catalytic hydrogenation (e.g. Pd—C) and then converted to the desired sulfonamide by reaction with the appropriate sulfonyl chloride in the presence of a base such as pyridine. Ultimate reduction of the amide via hydroboration furnishes the final compounds.

Of course, the reaction also applies to compounds wherein the (hetero)aromatic ring bound to thr azetidine group is a 5-membered heterocyclic radical, e.g. thienyl.

4.3 Synthesis of N-(piperidin-3-yl)-sulfonamides

Further to the above-described syntheses (routes A, B and C), compounds I, wherein n is 2 and E is $NR^5$ (piperidin-3-yl sulfonamides) may be prepared by starting from commercially available 3-aryl or 3-hetaryl piperidines. These starting compounds may then be converted into the amino-substituted or halogenated derivative and then be subjected to the synthetic path of route A or B.

A skilled person will readily appreciate that compounds of the formula I can also be obtained from structurally similar compounds by functional group interconversion. In particular N-bound radicals $R^a$ can be introduced into compounds of the formula I by reacting the corresponding halogen compound, i.e. a compound of the formula I, which instead of $R^a$ carries a halogen atom, in particular a bromine or iodine atom, with a primary or secondary amine in the presence of a base, preferably also in the presence of a palladium catalyst in terms of a Buchwald-Hartwig reaction.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The sulfonylchlorides Cl—$SO_2$—Ar are either commercially available or can be prepared according to standard synthetic methods. Sulfonylchlorides containing a fluorinated radical $R^a$ may be prepared by different synthetic routes, e.g. by reacting suitable hydroxy or oxo precursor (e.g. a compound Cl—$SO_2$—Ar, carrying a hydroxy or oxo substituted radical) with fluorinating reagents like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl) amine; Journal of Fluorine Chemistry, 1989, 43, 371-377).

More conventionally, the hydroxy group of an aromatic compound which carries a hydroxy substituted radical but not a chlorosulfonyl group, is trans-formed into a leaving group which is then replace by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorous pentachloride (Eur. J. Med. Chem., 2002, 36, 809-828) and the like, yields the desired sulfonylchloride (Tetrahedron Letters, 1991, 33, 50 7787-7788)) Sulfonylchlorides may also be prepared by diazotation of suitable amine precursor Ar—$NH_2$ with sodium nitrite under acidic conditions and reaction with sulfur dioxide in acetic acid (scheme (iii); J. Org. Chem., 1960, 25, 1824-26;); by oxidation of suitable heteroaryl-thiols HS—Ar or heteroaryl-benzyl-thioethers $C_6H_5$—$CH_2$—S—Ar with chlorine (Synthesis, 1998, 36-38; J. Am. Chem. Soc., 1950, 74, 4890-92;) directly to the corresponding sulfonyl chlorides. The further are known in the art or may be prepared by standard methods. E.g. mercapto-pyrimidines or pyrimidinyl-benzylthioether precursors can e.g. be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645).

In the following schemes 6 to 8 several routes are shown which are suitable to prepare benzenesulfonyl chlorides carrying a fluorinated propyl radical.

Scheme 6:

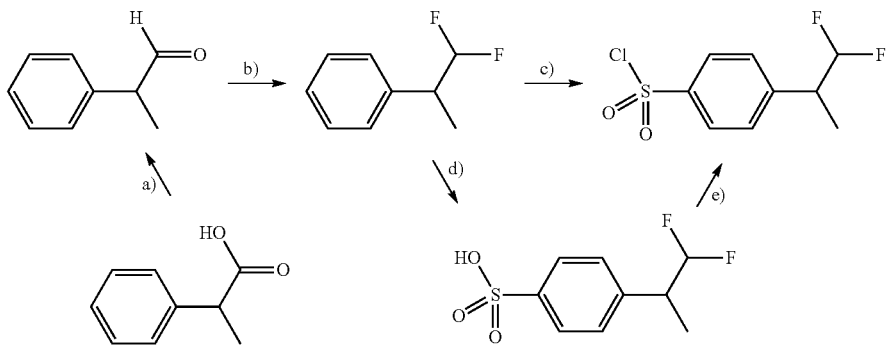

The 4-(1,1-difluoropropan-2-yl)benzene-1-sulfonyl chloride intermediate can be prepared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, $SO_2Cl_2$). The ester can be reduced to the corresponding 2-phenyl propanal by a reducing agent such as DIBAL (diisobutylaluminium hydride). The aldehyde is converted to the 1,1-difluoro-2-propyl derivative by reaction with a suitable fluorinating reagent like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 6 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 7:

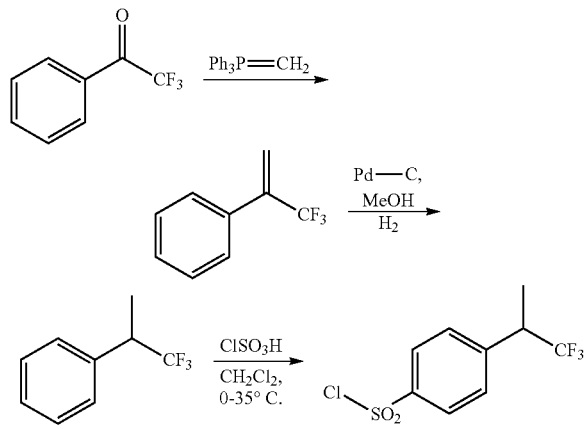

4-(1,1,1-Trifluoropropan-2-yl)benzene-1-sulfonyl chloride intermediate can be prepared from the commercially available 2,2,2-trifluoro-1-phenylethanone by a synthetic route shown in scheme 7. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 6.

The synthesis of scheme 7 can also be performed using a chiral catalyst for the alkene hydrogenation to allow the preparation of the corresponding chiral 4-(1,1,1-trifluoropropan-2-yl)benzene-1-sulfonyl chlorides.

Scheme 8:

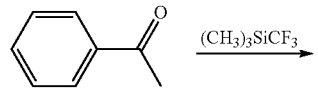

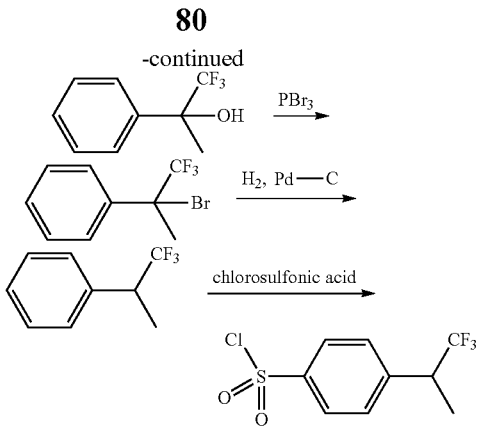

The 4-(1,1,1-trifluoropropan-2-yl)benzene-1-sulfonyl chloride can be also prepared from the commercially available 1-phenyl-ethanone by a four step procedure as shown in scheme 8. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, α1-adrenergic and/or α2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$ values) of as a rule less than 50 nM (nmol/1), preferably of less than 10 nM and, in particular of less than 5 nM. The displacement of $[^{125}I]$-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of $[^3H]SCH23390$, $[^{125}I]$ iodosulpride or $[^{125}I]$ spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distracted-ness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gillesde-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxide or d-chloroform, if not stated otherwise, on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of the Intermediates a. Preparation of Sulfonyl Chlorides a.1 4-((S)-2-Fluoro-1-methyl-ethyl)-benzenesulfonyl chloride a.1.1 Toluene-4-sulfonic acid (S)-2-phenyl-propyl ester To a solution of 20 g of (S)-(−)-2-phenyl-1-propanol in 240 ml of dichloromethane was added in portions 28 g of p-toluenesulfonyl chloride (146.8 mmol). After stirring for 18 h at room temperature, the organic phase was washed with 100 ml of water, dried over magnesium sulfate, filtered, and the solvent evaporated under reduced pressure to yield 43 g of the title compound.

$^1$H-NMR (CDCl$_3$, 400 MHz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

a.1.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethylenglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexyane/ethyl acetate 15% as eluent. 2.85 g of the desired product were isolated, containing ~25% of the elimination side product.

$^1$H-NMR (CDCl$_3$, 400 MHz): δ [ppm]7.2-7.4 (m, 5H), 4.3-4.6 (several m, 2H), 3.15 (m, 1H). 1.3 (m, 3H).

a.1.3 4-((S)-2-Fluoro-1-methyl-ethyl)-benzenesulfonyl chloride 3.5 g of ((S)-2-fluoro-1-methyl-ethyl)-benzene (25.32 mmol) were dissolved in 80 ml of dichloromethane. At 0-5° C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml of water, and the organic layer was dried over magnesium sulfate, filtered, and the solvent evaporated under reduced pressure. The crude product was purified via silica gel chromatography with n-heptane-dichloromethane (6:4) as eluent to give 1.5 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.2 4-((R)-2-Fluoro-1-methyl-ethyl)-benzenesulfonyl chloride a.2.1 Toluene-4-sulfonic acid (R)-2-phenyl-propyl ester Following the procedure analogous to that used for the synthesis of toluene-4-sulfonic acid (S)-2-phenyl-propyl ester, but using (R)-2-phenyl-1-propanol, the title compound was prepared a.2.2 ((R)-2-Fluoro-1-methyl-ethyl)-benzene The title compound was prepared as described above for the synthesis of ((S)-2-fluoro-1-methyl-ethyl)-benzene, but using toluene-4-sulfonic acid (R)-2-phenyl-propyl ester instead of toluene-4-sulfonic acid (S)-2-phenyl-propyl ester.

$^1$H-NMR (CDCl$_3$, 400 MHz): δ [ppm] 7.2-7.4 (m, 5H), 4.3-4.6 (several m, 2H), 3.15 (m, 1H). 1.3 (m, 3H).

a.2.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane, were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer dried over magnesium sulfate, filtered, and the solvent evaporated under reduced pressure. The crude product was purified via silica gel chromatography with n-heptane-dichloromethane (1:1) as eluent to give 0.261 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.3 4-(2-Fluoro-1-methyl-ethyl)-benzenesulfonyl chloride

Following the procedures analogous to that used for the preparation of 4-((S)-2-fluoro-1-methyl-ethyl)-benzenesulfonyl chloride, but starting with 2-phenyl-1-propanol in step a.3.1, the title compound was prepared.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.4 4-(2-Fluoro-1-fluoromethyl-ethyl)-benzenesulfonyl chloride a.4.1 (2-Fluoro-1-fluoromethyl-ethyl)benzene 4 g of 3-phenylglutaric acid (19.21 mmol) were suspended in 350 ml of dichloromethane. At room temperature, 6.5 g of xenon difluoride (38.42 mmol) were added and the reaction mixture was stirred at room temperature for 18 h. The organic phase was washed once with 975 ml of 6% aqueous sodium hydrogencarbonate, dried over magnesium sulfate, filtered, and the solvent evaporated. The remaining residue was distilled at a bath temperature of 123° C. at 21 mm to yield 0.78 g of the title compound that contained ~50% of 4-(2-Fluoro-1-methyl-ethyl)benzene.

$^1$H-NMR (CDCl$_3$, 400 MHz): δ [ppm] 7.2-7.4 (m, 5H), 4.6-4.8 (dd, 4H), 3.3 (m, 1H).

a.4.2 4-(2-Fluoro-1-fluoromethyl-ethyl)-benzenesulfonyl chloride

Following the procedures analogous to that used for the preparation of 4-((S)-2-fluoro-1-methyl-ethyl)-benzenesulfonyl chloride, but using 5 equivalents. of chlorosulfonic acid, 0.12 g of the title compound were obtained.

$^1$H-NMR (CDCl$_3$, 400 MHz): δ [ppm] 8.05 (d, 2H), 7.55 (d, 2H), 4.75 (dd, 4H), 3.4 (m, 1H).

a.5 4-(3,3,3-Trifluoropropyl)-benzenesulfonyl chloride 2.9 g were obtained from commercially available (3,3,3-trifluoropropyl)-benzene following the procedure used for the synthesis of 4-((S)-2-fluoro-1-methyl-ethyl)benzenesulfonyl chloride described above.

$^1$H-NMR (CDCl$_3$, 400 MHz): δ [ppm] 8.0 (d, 2H), 7.45 (d, 2H), 3.0 (t, 2H), 2.45 (m, 2H).

a.6 4-(2,2,2-Trifluoroethyl)-benzenesulfonyl chloride

The product was obtained from commercially available (2,2,2-trifluoroethyl)benzene following the procedure as described in J. Org. Chem., 1960, 25, 1824-26.

$^1$H-NMR (CDCl$_3$, 400 MHz): δ [ppm] 8.05 (d, 2H), 7.55 (d, 2H), 3.5 (q, 2H).

a.7 4-(3-Fluoropropyl)-benzenesulfonyl chloride a.7.1 (3-Fluoropropyl)-benzene 15.6 g of diethylaminosulfurtrifluoride (DAST, 96.91 mmol) were dissolved in 18 ml of dichloromethane. At 0-5° C., 12 g of 3-phenyl-1-propanol (88.1 mmol) dissolved in 30 ml of dichloromethane, were added dropwise. The reaction mixture was stirred for 18 h, and, after addition of 30 ml of dichloromethane, poured onto 100 ml of ice water. The organic layer was separated, dried over magnesium sulfate, filtered, and the solvent evaporated. The crude product was purified by distillation at a bath temperature of 106° C. at 20 mm to yield 7.4 g of the title compound.

$^1$H-NMR (CDCl$_3$, 400 MHz): δ [ppm] 7.1-7.3 (m, 5H), 4.4 (dt, 2H), 2.7 (m, 2H). 2.0 (m, 2H).

a.7.2 4-(3-Fluoropropyl)-benzenesulfonyl chloride 4.1 g of (3-fluoro-propyl)-benzene (29.67 mmol) were dissolved in 40 ml of dichloromethane. At 0-5° C., 6.91 g of chlorosulfonic acid (59.34 mmol), dissolved in 10 ml of dichloromethane, were added dropwise. The reaction mixture was stirred for 45 min at 0-5° C. and then added to a solution of 6.8 g of phosphorous pentachloride (32.63 mmol) dissolved in 50 ml of dichloromethane. The reaction mixture was stirred for 1 h at 5-10° C. The solvent was evaporated, 150 ml of diethyl ether added, washed once with 150 ml of ice water, and the organic layer dried over magnesium sulfate, filtered, and the solvent evaporated under reduced pressure. The crude product was purified via silica gel chromatography with n-heptane-dichloromethane (11:9) as eluent to give 5.5 g of the title compound.

$^1$H-NMR (CDCl$_3$, 400 MHz): δ [ppm] 7.95 (d, 2H), 7.45 (d, 2H), 4.5 (dt, 2H), 2.9 (t, 2H), 2.05 (m, 2H).

a.8 4-(2,2-Difluoro-cyclopropyl)-benzenesulfonyl chloride 2.07 g of were obtained from commercially available (2,2-difluorocyclopropyl)benzene following the procedure used for the synthesis of (3-fluoropropyl)benzenesulfonyl chloride with the exception that only 1.1 equivalents of phosphorous pentachloride were used.

$^1$H-NMR (CDCl$_3$, 400 MHz): δ [ppm] 8.0 (d, 2H), 7.45 (d, 2H), 2.85 (m, 1H), 2.0 (m, 1H), 1.75 (m, 1H).

a.9 3-Bromo-4-trifluoromethoxy-benzenesulfonyl chloride 2.0 g of 1-bromo-2-(trifluoro-methoxy)benzene (8.3 mmol) were dissolved in 30 ml of dichloromethane. At 0-5° C., 1.06 g of chlorosulfonic acid (9.13 mmol), dissolved in 3 ml of dichloromethane, were added dropwise. The reaction mixture was stirred for 30 min at room temperature. Additional 5.5 equivalents of chlorosulfonic in dichloromethane were added to drive the reaction to completion. Standard work-up was followed and silica gel chromatography with n-heptane-dichloromethane (6:4) as eluent gave 2.19 g of the title compound.

$^1$H-NMR (CDCl$_3$, 400 MHz): δ [ppm] 8.3 (d, 1H), 8.05 (dd, 1H), 7.5 (dd, 1H).

a.10 4-(2-Fluoroethyl)-benzenesulfonyl chloride
a.10.1 (2-Fluoroethyl)-benzene 6.8 g of the title compound were obtained from commercially available 2-phenylethanol following the procedure used for the synthesis of (3-fluoropropyl)benzene.

$^1$H-NMR (CDCl$_3$, 400 MHz): δ [ppm] 7.1-7.3 (m, 5H), 4.6 (m, 1H), 4.45 (m, 1H), 2.95 (m, 1H), 2.9 (m, 1H).

a.10.2 4-(2-Fluoroethyl)-benzenesulfonyl chloride 3.55 g were obtained following the procedure used for the synthesis of 4-((R)-2-fluoro-1-methyl-ethyl)-benzenesulfonyl chloride.

$^1$H-NMR (CDCl$_3$, 400 MHz): δ [ppm] 8.0 (d, 2H), 7.5 (d, 2H), 4.7 (dt, 2H), 3.05-3.2 (dt, 2H).

a.11 5-Propylthiophene-2-sulfonyl chloride

Following the procedures analogous to that used for the preparation of (3-fluoropropyl)-benzenesulfonyl chloride, but using only 1 equivalent of phosphorous pentachloride, the title compound was prepared.

$^1$H-NMR (CDCl$_3$, 400 MHz): δ [ppm] 7.7 (d, 1H), 6.85 (d, 1H), 2.9 (t, 2H), 1.75 (m, 2H), 1.0 (t, 3H).

a.12 4-(1-Methyl-1H-pyrazol-4-yl)-benzenesulfonyl chloride
a.12.1 1-Methyl-4-phenyl-1H-pyrazole 1 g of 2-phenylmalonaldehyde (6.75 mmol) were dissolved in 25 ml of ethanol. 0.36 ml of N-methyl-hydrazine (6.75 mmol) were added, the reaction mixture was stirred under reflux for 4 h, the solvent evaporated under reduced pressure to yield 1.09 g of the product.

ESI-MS: 159.1 [M+H]+

$^1$H-NMR (CDCl$_3$, 400 MHz): δ [ppm] 7.75 (s, 1H), 7.6 (s, 1H), 7.45 (d, 2H), 7.35 (t, 2H), 7.2 (t, 1H), 3.9 (s, 3H)

a.12.2 4-(1-Methyl-1H-pyrazol-4-yl)-benzenesulfonyl chloride 0.5 g of 1-methyl-4-phenyl-1H-pyrazole (3.16 mmol) were dissolved in 20 ml of dichloromethane. At 0° C., 0.232 ml of chlorosulfonic acid were added and the reaction mixture was stirred for 1 h under ice cooling. Additional 0.7 ml of chlorosulfonic acid were added, the mixture was stirred at 0° C. for 30 minutes and then 90 minutes at 50° C. The two phases were separated and the lower layer put on ice, extracted twice with diethyl ether, dried over magnesium sulfate, filtered, and the solvent evaporated under reduced pressure to yield 0.496 g of the product.

$^1$H-NMR (CDCl$_3$, 400 MHz): δ [ppm] 8.0 (d, 2H), 7.85 (s, 1H), 7.75 (s, 1H), 7.65 (d, 2H), 4.0 (s, 3H).

a.13 4-(1,1,1-Trifluoropropan-2-yl)benzenesulfonyl chloride and 2-(1,1,1-trifluoropropan-2-yl)benzenesulfonyl chloride Prepared on a 14 g scale following the procedure outlined in Scheme 7. 2-(1,1,1-Trifluoropropan-2-yl)benzenesulfonyl chloride is a by-product of the reaction.

4-(1,1,1-Trifluoropropan-2-yl)benzenesulfonyl chloride

MS (ESI) m/z: 273.1 [M+H]+
$^1$H-NMR (DMSO-d$_6$): δ [ppm] 7.62 (d, 2H), 7.33 (d, 2H), 3.81 (m, 1H), 1.42 (d, 3H).

2-(1,1,1-Trifluoropropan-2-yl)benzenesulfonyl chloride

MS (ESI) m/z: 273.1 [M+H]+ a.14 4-(1,1-Difluoropropan-2-yl)benzenesulfonyl chloride and 2-(1,1-Difluoropropan-2-yl)benzene-1-sulfonyl chloride Prepared on an 11 g scale following the procedure outlined in Scheme 6. 2-(1,1-Difluoropropan-2-yl)benzene-1-sulfonyl chloride is a by-product of the reaction.

4-(1,1-Difluoropropan-2-yl)benzenesulfonyl chloride

MS (ESI) m/z: 255.0 [M+H]+
$^1$H-NMR (DMSO-d$_6$): δ [ppm] 8.03 (d, 2H), 7.55 (d, 2H), 5.88 (dt, 1H), 3.34 (m, 1H), 1.47 (d, 3H).
$^{13}$C-NMR (DMSO-d$_6$): δ [ppm] 146.43, 143.54, 129.77, 127.28, 117.06 (t), 43.76, 13.78.

2-(1,1-difluoropropan-2-yl)benzene-1-sulfonyl chloride

Isolated by chromatography on 110 mg scale.
MS (ESI) m/z: 255.0 [M+H]+
$^1$H-NMR (DMSO-d$_6$): δ [ppm] 8.15 (d, 1H), 7.77 (t, 1H), 7.70 (d, 1H), 7.54 (t, 1H), 5.99 (dt, 1H), 4.43 (m, 1H), 1.51 (d, 3H).
$^{13}$C-NMR (DMSO-d$_6$): δ [ppm] 143.45, 138.63, 135.53, 130.93, 129.04, 128.17, 116.61 (t), 38.38, 13.68.

b. Preparation of toluene-4-sulfonic acid 3-fluoro-propyl ester 5 g of 3-fluoro-propanol (64.03 mmol) and 18 ml of triethylamine (129.32 mmol) were dissolved in 50 ml of dichloromethane. At 0-5° C., 12.9 g toluene-4-sulfonylchloride (67.66 mmol) were added and the reaction mixture stirred at room temperature for 18 h. Standard work-up yielded 13.7 g of toluene-4-sulfonic acid 3-fluoro-propyl ester.

ESI-MS: 233.1 [M+H]+

II. Preparation of the Compounds I

Example 1

4-Isopropyl-N-[4-((S)-1-propyl-pyrrolidin-3-yl)-phenyl]-benzenesulfonamide hydrochloride 1.1 (S)-2-Phenyl-succinic acid dimethyl ester 5 g of (S)-2-phenyl succinic acid (25.75 mmol) were dissolved in 50 ml of methanol. At 4° C., 4.7 ml of thionyl chloride (64.37 mmol) were added dropwise. The reaction mixture was stirred at room temperature for 2 h, the solvents were evaporated under reduced pressure. The residue that remained was dissolved in diethyl ether, washed once with saturated aqueous NaHCO$_3$ solution, reextracted with diethyl ether, and the combined organic layers dried over magnesium sulfate, filtered, and evaporated to dryness to yield 5.8 g of the desired product.

ESI-MS: 223.1 [M+H]$^+$ 1.2 (S)-2-Phenyl-butane-1,4-diol 2.54 g of lithium aluminium hydride (66.95 mmol) were suspended under ice cooling in 25 ml of tetrahydrofuran. 5.8 g of (S)-2-phenyl succinic acid dimethyl ester (25.75 mmol) dissolved in 25 ml of tetrahydrofuran were added slowly at 5-10° C. Stirring was continued for 15 minutes and then 15 ml of tetrahydrofuran/water (1:1) were added dropwise. The suspension was adjusted to pH 3-4 with conc. hydrochloric acid, filtered and the filter washed with dichloromethane. The filtrate was evaporated to dryness, taken up in diethylether, washed with saturated sodium hydrogen carbonate solution, reextracted with diethylether, and the combined organic layers dried over magnesium sulfate, filtered, and the solvent evaporated under reduced pressure to yield 4.2 g of the diol.

ESI-MS: 189.1 [M+Na]$^+$ $^1$H-NMR (CDCl$_3$): δ [ppm] 7.25-7.4 (m, 2H), 7.15-7.3 (m, 3H), 4.2-4.35 (m, 2H), 3.2 (m, 1H), 3.1 (m, 1H), 2.1-2.3 (m, 3H).

1.3 Methanesulfonic acid (S)-4-methanesulfonyloxy-3-phenyl-butyl ester 4.19 g of (S)-2-phenyl-butane-1,4-diol (25.21 mmol) were dissolved in 50 ml of dichloromethane. 10.53 ml of triethylamine (75.6 mmol) were added, and, under ice cooling, 5 ml of methansulfonyl chloride (64.34 mmol). Stirring was continued for 15 minutes and then 40 ml of water were added. The organic phase was separated, and the aqueous phase extracted with dichloromethane. The combined organic layers were dried over magnesium sulfate, filtered, and the solvent evaporated under reduced pressure to yield 8.37 g of the product.

1.4 (S)-3-phenyl-1-propyl-pyrrolidine 2.0 g of methanesulfonic acid (S)-4-methanesulfonyloxy-3-phenyl-butyl ester (5.51 mmol) were dissolved in 5 ml of n-propylamine (60.82 mmol). The reaction mixture was stirred for 15 h at room temperature, diethyl ether added, the organic phase washed twice with water. The aqueous phase was reextraced once with diethylether, the organic layers combined, dried over magnesium sulfate, filtered, and the solvent evaporated under reduced pressure to yield 1.09 g of the product. ESI-MS: 190.1 [M+H]$^+$ 1.5 (S)-3-(4-Nitro-phenyl)-1-propyl-pyrrolidine 0.3 g of (S)-3-phenyl-1-propyl-pyrrolidine (1.48 mmol) was dissolved in 2 ml of conc. sulphuric acid under argon and ice cooling. 165.16 mg of potassium nitrate (1.63 mmol) were added in small portions. The reaction mixture was stirred for 15 minutes under ice cooling, for 15 h at room temperature, and poured onto crushed ice. The aqueous solution was made alkaline with 25% sodium hydroxide, extracted three times with diethyl ether, the aqueous phase reextracted once with diethylether, the organic layers combined, dried over magnesium sulfate, filtered, and the solvent evaporated under reduced pressure to yield 0.326 g of a brownish oil. A second reaction yielded another 0.919 g of the desired product.

ESI-MS: 235.1 [M+H]$^+$ $^1$H-NMR (CDCl$_3$): δ [ppm] 8.15 (d, 2H), 7.45 (d, 2H), 3.4-3.5 (m, 1H), 2.9-3.0 (m, 1H), 2.75 (m, 1H), 2.3-2.6 (m, 4H), 1.8-1.9 (m, 1H), 1.5-1.65 (m, 3H), 0.95 (m, 3H).

1.6 (S)-3-(4-Amino-phenyl)-1-propyl-pyrrolidine 0.907 g of (S)-3-(4-nitro-phenyl)-1-propyl-pyrrolidine (3.59 mmol) were dissolved in 20 ml of methanol, 7.0 g of tin dichloride (31.02 mmol) added, and the reaction mixture stirred under reflux for 1 h. The methanol was evaporated, 60 ml of 1 N sodium hydroxide and dichloromethane added, and the phases separated after extensive stirring. The aqueous phase was extracted twice with dichloromethane, the organic layers combined, dried over magnesium sulfate, filtered, and the solvent evaporated under reduced pressure to yield 0.744 g of the crude amino compound. ESI-MS: 205.2 [M+H]$^+$ $^1$H-NMR (DMSO-d$_6$): δ [ppm] 6.9 (d, 2H), 6.45 (d, 2H), 4.7 (s, broad, 2H), 3.1 (m, 1H), 2.85 (m, 1H), 2.65 (m, 1H), 2.55 (m, 1H), 2.25-2.45 (m, 3H), 2.1 (m, 1H), 1.65 (m, 1H), 1.4-1.5 (m, 2H), 0.85 (m, 3H).

1.7 4-Isopropyl-N-[4-((S)-1-propyl-pyrrolidin-3-yl)-phenyl]-benzenesulfonamide hydrochloride 0.4 g of (S)-3-(4-amino-phenyl)-1-propyl-pyrrolidine (1.96 mmol) and 0.407 mg of 4-isopropyl-phenylsulfonyl chloride (1.86 mmol) were dissolved in 15 ml of tetrahydrofuran. 0.82 ml of triethylamine (5.87 mmol) were added and the reaction mixture stirred for 15 h at room temperature. The solvents were evaporated under reduced pressure, the residue treated with water and adjusted to an alkaline pH with sodium hydroxide solution. The aqueous layer was extracted three times with diethyl ether, the organic layers combined, dried over magnesium sulfate, filtered, and the solvent evaporated under reduced pressure. The crude product was purified with silica gel chromatography with ethyl acetate/methanol (2.5-3%) as eluent, yielding 0.225 g of the purified product. This material was dissolved in 15 ml of diethyl ether and 1 ml of dichloromethane, 0.61 ml of 1 N HCl in diethyl ether added, and after formation of a precipitate, the suspension evaporated under reduced pressure to yield 0.235 g of a white precipitate.

ESI-MS: 387.2 [M+H]$^+$ $^1$H-NMR (DMSO-d$_6$): δ [ppm] 11.3 and 11.1 (2s, broad, 1H), 10.35 (m, 1H), 7.7 (d, 2H), 7.4 (d, 2H), 7.15-7.3 (m, 2H), 7.1 (m, 2H), 3.2-3.8 (several m, 4H), 2.85-3.15 (several m, 4H), 2.3 (m, 1H), 1.8-2.0 (m, 1H), 1.6-1.75 (m, 2H), 1.15 (d, 6H), 0.9 (m, 3H).

Example 2

4-(1,1-Dimethyl-propyl)-N-[4-((S)-1-propyl-pyrrolidin-3-yl)-phenyl]-benzenesulfonamide hydrochloride 0.219 g of the desired product were obtained following the same synthetic procedure as described for 4-isopropyl-N-[4-((S)-1-propyl-pyrrolidin-3-yl)-phenyl]-benzenesulfonamide hydrochloride using commercially available 4-(1,1-dimethylpropyl)benzenesulfonylchloride.

ESI-MS: 415.5 [M+H]$^+$ $^1$H-NMR (DMSO-d$_6$): δ [ppm] 11.3 and 11.1 (2s, broad, 1H), 10.3 (m, 1H), 7.7 (d, 2H), 7.5 (d, 2H), 7.1-7.3 (m, 2H), 7.1 (m, 2H), 3.15-3.8 (several m, 4H), 2.85-3.15 (several m, 3H), 2.3 (m, 1H), 1.8-2.0 (m, 1H), 1.5-1.75 (several m, 4H), 1.2 (s, 6H), 0.9 (m, 3H), 0.55 (m, 3H).

Example 3

4-(Isopropyl)-N-[4-((S)-1-allyl-pyrrolidin-3-yl)-phenyl]-benzenesulfonamide hydrochloride 3.1 (S)-1-Allyl-3-phenyl-pyrrolidine 1.3 g of the desired product were obtained following the same synthetic procedure as described for (S)-3-phenyl-1-propyl-pyrrolidine, using allylamine.

ESI-MS: 188.2 [M+H]$^+$ 3.2 (S)-1-Allyl-3-(4-nitro-phenyl)-pyrrolidine 1.27 g of the desired product were obtained following the same synthetic procedure as described for (S)-3-(4-nitro-phenyl)-1-propyl-pyrrolidine.

ESI-MS: 233.3 [M+H]$^+$ $^1$H-NMR (CDCl$_3$): δ [ppm] 8.15 (d, 2H), 7.4 (d, 2H), 5.85-6.0 (m, 1H), 5.2 (m, 1H), 5.1 (m, 1H), 3.4-3.5 (m, 1H), 3.05-3.2 (m, 2H), 3.0 (m, 1H), 2.75 (m, 2H), 2.6 (m, 1H), 2.3-2.4 (m, 1H), 1.8-1.9 (m, 1H).

3.3 (S)-1-Allyl-3-(4-amino-phenyl)-pyrrolidine 1.01 g of the desired product were obtained following the same synthetic procedure as described for (S)-3-(4-nitro-phenyl)-1-propyl-pyrrolidine.

ESI-MS: 203.1 [M+H]$^+$ 3.4 4-(Isopropyl)-N-[4-((S)-1-allyl-pyrrolidin-3-yl)-phenyl]-benzenesulfonamide hydrochloride 0.184 g of the desired product were obtained following the same synthetic procedure as described for 4-isopropyl-N-[4-((S)-1-propyl-pyrrolidin-3-yl)-phenyl]-benzenesulfonamide hydrochloride.

ESI-MS: 385.1 [M+H]$^+$ $^1$H-NMR (DMSO-d$_6$): δ [ppm] 11.8 and 11.5 (2s, broad, 1H), 10.45 (m, 1H), 7.7 (d, 2H), 7.4 (d, 2H), 7.2-7.3 (m, 21-1), 7.1 (m, 2H), 6.0 (m, 1H), 5.4-5.55 (m, 2H), 3.8 m (2H), 3.3-3.7 (several m, 3H), 3.2 (m, 1H), 2.9-3.1 (several m, 2H), 2.3 (m, 1H), 1.85-2.05 (m, 1H), 1.15 (s, 6H).

Example 4

4-(Isopropyl)-N-[4-((R)-1-allyl-pyrrolidin-3-yl)-phenyl]-benzenesulfonamide hydrochloride 4.1 (R)-1-Allyl-3-(4-nitro-phenyl)-pyrrolidine 2.1 g of the desired product were obtained following the same synthetic procedure as described for (S)-3-(4-nitro-phenyl)-1-propyl-pyrrolidine.

ESI-MS: 233.1 [M+H]$^+$ $^1$H-NMR (CDCl$_3$): δ [ppm] 8.15 (d, 2H), 7.4 (d, 2H), 5.85-6.0 (m, 1H), 5.2 (m, 1H), 5.1 (m, 1H), 3.4-3.5 (m, 1H), 3.05-3.2 (m, 2H), 3.0 (m, 1H), 2.75 (m, 2H), 2.6 (m, 1H), 2.3-2.4 (m, 1H), 1.8-1.9 (m, 1H).

4.2 (R)-1-Allyl-3-(4-amino-phenyl)-pyrrolidine 1.12 g of the desired product were obtained following the same synthetic procedure as described for (S)-1-allyl-3-(4-amino-phenyl)-1-propyl-pyrrolidine.

ESI-MS: 203.1 [M+H]$^+$ $^1$H-NMR (CDCl$_3$): δ [ppm]

4.3 4-(Isopropyl)-N-[4-((R)-1-allyl-pyrrolidin-3-yl)-phenyl]-benzenesulfonamide hydrochloride 0.138 g of the desired product were obtained following the same synthetic procedure as described for 4-isopropyl-N-4-[4-(S)-1-propyl-pyrrolidin-3-yl)-phenyl]-benzenesulfonamide hydrochloride.

ESI-MS: 385.1 [M+H]$^+$ $^1$H-NMR (DMSO-d$_6$): δ [ppm] 11.65 and 11.45 (2s, broad, 1H), 10.35 (m, 1H), 7.7 (d, 2H), 7.4 (d, 2H), 7.2-7.3 (m, 2H), 7.1 (m, 2H), 6.0 (m, 1H), 5.4-5.55 (m, 2H), 3.8 m (2H), 3.3-3.7 (several m, 3H), 3.2 (m, 1H), 2.9-3.1 (several m, 2H), 2.3 (m, 1H), 1.85-2.05 (m, 1H), 1.15 (s, 6H).

Example 5

4-(Isopropyl)-N-[4-((R)-1-propyl-pyrrolidin-3-yl)-phenyl]benzenesulfonamide hydrochloride 0.525 g of 4-(isopropyl)-N-[4-((R)-1-alkyl-pyrrolidin-3-yl)-phenyl]-benzenesulfonamide (1.37 mmol) were dissolved in 15 ml ethanol, 0.075 g Pd/C (10%) added, warmed to 80° C. and 0.861 g ammonium formiate (13.65 mmol) dissolved in 7.5 ml of water, added. After stirring for 15 h at room temperature, the catalyst was filtered off, washed with water and dichloromethane. The aqueous phase was adjusted to pH 9 with 1 N aq. sodium hydroxide, extracted twice with dichloromethane, and the combined organic layers washed with saturated sodium chloride solution, dried over magnesium sulfate, filtered, and the solvent evaporated to dryness to yield 0.55 g of a mixture of the N-propyl- and N-dealkylated products. This mixture was dissolved in 25 ml of dichloromethane, 0.116 ml of propionic aldehyde (1.6 mmol), 0.14 ml acetic acid (2.39 mmol) and 0.508 g sodium triacetoxyborohydride (2.39 mmol) added. After stirring for 1 h at room temperature, the mixture was evaporated to dryness, water added and the pH adjusted to pH 9 with 1 N aq. sodium hydroxide. The aqueous layer was extracted three times with diethyl ether, the organic layers combined, dried over magnesium sulfate, filtered, and evaporated to dryness. The crude product was purified via silica gel chromatography with ethyl acetate/methanol (17.5%). Fractions containing the product were combined, evaporated under reduced pressure, and the residue partitioned between alkaline (pH 9-10) aqueous and diethyl ether, followed by a second extraction with ethyl ether and one with ethyl acetate. The combined organic layers were dried over magnesium sulfate, filtered, and evaporated to dryness to yield 0.21 g of the purified product. The material was dissolved in 10 ml of diethyl ether, and 0.285 ml of 2 N HCl in diethyl ether added. The forming suspension was evaporated to dryness under reduced pressure to yield 0.201 g of the product as hydrochloride.

ESI-MS: 387.2 [M+H]$^+$ $^1$H-NMR (DMSO-d$_6$): δ [ppm] 11.4 and 11.3 (2s, broad, 1H), 10.35 (m, 1H), 7.7 (d, 2H), 7.4 (d, 2H), 7.15-7.3 (m, 2H), 7.1 (m, 2H), 3.2-3.8 (several m, 4H), 2.85-3.15 (several m, 4H), 2.3 (m, 1H), 1.8-2.0 (m, 1H), 1.6-1.75 (m, 2H), 1.15 (d, 6H), 0.9 (m, 3H).

Example 6

4-Ethyl-N-[4-((S)-1-propyl-pyrrolidin-3-yl)-phenyl]-benzenesulfonamide hydrochloride 0.096 g of the desired product were obtained following the same synthetic procedure as described for 4-isopropyl-N-[4-((S)-1-propyl-pyrrolidin-3-yl)-phenyl]-benzenesulfonamide hydrochloride using commercially available 4-ethyl-benzenesulfonylchloride.

ESI-MS: 373.3 [M+H]$^+$ $^1$H-NMR (DMSO-d$_6$): δ [ppm] 11.35 and 11.15 (2s, broad, 1H), 10.3 (m, 1H), 7.7 (d, 2H), 7.4 (d, 2H), 7.15-7.3 (m, 2H), 7.05 (m, 2H), 2.9-3.8 (several m, 7H), 2.6-2.7 (m, 2H), 2.3 (m, 1H), 1.8-2.0 (m, 1H), 1.6-1.75 (m, 2H), 1.2 (m, 3H), 0.9 (m, 3H).

Example 7

4-Trifluoromethoxy-N-[4-((S)-1-propyl-pyrrolidin-3-yl)-phenyl]-benzenesulfonamide hydrochloride 0.067 g of the desired product were obtained following the same synthetic procedure as described for 4-isopropyl-N-[4-((S)-1-propyl-pyrrolidin-3-yl)-phenyl]-benzenesulfonamide hydrochloride using commercially available 4-trifluoromethoxy-benzenesulfonylchloride.

ESI-MS: 429.1 [M+H]$^+$

¹H-NMR (DMSO-d₆): δ [ppm] 11.25 and 11.05 (2s, broad, 1H), 10.65 (m, 1H), 8.0 (m, broad, 4H), 7.2-7.35 (m, 2H), 7.1 (m, 2H), 2.9-3.8 (several m, 7H), 2.3 (m, 1H), 1.8-2.05 (m, 1H), 1.6-1.75 (m, 2H), 0.9 (m, 3H).

Example 8

4-Trifluoromethyl-N-[4-((S)-1-propyl-pyrrolidin-3-yl)-phenyl]-benzenesulfonamide hydrochloride 0.12 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-trifluoromethyl-benzenesulfonylchloride.

ESI-MS: 413.1 [M+H]⁺

¹H-NMR (DMSO-d₆): δ [ppm] 11.3 and 11.1 (2s, broad, 1H), 10.55 (m, 1H), 7.9 (d, 2H), 7.55 (d, 2H), 7.2-7.35 (m, 2H), 7.1 (m, 2H), 2.9-3.8 (several m, 7H), 2.3 (m, 1H), 1.8-2.05 (m, 1H), 1.6-1.75 (m, 2H), 0.9 (m, 3H).

Example 9

4-Difluoromethoxy-N-[4-((S)-1-propyl-pyrrolidin-3-yl)-phenyl]-benzenesulfonamide hydrochloride 0.125 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-difluoromethoxy-benzenesulfonylchloride.

ESI-MS: 411.1 [M+H]⁺

¹H-NMR (CDCl₃): δ [ppm] 7.8 (d, 2H), 7.0-7.2 (m, 6H), 7.1 (m, 2H), 6.55 (t, 1H), 3.25 (m, 1H), 3.0 (m, 1H), 2.85 (m, 1H), 2.65 (m, 1H), 2.4-2.55 (m, 3H), 2.25 (m, 1H), 1.8 (m, 1H), 1.5 (m, 2H), 0.9 (t, 3H).

Example 10

4-Methyl-N-[4-((S)-1-propyl-pyrrolidin-3-yl)-phenyl]-benzenesulfonamide hydrochloride 0.31 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-methyl-benzenesulfonylchloride.

ESI-MS: 359.1 [M+H]⁺

¹H-NMR (CDCl₃): δ [ppm] 7.7 (m, 1H), 7.2 (m, 1H), 7.05 (m, 1H), 3.3 (m, 1H), 3.0 (m, 1H), 2.85 (m, 1H), 2.65 (m, 1H), 2.2-2.6 (several m, 4H), 2.35 (s, 3H), 1.8 (m, 1H), 1.55 (m, 2H), 0.9 (m, 3H).

Example 11

6-Chloro-pyridine-3-sulfonic acid [4-((S)-1-propyl-pyrrolidin-3-yl)-phenyl]-amide 0.163 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 6-chloro-pyridine-sulfonylchloride.

ESI-MS: 380.1 [M+H]⁺

Example 12

4-Methoxy-N-[4-((S)-1-propyl-pyrrolidin-3-yl)-phenyl]-benzenesulfonamide 0.154 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-methoxy-benzenesulfonylchloride.

ESI-MS: 375.1 [M+H]⁺

¹H-NMR (CDCl₃): δ [ppm] 7.7 (m, 1H), 7.05 (m, 1H), 6.85 (m, 1H), 3.8 (s, 3H), 3.3 (m, 1H), 3.1 (m, 1H), 2.9 (m, 1H), 2.7 (m, 1H), 2.4-2.6 (several m, 3H), 2.3 (m, 1H), 1.8 (m, 1H), 1.55 (m, 2H), 0.9 (m, 3H).

Example 13

4-Chloro-N-[4-((S)-1-propyl-pyrrolidin-3-yl)-phenyl]-benzenesulfonamide 0.175 g of the desired product were obtained following the same synthetic procedure as described for 4-isopropyl-N-[4-((S)-1-propyl-pyrrolidin-3-yl)-phenyl]-benzenesulfonamide hydrochloride using commercially available 4-chloro-benzenesulfonylchloride.

ESI-MS: 379.05 [M+H]⁺

¹H-NMR (CDCl₃): δ [ppm] 7.7 (d, 2H), 7.35 (d, 2H), 7.0-7.2 (m, 4H), 7.1 (m, 2H), 3.3 (m, 1H), 3.05 (m, 1H), 2.85 (m, 1H), 2.65 (m, 1H), 2.4-2.55 (m, 3H), 2.25 (m, 1H), 1.8 (m, 1H), 1.55 (m, 2H), 0.9 (m, 3H).

Example 14

2,3-Dihydro-benzofuran-5-sulfonic acid [4-((S)-1-propyl-pyrrolidin-3-yl)-phenyl]-amide 0.207 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 2,3-Dihydro-benzofuran-5-sulfonylchloride.

ESI-MS: 387.1 [M+H]⁺

¹H-NMR (CDCl₃): δ [ppm] 7.5-7.6 (m, 2H), 7.15 (m, 2H), 6.95 (m, 2H), 6.7 (m, 1H), 4.65 (m, 2H), 3.35 (m, 1H), 3.2 (m, 2H), 3.0 (m, 1H), 2.8 (m, 1H), 2.6 (m, 1H), 2.3-2.5 (m, 3H), 2.2-2.3 (m, 1H), 1.8 (m, 1H), 1.5 (m, 2H), 0.9 (m, 3H).

Example 15

4-Bromo-3-fluoro-N-[4-((S)-1-propyl-pyrrolidin-3-yl)-phenyl]-benzenesulfonamide 0.289 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-bromo-3-fluorobenzene-sulfonylchloride.

ESI-MS: 441.0/443.0 [M+H]⁺

¹H-NMR (CDCl₃): δ [ppm] 7.65 (m, 1H), 7.5 (m, 1H), 7.4 (m, 1H), 7.15 (d, 2H), 7.0 (d, 2H), 3.3 (m, 1H), 3.0 (m, 1H), 2.8 (m, 1H), 2.65 (m, 1H), 2.35-2.5 (m, 3H), 2.3 (m, 1H), 1.8 (m, 1H), 1.5 (m, 2H), 0.9 (m, 3H).

Example 16

4-Bromo-3-fluoro-N-[2-((S)-1-propyl-pyrrolidin-3-yl)-phenyl]-benzenesulfonamide 0.02 g of the ortho product could be separated during purification of the major para product.
ESI-MS: 441.0/443.0 [M+H]$^+$
$^1$H-NMR (CDCl$_3$): δ [ppm] 7.5-7.7 (m, 3H), 7.1-7.2 (m, 3H), 7.0 (m, 1H), 3.5 (m, 1H), 3.3 (m, 1H), 3.1-3.2 (m, 2H), 2.7-2.9 (m, 3H), 2.3-2.4 (m, 1H), 1.9-2.1 (m, 2H), 1.6-1.8 (m, 2H), 0.9 (m, 3H).

Example 17

4-Bromo-2-fluoro-N-[4-((S)-1-propyl-pyrrolidin-3-yl)-phenyl]-benzenesulfonamide 0.387 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-bromo-2-fluorobenzene-sulfonylchloride.
ESI-MS: 441.0/443.0 [M+H]$^+$
$^1$H-NMR (CDCl$_3$): δ [ppm] 7.65 (m, 1H), 7.3-7.4 (m, 2H), 7.15 (d, 2H), 7.0 (d, 2H), 3.3 (m, 1H), 3.0 (m, 1H), 2.8 (m, 1H), 2.65 (m, 1H), 2.35-2.55 (m, 3H), 2.25 (m, 1H), 1.75 (m, 1H), 1.5 (m, 2H), 0.9 (m, 3H).

Example 18

4-Isopropyl-N-[4-((S)-pyrrolidin-3-yl)-phenyl]-benzenesulfonamide 0.515 g of 4-isopropyl-N-[4-((S)-1-allyl-pyrrolidin-3-yl)-phenyl]-benzenesulfonamide (1.34 mmol) were dissolved in 10 ml of tetrahydrofuran and added to a solution of 0.049 g tris-(dibenzylidenaceton)-dipalladium(0) (0.05 mmol) and 0.023 g of 1,4-bis(diphenylphospino)-butane (0.05 mmol) in 3 ml of tetrahydrofuran under argon, followed by addition of 0.227 mg of 2-mercapto benzoic acid (1.47 mmol) in 3 ml of tetrahydrofuran. The mixture was stirred for 2 h at room temperature, the solvent evaporated under reduced pressure and water containing 1 N hydrochlorid acid added to adjust the pH to acidic values. The aqueous phase was extracted three times with ethyl acetate, then adjusted to alkaline pH with 1 N sodium hydroxide, extracted twice with diethyl ether and twice with dichloromethane. The combined organic layers were dried over magnesium sulfate, filtered, and the solvent evaporated under reduced pressure to yield 0.215 g of the secondary amine.
ESI-MS: 345.1 [M+H]$^+$ Example 19

2-Fluoro-4-isopropenyl-N-[4-((S)-1-propyl-pyrrolidin-3-yl)-phenyl]-benzenesulfonamide 0.2 g of 2-fluoro-4-bromo-N-[4-((S)-1-propyl-pyrrolidin-3-yl)-phenyl]-benzenesulfonamide (0.45 mmol), 1.05 g of tributyl-isopropenyl-stannane (3.17 mmol) and 0.026 g of tetrakistriphenylphosphinpalladium(0) (0.02 mmol) were dissolved in 3 ml of tetrahydrofuran and stirred for 40 minutes at 150° C. in the microwave (CEM). The reaction mixture was filtered over celite, washed with methanol, and the filtrate evaporated to dryness under reduced pressure. The residue was purified via silica gel chromatography with cyclohexane/ethyl acetate (20%), ethyl acetate, and ethyl acetate/methanol (15%). Fractions containing the product were combined, the solvent evaporated to yield 0.176 g of the title product.
ESI-MS: 403.1 [M+H]$^+$
$^1$H-NMR (CDCl$_3$): δ [ppm] 7.7 (m, 1H), 7.2-7.3 (m, 2H), 7.1 (m, 2H), 7.0 (m, 2H), 5.45 (m, 1H), 5.25 (m, 1H), 3.3-3.4 (m, 1H), 2.6 (m, 1H), 2.25-2.35 (m, 1H), 2.1 (s, 3H), 1.8-1.9 (m, 2H), 1.55-1.7 (m, 3H), 1.2-1.4 (m, 3H), 0.9 (m, 3H).

Example 20

3-Fluoro-4-isopropenyl-N-[4-((S)-1-propyl-pyrrolidin-3-yl)-phenyl]-benzenesulfonamide 3-Fluoro-4-isopropenyl-N-[4-((S)-1-propyl-pyrrolidin-3-yl)-phenyl]-benzenesulfonamide were obtained following the same synthetic procedure as described for 2-fluoro-4-Isopropenyl-N-[4-((S)-1-propyl-pyrrolidin-3-yl)-phenyl]-benzenesulfonamide starting from 3-fluoro-4-bromo-N-[4-((S)-1-propyl-pyrrolidin-3-yl)-phenyl]-benzenesulfonamide yielding 0.17 g of the desired.
ESI-MS: 403.1 [M+H]$^+$
$^1$H-NMR (CDCl$_3$): δ [ppm] 7.3-7.5 (m, 3H), 7.15 (d, 2H), 7.0 (d, 2H), 5.3 (m, 2H), 3.35 (m, 1H), 2.6 (m, 2H), 2.3 (m, 1H), 2.1 (s, 3H), 1.8-1.9 (m, 2H), 1.55-1.7 (m, 3H), 1.2-1.4 (m, 1H), 0.9 (m, 4H).

Example 21

2-Fluoro-4-isopropyl-N-[4-((S)-1-propyl-pyrrolidin-3-yl)-phenyl]-benzenesulfonamide 0.161 g of 2-fluoro-4-isopropenyl-N-[4-((S)-1-propyl-pyrrolidin-3-yl)-phenyl]-benzenesulfonamide (0.37 mmol) were dissolved in 20 ml methanol, a tip of a spatula 10% Pd/C added, and the reaction mixture hydrogenated for 3 h at 50° C. The reaction mixture was filtered over celite, washed with methanol, and the filtrate evaporated to dryness under reduced pressure. The residue was purified via silica gel chromatography on a chromabond column with ethyl acetate and ethyl acetate/methanol (10%). Fractions containing the product were combined, the solvent evaporated to yield 0.11 g of the title product.
ESI-MS: 405.1 [M+H]$^+$
$^1$H-NMR (CDCl$_3$): δ [ppm] 7.7 (m, 1H), 6.9-7.2 (several m, 6H), 3.5-3.6 (m, 2H), 3.2-3.4 (m, 2H), 2.85-3.05 (m, 4H), 2.4 (m, 1H), 2.1 (m, 1H), 1.8 (m, 2H), 1.2 (d, 6H), 0.95 (m, 3H).

Example 22

3-Fluoro-4-isopropyl-N-[4-((S)-1-propyl-pyrrolidin-3-yl)-phenyl]-benzenesulfonamide 0.122 g of 3-fluoro-4-isopropyl-N-[4-((S)-1-propyl-pyrrolidin-3-yl)-phenyl]-benzenesulfonamide were obtained following the same synthetic procedure as described for 2-fluoro-4-isopropyl-N-[4-((S)-1-propyl-pyrrolidin-3-yl)-phenyl]-benzenesulfonamide starting from 3-fluoro-4-isopropenyl-N-[4-((S)-1-propyl-pyrrolidin-3-yl)-phenyl]-benzenesulfonamide.
ESI-MS: 405.1 [M+H]$^+$
$^1$H-NMR (CDCl$_3$): δ [ppm] 7.5 (m, 1H), 7.4 (m, 1H), 7.3 (m, 1H), 7.1 (d, 2H), 7.0 (d, 2H), 3.4 (m, 1H), 3.2 (m, 2H), 3.05 (m, 1H), 2.9 (m, 1H), 2.6-2.7 (m, 3H), 2.1 (m, 1H), 1.9 (m, 1H), 1.6-1.7 (m, 2H), 1.2 (d, 6H), 0.9 (m, 3H).

Example 23

4-Isopropoxy-N-[4-((S)-1-propyl-pyrrolidin-3-yl)-phenyl]-benzenesulfonamide hydrochloride 0.083 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-isopropoxy-benzene-sulfonylchloride.
ESI-MS: 403.3 [M+H]$^+$
$^1$H-NMR (DMSO-d$_6$): δ [ppm] 11.3 and 11.1 (2s, broad, 1H), 10.2 (m, 1H), 7.7 (d, 2H), 7.25 (m, 1H), 7.2 (m, 1H), 6.95-7.1 (m, 4H), 4.7 (m, 1H), 2.9-3.8 (several m, 7H), 2.3 (m, 1H), 1.85-2.0 (m, 1H), 1.7 (m, 2H), 1.2 (d, 6H), 0.9 (m, 3H).

Example 24

Indan-5-sulfonic acid [4-((S)-1-propyl-pyrrolidin-3-yl)-phenyl]-amide hydrochloride 0.15 g of the desired product were obtained following the same synthetic procedure as described for 4-Isopropyl-N-[4-((S)-1-propyl-pyrrolidin-3-yl)-phenyl]-benzenesulfonamide hydrochloride using commercially available indan-5-sulfonylchloride.
ESI-MS: 385.1 [M+H]$^+$
$^1$H-NMR (DMSO-d$_6$): δ [ppm] 11.3 and 11.1 (2s, broad, 1H), 10.25 (m, 1H), 7.6 (s, 1H), 7.5 (d, 1H), 7.35 (d, 1H), 7.25 (m, 1H), 7.2 (m, 1H), 7.05 (m, 2H), 3.2-3.8 (several m, 4H), 2.8-3.1 (several m, 7H), 2.3 (m, 1H), 1.8-2.05 (m, 3H), 1.6-1.7 (m, 2H), 0.9 (m, 3H).

Example 25

4-Bromo-N-[4-((S)-1-propyl-pyrrolidin-3-yl)-phenyl]-benzenesulfonamide hydrochloride 0.07 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-bromo-benzenesulfonylchloride.
ESI-MS: 425.0 [M+H]$^+$
$^1$H-NMR (DMSO-d$_6$): δ [ppm] 11.3 and 11.05 (2s, broad, 1H), 10.45 (m, 1H), 7.8 (d, 2H), 7.7 (d, 2H), 7.3 (m, 1H), 7.2 (m, 1H), 7.05 (m, 2H), 2.9-3.8 (several m, 7H), 2.3 (m, 1H), 1.85-2.05 (m, 1H), 1.6-1.8 (m, 2H), 0.9 (m, 3H).

Example 26

4-Acetyl-N-[4-((S)-1-propyl-pyrrolidin-3-yl)-phenyl]-benzenesulfonamide 0.159 g of the desired product were obtained following the same synthetic procedure as described for 4-Isopropyl-N-[4-((S)-1-propyl-pyrrolidin-3-yl)-phenyl]-benzenesulfonamide using commercially available 4-acetyl-benzene-sulfonylchloride.
ESI-MS: 387.1 [M+H]$^+$
$^1$H-NMR (CDCl$_3$): δ [ppm] 8.0 (d, 2H), 7.8 (d, 2H), 7.15 (d, 2H), 6.95 (d, 2H), 3.3 (m, 1H), 3.0 (m, 1H), 2.8 (m, 1H), 2.65 (m, 1H), 2.6 (s, 3H), 2.35-2.5 (m, 3H), 2.25 (m, 1H), 1.8 (m, 1H), 1.5 (m, 2H), 0.9 (m, 3H).

Example 27

4-Cyclopropyl-N-[4-((S)-1-propyl-pyrrolidin-3-yl)-phenyl]-benzenesulfonamide 0.3 g of 4-bromo-N-[4-((S)-1-propyl-pyrrolidin-3-yl)-phenyl]-benzenesulfonamide (0.71 mmol), 0.079 g of cyclopropylboronic acid (0.92 mmol), 0.526 g of potassium phosphate (2.48 mmol) and 0.02 g of ricyclohexylphosphin were dissolved in a mixture of 4 ml of toluene and 2 ml of water. After addition of 0.008 g of palladium(II)-acetate (0.04 mmol), the reaction mixture was stirred for 1 h at 100° C. in the microwave (CEM). The solution was decanted, the remaining suspension containing the catalyst washed again with ethyl acetate, the combined solvent extracts evaporated to dryness, redissolved in ethyl acetate and washed with water. The aqueous phase was reextracted once with ethyl acetate, the organic layers combined, dried over magnesium sulfate, filtered and evaporated under reduced pressure. The crude product was purified via silica gel chromatogrphay with dichloromethane, dichloromethane-methanol (5.5%). Fractions containing the product were combined, the solvent removed, to yield 0.066 g of the title product.
ESI-MS: 385.1 [M+H]$^+$
$^1$H-NMR (CDCl$_3$): δ [ppm] 7.65 (d, 2H), 6.95-7.15 (m, 6H), 3.3 (m, 1H), 3.1 (m, 1H), 2.9 (m, 1H), 2.75 (m, 1H), 2.5 (m, 3H), 2.35 (m, 1H), 2.0 (m, 1H), 1.8 (m, 2H), 1.55 (m, 2H), 1.25 (m, 1H), 1.0 (m, 1H), 0.9 (m, 3H), 0.7 (m, 1H).

Example 28

5-Bromo-thiophene-2-sulfonic acid [4-((S)-1-propyl-pyrrolidin-3-yl)-phenyl]-amide hydrochloride 0.05 g of the title product were obtained following the same synthetic procedure as described for 4-isopropyl-N-[4-((S)-1-propyl-pyrrolidin-3-yl)-phenyl]-benzenesulfonamide hydrochloride using commercially available 5-bromo-thiophene-2-sulfonylchloride.
ESI-MS: 431.0 [M+H]$^+$
$^1$H-NMR (DMSO-d$_6$): δ [ppm] 11.2 and 11.0 (2s, broad, 1H), 10.65 (m, 1H), 7.2-7.4 (several m, 4H), 7.1 (m, 2H), 3.0-3.8 (several m, 7H), 2.3 (m, 1H), 1.85-2.0 (m, 1H), 1.7 (m, 2H), 0.9 (m, 3H).

Example 29

5-Isopropenyl-thiophene-2-sulfonic acid [4-((S)-1-propyl-pyrrolidin-3-yl)-phenyl]-amide 0.154 g of the title product were obtained following the same synthetic procedure as described for 2-fluoro-4-Isopropenyl-N-[4-((S)-1-propyl-pyrrolidin-3-yl)-phenyl]-benzenesulfonamide starting from 5-bromo-thiophene-2-sulfonic acid [4-((S)-1-propyl-pyrrolidin-3-yl)-phenyl]-amide.
ESI-MS: 391.1 [M+H]$^+$
$^1$H-NMR (CDCl$_3$): δ [ppm] 7.3 (m, 1H), 7.25 (m, 1H), 7.2 (d, 2H), 7.05 (d, 2H), 6.9 (m, 1H), 5.4 (s, 1H), 5.1 (s, 1H), 3.3

(m, 1H), 3.05 (m, 1H), 2.9 (m, 1H), 2.7 (m, 1H), 2.5 (m, 2H), 2.3 (m, 1H), 2.05 (s, 3H), 1.85 (m, 1H), 1.6 (m, 2H), 1.3 (m, 1H), 0.9 (m, 3H).

Example 30

4-Propyl-N-[4-((S)-1-propyl-pyrrolidin-3-yl)-phenyl]-benzenesulfonamide hydrochloride 0.037 g of the title product were obtained following the same synthetic procedure as described for 4-Isopropyl-N-[4-((S)-1-propyl-pyrrolidin-3-yl)-phenyl]-benzenesulfonamide hydrochloride using commercially available 4-propyl-benzenesulfonylchloride.

ESI-MS: 387.2 [M+H]$^+$ $^1$H-NMR (DMSO-d$_6$): δ [ppm] 10.3 (m, 1H), 7.7 (d, 2H), 7.3 (d, 2H), 7.25 (m, 1H), 7.2 (m, 1H), 7.05 (m, 2H), 2.9-3.8 (several m, 7H), 2.55 (m, 2H), 2.3 (m, 1H), 1.85-2.0 (m, 1H), 1.7 (m, 2H), 1.55 (m, 2H), 0.9 (m, 3H), 0.8 (m, 3H).

Example 31

N-[6-(1-propyl-pyrrolidin-3-yl)-pyridin-3-yl]-4-isopropyl-benzene-sulfonamide 31.1 5-Nitro-2-vinyl-pyridine 0.5 g of 2-chloro-5-nitro-pyridine (3.15 mmol), 1.2 g of tributyl-vinyl-stannane (3.78 mmol), 0.036 g of tetrakistriphenylphosphinpalladium(0) (0.03 mmol), and 0.024 g of triphenylphosphin (0.09 mmol) were dissolved in 20 ml of toluene and stirred for 2 h under reflux. Upon cooling to room temperature, 10 ml of water were added, the agueous layer was extracted with ethyl acetate, and the combined organic layers were washed with saturated sodium chloride, dried over magnesium sulfate, filtered, and the solvent evaporated under reduced pressure. The crude product was purified via silica gel chromatography with cyclohexane/ethyl acetate (10%). Fractions containing the product were combined, the solvent evaporated to yield 0.528 g of the desired product.

ESI-MS: 151.1 [M+H]$^+$ $^1$H-NMR (CDCl$_3$): δ [ppm] 9.4 (s, 1H), 8.4 (m, 1H), 7.45 (m, 1H), 6.9 (q, 1H), 6.45 (m, 1H), 5.7 (m, 1H).

31.2 2-(1-Benzyl-pyrrolidin-3-yl)-5-nitro-pyridine 0.15 g of 5-nitro-2-vinyl-pyridine were dissolved in 2.5 ml of dichloromethane, 0.149 g of trifluoroacetic acid (1.31 mmol) were added, followed by slow addition of 0.928 g of N-benzyl-N-(methoxymethyl)-N-trimethylsilylmethylamine (3.91 mmol). Stirring was continued at room temperature for 1 h, before the reaction mixture was washed with aqueous sodium hydrogencarbonate, the aqueous layer reextracted with dichloromethane, the organic layers combined, dried over magnesium sulfate, filtered, and the solvent evaporated under reduced pressure. The crude product was purified via silica gel chromatography with ethyl acetate. Fractions containing the product were combined, the solvent evaporated to yield 0.186 g of the desired product.

ESI-MS: 284.1 [M+H]$^+$ $^1$H-NMR (CDCl$_3$): δ [ppm] 9.25 (m, 1H), 8.3 (m, 1H), 7.4 (m, 1H), 7.15-7.3 (m, 5H), 3.6 (d, 2H), 3.55 (m, 1H), 2.9 (m, 1H), 2.7 (m, 2H), 2.65 (m, 1H), 2.3 (m, 1H), 2.0 (m, 1H).

31.3 2-(1-Benzyl-pyrrolidin-3-yl)-5-amino-pyridine 0.181 g of 2-(1-benzyl-pyrrolidin-3-yl)-5-nitro-pyridine were dissolved in 10 ml of methanol and 1.15 g of tin dichloride SnCl$_2$ (5.11 mmol) were added in portions. Stirring was continued for 1 h under refluxing conditions. The solvent was evaporated, the residue treated with 1 N aqueous sodium hydroxide and ethyl acetate, and filtered. The two phases were separated, the aqueous phase was extracted twice with ethyl acetate, and the combined organic layers were dried over magnesium sulfate, filtered, and the solvent was evaporated under reduced pressure to yield 0.191 g of the crude amino product which was used in the next reaction without further purification.

ESI-MS: 254.1 [M+H]$^+$ 31.4 N-[6-(1-Benzyl-pyrrolidin-3-yl)-pyridin-3-yl]-4-isopropyl-benzene-sulfonamide 0.12 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-propyl-benzenesulfonylchloride. The crude product was thereby purified via silica gel chromatography on a cromabond column with ethyl acetate as eluent.

ESI-MS: 436.1 [M+H]$^+$ 31.5 N-[6-(Pyrrolidin-3-yl)-pyridin-3-yl]-4-isopropyl-benzene-sulfonamide 0.12 g of N-[6-(1-benzyl-pyrrolidin-3-yl)-pyridin-3-yl]-4-isopropyl-benzene-sulfonamide (0.28 mmol) were dissolved in 20 ml of methanol, a tip of a spatula 10% Pd/C was added, and the reaction mixture was hydrogenated for 2 h at room temperature and 4 h at 50° C. The catalyst was removed by filtration and the filtrate evaporated to dryness to yield 0.088 g of the desired debenzylated compound.

ESI-MS: 346.1 [M+H]$^+$ 31.6 N-[6-(1-propyl-pyrrolidin-3-yl)-pyridin-3-yl]-4-isopropyl-benzene-sulfonamide 0.088 g of N-[6-(1-benzyl-pyrrolidin-3-yl)-pyridin-3-yl]-4-isopropyl-benzene-sulfonamide (0.25 mmol) were dissolved in 10 ml of dichloromethane. 0.022 g of propionyl aldehyde (0.38 mmol), 0.023 g of acetic acid (0.38 mmol) and 0.081 g of sodium triacetoxyborohydride (0.38 mmol) were added and stirred for 1 h at room temperature. Water was added, the pH adjusted to 10 with 1 N sodium hydroxide, extracted three times with ethyl acetate, the organic layers combined and evaporated to dryness. The crude material was purified via silica gel chromatography with dichloromethane/methanol 20%. Fractions containing the product were combined and the solvent evaporated to yield 0.026 mg of the product.

ESI-MS: 388.1 [M+H]$^+$ $^1$H-NMR (CDCl$_3$): δ [ppm] 8.15 (m, 1H), 7.7 (d, 2H), 7.5 (m, 1H), 7.3 (d, 2H), 7.1 (m, 1H), 3.5 (m, 1H), 3.2 (m, 1H), 2.95 (m, 2H), 2.75 (m, 2H), 2.5-2.65 (m, 2H), 2.3 (m, 1H), 2.0 (m, 1H), 1.6 (m, 2H), 1.2 (m, 6H), 0.9 (m, 3H).

Example 32

4-Dimethylaminomethyl-N-[4-((S)-1-propyl-pyrrolidin-3-yl)-phenyl]-benzenesulfonamide 32.1 4-Formyl-N-[4-((S)-1-propyl-pyrrolidin-3-yl)-phenyl]-benzenesulfonamide 0.584 g of the desired product were obtained following the same synthetic procedure as described for 4-isopropyl-N-[4-((S)-1-propyl-pyrrolidin-3-yl)-phenyl]-benzenesulfonamide using commercially available 4-formyl-benzene-sulfonylchloride. The product was used in the subsequent step without further purification.

ESI-MS: 373.4 [M+H]$^+$ 32.2 4-Dimethylaminomethyl-N-[4-[(S)-1-propyl-pyrrolidin-3-yl]-phenyl]-benzenesulfonamide 0.3 g of 4-formyl-N-[4-((S)-1-propyl-pyrrolidin-3-yl)-phenyl]-benzenesulfonamide (0.81 mmol) were dissolved in 20 ml of dichloromethane, 0.6 ml of a 2 M solution of dimethylamine in tetrahydrofuran (1.21 mmol) added, followed by addition of 0.07 ml of acetic acid and 0.256 g sodium triacetoxyborohydride. The reaction mixture was stirred for 15 h at room temperature, water added, the pH adjusted to alkaline conditions with 1 N aqueous sodium hydroxide, and the aqueous layer extracted twice with diethylether. The combined ether extracts were dried over magnesium sulfate, filtered and the solvent evaporated under reduced pressure. The crude product was purified via preparative HPLC on a 40 mm Deltapak column with methanol/water/0.1% acetic acid. Fractions containing the product were combined, the solvent evaporated and the product isolated after extraction of an alkaline aqueous layer. (0.051 g).
ESI-MS: 402.1 [M+H]$^+$

Example 33

4-sec-Butyl-N-[4-((S)-1-propyl-pyrrolidin-3-yl)-phenyl]-benzenesulfonamide hydrochloride 0.082 g of the desired product were obtained following the same synthetic procedure as described for 4-isopropyl-N-[4-((S)-1-propyl-pyrrolidin-3-yl)-phenyl]-benzenesulfonamide hydrochloride using commercially available 4-sec-butylbenzenesulfonylchloride (ART-Chem).
ESI-MS: 401.1 [M+H]$^+$

Example 34

4-Bromo-3,6-difluoro-N-[4-(((S)-1-propyl-pyrrolidin-3-yl)-phenyl]-benzenesulfonamide 0.131 g of the desired product were obtained following the same synthetic procedure as described for 4-isopropyl-N-[4-((S)-1-propyl-pyrrolidin-3-yl)-phenyl]-benzenesulfonamide using commercially available 4-bromo-3,6-difluoro-benzenesulfonylchloride.
ESI-MS: 459.0/461.0 [M+H]$^+$
$^1$H-NMR (CDCl$_3$): δ [ppm] 7.55 (m, 1H), 7.4 (m, 1H), 7.15 (d, 2H), 7.0 (d, 2H), 4.7 (s, very broad, 2H), 3.3 (m, 1H), 3.0 (m, 1H), 2.85 (m, 1H), 2.7 (m, 1H), 2.4-2.6 (m, 3H), 2.25 (m, 1H), 1.8 (m, 1H), 1.55 (m, 2H), 0.85 (m, 3H).

Example 35

4-Isobutyl-N-[4-((S)-1-propyl-pyrrolidin-3-yl)-phenyl]-benzenesulfonamide hydrochloride 0.164 g of the desired product were obtained following the same synthetic procedure as described for 4-Isopropyl-N-[4-((S)-1-propyl-pyrrolidin-3-yl)-phenyl]-benzenesulfonamide hydrochloride using commercially available 4-isobutyl-benzenesulfonylchloride.
ESI-MS: 401.1 [M+H]$^+$
$^1$H-NMR (DMSO-d$_6$): δ [ppm] 11.3 and 11.1 (2s, broad, 1H), 10.3 (m, 1H), 7.7 (d, 2H), 7.3 (d, 2H), 7.25 (m, 1H), 7.2 (m, 1H), 7.05 (m, 2H), 2.9-3.8 (several m, 9H), 2.3 (m, 1H), 1.8-2.0 (m, 2H), 1.7 (m, 2H), 0.9 (m, 3H), 0.8 (m, 6H).

Example 36

4-Carboxy-N-[4-((S)-1-propyl-pyrrolidin-3-yl)-phenyl]-benzenesulfonamide 0.105 g of the desired product were obtained following the same synthetic procedure as described for 4-isopropyl-N-[4-((S)-1-propyl-pyrrolidin-3-yl)-phenyl]-benzenesulfonamide using commercially available 4-carboxy-benzenesulfonylchloride. The product however was finally isolated as precipitate from the aqueous layer through filtration, stirring with methanol, again filtration, and drying.
ESI-MS: 389.1 [M+H]$^+$
$^1$H-NMR (DMSO-d$_6$): δ [ppm] 10.25 (s, 1H), 9.6 (s, broad, 1H), 7.9 (d, 2H), 7.7-7.8 (m, 4H), 7.3 (d, 2H), 3.0-3.9 (several broad m, 7H), 2.4 (m, 1H), 2.0 (m, 1H), 1.7 (m, 2H), 0.9 (m, 3H).

Example 37

4-Cyclopentyl-N-[4-(S)-1-propyl-pyrrolidin-3-yl)-phenyl]-benzenesulfonamide hydrochloride 0.278 g of 4-bromo-N-[4-((S)-1-propyl-pyrrolidin-3-yl)-phenyl]-benzenesulfonamide (0.66 mmol) were dissolved in 5 ml tetrahydrofuran. 0.027 g of 1,1'-bis(diphenylphosphino) ferrocene (dppf)PdCl$_2$ (0.03 mmol) and 0.008 g of CuI (0.04 mmol) were added, followed by dropwise addition of 2 ml commercially available 0.5 M cyclopentylzincbromide in tetrahydrofuran. After stirring for 15 h at room temperature and further addition of cyclopentylzinkbromide, the reaction mixture was treated with ethyl acetate, washed with water, and the organic layer filtered over celite, washed with ethyl acetate, washed with water, and the organic layer dried over magnesium sulfate, filtered and the solvent removed under reduced pressure. The crude product was purified via preparative HPLC (Delta Pak column, 40 mm diameter) using methanol/water/0.1% acetic acid as eluent. Fractions containing the product were combined, methanol removed, and, after addition of 0.2 ml of 1 N hydrochlorid acid, the aqueous layer lyophilised to yield 0.0107 g of the product.
ESI-MS: 413.1 [M+H]$^+$
$^1$H-NMR (CDCl$_3$): δ [ppm] 12.4 & 12.3 (2s, broad, 1H), 7.7-7.9 (m, 3H), 7.25 (m, 2H), 7.0-7.2 (m, 3H), 4.0 (m, broad, 2H), 3.75 (m, broad, 1H), 2.5-3.0 (several m broad, 6H), 2.35 (m, broad, 1H), 1.5-2.1 (several m, broad, 10H), 1.0 (m, broad, 3H).

Example 38

4-Isopropyl-N-[4-((S)-1-(3-fluoro-propyl)-pyrrolidin-3-yl)-phenyl]-benzenesulfonamide 0.215 g of 4-isopropyl-N-[4-((S)-pyrrolidin-3-yl)-phenyl]-benzenesulfonamide (0.0.62 mmol) and 0.16 g of toluene-4-sulfonic acid 3-fluoro-propyl ester (0.69 mmol) were dissolved in 5 ml of dimethylformamide, 0.43 ml of triethylamine added and the reaction stirred for 1 h at 50° C. Additional toluene-4-sulfonic acid 3-fluoro-propyl ester and triethylamine were added to drive the reaction to completion. After stirring at room temperature for 15 h, the solvent was evaporated, the residue re-dissolved in dichloromethane, and the organic layer washed with 1 N aqueous sodium hydroxide. The aqueous phase was extracted twice with dichloromethane, the organic layers combined, dried over magnesium sulfate, filtered and the solvent evaporated. The crude product was purified via silica gel chromatography (chromabond column) using dichloromethane/methanol 0-3%. Fractions containing the product were collected and the solvent evaporated to yield 0.115 g of the desired product.
ESI-MS: 405.1 [M+H]$^+$
$^1$H-NMR (CDCl$_3$, 400 MHz): δ [ppm] 7.7 (d, 2H), 7.3 (d, 2H), 7.15 (d, 2H), 7.0 (d, 2H), 4.6 (m, 1H), 4.45 (m, 1H), 3.3

(m, 1H), 2.95 (m, 2H), 2.8 (m, 1H), 2.5-2.7 (several m, 3H), 2.45 (m, 1H), 2.25 (m, 1H), 1.75-2.0 (several m, 3H), 1.2 (m, 6H).

Example 39

3-Trifluoromethyl-N-[4-((S)-1-propyl-pyrrolidin-3-yl)-phenyl]-benzenesulfonamide 0.11 g of the desired product were obtained following the same synthetic procedure as described for 4-Isopropyl-N-[4-((S)-1-propyl-pyrrolidin-3-yl)-phenyl]-benzenesulfonamide using commercially available 3-trifluoromethyl-benzenesulfonylchloride.
ESI-MS: 427.2 [M+H]$^+$ Example 40

4-Butyloxy-N-[4-((S)-1-propyl-pyrrolidin-3-yl)-phenyl]-benzenesulfonamide

The desired product was obtained following the same synthetic procedure as described for 4-isopropyl-N-[4-((S)-1-propyl-pyrrolidin-3-yl)-phenyl]-benzenesulfonamide using commercially available 4-butyloxy-benzenesulfonylchloride.
ESI-MS: 417.3 [M+H]$^+$
$^1$H-NMR (CDCl$_3$, 400 MHz): δ [ppm] 7.7 (d, 2H), 7.15 (d, 2H), 6.95 (d, 2H), 6.85 (d, 2H), 5.6 (s, broad, 1H), 3.95 (t, 2H), 3.3 (m, 1H), 3.0 (m, 1H), 2.8 (m, 1H), 2.6 (m, 1H), 2.45 (m, 1H), 2.35 (m, 2H), 2.25 (m, 1H), 1.75 (m, 3H), 1.5 (m, 4H), 0.96 (m, 6H).

Example 41

4-(2,2-Difluorocyclopropyl)-N-[4-((S)-1-propyl-pyrrolidin-3-yl)-phenyl]-benzenesulfonamide The desired product were obtained following the same synthetic procedure as described for 4-Isopropyl-N-[4-((S)-1-propyl-pyrrolidin-3-yl)-phenyl]-benzenesulfonamide using 4-(2,2-difluoro-cyclopropyl)-benzenesulfonylchloride.
ESI-MS: 421.15 [M+H]$^+$
$^1$H-NMR (CDCl$_3$, 400 MHz): δ [ppm] 7.75 (d, 2H), 7.25 (d, 2H), 7.15 (d, 2H), 7.0 (d, 2H), 5.65 (bs, 1H), 3.3 (m, 1H), 3.05 (m, 1H), 2.85 (m, 1H), 2.75 (m, 1H), 2.65 (m, 1H), 2.45 (m, 3H), 2.3 (m, 1H), 1.9 (m, 1H), 1.8 (m, 1H), 1.65 (m, 1H), 1.55 (m, 2H), 0.95 (t, 3H).

Example 42

N-[3-(1-Propyl-pyrrolidin-3-yl)-phenyl]-4-trifluoromethoxy-benzenesulfonamide×HCl 42.1 3-[3-(4-Trifluoromethoxy-benzenesulfonylamino)-phenyl]-pyrrolidine-1-carboxylic acid methyl ester
To a solution of 3-(3-amino-phenyl)-pyrrolidine-1-carboxylic acid methyl ester (500 mg, 2.27 mmol) and triethylamine (500 mg, 4.94 mmol) in THF (20 ml) at 10° C. 4-trifluoromethoxy-benzenesulfonylchloride (600 mg, 2.3 mop was added. The mixture was allowed to come to room temperature and was stirred for 16 h. The mixture was poured into water and extracted three times with ethyl acetate. The organic layer was washed with water and saturated sodium chloride solution, dried over MgSO$_4$ and evaporated under reduced pressure to give the product as a brown oil (1 g, 99%).

42.2 N-(3-Pyrrolidin-3-yl-phenyl)-4-trifluoromethoxy-benzenesulfonamide
3-[3-(4-Trifluoromethoxy-benzenesulfonylamino)-phenyl]-pyrrolidine-1-carboxylic acid methyl ester (500 mg, 1.13 mmol) and HCl (8M, 137.82 mmol) in EtOH (10 ml) were heated under reflux for 48 h. The mixture was extracted twice with ethyl acetate and then NaOH (2M) was added. The aqueous phase was extracted twice with ethyl acetate. The combined organic layers were washed with water and saturated sodium chloride solution, dried over MgSO$_4$ and evaporated under reduced pressure to give the product as a brown oil (200 mg, 46%).

42.3 N-[3-(1-Propyl-pyrrolidin-3-yl)-phenyl]-4-trifluoromethoxy-benzenesulfonamide×HCl
A solution of N-(3-pyrrolidin-3-yl-phenyl)-4-trifluoromethoxy-benzenesulfonamide (200 mg, 0.52 mmol), acetic acid (30 μl, 0.52 mmol) and propionic aldehyde (30 mg, 0.52 mmol) were stirred in dichloromethane (20 ml) for 30 min at room temperature before sodium triacetoxyborohydride (165 mg, 0.78 mmol) was added in portions at 15° C. The mixture was stirred for 16 h at room temperature. The mixture was poured into water/dichloromethane (1/1) and the organic layer was washed with water, dried over MgSO$_4$ and evaporated under reduced pressure. The residue was purified by column chromatography (CH$_2$Cl$_2$/methanol–2%, 3%, 4%, 6%) to give a brown oil. To a solution of this oil in diethylether HCl in diethylether (1M) was added and the mixture was evaporated under reduced pressure to give the product as a white foam, which was dried in vacuo (55 mg, 23%).
MS (ESI) m/z: 429.15 [M+H]$^+$
$^1$H-NMR (DMSO-d$_6$): δ [ppm] 11.0-11.2 (m, 1H), 10.6 (s, 1H), 7.90-7.95 (m, 2H), 7.60-7.65 (m, 2H), 7.20-7.25 (m, 1H), 6.95-7.10 (m, 3H), 3.35-3.80 (m, 3H), 3.20-3.30 (m, 1H), 3.05-3.15 (m, 2H), 2.90-3.05 (m, 1H), 2.25-2.35 (m, 1H), 1.85-2.05 (m, 1H), 1.65-1.80 (m, 2H), 0.90-1.00 (m, 3H).

Example 43

4-Isopropyl-N-[3-(1-propyl-pyrrolidin-3-yl)-phenyl]-benzenesulfonamide×HCl 43.1 3-[3-(4-Isopropyl-benzenesulfonylamino)-phenyl]-pyrrolidine-1-carboxylic acid methyl ester
To a solution of 3-(3-amino-phenyl)-pyrrolidine-1-carboxylic acid methyl ester (500 mg, 2.27 mmol) and triethylamine (500 mg, 4.94 mmol) in THF (20 ml) at 10° C. 4-isopropyl-benzenesulfonylchloride (500 mg, 2.27 mmol) was added. The mixture was allowed to come to room temperature and was stirred for 16 h. The mixture was poured into water and extracted three times with ethyl acetate. The organic layer was washed with water and saturated sodium chloride solution, dried over MgSO$_4$ and evaporated under reduced pressure to give the product as a brown oil (1 g, 100%).

43.2 4-Isopropyl-N-(3-pyrrolidin-3-yl-phenyl)-benzenesulfonamide
3-[3-(4-Isopropyl-benzenesulfonylamino)-phenyl]-pyrrolidine-1-carboxylic acid methyl ester (900 mg, 1.13 mmol) and HCl (8M, 273.90 mmol) in EtOH (20 ml) were heated to reflux for 48 h. The mixture was extracted twice with ethyl acetate and then NaOH (2M) was added. The aqueous phase was extracted twice with ethyl acetate. The combined organic layers were washed with water and saturated sodium chloride solution, dried over MgSO$_4$ and evaporated under reduced pressure to give the product as a brown oil (100 mg, 13%).

43.3 4-Isopropyl-N-[3-(1-Propyl-pyrrolidin-3-yl)-phenyl]-benzenesulfonamide×HCl

A solution of 4-isopropyl-N-(3-pyrrolidin-3-yl-phenyl)-benzenesulfonamide (100 mg, 0.29 mmol), acetic acid (20 µl, 0.29 mmol) and propionic aldehyde (16.86 mg, 0.29 mmol) were stirred in dichloromethane (20 ml) for 30 min at room temperature before sodium triacetoxyborohydride (123 mg, 0.58 mmol) was added in portions at room temperature. The mixture was stirred for 16 h at room temperature. The mixture was poured into saturated aqueous $NaHCO_3$/dichloromethane (1/1) and the organic layer was washed with water and saturated sodium chloride solution, dried over $MgSO_4$ and evaporated under reduced pressure. The residue was purified by column chromatography ($CH_2Cl_2$/methanol–2%, 4%, 6%). To a solution of the purified product in diethylether HCl in diethylether (1M) was added and the mixture was evaporated under reduced pressure to give the product as a white foam, which was dried in vacuo (55 mg, 45%).

MS (ESI) m/z: 387.15 $[M+H]^+$ $^1$H-NMR ($CDCl_3$): δ [ppm] 8.95-9.15-(m, 1H), 7.72-7.82 (m, 2H), 6.85-7.31 (m, 6H), 3.85-4.05 (m, 1H), 3.65-3.79 (m, 1H), 3.25-3.56 (m, 1H), 3.0-3.2 (m, 2H), 2.78-3.0 (m, 2H), 2.43-2.55 (m, 1H), 1.80-2.40 (m, 5H), 1.12-1.21 (m, 6H), 0.9-1.02 (m, 3H).

Example 44

N-[3-(1-Cyclopropylmethyl-pyrrolidin-3-yl)-phenyl]-4-isopropyl-benzenesulfonamide×HCl A solution of 4-isopropyl-N-(3-pyrrolidin-3-yl-phenyl)-benzenesulfonamide (100 mg, 0.29 mmol), acetic acid (20 µl, 0.29 mmol) and cyclopropanecarbaldehyde (20.35 mg, 0.29 mmol) were stirred in dichloromethane (20 ml) for 30 min at room temperature before sodium triacetoxyborohydride (123 mg, 0.58 mmol) was added in portions at room temperature. The mixture was stirred for 16 h at room temperature. The mixture was poured into saturated aqueous $NaHCO_3$/dichloromethane (1/1) and the organic layer was washed with water and saturated sodium chloride solution, dried over $MgSO_4$ and evaporated under reduced pressure. The residue was purified by column chromatography ($CH_2Cl_2$/methanol–2%, 4%, 6%). To a solution of the purified product in diethylether HCl in diethylether (1M) was added and the mixture was evaporated under reduced pressure to give the product as a brown foam, which was dried in vacuo (50 mg, 40%).

MS (ESI) m/z: 399.25 $[M+H]^+$ $^1$H-NMR ($CDCl_3$): δ [ppm] 9.05-9.35-(m, 1H), 7.72-7.81 (m, 2H), 6.82-7.35 (m, 6H), 3.69-4.05 (m, 2H), 2.70-3.25 (m, 5H), 2.0-2.55 (m, 3H), 1.1-1.3 (m, 7H), 0.6-0.8 (m, 2H), 0.47-0.5 (m, 2H).

Example 45

N-[3-(1-Allyl-pyrrolidin-3-yl)-phenyl]-4-isopropyl-benzenesulfonamide×HCl

A solution of 4-isopropyl-N-(3-pyrrolidin-3-yl-phenyl)-benzenesulfonamide (100 mg, 0.29 mmol), allylbromide (38 mg, 0.31 mmol), potassium carbonate (60 mg, 0.43 mmol), and potassium fluoride (0.2 mg, 0.003 mmol) in acetone (20 ml) were heated to reflux for 4 h. The mixture was evaporated under reduced pressure and the residue was partitioned between ethyl acetate and water. The organic layer was washed with saturated sodium chloride solution, dried over $MgSO_4$ and evaporated under reduced pressure. The residue was purified by column chromatography ($CH_2Cl_2$/methanol–2%, 4%, 6%). To a solution of the purified product in dichloromethane HCl in diethylether (1M) was added and the mixture was evaporated under reduced pressure to give the product as a brown foam, which was dried in vacuo (25 mg, 21%).

MS (ESI) m/z: 385.15 $[M+H]^+$ $^1$H-NMR ($CDCl_3$): δ [ppm] 8.79-8.95-(m, 1H), 7.72-7.81 (m, 2H), 6.85-7.30 (m, 6H), 6.05-6.20 (m, 1H), 5.43-5.56 (m, 2H), 3.10-3.95 (m, 6H), 2.80-2.95 (m, 1H), 1.90-2.55 (m, 3H), 1.15-1.25 (m, 6H).

Example 46

4-Isopropyl-N-[6-(1-propyl-azetidin-3-yl)-pyridin-3-yl]-benzenesulfonamide 46.1 3-Hydroxy-azetidine-1-carboxylic acid tert-butyl ester To a degassed solution of 1-benzhydryl-azetidin-3-ol (4.75 g, 19.84 mmol) in methanol (methanol) (150 ml) were added ammonium formate (8.76 g, 138.91 mmol), 10% Pd/C (450 mg) and $Boc_2O$ (di-tert-butyl dicarbonate) (13 g, 59.56 mmol). The resulting suspension was heated to reflux under $N_2$ for 1 h. It was then cooled down to room temperature, filtered through a short pad of celite and concentrated. The residue was dissolved in $CH_2Cl_2$ and washed with water. The organic layer was dried ($Na_2SO_4$) and evaporated. The raw substance was chromatographed on silica gel (heptane:ethyl acetate (ethyl acetate), 1:1) to afford the title compound (3.30 g, 96%) as white crystals.

MS (ESI+) m/z=118.1 $[M-tBu+H]^+$ $^1$H NMR (400 MHz, $CDCl_3$): δ (ppm) 1.43 (s, 9H), 2.35 (d, J=6.2 Hz, 1H), 3.80 (dd, J=10.4, 4.4 Hz, 2H), 4.15 (dd, J=9.6, 6.7 Hz, 2H), 4.58 (m, 1H).

46.2 3-Iodo-azetidine-1-carboxylic acid tert-butyl ester

A solution of 3-hydroxy-azetidine-1-carboxylic acid tert-butyl ester (3.35 g, 19.34 mmol) in toluene (200 ml) was treated with imidazole (3.95 g, 58.01 mmol), triphenylphosphine (10.14 g, 38.65 mmol) and $I_2$ (7.36 g, 28.99 mmol). The mixture was heated at 100° C. for 1 h, cooled down to room temperature and next poured into saturated aqueous $NaHCO_3$ (30 ml). Excess triphenylphosphine was destroyed by addition of iodine until $I_2$ coloration persisted in organic layer. The latter was washed with 5% aqueous $Na_2S_2O_3$, dried over $Na_2SO_4$ and evaporated. Purification of the crude product by flash column chromatography (heptane:ethyl acetate, 2:1) provides the title compound (5.19 g, 95%) as a light yellow oil.

MS (ESI+) m/z=227.9 $[M-tBu+H]^+$ $^1$H NMR (400 MHz, $CDCl_3$): δ (ppm) 1.44 (s, 9H), 4.29 (dd, J=10.4, 5.4 Hz, 2H), 4.47 (m, 1H), 4.64 (dd, J=9.5, 8.0 Hz, 2H).

46.3 3-(5-Nitro-pyridin-2-yl)-azetidine-1-carboxylic acid tert-butyl ester

Zn dust (520 mg, 7.95 mmol) was vigorously stirred in THF (2 ml) under nitrogen and 1,2 dibromoethane (84 µl, 0.97 mmol) was added. The suspension was then heated at 80° C. for 8 min and next allowed to cool to room temperature. Trimethylsilyl chloride (115 µl, 0.92 mmol) in THF (1 ml) was then added and the mixture further stirred at room temperature for 45 min. A solution of 3-iodo-azetidine-1-carboxylic acid tert-butyl ester (1.74 g, 6.14 mmol) in THF (2 ml) was then added dropwise to the solution over a period of 15 min and the reaction mixture stirred at room temperature for 2 h. $Pd_2(dba)_3$ (90 mg, 0.10 mmol) and P(2-furyl)$_3$ (85 mg, 0.36 mmol) were then added to the mixture, followed by 2-bromo-5-nitropyridine (1.37 g, 6.74 mmol) in THF (4 ml). The mixture was then heated at 55° C. for 3 h, cooled to room temperature and quenched with saturated aqueous NaCl. Extraction with $CH_2Cl_2$, drying ($Na_2SO_4$) of the organic phase, filtration and evaporation in vacuo provided the crude material, which was purified by flash column chromatography (heptane:ethyl acetate, 3:1) to give the title compound (1.22 g, 71%) as a light yellow oil.

MS (ESI+) m/z=224.1 [M−tBu+H]$^+$ $^1$H NMR (400 MHz, CDCl$_3$): δ (ppm) 1.47 (s, 9H), 3.99 (m, 1H), 4.18 (dd, J=8.2, 6.1 Hz, 2H), 4.35 (t, J=8.6 Hz, 2H), 7.42 (d, J=8.5 Hz, 1H), 8.45 (dd, J=8.5, 2.6 Hz, 1H), 9.44 (d, J=2.4 Hz, 1H).

46.4  1-[3-(5-Nitro-pyridin-2-yl)-azetidin-1-yl]-propan-1-one

A solution of 3-(5-nitro-pyridin-2-yl)-azetidine-1-carboxylic acid tert-butyl ester (1.22 g, 4.36 mmol) in $CH_2Cl_2$ (100 ml) was treated with trifluoroacetic acid (TFA) (15 ml) and then stirred at room temperature for 2 h. After concentration, the raw mixture was digested in $CH_2Cl_2$ and washed with saturated aqueous NaHCO$_3$. The aqueous phase was extracted with $CH_2Cl_2$ (×3), the combined organic layers dried over Na$_2$SO$_4$ and evaporated. The raw material was next dissolved in THF (80 ml) and the solution cooled to 0° C. Propionyl chloride (460 μl, 5.26 mmol) and triethylamine (735 μl, 5.28 mmol) were next added, the mixture allowed to reach 20° C. and stirred for a further 12 h. It was then diluted with $CH_2Cl_2$ and washed successively with 1N aqueous HCl, saturated aqueous NaHCO$_3$ and water. The organic layer was dried (Na$_2$SO$_4$) and evaporated. The residue was chromatographied on silica gel (CH$_2$Cl$_2$:methanol, 49:1) to afford the title compound (880 mg, 85% for two steps) as a brown oil.

MS (ESI+) m/z=236.1 [M+H]$^+$ $^1$H NMR (400 MHz, CDCl$_3$): δ (ppm) 1.16 (t, J=7.5 Hz, 3H), 2.18 (q, J=7.5 Hz, 2H), 4.07 (m, 1H), 4.22 (dd, J=9.5, 6.0 Hz, 1H), 4.44 (m, 2H), 4.52 (t, J=8.4 Hz, 1H), 7.42 (d, J=8.5 Hz, 1H), 8.46 (dd, J=8.5, 2.6 Hz, 1H), 9.45 (d, J=2.5 Hz, 1H).

46.5  4-Isopropyl-N-[6-(1-propionyl-azetidin-3-yl)-pyridin-3-A-benzenesulfonamide 1-[3-(5-nitro-pyridin-2-yl)-azetidin-1-yl]-propan-1-one (340 mg, 1.44 mmol) was dissolved in ethanol (EtOH) (25 ml) and SnCl$_2$.2H$_2$O (1.63 g, 7.22 mmol) was added. The resulting mixture was refluxed for 8 h and the solvent next removed under vacuum. The raw material was dissolved in ethyl acetate and washed successively with 2N aqueous NaOH (×2) and water. The organic layer was dried (Na$_2$SO$_4$), filtered through a pad of celite and evaporated. Half of the crude material was then dissolved in $CH_2Cl_2$ (40 ml) and pyridine (115 μl, 1.41 mmol) followed by 4-isopropyl-benzenesulfonylchloride (190 μl, 1.05 mmol) were added dropwise. After stirring at room temperature overnight, the reaction mixture was diluted with $CH_2Cl_2$ and washed successively with 1N aqueous HCl, saturated aqueous NaHCO$_3$ and water. The organic layer was dried (Na$_2$SO$_4$) and evaporated. The residue was chromatographied on silica gel (heptane:ethyl acetate, 1:3) to afford the title compound (150 mg, 54% for two steps) as a light yellow oil.

MS (ESI+) m/z=388.1 [M+H]$^+$ $^1$H NMR (400 MHz, CDCl$_3$): δ (ppm) 1.14 (t, J=7.5 Hz, 3H), 1.24 (d, J=6.9 Hz, 6H), 2.14 (q, J=7.5 Hz, 2H), 2.94 (m, 1H), 3.87 (m, 1H), 4.10 (dd, J=9.7, 5.9 Hz, 1H), 4.34 (m, 2H), 4.42 (t, J=8.5 Hz, 1H), 7.12 (d, J=8.4 Hz, 1H), 7.31 (m, 3H), 7.59 (dd, J=8.4, 2.6 Hz, 1H), 7.71 (d, J=8.4 Hz, 2H), 8.25 (d, J=2.3 Hz, 1H).

46.6  4-Isopropyl-N-[6-(1-propionyl-azetidin-3-yl)-pyridin-3-yl]-benzenesulfonamide To a solution of 4-isopropyl-N-[6-(1-propionyl-azetidin-3-yl)-pyridin-3-yl]-benzenesulfonamide (150 mg, 0.38 mmol) in THF (15 ml) was added dropwise 1M BH$_3$. THF (3.8 ml) and the mixture was stirred at room temperature for 12 h. It was then quenched by careful addition of 1N aqueous HCl (10 ml) and the resulting solution was heated at reflux for 4 h. The solution was next cooled to room temperature, adjusted to pH~8 with 2 N NaOH solution and diluted with $CH_2Cl_2$. Separation of the layers, drying (Na$_2$SO$_4$) of the organic phase, filtration and evaporation in vacuo provided the crude material, which was purified by flash column chromatography (CH$_2$Cl$_2$:methanol, 95:5) to give the title compound (95 mg, 66%) as a light yellow oil.

MS (ESI+) m/z=374.1 [M+H]$^+$ $^1$H NMR (400 MHz, CDCl$_3$): δ (ppm) 0.93 (t, J=7.4 Hz, 3H), 1.24 (d, J=6.9 Hz, 6H), 1.47 (m, 2H), 2.62 (m, 2H), 2.94 (m, 1H), 3.44 (m, 2H), 3.90 (m, 3H), 7.15 (d, J=8.4 Hz, 1H), 7.31 (d, J=8.3 Hz, 2H), 7.52 (dd, J=8.4, 2.6 Hz, 1H), 7.70 (d, J=8.3 Hz, 2H), 8.22 (d, J=1.8 Hz, 1H).

Example 47

N-[6-(1-Propyl-azetidin-3-yl)-pyridin-3-yl]-4-trifluoromethoxy-benzenesulfonamide 47.1  N-[6-(1-Propionyl-azetidin-3-yl)-pyridin-3-yl]-4-trifluoromethoxy-benzenesulfonamide Following the same procedure as described above, the second half of the crude aminopyridine obtained in 46.5 was treated with pyridine (115 μl, 1.41 mmol) and 4-(trifluoromethoxy)benzenesulfonylchloride (180 μl, 1.06 mmol) in $CH_2Cl_2$ (40 ml). Purification of the crude product by flash column chromatography (heptane:ethyl acetate, 1:2) provides the title compound (130 mg, 42% for two steps) as a light yellow oil.

MS (ESI+) m/z=430.0 [M+H]$^+$ $^1$H NMR (400 MHz, CDCl$_3$): δ (ppm) 1.14 (t, J=7.5 Hz, 3H), 2.16 (q, J=7.5 Hz, 2H), 3.86 (m, 1H), 4.08 (dd, J=9.5, 6.1 Hz, 1H), 4.34 (m, 2H), 4.43 (t, J=8.4 Hz, 1H), 7.12 (d, J=8.4 Hz, 1H), 7.29 (d, J=8.3 Hz, 2H), 7.60 (dd, J=8.4, 2.6 Hz, 1H), 7.87 (d, J=8.9 Hz, 2H), 8.01 (bs, 1H), 8.28 (d, J=2.0 Hz, 1H).

47.2  N-[6-(1-Propyl-azetidin-3-yl)-pyridin-3-yl]-4-trifluoromethoxy-benzenesulfonamide Following the same procedure as described in Example 46.6, N-[6-(1-propionyl-azetidin-3-yl)-pyridin-3-yl]-4-trifluoromethoxy-benzenesulfonamide (130 mg, 0.30 mmol) in THF (15 ml) was treated with 1M BH$_3$. THF (3 ml). Purification of the crude product by flash column chromatography (CH$_2$Cl$_2$:methanol, 95:5) provides the title compound (75 mg, 60%) as a light yellow oil.

MS (ESI+) m/z=416.1 [M+H]$^+$ $^1$H NMR (400 MHz, CDCl$_3$): δ (ppm) 0.96 (t, J=7.4 Hz, 3H), 1.57 (m, 2H), 2.88 (t, J=7.7 Hz, 2H), 3.76 (t, J=8.1 Hz, 2H), 3.98 (m, 1H), 4.19 (t, J=8.3 Hz, 2H), 7.04 (d, J=8.4 Hz, 1H), 7.24 (d, J=8.4 Hz, 2H), 7.33 (bs, 1H), 7.50 (dd, J=8.3, 2.5 Hz, 1H), 7.90 (d, J=8.8 Hz, 2H), 8.33 (d, J=2.3 Hz, 1H).

Example 48

4-Isopropyl-N-[4-(1-propyl-azetidin-3-yl)-phenyl]-benzene sulfonamide 48.1  3-(4-Nitro-phenyl)-azetidine-1-carboxylic acid tert-butyl ester Following the same procedure as described in 46.3, the organozinc species was prepared using 3-iodo-azetidine-1-carboxylic acid tert-butyl ester (1.74 g, 6.14 mmol), Zn dust (520 mg, 7.95 mmol), 1,2 dibromoethane (84 μl, 0.97 mmol) and trimethylsilyl chloride (115 μl, 0.92 mmol). It was then coupled with 1-bromo-4-nitrobenzene (1.24 g, 6.13 mmol)

using Pd$_2$(dba)$_3$ (90 mg, 0.10 mmol) and P(2-furyl)$_3$ (85 mg, 0.36 mmol). Purification of the crude product by flash column chromatography (heptane:ethyl acetate, 4:1) provides the title compound (880 mg, 52%) as a light yellow oil.

MS (ESI+) m/z=223.1 [M−tBu+H]$^+$.

48.2 1-[3-(4-Nitro-phenyl)-azetidin-1-yl]-propan-1-one

Using the same procedure as described in 46.4, 3-(4-nitro-phenyl)-azetidine-1-carboxylic acid tert-butyl ester was deprotected with TFA (15 ml) in CH$_2$Cl$_2$ (100 ml) and the resulting amine treated with propionyl chloride (2900, 3.31 mmol) and triethylamine (470 μl, 3.37 mmol) in THF (80 ml). Purification of the crude product by flash column chromatography (heptane:ethyl acetate, 1:1) provides the title compound (570 mg, 87% for two steps) as a brown oil.

MS (ESI+) m/z=235.1 [M+H]$^{+1}$H NMR (400 MHz, CDCl$_3$): δ (ppm) 1.17 (t, J=7.5 Hz, 3H), 2.17 (q, J=7.5 Hz, 2H), 3.93 (m, 1H), 4.09 (dd, J=9.8, 5.9 Hz, 1H), 4.14 (dd, J=8.3, 6.0 Hz, 1H), 4.47 (t, J=9.3 Hz, 1H), 4.59 (t, J=8.6 Hz, 1H), 7.49 (d, J=8.7 Hz, 2H), 8.24 (d, J=8.7 Hz, 2H).

48.3 4-Isopropyl-N-[4-(1-propionyl-azetidin-3-yl)-phenyl]-benzenesulfonamide

Following the same procedure as described in 46.5, 1-[3-(4-nitro-phenyl)-azetidin-1-yl]-propan-1-one (480 mg, 2.04 mmol) in EtOH (20 ml) was treated with SnCl$_2$.2H$_2$O (2.25 g, 9.97 mmol) and half of the resulting aniline in CH$_2$Cl$_2$ (15 ml) was then treated with pyridine (140 μl, 1.71 mmol) and 4-isopropyl-benzensulfonylchloride (230 μl, 1.28 mmol). Purification of the crude product by flash column chromatography (heptane:ethyl acetate, 1:1) provided the title compound (140 mg, 36% for two steps) as a pale yellow gum.

MS (ESI+) m/z=387.1 [M+H]$^+$ 48.4 4-Isopropyl-N-[4-(1-propyl-azetidin-3-yl)-phenyl]benzene sulfonamide Following the same procedure as described in Example 46.6, 4-isopropyl-N-[4-(1-propionyl-azetidin-3-yl)-phenyl]-benzenesulfonamide (140 mg, 0.36 mmol) in THF (18 ml) was then treated with 1M BH$_3$. THF (3.6 ml). The crude material was chromatographied (ethyl acetate) to afford the title compound (90 mg, 67%) as a pale yellow oil.

MS (ESI+) m/z=373.1 [M+H]$^+$ $^1$H NMR (400 MHz, CDCl$_3$): δ (ppm) δ 0.93 (t, J=7.4 Hz, 3H), 1.24 (d, J=6.9 Hz, 6H), 1.38 (m, 2H), 2.41 (t, J=7.5 Hz, 2H), 2.94 (m, 1H), 3.03 (m, 2H), 3.67 (m, 3H), 7.01 (d, J=8.4 Hz, 2H), 7.16 (d, J=8.4 Hz, 2H), 7.28 (d, J=8.5 Hz, 2H), 7.68 (d, J=8.4 Hz, 2H).

Example 49

N-[4-(1-Propyl-azetidin-3-yl)-phenyl]-4-trifluoromethoxybenzene sulfonamide 49.1 N-[4-(1-Propionyl-azetidin-3-yl)-phenyl]-4-trifluoromethoxy-benzenesulfonamide Following the same procedure as described above, the second half of the resulting aniline from 48.3 was treated with pyridine (140 μl, 1.71 mmol) and 4-(trifluoromethoxy)benzensulfonylchloride (215 μl, 1.26 mmol) in CH$_2$Cl$_2$ (15 ml). Purification of the crude product by flash column chromatography (heptane:ethyl acetate, 2:1) provided the title compound (170 mg, 40% for two steps) as a pale yellow gum.

MS (ESI+) m/z=429.0 [M+H]$^+$ 49.3 N-[4-(1-Propyl-azetidin-3-yl)-phenyl]-4-trifluoromethoxybenzene sulfonamide Following the same procedure as described in Example 47.2, N-[4-(1-propionyl-azetidin-3-yl)-phenyl]-4-trifluoromethoxy-benzenesulfonamide (170 mg, 0.39 mmol) in THF (20 ml) was then treated with 1M BH$_3$. THF (3.9 ml). The crude material was chromatographied (ethyl acetate) to afford the title compound (86 mg, 52%) as a pale yellow oil.

MS (ESI+) m/z=415.1 [M+H]$^+$ $^1$H NMR (400 MHz, CDCl$_3$): δ (ppm) 0.90 (t, J=7.4 Hz, 3H), 1.38 (m, 2H), 2.43 (t, J=7.5 Hz, 2H), 3.05 (m, 2H), 3.68 (m, 3H), 7.01 (d, J=8.4 Hz, 2H), 7.18 (d, J=8.4 Hz, 2H), 7.25 (d, J=8.5 Hz, 2H), 7.79 (d, J=8.8 Hz, 2H).

Example 50

4-Bromo-N-[2-(1-propyl-pyrrolidin-3-yl)-pyrimidin-5-yl]-benzenesulfonamide 50.1 5-Bromo-2-vinyl-pyrimidine 5-Bromo-2-iodo-pyrimidine (9.15 g, 32.11 mmol) was dissolved in THF (150 ml) and Pd(PPh$_3$)$_4$ (18.85 g, 1.60 mmol) was added, followed by tributyl-vinyl-stannane (9.38 ml, 32.11 mmol). The resulting mixture was heated at 140° C. for 20 min under microwave irradiations, next filtered through a pad of celite and concentrated. The crude material was diluted with CH$_2$Cl$_2$ and washed with water. Separation of the layers, drying (Na$_2$SO$_4$) of the organic phase, filtration and evaporation in vacuo provided the crude material, which was purified by flash column chromatography (CH$_2$Cl$_2$) to give the title compound (4.05 g, 68%) as a volatile yellow oil crystallizing at 4° C.

$^1$H NMR (400 MHz, CDCl$_3$): δ (ppm) 5.77 (dd, J=10.5, 1.4 Hz, 1H), 6.62 (dd, J=17.3, 1.4 Hz, 1H), 6.83 (dd, J=17.3, 10.5 Hz, 1H).

50.2 5-Bromo-2-(1-propyl-pyrrolidin-3-yl)-pyrimidine

Methoxymethyl-propyl-trimethylsilanylethyl-amine (14.13 g, 74.61 mmol) in CH$_2$Cl$_2$ (4 ml) was added dropwise to a 0° C. cooled solution of 5-bromo-2-vinyl-pyrimidine (2 g, 10.80 mmol) and TFA (210 μl, 2.72 mmol) in CH$_2$Cl$_2$ (45 ml) over a period of 20 min. The reaction mixture was then stirred at room temperature for 2 h. The crude material was diluted with CH$_2$Cl$_2$, washed with saturated aqueous NaHCO$_3$ and the organic layer was dried over Na$_2$SO$_4$ and evaporated. The residue was chromatographied on silica gel (CH$_2$Cl$_2$:methanol, 97:3) to afford the title compound (1.03 g, 34%) as a brown oil.

MS (ESI+) m/z=271.9 [M+H]$^+$ 50.3 2-(1-Propyl-pyrrolidin-3-yl)-pyrimidin-5-ylamine. A dry flask was charged with 5-bromo-2-(1-propyl-pyrrolidin-3-yl)-pyrimidine (300 mg, 1.11 mmol), Pd$_2$(dba)$_3$ (tris(dibenzylideneacetonate) dipalladium (30 mg, 0.032 mmol)), rac-BINAP (2,2'-bis(diphenylphosphino)-1,1'-binaphthyl) (35 mg, 0.056 mmol), tBuONa (150 mg, 1.56 mmol), benzophenone imine (300 mg, 1.65 mmol) and toluene (4 ml). It was then evacuated, flushed with nitrogen and the mixture heated at 80° C. under microwave irradiations for 3 h. After filtration through a pad of celite, the solvent was removed under reduced pressure. The crude material was then dissolved in THF (10 ml) and 1 N aqueous HCl (3 ml) was added. The solution was stirred at room temperature for 45 min and the organic solvent was next removed under vacuo. The resulting aqueous phase was adjusted to pH-9 with 2 N NaOH solution, washed with heptane:ethyl acetate, 2:1 (50 ml) and concentrated to give the crude amine.

MS (ESI+) m/z=207.1 [M+H]$^+$ 50.4 4-Bromo-N-[2-(1-propyl-pyrrolidin-3-yl)-pyrimidin-5-yl]-benzenesulfonamide The crude 2-(1-propyl-pyrrolidin-3-yl)-pyrimidin-5-ylamine (about 1.11 mmol) was dissolved in CH$_2$Cl$_2$:pyridine, 9:1 (50 ml) and 4-bromobenzensulfonyl chloride (566 mg, 2.21 mmol) was added. After stirring at room temperature overnight, the reaction mixture was filtered and concentrated. The raw material was then dissolved in a solution of EtONa (400 mg, 5.87 mmol) in EtOH (35 ml) and the resulting solution was heated under reflux for 1 h. Silica gel (1 g) was next added to the mixture and the solvent removed under reduced pressure. Following flash column chromatography (CH$_2$Cl$_2$:methanol, 9:1) provides the title compound (100 mg, 21% for four steps) as a yellow gum.

MS (ESI+) m/z=426.9 [M+H]$^+$ $^1$H NMR (400 MHz, CDCl$_3$): rotamers δ (ppm) 0.99 (t, J=7.3 Hz, 3H), 1.84 (m, 2H), 2.33 (m, 1H), 2.53 (m, 1H), 3.05 (m, 1H), 3.17 (m, 1H), 3.46 (t, J=6.0 Hz, 2H), 3.70 (m, 2H), 3.86 (m, 1H), 5.67 (bs, 1H), 7.53 (d, J=8.4 Hz, 2H), 7.70-7.75 (2d, J=8.4 Hz, 2H), 8.44 (s, 2H).

Example 51

N-[2-(1-Propyl-pyrrolidin-3-yl)-pyrimidin-5-yl]-4-trifluoromethoxy-benzenesulfonamide Following the same procedure as described in Example 50.4, a crude 2-(1-propyl-pyrrolidin-3-yl)-pyrimidin-5-ylamine (about 0.74 mmol) obtained via the above mentioned protocol was treated with 4-(trifluoromethoxy)benzensulfonyl chloride (250 µl, 1.47 mmol) in CH$_2$Cl$_2$:pyridine, 9:1 (50 ml). Subsequent treatment with EtONa/EtOH and purification of the crude product by flash column chromatography (CH$_2$Cl$_2$:methanol, 9:1) provided the title compound (44 mg, 14% for four steps) as a yellow gum.

MS (ESI+) m/z=431.0 [M+H]$^+$ $^1$H NMR (400 MHz, CDCl$_3$): rotamers δ (ppm) 0.98 (t, J=7.3 Hz, 3H), 1.84 (m, 2H), 2.30 (m, 1H), 2.58 (m, 1H), 3.14 (m, 2H), 3.31 (m, 1H), 3.64 (m, 2H), 3.92 (m, 2H), 7.24 (m, 2H), 7.93-7.97 (2d, J=8.6 Hz, 2H), 8.44 (s, 2H).

Example 52

4-Isopropyl-N-[2-(1-propyl-pyrrolidin-3-yl)-pyrimidin-5-yl]-benzenesulfonamide

Following the same procedure as described in Example 50.4, a crude 2-(1-propyl-pyrrolidin-3-yl)-pyrimidin-5-ylamine (about 0.13 mmol) obtained via the above mentioned protocol was treated with 4-isopropylbenzensulfonyl chloride (56 µl, 0.31 mmol) in CH$_2$Cl$_2$:pyridine, 9:1 (50 ml). Subsequent treatment with EtONa/EtOH and purification of the crude product by flash column chromatography (CH$_2$Cl$_2$:methanol, 85:15) provided the title compound (26 mg, 50% for four steps) as a yellow gum.

MS (ESI+) m/z=389.1 [M+H]$^+$ $^1$H NMR (400 MHz, CDCl$_3$): rotamers δ (ppm) 0.96 (t, J=7.4 Hz, 3H), 1.21-1.23 (2d, J=6.9 Hz, 6H), 1.80 (m, 2H), 2.26 (m, 1H), 2.52 (m, 1H), 2.90 (m, 1H), 3.07 (m, 2H), 3.24 (m, 1H), 3.55 (m, 2H), 3.85 (m, 2H), 6.34 (bs, 1H), 7.25 (m, 2H), 7.76-7.81 (2d, J=8.2 Hz, 2H), 8.54 (s, 2H).

Example 53

N-{4-[(S)-1-(3-Hydroxy-propyl)-pyrrolidin-3-yl]-phenyl}-4-isopropyl-benzenesulfonamide 53.1 Acetic acid 3-{(S)-3-[4-(4-isopropyl-benzenesulfonylamino)-phenyl]-pyrrolidin-1-yl}-propyl ester 0.21 g of 4-isopropyl-N-[4-((S)-pyrrolidin-3-yl)-phenyl]-benzenesulfonamide (0.62 mmol) were dissolved in 5 ml dimethylformamide. 0.0019 mg of sodium iodide (0.01 mmol) and 0.13 ml of triethylamine (0.94 mmol) were added, followed by addition of 0.136 mg of 3-acetoxy-1-bromopropane (0.75 mmol). Stirring continued for 15 h at room temperature before the reaction mixture was poured onto 50 ml of crushed ice. The aqueous layer was extracted three times with ethyl acetate and the combined organic phases washed with water and saturated sodium chloride solution. The ethyl acetate phase was dried over magnesium sulfate, filtered, and evaporated to dryness under reduced pressure to yield 0.26 g of the crude product.

ESI-MS: 445.1 [M+H]$^+$ 53.2 N-{4-[(S)-1-(3-Hydroxy-propyl)-pyrrolidin-3-yl]-phenyl}-4-isopropylbenzene-sulfonamide 0.26 g of acetic acid 3-{(S)-3-[4-(4-isopropyl-benzenesulfonylamino)-phenyl]-pyrrolidin-1-yl}-propyl ester (0.58 mmol) were dissolved in 4 ml of tetrahydrofuran. 0.021 g lithium hydroxide (0.88 mmol) dissolved in 4 ml water were added and the reaction mixture stirred for 15 h at room temperature. An additional equivalent of lithium hydroxide was added and stirring continued for 24 h before the reaction mixture was diluted with water and extracted three times with ethyl acetate. The combined organic phases were dried over magnesium sulfate, filtered, and evaporated to dryness under reduced pressure to yield 0.157 g of the product.

ESI-MS: 403.3 [M+H]$^+$ $^1$H-NMR (CDCl$_3$): δ [ppm] 7.7 (d, 2H), 7.25 (m, 2H), 7.1 (d, 2H), 6.95 (d, 2H), 3.8 (m, 2H), 3.3 (m, 1H), 3.05 (m, 1H), 2.95 (m, 1H), 2.7-2.9 (m, 4H), 2.55 (m, 1H), 2.25 (m, 1H), 1.7-1.85 (m, 2H), 1.15-1.3 (broad, 7H).

Example 54

4-Cyclobutyl-N-[4-((S)-1-propyl-pyrrolidin-3-yl)-phenyl]-benzenesulfonamide

The title compound was prepared in an analogous manner to that described for Example 37.

ESI-MS: 399.1 [M+H]$^+$

Example 55

4-Oxazol-5-yl-N-[4-(1-propyl-azetidin-3-yl)-phenyl]-benzenesulfonamide 55.1 4-(1-Propyl-azetidin-3-yl)-phenylamine 1-(3-(4-Nitrophenyl)azetidin-1-yl)propan-1-one (3.16 g, 13.49 mmol) was dissolved in ethanol (200 ml) and SnCl$_2$.2H$_2$O (15.20 g, 67.45 mmol) was added. The resulting mixture was refluxed for 8 h and then the solvent was removed under vacuum. The raw material was dissolved in ethyl acetate and washed successively with 2N aqueous NaOH (×2) and water. The organic layer was dried (Na$_2$SO$_4$), filtered through a pad of celite and evaporated. The crude 1-[3-(4-amino-phenyl)-azetidin-1-yl]-propan-1-one was then dissolved in tetrahydrofuran (THF) (200 ml) and 1M LiAlH$_4$ in tetrahydrofuran (19.5 ml, 19.5 mmol) was added dropwise at 0° C. After stirring at room temperature for 2 h, the reaction mixture was carefully quenched with THF/H$_2$O 9:1 (20 ml) at 0° C., then filtered through a pad of celite and the solvents were removed under reduced pressure. The crude 4-(1-propyl-azetidin-3-yl)-phenylamine was used without any further purification for the next step.

MS (ESI+) m/z=191.1 [M+H]$^+$ 55.2 4-Oxazol-5-yl-N-[4-(1-propyl-azetidin-3-yl)-phenyl]-benzenesulfonamide The crude 4-(1-propyl-azetidin-3-yl)-phenylamine (40 mg, 0.21 mmol) was dissolved in CH$_2$Cl$_2$/pyridine 9:1 (10 ml) and 4-oxazol-5-yl-benzenesulfonyl chloride (51 mg, 0.21 mmol) was added. After stirring at room temperature for 2 h, the reaction mixture was diluted with $CH_2Cl_2$ and washed successively with 1N aqueous HCl, saturated aqueous $NaHCO_3$ and water. The organic layer was dried over $Na_2SO_4$ and evaporated. The residue was chromatographied on silica gel ($CH_2Cl_2$:methanol, 95:5) to afford the title compound (30 mg, 36%) as a white amorphous solid.

MS (ESI+) m/z=398.1 $[M+H]^+$
$^1$H NMR (400 MHz, $CDCl_3$): δ (ppm) 1.02 (t, J=7.4 Hz, 3H), 1.75 (m, 2H), 3.08 (m, 2H), 3.72 (m, 2H), 4.24 (m, 1H), 4.62 (m, 2H), 7.10 (m, 2H), 7.22 (d, J=7.9 Hz, 2H), 7.45 (s, 1H), 7.69 (d, J=8.4 Hz, 2H), 7.89 (d, J=8.3 Hz, 2H), 7.95 (s, 1H).

Example 56

4-(2-Fluoro-ethyl)-N-[4-(1-propyl-azetidin-3-yl)-phenyl]-benzenesulfonamide

Following the same procedure as described in example 55, 4-(1-propyl-azetidin-3-yl)phenylamine (100 mg, 0.52 mmol) in $CH_2Cl_2$/pyridine 9:1 (12 ml) was treated with 4-(2-fluoro-ethyl)-benzenesulfonyl chloride (117 mg, 0.52 mmol). Purification of the crude product by chromatography on reversed phase silica gel ($H_2O$+0.1% acetic acid:$CH_3CN$+0.1% acetic acid, 75:25) provided the title compound (11 mg, 6%) as a colourless gum.

MS (ESI+) m/z=377.1 $[M+H]^+$
$^1$H NMR (400 MHz, $CDCl_3$): δ (ppm) 0.97 (t, J=7.4 Hz, 3H), 1.59 (m, 2H), 2.89 (m, 2H), 3.00 (t, J=6.0 Hz, 1H), 3.06 (t, J=6.0 Hz, 1H), 3.76 (m, 2H), 4.05 (m, 1H), 4.29 (m, 2H), 4.57 (t, J=6.0 Hz, 1H), 4.69 (t, J=6.0 Hz, 1H), 7.08 (d, J=8.5 Hz, 2H), 7.12 (d, J=8.5 Hz, 2H), 7.32 (d, J=8.2 Hz, 2H), 7.71 (d, J=8.2 Hz, 2H).

Example 57

4-(3-Fluoro-propyl)-N-[4-(1-propyl-azetidin-3-yl)-phenyl]-benzenesulfonamide

Following the same procedure as described in example 55, 4-(1-propyl-azetidin-3-yl)phenylamine (100 mg, 0.52 mmol) in $CH_2Cl_2$/pyridine 1:1 (12 ml) was treated with 4-(3-fluoro-propyl)-benzenesulfonyl chloride (161 mg, 0.68 mmol). Purification of the crude product by chromatography on reversed phase silica gel ($H_2O$+0.1% acetic acid:$CH_3CN$+0.1% acetic acid, 75:25) provided the title compound (40 mg, 20%) as a colourless gum.

MS (ESI+) m/z=391.3 $[M+H]^+$
$^1$H NMR (400 MHz, $CDCl_3$): δ (ppm) 0.96 (t, J=7.4 Hz, 3H), 1.66 (m, 2H), 1.97 (m, 2H), 2.76 (m, 2H), 3.08 (m, 1H), 3.25 (m, 1H), 3.73 (m, 2H), 4.21 (m, 1H), 4.34 (t, J=5.7 Hz, 1H), 4.46 (t, J=5.7 Hz, 1H), 4.66 (m, 2H), 7.04 (d, J=8.3 Hz, 2H), 7.12 (d, J=8.3 Hz, 2H), 7.25 (d, J=8.1 Hz, 2H), 7.70 (d, J=8.3 Hz, 2H), 8.17 (s, 1H).

Example 58

4-Bromo-N-[4-(1-propyl-azetidin-3-yl)-phenyl]-benzenesulfonamide

Following the same procedure as described in example 55, 4-(1-propyl-azetidin-3-yl)phenylamine (1 g, 5.25 mmol) in $CH_2Cl_2$/pyridine 9:1 (50 ml) was treated with 4-bromobenzenesulfonyl chloride (1.34 g, 5.25 mmol). Purification of the crude product by flash column chromatography ($CH_2Cl_2$:methanol, 95:5) provided the title compound (1.1 g, 51%) as a colourless gum.

MS (ESI+) m/z=410.0 $[M+H]^+$
$^1$H NMR (400 MHz, $CDCl_3$): δ (ppm) 0.92 (t, J=7.4 Hz, 3H), 1.47 (m, 2H), 2.60 (m, 2H), 3.28 (m, 2H), 3.78 (m, 1H), 3.91 (m, 2H), 6.07 (bs, 1H), 7.07 (d, J=8.4 Hz, 2H), 7.13 (d, J=8.4 Hz, 2H), 7.53 (d, J=8.5 Hz, 2H), 7.64 (d, J=8.5 Hz, 2H).

Example 59

4-((R)-2-Fluoro-1-methyl-ethyl)-N-[4-(1-propyl-azetidin-3-yl)-phenyl]-benzenesulfonamide Following the same procedure as described in example 55, 4-(1-propyl-azetidin-3-yl)phenylamine (150 mg, 0.78 mmol) in $CH_2Cl_2$/pyridine 1:1 (12 ml) was treated with 4-((R)-2-fluoro-1-methyl-ethyl)-benzenesulfonyl chloride (242 mg, 1.02 mmol). Purification of the crude product by chromatography on reversed phase silica gel ($H_2O$+0.1% acetic acid:$CH_3CN$+0.1% acetic acid, 75:25) provided the title compound (15 mg, 5%) as a colourless gum.

MS (ESI+) m/z=391.1 $[M+H]^+$
$^1$H NMR (400 MHz, $CDCl_3$): δ (ppm) 0.93 (t, J=7.3 Hz, 3H), 1.27 (m, 3H), 1.60 (m, 2H), 2.99 (m, 2H), 3.13 (m, 1H), 3.86 (m, 2H), 4.10 (m, 1H), 4.42 (m, 5H), 4.36 (m, 1H), 4.49 (m, 1H), 7.07 (m, 4H), 7.27 (d, J=8.3 Hz, 2H), 7.74 (d, J=8.3 Hz, 2H).

Example 60

4-((S)-2-Fluoro-1-methyl-ethyl)-N-[4-(1-propyl-azetidin-3-yl)-phenyl]-benzenesulfonamide Following the same procedure as described in example 55, 4-(1-propyl-azetidin-3-yl)phenylamine (110 mg, 0.57 mmol) in $CH_2Cl_2$/pyridine 1:1 (12 ml) was treated with 4-((S)-2-fluoro-1-methyl-ethyl)-benzenesulfonyl chloride (178 mg, 0.75 mmol). Purification of the crude product by flash column chromatography ($CH_2Cl_2$:methanol, 95:5) provided the title compound (50 mg, 22%) as a gum.

MS (ESI+) m/z=391.1 $[M+H]^+$
$^1$H NMR (400 MHz, $CDCl_3$): δ (ppm) 0.93 (t, J=7.3 Hz, 3H), 1.27 (m, 3H), 1.60 (m, 2H), 2.92 (m, 2H), 3.15 (m, 1H), 3.73 (m, 2H), 4.06 (m, 1H), 4.32 (m, 2H), 4.36 (m, 1H), 4.49 (m, 1H), 7.07 (m, 4H), 7.28 (d, J=8.3 Hz, 2H), 7.74 (d, J=8.3 Hz, 2H).

Example 61

N-[4-(1-Propyl-azetidin-3-yl)-phenyl]-4-(3,3,3-trifluoro-propyl)-benzenesulfonamide Following the same procedure as described in example 55, 4-(1-propyl-azetidin-3-yl)phenylamine (100 mg, 0.52 mmol) in $CH_2Cl_2$/pyridine 9:1 (12 ml) was treated with 4-(3,3,3-trifluoro-propyl)-benzenesulfonyl chloride (214 mg, 0.78 mmol). Purification of the crude product by flash column chromatography ($CH_2Cl_2$:methanol, 95:5) provided the title compound (26 mg, 11%) as a colourless gum.

MS (ESI+) m/z=427.1 $[M+H]^+$
$^1$H NMR (400 MHz, $CDCl_3$): δ (ppm) 0.99 (t, J=7.4 Hz, 3H), 1.73 (m, 2H), 2.36 (m, 2H), 2.87 (m, 2H), 3.10 (m, 2H), 3.70-4.20 (m, 5H), 7.15 (m, 4H), 7.24 (d, J=8.5 Hz, 2H), 7.79 (d, J=8.3 Hz, 2H).

Example 62

N-[4-(1-Propyl-azetidin-3-yl)-phenyl]-4-(2,2,2-trifluoro-ethyl)-benzenesulfonamide Following the same procedure as described in example 55, 4-(1-propyl-azetidin-3-yl)phenylamine (100 mg, 0.52 mmol)

in CH$_2$Cl$_2$/pyridine 9:1 (10 ml) was treated with 4-(3,3,3-trifluoro-ethyl)-benzenesulfonyl chloride (163 mg, 0.63 mmol). Purification of the crude product by flash column chromatography (CH$_2$Cl$_2$:methanol, 95:5) provided the title compound (65 mg, 30%) as a colourless gum.

MS (ESI+) m/z=413.1 [M+H]$^+$ $^1$H NMR (400 MHz, CDCl$_3$): δ (ppm) 0.98 (t, J=7.4 Hz, 3H), 1.71 (m, 2H), 3.09 (m, 2H), 3.38 (m, 2H), 3.66-4.75 (m, 5H), 7.13 (m, 4H), 7.33 (d, J=8.0 Hz, 2H), 7.83 (d, J=8.1 Hz, 2H).

Example 63

N-[4-(1-Propyl-azetidin-3-yl)-phenyl]-4-(2,2,2-trifluoro-1-methyl-ethyl)benzenesulfonamide Following the same procedure as described in example 55, 4-(1-propyl-azetidin-3-yl)phenylamine (100 mg, 0.52 mmol) in CH$_2$Cl$_2$/pyridine 9:1 (15 ml) was treated with 4-(2,2,2-trifluoro-1-methyl-ethyl)-benzenesulfonyl chloride (145 mg, 0.52 mmol). Purification of the crude product by flash column chromatography (CH$_2$Cl$_2$:methanol, 95:5) provided the title compound (40 mg, 18%) as a pale yellow gum.

MS (ESI+) m/z=427.1 [M+H]$^+$ $^1$H-NMR (400 MHz, CDCl$_3$): δ (ppm) 0.98 (t, J=7.4 Hz, 3H), 1.49 (d, J=7.2 Hz, 3H), 1.68 (m, 2H), 3.02-3.21 (m, 2H), 3.47 (m, 1H), 3.68-4.70 (m, 5H), 7.07 (d, J=8.6 Hz, 2H), 7.12 (d, J=8.5 Hz, 2H), 7.40 (d, J=8.2 Hz, 2H), 7.76 (d, J=8.3 Hz, 2H).

Example 64

4-(2,2-Difluoro-1-methyl-ethyl)-N-[4-(1-propyl-azetidin-3-yl)-phenyl]-benzenesulfonamide Following the same procedure as described in example 55, 4-(1-propyl-azetidin-3-yl)phenylamine (150 mg, 0.78 mmol) in CH$_2$Cl$_2$/pyridine 1:1 (12 ml) was treated with 4-(2,2-difluoro-1-methyl-ethyl)-benzenesulfonyl chloride (321 mg, 1.26 mmol). Purification of the crude product by flash column chromatography (CH$_2$Cl$_2$:methanol, 95:5) provided the title compound (40 mg, 18%) as a colourless gum.

MS (ESI+) m/z=409.1 [M+H]$^+$ $^1$H-NMR (400 MHz, CDCl$_3$): δ (ppm) 0.97 (t, J=7.4 Hz, 3H), 1.36 (m, 3H), 1.69 (m, 2H), 3.07 (m, 2H), 3.17 (m, 1H), 3.54-4.65 (m, 5H), 5.76 (td, J=3.5 Hz, 1H), 7.11 (m, 4H), 7.30 (d, J=8.1 Hz, 2H), 7.78 (d, J=8.3 Hz, 2H).

Example 65

N-[4-((S)-1-Propyl-pyrrolidin-3-yl)-phenyl]-4-[1,2,3]thiadiazol-4-yl-benzenesulfonamide Sulfonamide coupling was achieved by following a procedure analogous to that described in example 55. Yield: 75 mg (52%).

MS (ESI) m/z: 429.0 [M+H]$^+$ $^1$H-NMR (DMSO-d$_6$): δ [ppm] 9.75 (s, 1H), 8.29 (d, 2H), 7.91 (d, 2H), 7.13 (d, 2H), 7.04 (d, 1H), 3.16 (m, 1H), 2.83 (m, 1H), 2.60 (t, 1H, J=7.3 Hz, 2H), 2.23 (m, 3H), 2.15 (m, 1H), 1.65 (m, 1H), 1.43 (m, 2H), 0.85 (t, J=7.3 Hz, 3H).

Example 66

N-[2-((S)-1-Propyl-pyrrolidin-3-yl)-phenyl]-4-[1,2,3]thiadiazol-4-yl-benzenesulfonamide Sulfonamide coupling was achieved by following a procedure analogous to that described in example 55. Yield: 15 mg (10%)

MS (ESI) m/z: 429.0 [M+H]$^+$ $^1$H-NMR (DMSO-d$_6$): δ [ppm] 9.73 (s, 1H), 8.30 (d, 2H), 7.88 (d, 2H), 7.12 (t, 1H), 6.98 (m, 3H), 3.16 (m, 1H), 2.81 (m, 1H), 2.60 (t, 1H, J=7.3 Hz, 2H), 2.23 (m, 3H), 2.14 (m, 1H), 1.58 (m, 1H), 1.39 (m, 2H), 0.82 (t, J=7.3 Hz, 3H).

Example 67

N-[4-((S)-1-Propyl-pyrrolidin-3-yl)-phenyl]-4-pyrrolidin-1-yl-benzenesulfonamide Starting from 4-bromo-N[4-((S)-1-propyl-pyrrolidin-3-yl)-phenyl]benzenesulfonamide obtained in example 25 and following a procedure in analogy to example 50; (pyrrolidine, BINAP, tert-NaOC$_4$H$_9$, Pd$_2$(dba)$_3$, 140° C. MW (microwave)) the title compound was obtained. Chromatography CH$_2$Cl$_2$-methanol 9:1. Yield: 36 mg (14%).

MS (ESI) m/z: 414.1 [M+H]$^+$ $^1$H-NMR (DMSO-d$_6$): δ [ppm] 9.85 (br s, 1H), 7.50 (d, 2H), 7.11 (d, 2H), 7.00 (d, 2H), 6.51 (d, 2H), 3.30 (m, 6H), 2.91 (m, 2H), 2.63 (m, 3H), 2.19 (m, 1H), 1.87 (m, 4H), 1.73 (m, 1H), 1.51 (m, 2H), 0.85 (t, J=7.3 Hz, 3H).

Example 68

N-[4-((S)-1-Propyl-pyrrolidin-3-yl)-phenyl]-4-trifluoromethylsulfanyl-benzenesulfonamide 4-((S)-1-Propyl-pyrrolidin-3-yl)phenylamino (50 mg, 0.24 mmol) was dissolved in THF (5 ml) at −78° C. and potassium hexamethyldisilazide (146 mg, 0.73 mmol) added. The solution was stirred at −78° C. for 1 hour and then 4-(trifluoromethylthio)benzene-1-sulfonyl fluoride (64 mg, 0.24 mmol) was added and the solution was allowed to reach room temperature over night. The solvent was removed in vacuo and the residue partitioned between ethyl acetate and NaOH (2M). The organic extract was separated, dried (MgSO$_4$), filtered and concentrated to give the product (97 mg, yield 89%).

MS (ESI) m/z: 445.0 [M+H]$^+$ $^1$H-NMR (DMSO-d$_6$): δ [ppm] 10.27 (br s, 1H), 7.87 (m, 2H), 7.68 (m, 2H), 7.19 (d, 2H), 7.03 (d, 2H), 3.30 (m, 2H), 3.16 (m, 2H), 2.82 (m, 3H), 2.26 (m, 1H), 1.82 (m, 1H), 1.53 (m, 2H), 0.88 (t, J=7.3 Hz, 3H).

Example 69

N-[4-((S)-1-Propyl-pyrrolidin-3-yl)-phenyl]-4-pyrazol-1-yl-benzenesulfonamide

Sulfonamide coupling was achieved by following a procedure analogous to that described in example 55.2; 2 mg (34%) of the title compound were obtained.

MS (ESI) m/z: 411.1 [M+H]$^+$ $^1$H-NMR(CH$_3$OH-d$_4$): δ [ppm] 8.30 (s, 1H), 7.84 (m, 4H), 7.72 (s, 1H), 7.19 (d, 2H), 7.08 (d, 2H), 6.52 (s, 1H), 3.50 (m, 2H), 3.30 (m, 2H), 2.96 (m, 2H), 2.38 (m, 1H), 2.02 (m, 1H), 1.68 (m, 2H), 0.96 (t, J=7.3 Hz, 3H).

Example 70

4-Oxazol-5-yl-N-[4-((S)-1-propyl-pyrrolidin-3-yl)-phenyl]-benzenesulfonamide

Sulfonamide coupling was achieved by following a procedure analogous to that described in example 55.2. 148 mg (yield 84%) of the title compound were obtained.

MS (ESI) m/z: 412.1 [M+H]$^+$ $^1$H-NMR(CH$_3$OH-d$_4$): δ [ppm] 8.28 (s, 1H), 7.79 (m, 4H), 7.62 (s, 1H), 7.20 (d, 2H), 7.13 (d, 2H), 3.69 (m, 1H), 3.53 (m, 1H), 3.47 (m, 2H), 3.12 (m, 3H), 2.38 (m, 1H), 2.10 (m, 1H), 1.75 (m, 2H), 0.99 (t, J=7.3 Hz, 3H).

Example 71

4-Oxazol-5-yl-N-[2-((S)-1-propyl-pyrrolidin-3-yl)-phenyl]-benzenesulfonamide

Sulfonamide coupling was achieved by following a procedure analogous to that described in example 55.2. 11 mg (yield 6%) of the title compound were obtained.

MS (ESI) m/z: 412.1 [M+H]$^+$ $^1$H-NMR(CH$_3$OH-d$_4$): δ [ppm] 8.29 (s, 1H), 7.82 (m, 4H), 7.66 (s, 1H), 7.21 (m, 1H), 7.06 (m, 3H), 3.61 (m, 1H), 3.50 (m, 1H), 3.37 (m, 2H), 3.03 (m, 3H), 2.38 (m, 1H), 2.05 (m, 1H), 1.69 (m, 2H), 0.99 (t, J=7.3 Hz, 3H).

Example 72

4-(2-Oxo-pyrrolidin-1-yl)-N-[4-((S)-1-propyl-pyrrolidin-3-yl)-Phenyl]-benzenesulfonamide Sulfonamide coupling was achieved by following a procedure analogous to that described in example 55.2. 86 mg (yield 66%) of the title compound were obtained.

MS (ESI) m/z: 428.1 [M+H]$^+$ $^1$H-NMR (CDCl$_3$): δ [ppm] 7.72 (m, 4H), 7.12 (d, 2H), 7.01 (d, 2H), 3.83 (t, 2H), 3.32 (m, 1H), 3.14 (m, 1H), 2.92 (m, 1H), 2.81 (m, 1H), 2.53 (m, 5H), 2.27 (m, 1H), 2.13 (m, 2H), 1.83 (m, 1H), 1.52 (m, 2H), 0.91 (t, J=7.3 Hz, 3H).

Example 73

4-Furan-2-yl-N-[4-((S)-1-propyl-pyrrolidin-3-yl)-phenyl]-benzenesulfonamide

Starting from 4-bromo-N[4-((S)-1-propyl-pyrrolidin-3-yl)-phenyl]benzenesulfonamide obtained in example 25 and following a procedure in analogy to example 19 the title compound (92 mg (yield 76%)) was obtained.

MS (ESI) m/z: 412.1 [M+H]$^+$ $^1$H-NMR(CH$_3$OH-d$_4$): δ [ppm] 7.73 (s, 4H), 7.61 (s, 1H), 7.19 (d, 2H), 7.12 (d, 2H), 6.91 (s, 1H), 6.52 (s, 1H), 3.95-3.40 (m, 5H), 3.32 (m, 1H), 3.20 (m, 2H), 2.15 (m, 1H), 1.74 (m, 2H), 0.99 (t, J=7.3 Hz, 3H).

Example 74

N-[4-((S)-1-Propyl-pyrrolidin-3-yl)-phenyl]-4-pyrrol-1-yl-benzenesulfonamide

Sulfonamide coupling was achieved by following a procedure analogous to that described in example 55. 86 mg (yield 66%) of the title compound were obtained.

MS (ESI) m/z: 411.1 [M+H]$^+$ $^1$H-NMR(CH$_3$OH-d$_4$): δ [ppm]7.78 (d, 2H), 7.76 (s, 1H), 7.61 (d, 2H), 7.26 (s, 1H), 7.18 (d, 2H), 7.09 (d, 2H), 6.31 (s, 1H), 3.36 (m, 2H), 3.17 (m, 1H), 3.08 (m, 1H), 2.82 (m, 3H), 2.32 (m, 1H), 1.95 (m, 1H), 1.62 (m, 2H), 0.97 (t, J=7.4 Hz, 3H).

Example 75

4-Azetidin-1-yl-N-[4-((S)-1-propyl-pyrrolidin-3-yl)-phenyl]-benzenesulfonamide

The title compound was prepared in analogy to the procedure described in example 67. 9 mg (yield 11%) of the title compound were obtained.

MS (ESI) m/z: 400.2 [M+H]$^+$ $^1$H-NMR(CH$_3$OH-d$_4$): δ [ppm] 7.50 (d, 2H), 7.12 (d, 2H), 7.03 (d, 2H), 6.31 (d, 2H), 3.89 (m, 4H), 3.49 (m, 2H), 3.26 (m, 2H), 2.92 (m, 3H), 2.33 (m, 3H), 2.02 (m, 1H), 1.68 (m, 2H), 0.97 (t, J=7.3 Hz, 3H).

Example 76

4-(2-Oxo-oxazolidin-3-yl)-N-[4-((S)-1-propyl-pyrrolidin-3-yl)-phenyl]-benzenesulfonamide The title compound was prepared in analogy to the procedure described in example 67. 7 mg (yield 10%) of the title compound were obtained.

MS (ESI) m/z: 430.2 [M+H]$^+$ $^1$H-NMR (CDCl$_3$): δ [ppm] 7.74 (d, 2H), 7.68 (d, 2H), 7.14 (d, 2H), 7.07 (d, 2H), 4.50 (m, 2H), 4.10 (m, 2H), 3.50 (m, 4H), 2.96 (m, 3H), 2.37 (m, 1H), 2.01 (m, 1H), 1.68 (m, 2H), 0.98 (t, J=7.3 Hz, 3H).

Example 77

4-(2,2-Difluoro-1-methyl-ethyl)-N-[4-((S)-1-propyl-pyrrolidin-3-yl)-phenyl]-benzenesulfonamide Sulfonamide coupling was achieved by following a procedure analogous to that described in example 55.2. Purification by chromatography ethyl acetate-CH$_2$Cl$_2$ 1:1 gave 36 mg (yield 12%) of the title compound.

MS (ESI) m/z: 423.1 [M+H]$^+$ $^1$H-NMR (CDCl$_3$): δ [ppm] 7.74 (d, 2H), 7.52 (d, 2H), 7.14 (d, 2H), 7.03 (d, 2H), 6.14 (m, 1H), 3.30 (m, 5H), 2.82 (m, 1H), 2.65 (t, 1H, J=7.3 Hz, 2H), 2.39 (m, 2H), 2.15 (m, 1H), 1.65 (m, 1H), 1.41 (m, 1H), 1.31 (d, 3H), 0.98 (t, J=7.3 Hz, 3H).

Example 78

N-[4-((S)-1-Propyl-pyrrolidin-3-yl)-phenyl]-4-(2,2,2-trifluoro-1-methyl-ethyl)benzenesulfonamide Sulfonamide coupling was achieved by following a procedure analogous to that described in example 55.2. 57 mg (yield 43%) of the title compound were obtained.

MS (ESI) m/z: 441.1 [M+H]$^+$ $^1$H-NMR(CH$_3$OH-d$_4$): δ [ppm] 7.72 (d, 2H), 7.49 (d, 2H), 7.12 (d, 2H), 7.03 (d, 2H), 3.65 (m, 2H), 3.24 (m, 1H), 3.10 (m, 1H), 2.90 (m, 1H), 2.70 (m, 1H), 2.51 (m, 3H), 2.25 (m, 1H), 1.82 (m, 1H), 1.57 (m, 2H), 1.47 (d, 3H), 0.94 (t, J=7.3 Hz, 3H).

Example 79

Benzofuran-2-sulfonic acid [4-((S)-1-propyl-pyrrolidin-3-yl)-phenyl]-amide

Sulfonamide coupling was achieved by following a procedure analogous to that described in example 55.2. Chromatography (using ethyl acetat-methanol) 1-50% gave 52 mg (yield 24%) of the title compound.
MS (ESI) m/z: 385.1 [M+H]+
$^1$H-NMR (DMSO-d$_6$): δ [ppm] 10.50 (br s, 1H), 7.76 (d, 1H), 7.70 (d, 1H), 7.55 (m, 3H), 7.34 (m, 1H), 7.18 (d, 2H), 7.10 (d, 2H), 3.10 (m, 1H), 2.90 (m, 1H), 2.61 (m, 5H), 2.22 (m, 1H), 1.76 (m, 1H), 1.52 (m, 3H), 0.86 (t, J=7.3 Hz, 3H).

Example 80

5-Isoxazol-5-yl-thiophene-2-sulfonic acid [4-((S)-1-propyl-pyrrolidin-3-yl)-phenyl]-amide 4-((S)-1-Propyl-pyrrolidin-3-yl)-phenylamine (100 mg, 0.49 mmol) was dissolved in tetrahydrofuran (5 ml). Subsequently, dimethylaminopyridine (24 mg, 0.20 mmol) and 5-(5-isoxazyl)thiophene-2-sulfonyl chloride (159 mg, 0.64 mmol) were added and the reaction mixture stirred overnight at room temperature. The solvent was evaporated under reduced pressure, the residue treated with water and ethyl acetate. The organic layer was dried over magnesium sulfate, filtered, and the solvent evaporated under reduced pressure to give the crude product. The crude product was purified with silica gel chromatography with dichloromethane/methanol (100:0 to 96:4) as eluent, yielding the purified product (67 mg, 33%).
MS (ESI) m/z: 418.1 [M+H]+
$^1$H-NMR (DMSO-d$_6$): δ [ppm] 8.65 (s, 1H), 7.63 (d, 1H), 7.58 (d, 1H), 7.24 (d, 2H), 7.12 (m, 3H), 7.07 (s, 1H), 4.02 (m, 1H), 3.16 (d, 2H), 3.10 (m, 3H), 2.28 (m, 1H), 1.91 (m, 1H), 1.58 (m, 2H), 0.88 (t, J=7.3 Hz, 3H).

Example 81

5-Isoxazol-3-yl-thiophene-2-sulfonic acid [4-((S)-1-propyl-pyrrolidin-3-yl)-phenyl]-amide Sulfonamide coupling was achieved by following a procedure analogous to that described in example 80. The title compound was obtained in an amount of 66 mg; yield 32%.
MS (ESI) m/z: 418.1 [M+H]+
$^1$H-NMR (DMSO-d$_6$): δ [ppm] 8.72 (s, 1H), 7.68 (d, 1H), 7.62 (d, 1H), 7.24 (d, 2H), 7.14 (m, 3H), 7.09 (s, 1H), 4.08 (m, 1H), 3.16 (d, 2H), 3.10 (m, 3H), 2.33 (m, 1H), 1.97 (m, 1H), 1.62 (m, 2H), 0.92 (t, J=7.3 Hz, 3H).

Example 82

5-Oxazol-5-yl-thiophene-2-sulfonic acid [4-((S)-1-propyl-pyrrolidin-3-yl)-phenyl]-amide Sulfonamide coupling was achieved by following a procedure analogous to that described in example 80; title compound was obtained in an amount of 110 mg (yield 54%).
MS (ESI) m/z: 418.1 [M+H]+
$^1$H-NMR(CH$_3$OH-d$_4$): δ [ppm]8.70 (s, 1H), 7.68 (d, 1H), 7.62 (d, 1H), 7.36 (d, 2H), 7.14 (m, 3H), 7.09 (s, 1H), 4.05 (m, 1H), 3.18 (d, 2H), 3.04 (m, 2.32 (m, 1H), 1.93 (m, 1H), 1.59 (m, 2H), 0.91 (t, J=7.3 Hz, 3H).

Example 83

N-(4-Azetidin-3-yl-phenyl)-4-(2,2-difluoro-1-methyl-ethyl)-benzenesulfonamide

Step 1: Sulfonamide coupling using 4-(1,1-difluoropropan-2-yl)benzene-1-sulfonyl chloride, following a procedure in analogy to that used in example 55. 90 mg (29%) of the title compound were obtained.
MS (ESI) m/z: 467.1 [M+H]+

Step 2: boc deprotection, following a procedure in analogy to that used in example 46.4. 77 mg (100%) of the title compound were obtained.
MS (ESI) m/z: 367.1 [M+H]+

Example 84

4-Isopropyl-N-[4-((S)-1-ethyl-pyrrolidin-3-yl)-phenyl]-benzenesulfonamide 0.3 g of 4-Isopropyl-N—((S)-4-pyrrolidin-3-yl-phenyl)-benzenesulfonamide (0.87 mmol) were dissolved in 20 ml dichloromethane. After addition of 0.07 ml of acetic acid, 0.073 ml of acetaldehyde (1.31 mmol) and 0.277 g of sodium triacetoxyborohydride (1.31 mmol), the reaction mixture was stirred at room temperature for 30 minutes. The solvent was evaporated, the residue dissolved in water and the pH adjusted to pH 8-9 with aqueous sodium hydroxide solution. The aqueous phase was extracted three times with diethyl ether, the combined organic phases dried over magnesium sulfate, filtered, and the solvent evaporated under reduced pressure. The crude product was purified via silica gel chromatography (chromabond column) with dichloromethane, dichloromethane/methanol 4% as eluent to yield 64 mg of the title compound.
ESI-MS: 373.25 [M+H]+
$^1$H-NMR (CDCl$_3$, 400 MHz): δ [ppm] 7.7 (d, 2H), 7.3 (d, 2H), 7.15 (d, 2H), 7.0 (d, 2H), 6.1 (bs, 1H), 3.35 (m, 1H), 3.1 (m, 1H), 2.95 (m, 2H), 2.65 (m, 2H), 2.55 (m, 1H), 2.45 (m, 1H), 2.3 (m, 1H), 1.85 (m, 1H), 1.25 (d, 6H), 1.15 (t, 3H).

Example 85

4-Isopropyl-N-[4-((S)-1-methyl-pyrrolidin-3-yl)-phenyl]-benzenesulfonamide

4-Isopropyl-N-[4-((S)-1-methyl-pyrrolidin-3-yl)-phenyl]-benzenesulfonamide was prepared as described for example 84, but using aqueous formaldehyde solution as source for the carbonyl reagent.
ESI-MS: 359.2 [M+H]+
$^1$H-NMR (CDCl$_3$, 400 MHz): δ [ppm] 7.7 (d, 2H), 7.3 (d, 2H), 7.1 (d, 2H), 7.0 (d, 2H), 6.0 (s, broad, 1H), 3.3 (m, 1H), 3.0 (m, 1H), 2.95 (m, 1H), 2.85 (m, 1H), 2.7 (m, 1H), 2.5 (m, 1H), 2.4 (s, 3H), 2.3 (m, 1H), 1.8 (m, 1H), 1.2 (m, 6H).

According to the examples described above, the examples 86 to 93 were prepared. The compounds are characterised by the following physical data.

Example 86

4-(2-Fluoro-ethyl)-N-[4-((S)-1-propyl-pyrrolidin-3-yl)-phenyl]-benzenesulfonamide, hydrochloride ESI-MS: 391.4 [M+H]+
$^1$H-NMR (DMSO-d$_6$, 400 MHz): δ [ppm] 11.35 (bs, 1H), 10.35 (m, 1H), 7.75 (d, 2H), 7.45 (d, 2H), 7.35 (m, 2H), 7.1 (m, 2H), 4.7 (m, 1H), 4.6 (m, 1H), 3.8-3.2 (m, 5H), 3.15-2.95 (m, 4H), 2.3 (m, 1H), 2.0 (m, 1H), 1.7 (m, 2H), 0.9 (t, 3H).

Example 87

4-((S)-2-Fluoro-1-methyl-ethyl)-N-[4-((S)-1-propyl-pyrrolidin-3-yl)-phenyl]-benzenesulfonamide ESI-MS: 405.15 [M+H]+
$^1$H-NMR (CDCl$_3$, 400 MHz): δ [ppm] 7.75 (d, 2H), 7.3 (d, 2H), 7.15 (d, 2H), 7.0 (d, 2H), 5.35 (bs, 1H), 4.5 (m, 1H), 4.4

(m, 1H), 3.3 (m, 1H), 3.15 (m, 1H), 3.05 (m, 1H), 2.85 (m, 1H), 2.65 (m, 1H), 2.5 (m, 1H), 2.45 (m, 2H), 2.3 (m, 1H), 1.8 (m, 1H), 1.55 (m, 2H), 1.3 (d, 3H), 0.9 (t, 3H).

Example 88

N-[4-((S)-1-Propyl-pyrrolidin-3-yl)-phenyl]-4-(3,3,3-trifluoro-Propyl)-benzenesulfonamide ESI-MS: 441.1 [M+H]$^+$
$^1$H-NMR (CDCl$_3$, 400 MHz): δ [ppm] 7.75 (d, 2H), 7.25 (d, 2H), 7.1 (d, 2H), 7.0 (d, 2H), 5.7 (bs, 1H), 3.3 (m, 1H), 3.05 (m, 1H), 2.9 (m, 3H), 2.7 (m, 1H), 2.2-2.6 (several m, 6H), 1.8 (m, 1H), 1.55 (m, 2H), 0.9 (t, 3H).

Example 89

5-Propyl-thiophene-2-sulfonic acid [4-((S)-1-propyl-pyrrolidin-3-yl)-phenyl]-amide ESI-MS: 393.1 [M+H]$^+$
$^1$H-NMR (CDCl$_3$, 400 MHz): δ [ppm] 7.3 (d, 1H), 7.2 (d, 2H), 7.05 (d, 2H), 6.65 (d, 1H), 3.35 (m, 1H), 3.1 (m, 1H), 2.9 (m, 1H), 2.75 (m, 3H), 2.5 (m, 3H), 2.3 (m, 1H), 1.85 (m, 1H), 1.5-1.7 (m, 4H), 0.9 (m, 6H).

Example 90

N-[4-((R)-1-Allyl-pyrrolidin-3-yl)-phenyl]-4-(2,2-difluoro-cyclopropyl)benzenesulfonamide ESI-MS: 419.1 [M+H]$^+$
$^1$H-NMR (CDCl$_3$, 400 MHz): δ [ppm] 7.65 (d, 2H), 7.2 (d, 2H), 7.05 (d, 2H), 6.95 (d, 2H), 6.0 (bs, 1H), 5.8 (m, 1H), 5.15 (d, 1H), 5.05 (d, 1H), 3.25 (m, 1H), 3.1 (m, 2H), 2.95 (m, 1H), 2.8 (m, 1H), 2.7 (m, 1H), 2.6 (m, 1H), 2.4 (m, 1H), 2.2 (m, 1H), 1.8 (m, 1H), 1.7 (m, 1H), 1.55 (m, 1H).

Example 91

5-Methyl-pyridine-2-sulfonic acid [4-((S)-1-propyl-pyrrolidin-3-yl)-phenyl]-amide ESI-MS: 360.1 [M+H]$^+$
$^1$H-NMR (CDCl$_3$, 400 MHz): δ [ppm] 8.5 (s, 1H), 7.9 (bs, 1H), 7.8 (d, 1H), 7.6 (d, 1H), 7.15 (d, 2H), 7.1 (d, 2H), 3.25 (m, 1H), 3.0 (m, 1H), 2.85 (m, 1H), 2.6 (m, 1H), 2.5 (m, 1H), 2.4 (m, 2H), 2.4 (s, 3H), 2.2 (m, 1H), 1.75 (m, 1H), 1.5 (m, 2H), 0.9 (t, 3H).

Example 92

4-(3-Fluoro-propyl)-N-[4-((S)-1-propyl-pyrrolidin-3-yl)-phenyl]-benzenesulfonamide ESI-MS: 405.1 [M+H]$^+$
$^1$H-NMR (CDCl$_3$, 400 MHz): δ [ppm] 7.7 (d, 2H), 7.25 (d, 2H), 7.1 (d, 2H), 7.0 (d, 2H), 6.3 (bs, 1H), 4.4 (dt, 2H), 3.3 (m, 1H), 3.0 (m, 1H), 2.85 (m, 1H), 2.8 (m, 2H), 2.7 (m, 1H), 2.55 (m, 1H), 2.45 (m, 2H), 2.3 (m, 1H), 2.0 (m, 2H), 1.8 (m, 1H), 1.55 (m, 2H), 0.9 (t, 3H).

Example 93

4-((R)-2-Fluoro-1-methyl-ethyl)-N-[4-((S)-1-propyl-pyrrolidin-3-yl)-phenyl]-benzenesulfonamide ESI-MS: 405.15 [M+H]$^+$
$^1$H-NMR (CDCl$_3$, 400 MHz): δ [ppm] 7.75 (d, 2H), 7.3 (d, 2H), 7.15 (d, 2H), 7.0 (d, 2H), 5.5 (bs, 1H), 4.5 (m, 1H), 4.4 (m, 1H), 3.3 (m, 1H), 3.15 (m, 1H), 3.05 (m, 1H), 2.85 (m, 1H), 2.65 (m, 1H), 2.5 (m, 1H), 2.45 (m, 2H), 2.3 (m, 1H), 1.8 (m, 1H), 1.55 (m, 2H), 1.3 (d, 3H), 0.9 (t, 3H).

Example 94

N-[4-((S)-1-Cyclopropylmethyl-pyrrolidin-3-yl)-phenyl]-4-isopropyl-benzenesulfonamide N-[4-((S)-1-Cyclopropylmethyl-pyrrolidin-3-yl)-phenyl]-4-isopropyl-benzenesulfonamide was prepared as described for 4-isopropyl-N-[4-((S)-1-ethyl-pyrrolidin-3-yl)-phenyl]-benzenesulfonamide in example 84, but using cyclopropylcarbaldehyde as carbonyl reagent.

ESI-MS: 399.1 [M+H]$^+$
$^1$H-NMR (CDCl$_3$, 400 MHz): δ [ppm] 7.65 (d, 2H), 7.25 (d, 2H), 7.1 (d, 2H), 6.95 (d, 2H), 5.25 (s, 1H), 3.3 (m, 1H), 3.15 (m, 1H), 2.9 (m, 2H), 2.65 (m, 1H), 2.6 (m, 1H), 2.4 (m, 1H), 2.35 (m, 2H), 2.25 (m, 1H), 1.75 (m, 1H), 1.2 (d, 6H), 0.9 (m, 1H), 0.45 (d, 2H), 0.1 (d, 2H).

According to the examples described above, the examples 95 to 119 were prepared. The compounds are characterised by the following physical data.

Example 95

4-(2-Fluoro-1-fluoromethyl-ethyl)-N-[4-((S)-1-propyl-pyrrolidin-3-yl)-phenyl]-benzenesulfonamide ESI-MS: 423.15 [M+H]$^+$
$^1$H-NMR (CDCl$_3$, 400 MHz): δ [ppm] 7.75 (d, 2H), 7.35 (d, 2H), 7.15 (d, 2H), 7.0 (d, 2H), 5.3 (s, 1H), 4.75 (d, 2H), 4.65 (d, 2H), 3.3 (m, 1H), 3.05 (m, 1H), 2.85 (m, 2H), 2.65 (m, 1H), 2.45 (m, 4H), 2.3 (m, 1H), 1.8 (m, 1H), 1.55 (m, 2H), 0.9 (t, 3H).

Example 96

N-{4-[(S)-1-(2-Fluoro-ethyl)-pyrrolidin-3-yl]-phenyl}-4-isopropyl-benzenesulfonamide ESI-MS: 391.1 [M+H]$^+$
$^1$H-NMR (CDCl$_3$, 400 MHz): δ [ppm] 7.7 (d, 2H), 7.3 (d, 2H), 7.15 (d, 2H), 7.0 (d, 2H), 4.63 (t, 1H), 4.5 (t, 1H), 3.3 (m, 1H), 3.1 (m, 1H), 2.7-3.0 (several m, 5H), 2.5 (m, 1H), 2.25 (m, 1H), 1.8 (m, 1H), 1.2 (d, 6H).

Example 97

4-Isopropyl-N-[4-((S)-1-propionyl-pyrrolidin-3-yl)-phenyl]-benzenesulfonamide

ESI-MS: 401.15 [M+H]$^+$
$^1$H-NMR (CDCl$_3$, 400 MHz): δ [ppm] 7.7 (d, 2H), 7.3 (m, 3H), 7.1 (m, 3H), 4.0 (m, 0.5H), 3.8 (m, 2H), 3.65 (m, 0.5H), 3.5 (m, 1H), 3.35 (m, 2H), 2.95 (sept, 1H), 2.8 (m, 3H), 1.95 (m, 1H), 1.2 (d, 6H), 1.15 (m, 3H).

Example 98

N-[4-((S)-1-Propyl-pyrrolidin-3-yl)-phenyl]-3-trifluoromethoxy-benzenesulfonamide ESI-MS: 429.15 [M+H]$^+$
$^1$H-NMR (CDCl$_3$, 400 MHz): δ [ppm] 7.7 (d, 1H), 7.55 (s, 1H), 7.5 (t, 1H), 7.4 (d, 1H), 7.15 (d, 2H), 6.95 (d, 2H), 5.3 (bs, 1H), 3.3 (m, 1H), 3.05 (m, 1H), 2.85 (m, 1H), 2.65 (m, 1H), 2.5 (m, 1H), 2.45 (m, 2H), 2.3 (m, 1H), 1.8 (m, 1H), 1.55 (m, 2H), 0.9 (t, 3H).

Example 99

N-[2-((S)-1-Propyl-pyrrolidin-3-yl)-phenyl]-3-trifluoromethoxy-benzenesulfonamide

ESI-MS: 429.15 [M+H]$^+$

Example 100

N-[4-((S)-1-Propyl-pyrrolidin-3-yl)-phenyl]-2-trifluoromethyl-benzenesulfonamide ESI-MS: 413.15 [M+H]$^+$
$^1$H-NMR (CDCl$_3$, 400 MHz): δ [ppm] 8.0 (d, 1H), 7.85 (d, 1H), 7.65 (t, 1H), 7.55 (t, 1H), 7.1 (d, 2H), 6.95 (d, 2H), 5.9 (bs, 1H), 3.3 (m, 1H), 3.0 (m, 1H), 2.8 (m, 1H), 2.6 (m, 1H), 2.45 (m, 1H), 2.4 (m, 2H), 2.25 (m, 1H), 1.75 (m, 1H), 1.55 (m, 2H), 0.95 (t, 3H).

Example 101

N-[4-((S)-1-Allyl-pyrrolidin-3-yl)-phenyl]-4-trifluoromethoxy-benzenesulfonamide ESI-MS: 427.1 [M+H]$^+$
$^1$H-NMR (DMSO-d$_6$, 400 MHz): δ [ppm] 11.3 (bd, 1H), 10.45 (m, 1H), 7.9 (d, 2H), 7.55 (d, 2H), 7.25 (m, 2H), 7.1 (d, 2H), 6.0 (m, 1H), 5.5 (m, 1H), 5.45 (m, 1H), 3.8 (m, 2H), 2.9-3.75 (several m, 5H), 2.3 (m, 1H), 1.95 (m, 1H).

Example 102

N—((S)-4-Pyrrolidin-3-yl-phenyl)-4-trifluoromethoxy-benzenesulfonamide
ESI-MS: 387.05 [M+H]$^+$
$^1$H-NMR (DMSO-d$_6$, 400 MHz): δ [ppm] 7.85 (d, 2H), 7.45 (d, 2H), 7.05 (d, 2H), 6.95 (d, 2H), 5.2 (m, 1H), 3.3 (m, 1H), 3.1 (m, 2H), 3.05 (m, 1H), 2.7 (m, 1H), 2.15 (m, 1H), 1.7 (m, 1H)

Example 103

N-[4-((S)-1-Propyl-pyrrolidin-3-yl)-phenyl]-4-(2,2,2-trifluoro-ethyl)benzenesulfonamide ESI-MS: 427.2 [M+H]$^+$
$^1$H-NMR (CDCl$_3$, 400 MHz): δ [ppm] 7.8 (d, 2H), 7.4 (d, 2H), 7.15 (d, 2H), 7.0 (d, 2H), 5.7 (bs, 1H), 3.4 (m, 2H), 3.3 (m, 1H), 3.05 (m, 1H), 2.85 (m, 1H), 2.7 (m, 1H), 2.5 (m, 3H), 2.3 (m, 1H), 1.8 (m, 1H), 1.55 (m, 2H), 0.9 (t, 3H).

Example 104

N-[4-((S)-1-Ethyl-pyrrolidin-3-yl)-phenyl]-4-trifluoromethoxy-benzenesulfonamide ESI-MS: 415.1 [M+H]$^+$
$^1$H-NMR (CDCl$_3$, 400 MHz): δ [ppm] 7.8 (d, 2H), 7.25 (d, 2H), 7.15 (d, 2H), 7.0 (d, 2H), 4.9 (bs, 1H), 3.3 (m, 1H), 3.05 (m, 1H), 2.85 (m, 1H), 2.5-2.7 (several m, 3H), 2.45 (m, 1H), 2.3 (m, 1H), 1.8 (m, 1H), 1.15 (t, 3H).

Example 105

5-Chloro-thiophene-2-sulfonic acid [4-((S)-1-propyl-pyrrolidin-3-yl)-phenyl]-amide ESI-MS: 385.0 [M+H]$^+$
$^1$H-NMR (CDCl$_3$, 400 MHz): δ [ppm] 7.25 (d, 1H), 7.2 (d, 2H), 7.0 (d, 2H), 6.8 (d, 1H), 5.1 (bs, 1H), 3.3 (m, 1H), 3.05 (m, 1H), 2.85 (m, 1H), 2.7 (m, 1H), 2.4-2.6 (several m, 3H), 2.3 (m, 1H), 1.8 (m, 1H), 1.55 (m, 2H), 0.9 (t, 3H).

Example 106

N-[4-((S)-1-Allyl-pyrrolidin-3-yl)-phenyl]-4-((S)-2-fluoro-1-methyl-ethyl)benzenesulfonamide

ESI-MS: 403.4 [M+H]$^+$

Example 107

N-[4-((S)-1-Allyl-pyrrolidin-3-yl)-phenyl]-4-(3-fluoro-propyl)-benzene sulfonamide

ESI-MS: 403.15 [M+H]$^+$

Example 108

4-(3-Fluoro-propyl)-N—((S)-4-pyrrolidin-3-yl-phenyl)-benzenesulfonamide

ESI-MS: 363.1 [M+H]$^+$
$^1$H-NMR (DMSO-d$_6$, 400 MHz): δ [ppm] 7.7 (d, 2H), 7.4 (d, 2H), 7.1 (d, 2H), 7.0 (d, 2H), 4.6 (bs), 4.5 (m, 1H), 4.35 (m, 1H), 3.15 (m, 1H), 3.0 (m, 2H), 2.9 (m, 1H), 2.7 (m, 2H), 2.6 (m, 1H), 2.05 (m, 1H), 1.95 (m, 1H), 1.9 (m, 1H), 1.6 (m, 1H).

Example 109

4-((S)-2-Fluoro-1-methyl-ethyl)-N—((S)-4-pyrrolidin-3-yl-Phenyl)-benzenesulfonamide ESI-MS: 363.05 [M+H]$^+$
$^1$H-NMR(CH$_3$OH-d$_4$, 400 MHz): δ [ppm] 7.7 (d, 2H), 7.4 (d, 2H), 7.1 (d, 2H), 7.0 (d, 2H), 4.5 (m, 1H), 4.4 (m, 1H), 2.95-3.35 (several m, 6H), 2.7 (m, 1H), 2.2 (m, 1H), 1.3 (d, 3H).

Example 110

4-((R)-2-Fluoro-1-methyl-ethyl)-N—((S)-4-pyrrolidin-3-yl-phenyl)-benzenesulfonamide ESI-MS: 363.1 [M+H]$^+$
$^1$H-NMR (acetic acid-d$_4$, 400 MHz): δ [ppm] 7.7 (d, 2H), 7.4 (d, 2H), 7.2 (m, 4H), 4.55 (m, 1H), 4.45 (m, 1H), 3.8 (m, 1H), 3.65 (m, 1H), 3.5 (m, 2H), 3.2 (m, 2H), 2.4 (m, 1H), 2.05 (m, 1H), 1.3 (d, 3H).

Example 111

N-[4-((S)-1-Methyl-pyrrolidin-3-yl)-phenyl]-4-trifluoromethoxy-benzenesulfonamide ESI-MS: 401.1 [M+H]$^+$
$^1$H-NMR (DMSO-d$_6$, 400 MHz): δ [ppm] 7.9 (d, 2H), 7.55 (d, 2H), 7.15 (d, 2H), 7.0 (d, 2H), 3.2 (m, 1H), 2.8 (m, 2H), 2.6 (m, 2H), 2.3 (m, 1H), 2.25 (s, 3H), 2.15 (m, 1H), 1.65 (m, 1H).

Example 112

N-[4-((R)-1-Allyl-pyrrolidin-3-yl)-phenyl]-4-(2,2,2-trifluoro-1-methyl-ethyl)benzenesulfonamide

ESI-MS: 439.1 [M+H]$^+$ $^1$H-NMR (CDCl$_3$, 400 MHz): δ 7.8 (d, 2H), 7.4 (d, 2H), 7.15 (d, 2H), 7.0 (d, 2H), 5.9 (m, 1H), 5.2 (d, 1H), 5.1 (d, 1H), 3.45 (m, 1H), 3.3 (m, 1H), 3.2 (m, 2H), 3.1 (m, 1H), 2.9 (m, 1H), 2.7 (m, 1H), 2.5 (m, 1H), 2.3 (m, 1H), 1.8 (m, 1H), 1.5 (d, 3H).

Example 113

N-[4-((S)-1-Allyl-pyrrolidin-3-yl)-phenyl]-4-((R)-2-fluoro-1-methyl-ethyl)benzenesulfonamide

ESI-MS: 403.1 [M+H]$^+$ $^1$H-NMR (CDCl$_3$, 400 MHz): δ [ppm] 7.75 (d, 2H), 7.3 (d, 2H), 7.15 (d, 2H), 7.0 (d, 2H), 5.9 (m, 1H), 5.2 (d, 1H), 5.1 (d, 1H), 4.5 (m, 1H), 4.4 (m, 1H), 3.3 (m, 1H), 3.1-3.2 (m, 3H), 3.0 (m, 1H), 2.8 (m, 1H), 2.65 (m, 1H), 2.4 (m, 1H), 2.25 (m, 1H), 1.8 (m, 1H), 1.3 (d, 3H).

Example 114

N-{4-[(S)-1-(3-Fluoro-propyl)-pyrrolidin-3-yl]-phenyl}-4-trifluoromethoxy-benzenesulfonamide

ESI-MS: 447.1 [M+H]$^+$ $^1$H-NMR (DMSO-d$_6$, 400 MHz): δ [ppm] 10.25 (bs, 1H), 7.85 (d, 2H), 7.55 (d, 2H), 7.15 (d, 2H), 7.0 (d, 2H), 4.55 (t, 1H), 4.4 (t, 1H), 3.2 (m, 1H), 2.85 (m, 1H), 2.6 (m, 2H), 2.5 (m, 2H), 2.35 (m, 1H), 2.15 (m, 1H), 1.8 (m, 1H), 1.75 (m, 1H), 1.65 (m, 1H).

Example 115

4-Methanesulfonyl-N-[4-((S)-1-propyl-pyrrolidin-3-yl)-phenyl]-benzenesulfonamide

ESI-MS: 423.1 [M+H]$^+$ $^1$H-NMR (CDCl$_3$, 400 MHz): δ [ppm] 7.95 (m, 4H), 7.1 (d, 2H), 7.0 (d, 2H), 6.2 (bs, 1H), 3.3 (m, 1H), 3.1 (m, 1H), 3.05 (s, 3H), 2.9 (m, 1H), 2.75 (m, 1H), 2.5 (m, 3H), 2.3 (m, 1H), 1.8 (m, 1H), 1.55 (m, 2H), 0.9 (t, 3H).

Example 116

N-[4-((S)-1-Propyl-pyrrolidin-3-yl)-phenyl]-4-ureido-benzenesulfonamide

ESI-MS: 403.1 [M+H]$^+$

Example 117

4-Cyano-N-[4-((S)-1-propyl-pyrrolidin-3-yl)-phenyl]-benzenesulfonamide

ESI-MS: 370.1 [M+H]$^+$ $^1$H-NMR (CDCl$_3$, 400 MHz): δ [ppm] 7.85 (d, 2H), 7.7 (d, 2H), 7.1 (d, 2H), 6.95 (d, 2H), 6.0 (bs, 1H), 3.3 (m, 1H), 3.1 (m, 1H), 2.85 (m, 1H), 2.75 (m, 1H), 2.5 (m, 3H), 2.3 (m, 1H), 1.8 (m, 1H), 1.55 (m, 2H), 0.9 (t, 3H).

Example 118

4-(1-Methyl-1H-pyrazol-4-yl)-N-[4-((S)-1-propyl-pyrrolidin-3-yl)-phenyl]-benzenesulfonamide

ESI-MS: 425.1 [M+H]$^+$ $^1$H-NMR (CDCl$_3$, 400 MHz): δ [ppm] 7.75 (s, 1H), 7.7 (d, 2H), 7.65 (s, 1H), 7.45 (d, 2H), 7.1 (d, 2H), 7.0 (d, 2H), 3.9 (s, 3H), 3.3 (m, 1H), 3.05 (m, 1H), 2.85 (m, 1H), 2.7 (m, 1H), 2.5 (m, 3H), 2.3 (m, 1H), 1.8 (m, 1H), 1.55 (m, 2H), 0.9 (t, 3H).

Example 119

1-Ethyl-1H-pyrazole-4-sulfonic acid [4-((S)-1-propyl-pyrrolidin-3-yl)phenyl]-amide hydrochloride

ESI-MS: 363.1 [M+H]$^+$ $^1$H-NMR (CDCl$_3$, 400 MHz): δ [ppm] 7.65 (s, 1H), 7.6 (s, 1H), 7.15 (d, 2H), 7.0 (d, 2H), 4.25 (bs, 1H), 4.1 (q, 2H), 3.3 (m, 1H), 3.0 (m, 1H), 2.8 (m, 1H), 2.65 (m, 1H), 2.4-2.55 (m, 3H), 2.3 (m, 1H), 1.8 (m, 1H), 1.55 (m, 2H), 1.4 (t, 3H), 0.9 (t, 3H).

Example 120

4-Morpholin-4-yl-N-[4-((S)-1-propyl-pyrrolidin-3-yl)-phenyl]-benzenesulfonamide hydrochloride A solution of 0.07 g of rac-2,2'-bis(diphenylphosphino)-1,1'-binaphthalene (BINAP, 0.11 mmol) and 0.043 g tris(dibenzylidenacetone) dipalladium(0) (0.05 mmol) in 5 ml of tetrahydrofuran were added dropwise to a solution of 0.25 g of 4-bromo-N-[4-((S)-1-propyl-pyrrolidin-3-yl)-phenyl]-benzenesulfonamide (from example 25 (0.59 mmol)), 0.078 ml morpholine (0.9 mmol), and 0.104 g of sodium tert.-butylate (1.08 mmol) in 20 ml tetrahydrofuran. The reaction mixture was refluxed for 5½ h, and, after additional addition of 0.04 ml of morpholine, for another 2 h. After evaporation, the residue was treated with water, extracted twice with diethyl ether and dichloromethane each, and the combined organic layers dried over magnesium sulfate, filtered, and the solvent evaporated. The thus obtained crude product was purified via silica gel chromatography using a gradient of dichloromethane/methanol 0-12%.

ESI-MS: 430.2 [M+H]$^+$ $^1$H-NMR (DMSO-d$_6$, 400 MHz): δ [ppm] 11.25 (d broad, 1H), 10.05 (m, 1H), 9.4 (bs, 1H), 7.6 (d, 2H), 7.25 (d, 1H), 7.2 (d, 1H), 7.05 (m, 2H), 7.0 (d, 2H), 3.8 (m, 2H), 3.5-3.8 (m, 5H), 3.2 (m, 4H), 3.0-3.1 (m, 4H), 2.3 (m, 1H), 1.9 (m, 1H), 1.7 (m, 2H), 0.9 (t, 3H).

According to the examples described above, the examples 121 to 132 were prepared. The compounds are characterised by the following physical data.

Example 121

4-Benzyloxy-N-[4-((S)-1-propyl-pyrrolidin-3-yl)-phenyl]-benzenesulfonamide

ESI-MS: 451.1 [M+H]$^+$

Example 122

4-Hydroxy-N-[4-((S)-1-propyl-pyrrolidin-3-yl)-phenyl]-benzenesulfonamide

ESI-MS: 361.1 [M+H]$^+$ $^1$H-NMR (DMSO-d$_6$, 400 MHz): δ [ppm] 10.0 (bs, 1H), 7.55 (d, 2H), 7.1 (d, 2H), 7.0 (d, 2H), 6.85 (d, 2H), 3.15 (m, 1H), 2.85 (m, 1H), 2.6 (m, 2H), 2.3-2.45 (m, 3H), 2.15 (m, 1H), 1.65 (m, 1H), 1.4 (m, 2H), 0.85 (t, 3H).

Example 123

N-[4-((S)-1-Propyl-pyrrolidin-3-yl)-phenyl]-4-vinyl-benzenesulfonamide

ESI-MS: 371.1 [M+H]$^+$
$^1$H-NMR (CDCl$_3$, 400 MHz): δ [ppm] 7.7 (d, 2H), 7.4 (d, 2H), 7.15 (d, 2H), 7.0 (d, 2H), 6.7 (q, 1H), 5.8 (d, 1H), 5.4 (d, 1H), 4.25 (bs, 1H), 3.3 (m, 1H), 3.0 (m, 1H), 2.8 (m, 1H), 2.6 (m, 1H), 2.35-2.5 (m, 3H), 2.25 (m, 1H), 1.8 (m, 1H), 1.5 (m, 2H), 0.9 (t, 3H).

Example 124

N-[2-((S)-1-Propyl-pyrrolidin-3-yl)-phenyl]-4-vinyl-benzenesulfonamide

ESI-MS: 371.1 [M+H]$^+$
$^1$H-NMR (CDCl$_3$, 400 MHz): δ [ppm] 7.75 (d, 2H), 7.4 (d, 2H), 7.05-7.2 (m, 3H), 6.95 (d, 1H), 6.65 (q, 1H), 5.8 (d, 1H), 5.35 (d, 1H), 5.0 (bs), 3.45 (m, 1H), 3.3 (m, 1H), 3.15 (m, 1H), 3.1 (m, 1H), 2.65-2.8 (m, 3H), 2.3 (m, 1H), 1.9 (m, 1H), 1.7 (m, 2H), 0.9 (t, 3H).

Example 125

4-Fluoro-N-[4-((S)-1-propyl-pyrrolidin-3-yl)-phenyl]-benzenesulfonamide hydrochloride ESI-MS: 363.1 [M+H]$^+$
$^1$H-NMR (DMSO-d$_6$, 400 MHz): δ [ppm] 11.25 (bd, 1H), 10.4 (m, 1H), 7.8 (m, 2H), 7.4 (m, 2H), 7.3 (d, 1H), 7.25 (d, 1H), 7.1 (m, 2H), 3.2-3.8 (m, 5H), 2.9-3.1 (m, 2H), 2.3 (m, 1H), 1.95 (m, 1H), 1.7 (m, 2H), 0.9 (t, 3H).

Example 126

3,4-Difluoro-N-[4-((S)-1-propyl-pyrrolidin-3-yl)-phenyl]-benzenesulfonamide hydrochloride ESI-MS: 381.2 [M+H]$^+$
$^1$H-NMR (DMSO-d$_6$, 400 MHz): δ [ppm] 11.25 (bd, 1H), 10.55 (m, 1H), 7.85 (t, 1H), 7.65 (m, 2H), 7.3 (d, 1H), 7.25 (d, 1H), 7.1 (m, 2H), 3.2-3.8 (m, 5H), 2.9-3.15 (m, 2H), 2.3 (m, 1H), 1.95 (m, 1H), 1.7 (m, 2H), 0.9 (t, 3H).

Example 127

4-(3,3-Difluoro-pyrrolidin-1-yl)-N-[4-((S)-1-propyl-pyrrolidin-3-yl)-phenyl]-benzenesulfonamide

ESI-MS: 450.1 [M+H]$^+$

Example 128

N-[4-(1-Benzyl-pyrrolidin-3-yl)-3-fluoro-phenyl]-4-isopropyl-benzenesulfonamide 128.1 2-Fluoro-4-nitro-1-vinyl-benzene
$^1$H-NMR (CDCl$_3$, 400 MHz): δ [ppm] 8.0 (m, 1H), 7.95 (m, 1H), 7.65 (m, 1H), 6.9 (dd 1H), 6.0 (m, 1H), 5.6 (m, 1H).
128.2 1-Benzyl-3-(2-fluoro-4-nitro-phenyl)-pyrrolidine
ESI-MS: 301.1 [M+H]$^+$
128.3 1-Benzyl-3-(2-fluoro-4-amino-phenyl)-pyrrolidine
ESI-MS: 271.1 [M+H]$^+$
128.4 N-[4-(1-Benzyl-pyrrolidin-3-yl)-3-fluoro-phenyl]-4-isopropyl-benzenesulfonamide
ESI-MS: 453.15 [M+H]$^+$ According to the examples described above, the examples 129 to 131 were prepared.

The compounds are characterised by the following physical data.

Example 129

N-(3-Fluoro-4-pyrrolidin-3-yl-phenyl)-4-isopropyl-benzenesulfonamide

ESI-MS: 363.15 [M+H]$^+$

Example 130

N-[3-Fluoro-4-(1-propyl-pyrrolidin-3-yl)-phenyl]-4-isopropyl-benzenesulfonamide, hydrochloride ESI-MS: 405.15 [M+H]$^+$
$^1$H-NMR (DMSO-d$_6$, 400 MHz): δ [ppm] 11.2 (bs, 1H), 10.65 (m, 1H), 7.75 (d, 2H), 7.45 (m, 3H), 6.95 (m, 2H), 3.85-3.2 (m, 4H), 3.15-2.9 (m, 4H), 2.3 (m, 1H), 2.05 (m, 1H), 1.7 (m, 2H), 1.2 (d, 6H), 0.9 (t, 3H).

Examples 131

(−)-N-[6-(1-Propyl-pyrrolidin-3-yl)-pyridin-3-yl]-4-isopropyl-benzene-sulfonamide The racemic compound, N-[6-(1-propyl-pyrrolidin-3-yl)-pyridin-3-yl]-4-isopropyl-benzenesulfonamide, was subjected to a chiral chromatography on a preparative CHIRACEL AD column using n-hexane/ethanol/triethylamine (85:15:1) as eluent. Fractions containing only the desired enantiomer are analysed by analytical chiral HPLC and were combined.
ESI-MS: 388.1 [M+H]$^+$
[α]$_D$: −18.1°

Example 132

(+)-N-[6-(1-Propyl-pyrrolidin-3-yl)-pyridin-3-yl]-4-isopropyl-benzene-sulfonamide, hydrochloride The racemic compound, N-[6-(1-propyl-pyrrolidin-3-yl)-pyridin-3-yl]-4-isopropyl-benzenesulfonamide, was subjected to a chiral chromatography on a preparative CHIRACEL AD column using n-hexane/ethanol/triethylamine (85:15:1) as eluent. Fractions containing only the desired enantiomer are analysed by analytical chiral HPLC and were combined.
ESI-MS: 388.1 [M+H]$^+$
[α]$_D$: +17.2°

Example 133

N-[4-((S)-1-Propyl-piperidin-3-yl)-phenyl]-4-trifluoromethoxy-benzenesulfonamide 133.1 (S)-3-Phenyl-1-propyl-piperidine
1 g (6.2 mmol) of commercially available (S)-3-phenylpiperidine was dissolved in dichloromethane and 0.37 ml acetic acid (6.51 mmol). After addition of 0.5 ml of propanal (6.93 mmol) and 1.97 g of sodium triacetoxyborohydride (9.3 mmol), the reaction mixture was stirred at room temperature for 18 h. Water was added, the layers separated, and the aqueous phase extracted with dichloromethane. The combined organic layers were dried over magnesium sulfate, filtered, and evaporated to dryness to yield 1.1 g of (S)-3-phenyl-1-propyl-piperidine.

ESI-MS: 204.1 [M+H]$^+$ 133.2 (S)-3-(4-Nitro-phenyl)-1-propyl-piperidine

ESI-MS: 249.1 [M+H]$^+$ $^1$H-NMR (CDCl$_3$, 400 MHz): δ [ppm] 8.15 (d, 2H), 7.4 (d, 2H), 2.95 (m, 4H), 2.3 (m, 2H), 1.9-2.1 (m, 3H), 1.65-1.85 (m, 2H), 1.4-1.6 (m, 2H), 0.9 (t, 3H).

133.3 (S)-3-(4-Amino-phenyl)-1-propyl-piperidine

ESI-MS: 219.1 [M+H]$^+$ 133.4 N-[4-((S)-1-Propyl-piperidin-3-yl)-phenyl]-4-trifluoromethoxy-benzenesulfonamide Following a procedure analogous to that described in example 55.2 sulfonamide coupling was achieved

ESI-MS: 443.1 [M+H]$^+$ $^1$H-NMR (CDCl$_3$, 400 MHz): δ [ppm] 7.8 (d, 2H), 7.2 (d, 2H), 7.1 (d, 2H), 7.0 (d, 2H), 6.7 (bs, 1H), 3.0 (m, 2H), 2.8 (m, 1H), 2.35 (m, 2H), 1.95 (m, 2H), 1.85 (m, 1H), 1.75 (m, 2H), 1.5 (m, 2H), 1.4 (m, 1H), 0.9 (t, 3H).

Example 134

N-[2-Fluoro-4-(1-propyl-pyrrolidin-3-yl)-phenyl]-4-isopropyl-benzenesulfonamide, hydrochloride 134.1 2-Fluoro-1-nitro-4-vinyl-benzene 4-Bromo-2-fluoro-1-nitro-benzene (691 mg, 3.14 mmol), tributyl-vinyl-stannane (1.2 g, 3.77 mmol), triphenylphospine (49 mg, 0.19 mmol) and tetrakistriphenylphosphinpalladium(0) (73 mg, 0.06 mmol) were dissolved in toluene (25 ml) and stirred for 5 hours at reflux. The reaction mixture was concentrated in vacuo. The residue was partitioned between water (25 ml) and diethyl ether (50 ml). The organic phase was separated, dried over MgSO$_4$, filtered and concentrated in vacuo to yield an oil (1.8 g). The residue was purified via silica gel chromatography with cyclohexane/ethyl acetate (gradient 0-5%). Fractions containing the product were combined and the solvent evaporated to give an oil (360 mg, 69%).

134.2 1-Benzyl-3-(3-fluoro-4-nitro-phenyl)-pyrrolidine

2-Fluoro-1-nitro-4-vinyl-benzene (360 mg, 2.15 mmol) was dissolved in dichloromethane (2 ml), trifluoroacetic acid (70 µl, 0.88 mmol) was added, followed by slow addition of N-benzyl-N-(methoxymethyl)-N-trimethylsilylmethylamine (633 mg, 2.67 mmol). Stirring was continued for 2 h at room temperature. Another portion of N-benzyl-N(methoxymethyl)-N-trimethylsilylmethylamine (300 mg, 1.26 mmol) was added and stirring continued for another 30 minutes. The reaction mixture was diluted with ethyl acetate (25 ml), washed with aqueous NaHCO$_3$ (15 ml). The organic layer was dried over magnesium sulfate, filtered, and the solvent evaporated under reduced pressure to yield an oil (900 mg). The crude product was purified via silica gel chromatography with cyclohexane/ethyl acetate (gradient 0-25%). Fractions containing the product were combined, the solvent evaporated to yield an oil (550 mg, 85%).

ESI-MS: 301.1 [M+H]$^+$ 134.3 4-(1-Benzyl-pyrrolidin-3-yl)-2-fluoro-phenylamine

1-Benzyl-3-(3-fluoro-4-nitro-phenyl)-pyrrolidine (550 mg, 1.83 mmol) was dissolved in methanol (30 ml), tin dichloride (3.125 g, 16.48 mmol) was added, and the reaction mixture stirred at reflux for 2 h. The methanol was evaporated, 1 N sodium hydroxide (60 ml) and ethyl acetate were added and stirring continued. The tin salts were filtered off, the organic phase was separated, dried over magnesium sulfate, filtered, and the solvent evaporated under reduced pressure to yield an oil (400 mg).

ESI-MS: 271.1 [M+H]$^+$ 134.4 N-[4-(1-Benzyl-pyrrolidin-3-yl)-2-fluoro-phenyl]-4-isopropyl-benzenesulfonamide 4-(1-Benzyl-pyrrolidin-3-yl)-2-fluoro-phenylamine (400 mg, 1.48 mmol) and 4-isopropyl-phenylsulfonyl chloride (324 mg, 1.48 mmol) were dissolved in tetrahydrofuran (25 ml). Triethylamine (0.62 ml, 4.44 mmol) was added and the reaction mixture stirred over night at room temperature (10% conversion) and subsequently refluxed for 4 h (30% conversion). Small portions of 4-isopropyl-phenylsulfonyl chloride and triethylamine were added and the reaction mixture was stirred 15 min at 150° C. in the microwave (CEM). This procedure was repeated until complete conversion was observed. The solvent was evaporated under reduced pressure, the residue treated with ethyl acetate (50 ml) and extracted twice with slightly acidic water. The organic layer was dried over magnesium sulfate, filtered, and the solvent evaporated under reduced pressure to give an oil (170 mg, 21%).

ESI-MS: 453.1 [M+H]$^+$ 134.5 N-(2-Fluoro-4-pyrrolidin-3-yl-phenyl)-4-isopropyl-benzenesulfonamide A mixture of N-[4-(1-benzyl-pyrrolidin-3-yl)-2-fluoro-phenyl]-4-isopropyl-benzenesulfonamide (170 mg, 0.31 mmol) and 10% palladium on carbon (20 mg) in ethyl acetate (25 ml) and acetic acid (10 ml) was hydrogenated over night (20% conversion). The reaction mixture was irradiated with an infra-red lamp for 3 h (complete conversion). The catalyst was filtered, and the solvent was removed under vacuum to yield an oil (45 mg, 64% purity, 26%).

ESI-MS: 363.1 [M+H]$^+$ 134.6 N-[2-Fluoro-4-(1-propyl-pyrrolidin-3-yl)-phenyl]-4-isopropyl-benzenesulfonamide, hydrochloride N-(2-Fluoro-4-pyrrolidin-3-yl-phenyl)-4-isopropyl-benzenesulfonamide (45 mg, 0.08 mmol) and propionaldehyde (4.7 mg, 0.08 mmol) were dissolved in tetrahydrofuran (5 ml). Acetic acid (10 µl, 0.12 mmol) and sodium trisacetoxyborohydride (34 mg, 0.16 mmol) were sequentially added to the reaction mixture and stirred for 30 minutes at room temperature. The reaction mixture was concentrated and the residue was dissolved in aqueous NaHCO$_3$ (10 ml) and extracted with diethyl ether (30 ml). The organic phase was separated, dried over magnesium sulfate, filtered, and evaporated to dryness to yield an oil (45 mg). The residue was dissolved in diethyl ether (25 ml) and HCl in ether was added and stirred overnight. The solvent was decanted and to the residue was added 3 ml of H$_2$O. This solution was lyophilisated to yield the pure product (32 mg, 91%).

ESI-MS: 405.1 [M+H]$^+$ $^1$H-NMR(CH$_3$OH-d$_4$): δ [ppm] 7.7 (d, 2H), 7.4 (m, 3H), 7.0 (m, 2H), 3.4 (m, 2H), 3.2-2.9 (m, 4H), 2.8 (m, 2H), 2.4 (m, 1H), 2.0 (m, 1H), 1.6 (m, 2H), 1.2 (d, 6H), 1.0 (t, 3H).

Example 135

4-Isopropyl-N-(2-methoxy-4-pyrrolidin-3-yl-phenyl)-benzenesulfonamide, acetate 135.1 4-Bromo-2-methoxy-1-nitro-benzene To a solution of 4-bromo-2-fluoro-1-nitro-benzene (2.0 g, 9.09 mmol) in methanol (50 ml) was added sodium methanolate (30% in methanol) (1.64 g, 9.09 mmol). The reaction mixture was stirred at room temperature overnight. The reaction mixture was concentrated and the residue was dissolved in water (30 ml) and extracted twice with ethyl acetate. The combined organic phases were washed with water. The organic phase was separated, dried over magnesium sulfate, filtered, and evaporated to dryness to yield a crystalline solid (2.1 g, 99%).

$^1$H-NMR (DMSO-d$_6$): δ [ppm] 7.9 (d, 1H), 7.6 (s, 1H), 7.3 (d, 1H), 4.0 (s, 3H).

135.2 2-Methoxy-1-nitro-4-vinyl-benzene

4-Bromo-2-methoxy-1-nitro-benzene (691 mg, 3.14 mmol), tributyl-vinyl-stannane (1.2 g, 3.77 mmol), triphenylphospine (49 mg, 0.19 mmol) and tetrakistriphenylphosphinpalladium(0) (73 mg, 0.06 mmol) were dissolved in toluene (25 ml) and stirred for 5 hours at reflux. The reaction mixture was concentrated in vacuo. The residue was partitioned between water (25 ml) and diethyl ether (50 ml). The organic phase was separated, dried over MgSO$_4$, filtered and concentrated in vacuo to yield an oil (2.0 g). The residue was purified via silica gel chromatography with cyclohexane/ethyl acetate (gradient 0-25%). Fractions containing the product were combined, the solvent evaporated to give an oil (435 mg, 72%).

135.3 1-Benzyl-3-(3-methoxy-4-nitro-phenyl)-pyrrolidine

2-Methoxy-1-nitro-4-vinyl-benzene (435 mg, 2.43 mmol) was dissolved in dichloromethane (2 ml), trifluoro acetic acid (80 µl, 1.0 mmol) was added, followed by slow addition of N-benzyl-N-(methoxymethyl)-N-trimethylsilylmethylamine (715 mg, 3.01 mmol). Stirring was continued for 2 h at room temperature. Another portion of N-benzyl-N-(methoxymethyl)-N-trimethylsilylmethylamine (300 mg, 1.26 mmol) was added and stirring continued for another 30 minutes. The reaction mixture was diluted with ethylacetate (25 ml), washed with aqueous NaHCO$_3$ (15 ml). The organic layer was dried over magnesium sulfate, filtered, and the solvent evaporated under reduced pressure to yield an oil (970 mg). The crude product was purified via silica gel chromatography with cyclohexane/ethyl acetate (gradient 0-50%). Fractions containing the product were combined, the solvent evaporated to yield an oil (320 mg, 46%).

ESI-MS: 313.1 [M+H]$^+$ 135.4 4-(1-Benzyl-pyrrolidin-3-yl)-2-methoxy-phenylamine 1-Benzyl-3-(3-methoxy-4-nitro-phenyl)-pyrrolidine (350 mg, 1.12 mmol) was dissolved in methanol (20 ml), tin dichloride (1.912 g, 10.08 mmol) was added, and the reaction mixture stirred at reflux for 2 h. The methanol was evaporated, 1 N sodium hydroxide (50 ml) and ethyl acetate were added and stirring continued. The tin salts were filtered off, the organic phase was separated, dried over magnesium sulfate, filtered, and the solvent evaporated under reduced pressure to yield an oil (220 mg, 70%).

ESI-MS: 283.1 [M+H]$^+$ 135.5 N-[4-(1-Benzyl-pyrrolidin-3-yl)-2-methoxy-phenyl]-4-isopropylbenzenesulfonamide 4-(1-Benzyl-pyrrolidin-3-yl)-2-methoxy-phenylamine (220 mg, 0.78 mmol) and 4-isopropylphenylsulfonyl chloride (170 mg, 0.78 mmol) were dissolved in tetrahydrofuran (20 ml). Triethylamine (0.32 ml, 2.34 mmol) was added and the reaction mixture stirred over night at room temperature (10% conversion) and subsequently refluxed for 4 h (70% conversion). One small portion of 4-isopropylphenylsulfonyl chloride and triethylamine were added and the reaction mixture was stirred 15 min at 150° C. in the microwave (CEM). The solvent was evaporated under reduced pressure, the residue treated with ethyl acetate (50 ml) and extracted twice with slightly acidic water. The organic layer was dried over magnesium sulfate, filtered, and the solvent evaporated under reduced pressure to give an oil (470 mg). The crude product was purified via silica gel chromatography with cyclohexane/ethyl acetate (gradient 0-100%). Fractions containing the product were combined, the solvent evaporated to yield an oil (143 mg, 40%).

ESI-MS: 465.1 [M+H]$^+$ 135.6 4-Isopropyl-N-(2-methoxy-4-pyrrolidin-3-yl-phenyl)-benzenesulfonamide, acetate A mixture of N-[4-(1-benzyl-pyrrolidin-3-yl)-2-methoxy-phenyl]-4-isopropyl-benzenesulfonamide (143 mg, 0.31 mmol) and 10% palladium on carbon (20 mg) in ethyl acetate (20 ml) and acetic acid (20 ml) was hydrogenated for 4 h at room temperature. The catalyst was filtered, and the solvent was removed under vacuum to yield an oil (100 mg, 71%).

ESI-MS: 375.2 [M+H]$^+$ $^1$H-NMR (D$_2$O): δ [ppm] 7.6 (d, 2H), 7.4 (d, 2H), 7.3 (d, 1H), 6.9 (d, 1H), 6.8 (s, 1H), 3.7 (m, 1H), 3.6-3.4 (m, 6H), 3.2 (m, 1H), 3.0 (m, 1H), 2.4 (m, 1H), 2.1 (m, 1H), 1.2 (d, 6H).

Example 136

4-Isopropyl-N-[2-methoxy-4-(1-propyl-pyrrolidin-3-yl)-phenyl]-benzenesulfonamide, hydrochloride 4-Isopropyl-N-(2-methoxy-4-pyrrolidin-3-yl-phenyl)-benzenesulfonamide, acetate (40 mg, 0.09 mmol) and propionaldehyde (5.1 mg, 0.09 mmol) were dissolved in tetrahydrofuran (5 ml). Acetic acid (10 µl, 0.12 mmol) and sodium trisacetoxyborohydride (37 mg, 0.18 mmol) were sequentially added to the reaction mixture and stirred for 30 minutes at room temperature. The reaction mixture was concentrated and the residue was dissolved in aqueous NaHCO$_3$ (10 ml) and extracted with diethyl ether (30 ml). The organic phase was separated, dried over magnesium sulfate, filtered, and evaporated to dryness to yield an oil (30 mg). The residue was dissolved in diethyl ether (25 ml) and HCl in ether was added and stirred overnight. The solvent was decanted and to the residue was added 3 ml of H$_2$O. This solution was lyophilisated to yield the pure product (23 mg, 48%).

ESI-MS: 417.1 [M+H]$^+$ $^1$H-NMR(CH$_3$OH-d$_4$): δ [ppm] 7.6 (d, 2H), 7.4 (d, 2H), 7.3 (d, 1H), 6.9 (d, 1H), 6.8 (s, 1H), 3.5 (m, 5H), 3.3-3.2 (m, 2H), 3.0-2.9 (m, 4H), 2.4 (m, 1H), 2.0 (m, 1H), 1.7 (m, 2H), 1.2 (d, 6H), 1.0 (t, 3H).

Example 137

N-[4-(1-Allyl-pyrrolidin-3-yl)-2-methoxy-phenyl]-4-isopropyl-benzenesulfonamide, hydrochloride To 4-isopropyl-N-(2-Methoxy-4-pyrrolidin-3-yl-phenyl)-benzenesulfonamide, acetate (40 mg, 0.09 mmol) in N,N-dimethylformamide (5 ml) was added allyl bromide (8 µl, 0.1 mmol) and K$_2$CO$_3$ (36 mg, 0.26 mmol). The reaction mixture was stirred at room temperature for 2 h. The reaction mixture was diluted with water (35 ml) and extracted twice with diethyl ether (20 ml). The organic phase was separated, dried over magnesium sulfate, filtered, and evaporated to dryness to yield an oil (36 mg). The residue was dissolved in diethyl ether (25 ml) and HCl in ether was added and stirred overnight. The solvent was decanted and to the residue was added 3 ml H$_2$O. This solution was lyophilisated to yield the pure product (17 mg, 37%).

ESI-MS: 415.1 [M+H]$^+$ $^1$H-NMR(CH$_3$OH-d$_4$): δ [ppm] 7.6 (d, 2H), 7.3 (m, 3H), 6.8 (d, 1H), 6.7 (s, 1H), 5.9 (m, 1H), 5.3 (d, 1H), 5.2 (d, 1H), 3.4 (s, 3H), 3.2 (m, 1H), 3.0-2.9 (m, 3H), 2.6 (m, 1H), 2.3 (m, 1H), 1.9 (m, 1H), 1.2 (d, 6H).

Example 138

4-Isopropyl-N-[4-(1-propyl-piperidin-3-yl)-phenyl]-benzenesulfonamide, hydrochloride 138.1 3-Phenyl-1-propyl-piperidine 3-Phenyl-piperidine (4.0 g, 24.81 mmol) and propionaldehyde (1.8 ml, 24.81 mmol) were dissolved in tetrahydrofuran (100 ml). Acetic acid (2.14 ml, 37.21 mmol) and sodium trisacetoxyborohydride (10.515 g, 49.61 mmol) were sequentially added to the reaction mixture and stirred for 1 hour at room temperature. The reaction mixture was concentrated and the residue was dissolved in aqueous NaHCO$_3$ solution (50 ml) and diethyl ether (100 ml). The organic phases was dried over magnesium sulfate, filtered, and evaporated to dryness to yield the crude product (4.6 g, 87% purity).

ESI-MS: 204.15 [M+H]$^+$ 138.2 3-(4-Nitro-phenyl)-1-propyl-piperidine

To ice cooled 3-phenyl-1-propyl-piperidine (4.6 g, 19.73 mmol) and KNO$_3$ (2.254 g, 22.29 mmol) was added concentrated H$_2$SO$_4$. The reaction mixture was allowed to warm to room temperature and stirred for another 30 minutes. To the reaction mixture was added cautiously ice and subsequently the pH was adjusted to 9-10. The aqueous phase was extracted several times with ethyl acetate. The organic phases was dried over magnesium sulfate, filtered, and evaporated to dryness to yield the crude product (5.2 g, 81% purity).

ESI-MS: 249.15 [M+H]$^+$ 138.3 4-(1-Propyl-piperidin-3-yl)-phenylamine 3-(4-Nitro-phenyl)-1-propyl-piperidine (5.2 g, 1.86 mmol) was dissolved in methanol (35 ml), tin dichloride (3.78 g, 16.74 mmol) was added, and the reaction mixture stirred at reflux for 2 h and overnight at room temperature. The methanol was evaporated, 1 N sodium hydroxide (50 ml) and ethyl acetate were added and stirring continued. The tin salts were filtered off, the organic phase was separated, dried over magnesium sulfate, filtered, and the solvent evaporated under reduced pressure to yield an the crude product (450 mg, 90% purity).

138.4 4-Isopropyl-N-[4-(1-propyl-piperidin-3-yl)-phenyl]-benzenesulfonamide, hydrochloride 4-(1-Propyl-piperidin-3-yl)-phenylamine (600 mg, 1.65 mmol) and 4-isopropyl-phenylsulfonyl chloride (397 mg, 1.81 mmol) were dissolved in tetrahydrofuran (25 ml). Triethylamine (760 µl, 5.44 mmol) was added and the reaction mixture stirred for 72 hours at room temperature. The solvent was evaporated under reduced pressure, the residue treated with diethyl ether (50 ml) and three times extracted with water (3×30 ml). The organic phase was treated with 1 molar HCl solution. The acidic aqueous solution was made alkaline with NaOH solution to pH 9-10 and then extracted with ethyl acetate (25 ml). The organic phase was dried over magnesium sulfate, filtered, and the solvent evaporated under reduced pressure to give the crude product (580 mg). The crude product was purified via silica gel chromatography with ethyl acetate. Fractions containing the product were combined, the solvent evaporated to yield the pure product which was then converted into the hydrochloride salt via adding a solution of 1 N HCl in diethyl ether. The precipitate was filtered off and dried in vacuo to give the pure product (283 mg, 39%).

ESI-MS: 401.15 [M+H]$^+$ $^1$H-NMR (DMSO-d$_6$, 400 MHz): δ [ppm] 10.3 (s, 1H), 10.25 (bs, 1H), 7.7 (d, 2H), 7.45 (d, 2H), 7.15 (d, 2H), 7.1 (d, 2H), 3.45 (m, 1H), 3.35 (m, 1H), 3.1-2.8 (m, 6H), 1.9 (m, 2H), 1.85 (m, 1H), 1.75 (m, 2H), 1.55 (m, 1H), 1.2 (d, 6H), 0.9 (t, 3H).

Following a procedure analogous to example 138.4 the compounds of examples 139 to 142 were prepared. The compounds are characterised by the following physical data.

Example 139

N-[4-(1-Propyl-piperidin-3-yl)-phenyl]-4-trifluoromethoxy-benzenesulfonamide, hydrochloride

ESI-MS: 443.15 [M+H]$^+$ $^1$H-NMR (DMSO-d$_6$, 400 MHz): δ [ppm] 10.5 (s, 1H), 10.15 (bs, 1H), 7.9 (d, 2H), 7.6 (d, 2H), 7.2 (d, 2H), 7.1 (d, 2H), 3.45 (m, 2H), 3.1-2.8 (m, 5H), 1.9 (m, 2H), 1.85 (m, 1H), 1.7 (m, 2H), 1.55 (m, 1H), 0.9 (t, 3H).

Example 140

4-Difluoromethoxy-N-[4-(1-propyl-piperidin-3-yl)-phenyl]-benzenesulfonamide, hydrochloride

ESI-MS: 425.15 [M+H]$^+$ $^1$H-NMR (DMSO-d$_6$, 400 MHz): δ [ppm] 10.4 (s, 1H), 10.15 (bs, 1H), 7.85 (d, 2H), 7.4 (t, J=70 Hz, 1H), 7.35 (d, 2H), 7.15 (d, 2H), 7.1 (d, 2H), 3.45 (m, 1H), 3.4 (m, 1H), 3.1-2.8 (m, 5H), 1.9 (m, 2H), 1.85 (m, 1H), 1.75 (m, 2H), 1.55 (m, 1H), 0.9 (t, 3H).

Example 141

N-[4-(1-Propyl-piperidin-3-yl)-phenyl]-4-(2,2,2-trifluoro-ethyl)-benzenesulfonamide, hydrochloride

ESI-MS: 441.15 [M+H]$^+$ $^1$H-NMR (DMSO-d$_6$, 400 MHz): δ [ppm] 10.4 (s, 1H), 10.2 (bs, 1H), 7.8 (d, 2H), 7.55 (d, 2H), 7.15 (d; 2H), 7.1 (d, 2H), 3.8 (q, 2H), 3.45 (m, 1H), 3.4 (m, 1H), 3.1-2.8 (m, 5H), 1.9 (m, 2H), 1.85 (m, 1H), 1.7 (m, 2H), 1.55 (m, 1H), 0.9 (t, 3H).

Example 142

4-(2,2-Difluoro-cyclopropyl)-N-[4-(1-propyl-piperidin-3-yl)-phenyl]-benzenesulfonamide, hydrochloride

ESI-MS: 435.15 [M+H]$^+$ $^1$H-NMR (DMSO-d$_6$, 400 MHz): δ [ppm] 10.35 (s, 1H), 10.15 (bs, 1H), 7.75 (d, 2H), 7.45 (d, 2H), 7.15 (d, 2H), 7.1 (d, 2H), 3.45 (m, 1H), 3.4 (m, 1H), 3.15-2.8 (m, 5H), 2.05 (m, 2H), 1.9 (m, 2H), 1.8 (m, 1H), 1.7 (m, 2H), 1.55 (m, 1H), 0.9 (t, 3H).

Example 143

N-(3-Piperidin-3-yl-phenyl)-4-trifluoromethoxy-benzenesulfonamide 143.1 3-[3-(4-Trifluoromethoxy-benzenesulfonylamino)-phenyl]-piperidine-1-carboxylic acid tert-butyl ester 3-(3-Amino-phenyl)-piperidine-1-carboxylic acid tert-butyl ester (500 mg, 1.81 mmol) and dimethylaminopyridine (30 mg, 0.25 mmol) were dissolved in tetrahydrofuran (40 ml). 4-Trifluoromethoxyphenylsulfonyl chloride (519 mg, 1.99 mmol) was added and the reaction mixture stirred for 2 hours at room temperature. Additional quantities of trifluoromethoxyphenylsulfonyl chloride was added until the 3-(3-amino-phenyl)piperidine-1-carboxylic acid tert-butyl ester was completely consumed to give the bissulfonylated product. The solvent was evaporated under reduced pressure, the residue treated with water (25 ml) and diethyl ether (50 ml). The organic phases was dried over magnesium sulfate, filtered, and the solvent evaporated under reduced pressure. In an inert atmosphere, the residue was dissolved in ethanol (30 ml) and small pieces of metallic sodium were added and the reaction mixture was stirred for 1 hour at room temperature. The solvent was evaporated under reduced pressure, the residue treated with water (25 ml) and diethyl ether (50 ml). The organic phases was dried over magnesium sulfate, filtered, and the solvent evaporated under reduced pressure to give the crude product (385 mg). The crude product was purified via silica gel chromatography with dichloromethane/methanol (gradient 100:0-97:3). Fractions containing the product were combined, the solvent evaporated to yield the pure product (340 mg, 36%).

ESI-MS: 445.05 [M+H—C(CH$_3$)$_3$]$^+$ 143.2 N-(3-Piperidin-3-yl-phenyl)-4-trifluoromethoxy-benzenesulfonamide 3-[3-(4-Trifluoromethoxy-benzenesulfonylamino)-phenyl]-piperidine-1-carboxylic acid tert-butyl ester (340 mg, 0.66 mmol) was dissolved in dichloromethane (30 ml). Trifluoroacetic acid (2 ml) was added and the reaction mixture was stirred at room temperature for 1 hour. The reaction mixture was evaporated to dryness. Aqueous NaHCO$_3$ solution (10 ml) was added and extracted twice with ethyl acetate (25 ml). The combined organic phases were dried over magnesium sulfate, filtered, and evaporated to dryness to yield the pure product (250 mg, 95% yield).

ESI-MS: 401.05 [M+H]$^+$ $^1$H-NMR (DMSO-d$_6$, 400 MHz): δ [ppm] 7.85 (d, 2H), 7.5 (d, 2H), 7.1 (t, 1H), 6.9 (d, 1H), 6.85 (m, 2H), 2.95 (m, 2H), 2.5 (m, 3H), 1.75 (m, 1H), 1.65 (m, 1H), 1.45 (m, 2H).

Example 144

4-Isopropyl-N-(3-piperidin-3-yl-phenyl)benzenesulfonamide 144.1 3-[3-(4-Isopropyl-benzenesulfonylamino)-phenyl]-piperidine-1-carboxylic acid tert-butyl ester The title compound was prepared similar to a procedure as described in example 143.1

ESI-MS: 403.15 [M+H—C(CH$_3$)$_3$]$^+$ 144.2 4-Isopropyl-N-(3-piperidin-3-yl-phenyl)-benzenesulfonamide The title compound was prepared similar to a procedure as described in example 144.1

ESI-MS: 359.15 [M+H]$^+$ $^1$H-NMR (DMSO-d$_6$, 400 MHz): δ [ppm] 7.75 (d, 2H), 7.4 (d, 2H), 7.1 (t, 1H), 6.9 (d, 1H), 6.85 (m, 2H), 2.95 (m, 2H), 2.85 (m, 1H), 2.5-2.35 (m, 3H), 1.75 (m, 1H), 1.6 (m, 1H), 1.4 (m, 2H), 1.2 (d, 6H).

Example 145

N-[3-(1-Propyl-piperidin-3-yl)-phenyl]-4-trifluoromethoxy-benzenesulfonamide, hydrochloride N-(3-Piperidin-3-yl-phenyl)-4-trifluoromethoxy-benzenesulfonamide (60 mg, 0.15 mmol) and propionaldehyde (11 µl, 0.15 mmol) were dissolved in tetrahydrofuran (10 ml). Acetic acid (14 mg, 0.22 mmol) and sodium trisacetoxyborohydride (64 mg, 0.30 mmol) were sequentially added to the reaction mixture and stirred for 1 hour at room temperature. The reaction mixture was concentrated and the residue was dissolved in aqueous NaHCO$_3$ solution (5 ml) and diethyl ether (25 ml). The organic phases were dried over magnesium sulfate, filtered, and evaporated to dryness to yield the crude product (62 mg). The crude product was purified via silica gel chromatography with dichloromethane/methanol (gradient 100:0-75:25). Fractions containing the product were combined, the solvent evaporated to yield the pure product (42 mg) which was converted into the hydrochloride salt (45 mg, 63%).

ESI-MS: 443.15 [M+H]$^+$ $^1$H-NMR (DMSO-d$_6$, 400 MHz): δ [ppm] 10.45 (s, 1H), 10.25 (bs, 1H), 7.9 (d, 2H), 7.55 (d, 2H), 7.25 (t, 1H), 7.0 (m, 3H), 3.45 (m, 1H), 3.35 (m, 1H), 3.1-2.85 (m, 6H), 1.9 (m, 2H), 1.75 (m, 3H), 1.55 (m, 1H), 0.9 (t, 3H).

Example 146

4-Isoproply-N-[3-(1-propyl-piperidin-3-yl)-phenyl]-benzenesulfonamide, hydrochloride The title compound was prepared in a procedure analogous to that described in example 145.

ESI-MS: 401.25 [M+H]$^+$ $^1$H-NMR (DMSO-d$_6$, 400 MHz): (δ [ppm] 10.3 (s, 1H), 10.15 (bs, 1H), 7.7 (d, 2H), 7.45 (d, 2H), 7.2 (t, 1H), 7.0 (m, 2H), 6.95 (d, 1H), 3.45 (m, 1H), 3.35 (m, 1H), 3.05-2.85 (m, 6H), 1.9 (m, 2H), 1.75 (m, 3H), 1.55 (m, 1H), 1.2 (d, 6H), 0.9 (t, 3H).

III. Examples of Galenic Administration Forms

A) Tablets

Tablets of the following composition are pressed on a tablet press in the customary manner:

40 mg of substance from Example 8
120 mg of corn starch
13.5 mg of gelatin
45 mg of lactose
2.25 mg of Aerosil® (chemically pure silicic acid in submicroscopically fine dispersion)
6.75 mg of potato starch (as a 6% paste)

B) Sugar-Coated Tablets 20 mg of substance from Example 8
60 mg of core composition
70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

Receptor Binding Studies:

The substance to be tested was either dissolved in methanol/Chremophor® (BASFAG) or in dimethyl sulfoxide and then diluted with water to the desired concentration.

Dopamine D$_3$ Receptor:

The assay mixture (0.250 ml) was composed of membranes derived from ~10$^6$ HEK-293 cells possessing stably expressed human dopamine D$_3$ receptors, 0.1 nM [$^{125}$I]-iodosulpride and incubation buffer (total binding) or, in addition, test substance (inhibition curve) or 1 µM spiperone (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin, 10 μM quinolone and 0.1% ascorbic acid (prepared fresh daily). The buffer was adjusted to pH 7.4 with HCl.

Dopamine D$_{2L}$ Receptor:

The assay mixture (1 ml) was composed of membranes from ~10$^6$ HEK-293 cells possessing stably expressed human dopamine D$_{2L}$ receptors (long isoform) and 0.01 nM [$^{125}$I] iodospiperone and incubation buffer (total binding) or, in addition, test substance (inhibition curve) or 1 μM haloperidol (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptro binding studies are expressed as receptor binding constants K$_i$(D$_2$) and K$_i$(D$_3$), respectively, as herein before described, and given in table 6.

In these tests, the compounds according to the invention exhibit very good affinities for the D$_3$ receptor (<50 nM, or <10 nM, frequently <5 nM) and bind selectively to the D$_3$ receptor.

The results of the binding tests are given in table 6.

TABLE 6

| Example | K$_i$(D3)* [nM] | K$_i$(D2)* [nM] | K$_i$(D2)*/K$_i$(D3)* |
|---|---|---|---|
| 1 | 0.09 | 7.6 | 89 |
| 2 | 0.24 | 2.3 | 9 |
| 3 | 0.17 | 13.8 | 91 |
| 4 | 3.16 | 403 | 127 |
| 5 | 2.9 | 267 | 93 |
| 6 | 0.45 | 20.1 | 45 |
| 7 | 3.5 | 212 | 61 |
| 8 | 4.1 | 235 | 57 |
| 9 | 2.6 | 129 | 49 |
| 10 | 1.9 | 111 | 60 |
| 12 | 3.0 | 131 | 43 |
| 13 | 3.1 | 168 | 54 |
| 14 | 3.4 | 123 | 37 |
| 15 | 1.9 | 74 | 39 |
| 16 | 12.6 | 393 | 31 |
| 17 | 3.1 | 126 | 41 |
| 18 | 2.3 | 90 | 39 |
| 19 | 0.48 | 12.6 | 26 |
| 20 | 0.3 | 7.3 | 24 |
| 21 | 0.4 | 11 | 27 |
| 23 | 1.07 | 46.6 | 44 |
| 24 | 1.2 | 72 | 60 |
| 25 | 1.6 | 95 | 60 |
| 26 | 28.1 | 1278 | 46 |
| 27 | 0.23 | 7.1 | 30 |
| 28 | 3.3 | 133 | 41 |
| 29 | 0.67 | 27.3 | 41 |

TABLE 6-continued

| Example | K$_i$(D3)* [nM] | K$_i$(D2)* [nM] | K$_i$(D2)*/K$_i$(D3)* |
|---|---|---|---|
| 30 | 0.28 | 11.7 | 42 |
| 31 | 10.8 | 257 | 24 |
| 33 | 0.17 | 5.47 | 33 |
| 34 | 5.1 | 174 | 34 |
| 35 | 0.3 | 7.4 | 24 |
| 37 | 0.15 | 3.25 | 22 |
| 38 | 0.29 | 6.3 | 21 |
| 40 | 0.46 | 18.2 | 40 |
| 41 | 0.44 | 13.5 | 30 |
| 46 | 49 | 1,830 | 37 |
| 48 | 2.1 | 137 | 65 |
| 49 | 46 | 1,808 | 39 |
| 53 | 0.41 | 5.85 | 14 |
| 54 | 0.32 | 8.73 | 27 |
| 55 | 7.11 | 1175 | 165 |
| 56 | 24.4 | 2661.2 | 109 |
| 57 | 7.18 | 880 | 123 |
| 58 | 39.80 | 2940.0 | 74 |
| 59 | 6.41 | 1525 | 238 |
| 60 | 7.63 | 7780 | 1019 |
| 61 | 21.3 | — | — |
| 62 | 25.2 | 3545 | 141 |
| 63 | 5.75 | 647.21 | 113 |
| 64 | 2.10 | 344 | 164 |
| 65 | 6.79 | 197 | 29 |
| 67 | 0.35 | 3.88 | 11 |
| 68 | 3.00 | 142 | 47 |
| 69 | 2.51 | 90.3 | 36 |
| 70 | 0.84 | 37.3 | 44 |
| 71 | 4.79 | 52.3 | 11 |
| 72 | 35.1 | 473 | 13 |
| 73 | 0.61 | 6.73 | 11 |
| 74 | 0.69 | 10.5 | 15 |
| 75 | 0.63 | 12.2 | 19 |
| 77 | 1.33 | 50 | 37 |
| 78 | 1.40 | 41.9 | 30 |
| 79 | 13.5 | 1111 | 82 |
| 80 | 37.6 | 1095 | 29 |
| 81 | 31.3 | 1162.0 | 37 |
| 82 | 5.59 | 437 | 78 |
| 84 | 0.95 | 16.2 | 17 |
| 85 | 0.57 | 18.5 | 32 |
| 86 | 1.18 | 119 | 101 |
| 87 | 0.55 | 20.5 | 37 |
| 88 | 0.92 | 41 | 45 |
| 89 | 0.6 | 27 | 45 |
| 90 | 11 | 280 | 25 |
| 92 | 0.61 | 17.3 | 28 |
| 93 | 0.48 | 14.7 | 31 |
| 94 | 0.23 | 4.7 | 21 |
| 95 | 1.3 | 27.9 | 22 |
| 96 | 0.83 | 57.8 | 70 |
| 101 | 3.7 | 268 | 73 |
| 102 | 52 | 2714 | 52 |
| 103 | 1.2 | 45 | 38 |
| 104 | 8.3 | 352 | 43 |
| 105 | 6.1 | 309 | 51 |
| 107 | 0.42 | 45.8 | 108 |
| 108 | 11.2 | 203.8 | 18 |
| 109 | 7.4 | 257.9 | 35 |
| 110 | 6.6 | 895 | 135 |
| 111 | 16.4 | 723 | 44 |
| 112 | 10.3 | 1196 | 116 |
| 113 | 0.49 | 42.2 | 86 |
| 114 | 4.2 | 464 | 111 |
| 118 | 36.6 | 1169 | 32 |
| 120 | 2.0 | 174 | 86 |
| 121 | 3.7 | 163 | 44 |
| 122 | 43.9 | 1342 | 31 |
| 123 | 0.45 | 41 | 91 |
| 125 | 19.5 | 1305 | 67 |
| 126 | 34 | 1021 | 30 |
| 127 | 0.6 | 64.7 | 112 |
| 128 | 2.7 | 12.9 | 5 |
| 129 | 3.6 | 106.3 | 30 |
| 130 | 0.52 | 8.5 | 16 |
| 131 | 5.8 | 430 | 74 |
| 133 | 7.3 | 192.7 | 26 |

TABLE 6-continued

| Example | $K_i(D3)$* [nM] | $K_i(D2)$* [nM] | $K_i(D2)$*/$K_i(D3)$* |
|---|---|---|---|
| 134 | 0.76 | | 13 |
| 135 | 0.85 | | 17 |
| 136 | 0.27 | | 6 |
| 137 | 0.36 | | 12 |

*Receptor binding constants obtained according to the assays as described herein before

We claim:

1. A compound of the formula (I)

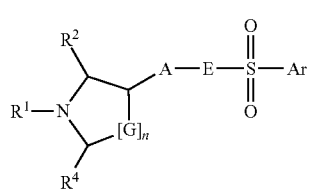

wherein n is 0;

G is $CH_2$ or $CHR_3$;

$R^1$ is H, $C_1$-$C_6$-alkyl, $C_1$-$C_6$-alkyl substituted by $C_3$-$C_6$-cycloalkyl, $C_1$-$C_6$ hydroxyalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl;

$R^2$, $R^3$ and $R^4$ are, independently of each other, H, methyl, fluoromethyl, di-fluoromethyl, or trifluoromethyl;

A is phenylene, pyridylene, pyrimidylene, pyrazinylene, pyridazinylene or thiophenylene, which can be substituted by one or more substituents selected from halogen, methyl, methoxy and $CF_3$;

E is $NR^5$ or $CH_2$, wherein $R^5$ is H or $C_1$-$C_3$-alkyl;

Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl, and where the cyclic radical Ar may carry 1, 2 or 3 substituents $R^a$;

$R^a$ is halogen, $C_1$-$C_6$-alkyl, fluorinated $C_1$-$C_6$-alkyl, $C_1$-$C_6$-hydroxyalkyl, $C_1$-$C_6$alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, benzyloxy, phenoxy, where the phenyl radical in the 3 last-mentioned radicals may be unsubstituted or may carry 1 to 3 substituents selected from $C_1$-$C_4$-alkyl, fluorinated $C_1$-$C_4$-alkyl and halogen, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, NH—C(O)—$NR^6R^7$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring, or is a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the heterocyclic ring may carry 1, 2 or 3 substituents selected from hydroxy, halogen, $C_1$-$C_6$ alkyl, fluorinated $C_1$-$C_6$-alkyl and $C_1$-$C_6$-alkoxy;

or a physiologically tolerated acid addition salt thereof.

2. The compound of claim 1,

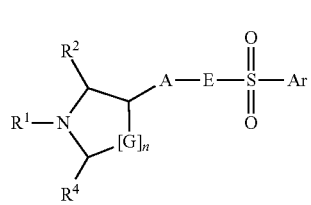

wherein $R^1$ is H, $C_1$-$C_6$-alkyl which may be substituted by $C_3$-$C_6$-cycloalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl; and Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S, and where the cyclic radical may carry 1, 2 or 3 substituents $R^a$ selected from the group consisting of halogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, CN, acetyl, carboxy, $NR^6R^7$, $NR^6R^7$—$C_1$-$C_6$-alkylene, where $R^6$ and $R^7$ are, independently of each other, H, $C_1$-$C_4$-alkyl or fluorinated $C_1$-$C_4$-alkyl or may form, together with N, a 4-, 5- or 6-membered saturated or unsaturated ring, and a saturated or unsaturated 5- or 6-membered heterocyclic ring comprising as ring members 1, 2 or 3 heteroatoms selected from N, O and S.

3. The compound of claim 1, wherein $R^1$ is hydrogen, methyl, ethyl, n-propyl, 2-fluoroethyl, 3-fluoropropyl, 3-hydroxypropyl, cyclo-propylmethyl or allyl.

4. The compound of claim 3, wherein $R^1$ is n-propyl or allyl.

5. The compound of claim 1, wherein $R^2$, $R^3$ and $R^4$ are H.

6. The compound of claim 1, wherein A is phenylene, pyridylene or pyrimidylene.

7. The compound of claim 1, wherein E is NH.

8. The compound of claim 1, wherein Ar is phenyl, thienyl, pyridyl, pyrimidyl, imidazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl or indanyl, which may be substituted as defined in claim 1.

9. The compound of claim 8, wherein Ar is phenyl, thienyl, pyridyl, benzofuranyl or indanyl, where the cyclic radical may carry 1, 2 or 3 substituents $R^a$ selected from the group consisting of halogen, $C_1$-$C_6$-alkyl, fluorinated $C_1$-C alkyl, $C_3$-$C_6$-cycloalkyl, fluorinated $C_3$-$C_6$-cycloalkyl, $C_1$-$C_6$- alkoxy, fluorinated $C_1$-$C_6$-alkoxy, CN, acetyl, carboxy, $NR^6R^7$, $NR^6R^7$—$C_1$-$C_6$-alkylene, where $R^6$ and $R^7$ are, independently of each other, H, $C_1$-$C_4$-alkyl or fluorinated $C_1$-$C_4$-alkyl or may form, together with N, a 4-, 5- or 6-membered saturated or unsaturated ring, and a saturated or unsaturated 5- or 6-membered heterocyclic ring comprising as ring members 1, 2 or 3 heteroatoms selected from N, O and S.

10. The compound of claim 8, wherein Ar is phenyl which carries 1, 2 or 3 substituents selected from the group consisting of halogen, $C_1$-$C_6$-alkyl, fluorinated $C_1$-$C_4$-alkyl, $C_1$-$C_4$-alkoxy, fluorinated $C_1$-$C_4$-alkoxy, $C_2$-$C_4$-alkenyl, fluorinated $C_2$-$C_4$-alkenyl, $CH_2N(CH_3)_2$, $NR^6R^7$, where $R^6$ and $R^7$ are independently of each other H, $C_1$-$C_4$-alkyl or fluorinated $C_1$-$C_4$-alkyl, $C_3$-$C_6$-cycloalkyl optionally substituted by halogen, acetyl or carboxyl, or Ar is thienyl, pyridyl, benzofuranyl or indanyl, which are optionally substituted by halogen, $C_1$-$C_4$-alkyl or $C_1$-$C_4$-alkenyl.

11. The compound of claim 1, wherein Ar carries one radical $R^a$ of the formula $R^{a\prime}$

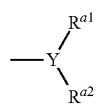

wherein
Y is N, CH or CF,
$R^{a1}$ and $R^{a2}$ are independently of each other selected from $C_1$-$C_2$-alkyl, fluorinated $C_1$-$C_2$-alkyl and $C_1$-$C_2$-alkoxy, provided for Y being CH or CF one of the radicals $R^{a1}$ or $R^{a2}$ may also be hydrogen or fluorine, or $R^{a1}$ and $R^{a2}$ together form a radical $(CH_2)_m$ wherein 1 or 2 of the hydrogen atoms may be replaced by fluorine, hydroxy, $C_1$-$C_2$-alkyl or $C_1$-$C_2$-alkoxy, wherein one $CH_2$ moiety may be replaced by O, S, SO, $SO_2$ or $NR^C$, wherein $R^C$ is H or $C_1$-$C_2$-alkyl, and wherein m is 2, 3, 4, 5 or 6.

12. The compound of claim 11, wherein the radical $R^{a\prime}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, cyclopropyl, cyclobutyl, 1-fluorocyclopropyl, 2-fluorocyclopropyl, (S)-2,2-difluorocyclopropyl and (R)-2,2-difluorocyclopropyl.

13. The compound of claim 11, wherein the radical $R^{a\prime}$ carries 1, 2, 3 or 4 fluorine atoms.

14. The compound of claim 1, wherein Ar is phenyl that carries a radical $R^a$ in the 4-position of the phenyl ring.

15. The compound of claim 1, wherein the absolute configuration at the carbon atom carrying the group A is (S).

16. The compound of claim 1, wherein Ar is phenyl which is substituted by a 5- or 6 membered heterocyclic radical selected from azetidinyl, pyrrolidinyl, oxopyrrolidinyl, oxooxazolidinyl, piperidinyl, piperazinyl, morpholinyl, thiomorpholinyl, 1-oxothiomorpholinyl, 1,1-dioxothiomorpholinyl, pyrrolyl, furanyl, thienyl, pyrazolyl, imidazolyl, oxazolyl, isoxazolyl, triazolyl, oxadiazolyl, furazanyl, thiadiazolyl, and tetrazolyl, where the heterocyclic radical may be unsubstituted or may carry 1 to 3 substituents selected from halogen, $C_1$-$C_4$-alkyl, fluorinated $C_1$-$C_4$-alkyl, $C_1$-$C_4$-alkoxy and hydroxy.

17. The compound of claim 16, wherein Ar is phenyl which is substituted by a 5- or 6 membered heterocyclic radical selected from azetidinyl, pyrrolidinyl, oxopyrrolidinyl, oxooxazolidinyl, morpholinyl, furanyl, thienyl, pyrazolyl, oxazolyl, isoxazolyl, and thiadiazolyl, where the heterocyclic radical may be unsubstituted or may carry 1 to 3 substituents selected from halogen and $C_1$-$C_4$-alkyl.

18. A pharmaceutical composition comprising at least one compound of claim 1, optionally together with at least one physiologically acceptable carrier or auxiliary substance.

19. A method for the treatment of acute or chronic signs, symptoms and/or malfunctions of a disease selected from the group consisting of Parkinson's disease, schizophrenia, depression, and anxiety, said method comprising administering an effective amount of at least one compound of claim 1 to a subject in need thereof.

20. The compound of formula (I) according to claim 1, that is 4-oxazol-4-yl-N-[4-(1-propyl-azetidin-3-yl)-phenyl]-benzenesulfonamide, or a physiologically tolerated acid addition salt thereof.

* * * * *